US012428448B1

(12) United States Patent  (10) Patent No.: US 12,428,448 B1
Fischer et al.  (45) Date of Patent: Sep. 30, 2025

(54) ALPHAVIRUS IMMUNOGENS AND METHODS OF USE

(71) Applicant: Triad National Security, LLC, Los Alamos, NM (US)

(72) Inventors: William M. Fischer, Los Alamos, NM (US); Peter T. Hraber, Los Alamos, NM (US)

(73) Assignee: Triad National Security, LLC, Los Alamos, NM (US)

( * ) Notice: Subject to any disclaimer, the term of this patent is extended or adjusted under 35 U.S.C. 154(b) by 902 days.

(21) Appl. No.: 17/590,166

(22) Filed: Feb. 1, 2022

Related U.S. Application Data

(60) Provisional application No. 63/144,551, filed on Feb. 2, 2021.

(51) Int. Cl.
  C07K 14/005 (2006.01)
  A61K 39/00 (2006.01)
  A61K 39/12 (2006.01)

(52) U.S. Cl.
  CPC ............ *C07K 14/005* (2013.01); *A61K 39/12* (2013.01); *A61K 2039/70* (2013.01); *C12N 2770/36122* (2013.01); *C12N 2770/36134* (2013.01)

(58) Field of Classification Search
  None
  See application file for complete search history.

(56) References Cited

U.S. PATENT DOCUMENTS 9,555,090 B2   1/2017  Dupuy et al.
2020/0345838 A1* 11/2020 Clark ................. C07K 16/2878

OTHER PUBLICATIONS

UniProt ID M1KF82_EEVV, V1 2013. https://rest.uniprot.org/unisave/M1KF82?format=txt&versions=1. Accessed Apr. 25, 2025. (Year: 2013).*
UniProt ID M1KF47_EEVV, V1 2013. https://rest.uniprot.org/unisave/M1KF47?format=txt&versions=1. Accessed Apr. 25, 2025. (Year: 2013).*
UniProt ID C7T0L5_EEVV, V1 2009. https://rest.uniprot.org/unisave/C7T0L5?format=txt&versions=1. Accessed Apr. 25, 2025. (Year: 2009).*
UniProt ID M1KF13_EEVV, V1 2013. https://rest.uniprot.org/unisave/M1KF13?format=txt&versions=1. Accessed Apr. 25, 2025. . (Year: 2013).*
UniProt ID A0A068BBW7_WEEV, V1 2014. https://rest.uniprot.org/unisave/A0A068BBW7?format=txt&versions=1. Accessed Apr. 25, 2025. (Year: 2014).*

(Continued)

*Primary Examiner* — Thomas J. Visone
*Assistant Examiner* — Katherine A. Willard
(74) *Attorney, Agent, or Firm* — Klarquist Sparkman, LLP

(57) ABSTRACT

Synthetic immunogenic polypeptides based on a curated set of natural alphavirus structural protein sequences are described. The polypeptides were computationally designed to provide optimal coverage of potential immunogenic epitopes of wild-type alphaviruses, including isolates of Venezuelan equine encephalitis virus, Western equine encephalitis virus, Eastern equine encephalitis virus and Chikungunya virus. Sets of immunogenic polypeptides, as well as nucleic acid molecules and vectors encoding the immunogenic polypeptides are also described. The disclosed compositions can be used to elicit an immune response against alphaviruses in a subject.

20 Claims, 2 Drawing Sheets

Specification includes a Sequence Listing.

(56) References Cited

OTHER PUBLICATIONS

UniProt ID C7DYC0_9VIRU, V1 2009. https://rest.uniprot.org/unisave/C7DYC0?format=txt&versions=1. Accessed Apr. 25, 2025. (Year: 2009).*

UniProt ID A1YZ44_EEEV, V1 2007. https://rest.uniprot.org/unisave/A1YZ44?format=txt&versions=1. Accessed Apr. 25, 2025. (Year: 2007).*

UniProt ID D2X872_EEEV, V1 2010. https://rest.uniprot.org/unisave/D2X872?format=txt&versions=1. Accessed Apr. 25, 2025. (Year: 2010).*

UniProt ID Q1H8W5_CHIKV, V1 2006. https://rest.uniprot.org/unisave/Q1H8W5?format=txt&versions=1. Accessed Apr. 25, 2025. (Year: 2006).*

UniProt ID M1JR58_EEVV, V1 2013. https://rest.uniprot.org/unisave/M1JR58?format=txt&versions=1. Accessed Apr. 25, 2025. (Year: 2013).*

UniProt ID M1KFF6_EEVV, V1 2013. https://rest.uniprot.org/unisave/M1KFF6?format=txt&versions=1. Accessed Apr. 25, 2025. (Year: 2013).*

UniProt ID C7T0M0_EEVV, V1 2009. https://rest.uniprot.org/unisave/C7T0M0?format=txt&versions=1. Accessed Apr. 25, 2025. (Year: 2009).*

UniProt ID W8R6F6_EEEV, V1 2014. https://rest.uniprot.org/unisave/W8R6F6?format=txt&versions=1. Accessed Apr. 25, 2025. (Year: 2014).*

UniProt ID D2KBQ2_CHIKV, V1 2010. https://rest.uniprot.org/unisave/D2KBQ2?format=txt&versions=1. Accessed Apr. 25, 2025. (Year: 2010).*

U.S. Appl. No. 17/590,166_alignments. Alignments of claimed SEQ ID Nos. to various deposited UniProt sequences. (Year: 2025).*

Theiler et al., "Graph-Based Optimization of Epitope Coverage for Vaccine Antigen Design" *Statist. Med.*, vol. 37:181-194, 2018.

Wolfe et al., "Perspective Piece: Current Strategic Thinking for the Development of a Trivalent Alphavirus Vaccine for Human Use," *Am. J. Trop. Med. Hyg.*, vol. 91:442-450, 2014.

\* cited by examiner

SEQUENCE LISTING

<160> NUMBER OF SEQ ID NOS: 26

<210> SEQ ID NO 1
<211> LENGTH: 1264
<212> TYPE: PRT
<213> ORGANISM: Artificial Sequence
<220> FEATURE:
<223> OTHER INFORMATION: Synthetic polypeptide

<400> SEQUENCE: 1

```
Met Asp Tyr Asp Ile Val Ser Ala Lys Met Phe Pro Phe Gln Pro Met
1               5                   10                  15

Tyr Pro Met Gln Pro Met Pro Tyr Arg Asn Pro Phe Ala Ala Pro Arg
                20                  25                  30

Arg Pro Trp Phe Pro Arg Thr Asp Pro Phe Leu Ala Met Gln Val Gln
            35                  40                  45

Glu Leu Thr Arg Ser Met Ala Asn Leu Thr Phe Lys Gln Arg Arg Asp
50                  55                  60

Ala Pro Pro Glu Gly Pro Pro Ala Lys Lys Pro Lys Arg Glu Ala Pro
65                  70                  75                  80

Gln Lys Gln Lys Gly Gly Gly Gln Gly Lys Lys Lys Asn Gln Gly
                85                  90                  95

Lys Lys Lys Ala Lys Thr Gly Pro Pro Asn Pro Lys Ala Gln Asn Gly
                100                 105                 110

Asn Lys Lys Lys Thr Asn Lys Lys Pro Gly Lys Arg Gln Arg Met Val
            115                 120                 125

Met Lys Leu Glu Ser Asp Lys Thr Phe Pro Ile Met Leu Glu Gly Lys
130                 135                 140

Ile Asn Gly Tyr Ala Cys Val Val Gly Lys Leu Phe Arg Pro Met
145                 150                 155                 160

His Val Glu Gly Lys Ile Asp Asn Asp Val Leu Ala Ala Leu Lys Thr
                165                 170                 175

Lys Lys Ala Ser Lys Tyr Asp Leu Glu Tyr Ala Asp Val Pro Gln Asn
            180                 185                 190

Met Arg Ala Asp Thr Phe Lys Tyr Thr His Glu Lys Pro Gln Gly Tyr
        195                 200                 205

Tyr Ser Trp His His Gly Ala Val Gln Tyr Glu Asn Gly Arg Phe Thr
210                 215                 220

Val Pro Lys Gly Val Gly Ala Lys Gly Asp Ser Gly Arg Pro Ile Leu
225                 230                 235                 240

Asp Asn Gln Gly Arg Val Val Ala Ile Val Leu Gly Gly Val Asn Glu
                245                 250                 255

Gly Ser Arg Thr Ala Leu Ser Val Val Met Trp Asn Glu Lys Gly Val
            260                 265                 270

Thr Val Lys Tyr Thr Pro Glu Asn Cys Glu Gln Trp Ser Leu Val Thr
        275                 280                 285

Thr Met Cys Leu Leu Ala Asn Val Thr Phe Pro Cys Ala Gln Pro Pro
290                 295                 300

Ile Cys Tyr Asp Arg Lys Pro Ala Glu Thr Leu Ala Met Leu Ser Val
305                 310                 315                 320

Asn Val Asp Asn Pro Gly Tyr Asp Glu Leu Leu Glu Ala Ala Val Lys
                325                 330                 335

Cys Pro Gly Arg Lys Arg Arg Ser Thr Glu Glu Leu Phe Lys Glu Tyr
            340                 345                 350

Lys Leu Thr Arg Pro Tyr Met Ala Arg Cys Ile Arg Cys Ala Val Gly
```

```
                355                 360                 365
Ser Cys His Ser Pro Ile Ala Ile Glu Ala Val Lys Ser Asp Gly His
    370                 375                 380

Asp Gly Tyr Val Arg Leu Gln Thr Ser Ser Gln Tyr Gly Leu Asp Ser
385                 390                 395                 400

Ser Gly Asn Leu Lys Gly Arg Thr Met Arg Tyr Asp Met His Gly Thr
                405                 410                 415

Ile Glu Glu Ile Pro Leu His Gln Val Ser Leu His Thr Ser Arg Pro
            420                 425                 430

Cys His Ile Val Asp Gly His Gly Tyr Phe Leu Leu Ala Arg Cys Pro
        435                 440                 445

Ala Gly Asp Ser Ile Thr Met Glu Phe Lys Lys Asp Ser Val Thr His
    450                 455                 460

Ser Cys Ser Val Pro Tyr Glu Val Lys Phe Asn Pro Val Gly Arg Glu
465                 470                 475                 480

Leu Tyr Thr His Pro Pro Glu His Gly Ala Glu Gln Ala Cys Gln Val
                485                 490                 495

Tyr Ala His Asp Ala Gln Asn Arg Gly Ala Tyr Val Glu Met His Leu
            500                 505                 510

Pro Gly Ser Glu Val Asp Ser Leu Val Ser Leu Ser Gly Ser Ser
        515                 520                 525

Val Thr Val Thr Pro Pro Ala Gly Thr Ser Ala Leu Val Glu Cys Glu
    530                 535                 540

Cys Gly Gly Thr Lys Ile Ser Glu Thr Ile Asn Thr Ala Lys Gln Phe
545                 550                 555                 560

Ser Gln Cys Thr Lys Lys Glu Gln Cys Arg Ala Tyr Arg Leu Gln Asn
                565                 570                 575

Asp Lys Trp Val Tyr Asn Ser Asp Lys Leu Pro Lys Ala Ala Gly Ala
            580                 585                 590

Thr Leu Lys Gly Lys Leu His Val Pro Phe Leu Leu Ala Asp Gly Lys
        595                 600                 605

Cys Thr Val Pro Leu Ala Pro Glu Pro Met Ile Thr Phe Gly Phe Arg
    610                 615                 620

Ser Val Ser Leu Lys Leu His Pro Lys Asn Pro Thr Tyr Leu Thr Thr
625                 630                 635                 640

Arg Gln Leu Ala Asp Glu Pro His Tyr Thr His Glu Leu Ile Ser Glu
                645                 650                 655

Pro Ala Val Arg Asn Phe Thr Val Thr Glu Lys Gly Trp Glu Phe Val
            660                 665                 670

Trp Gly Asn His Pro Pro Lys Arg Phe Trp Ala Gln Glu Thr Ala Pro
        675                 680                 685

Gly Asn Pro His Gly Leu Pro His Glu Val Ile Thr His Tyr Tyr His
    690                 695                 700

Arg Tyr Pro Met Ser Thr Ile Leu Gly Leu Ser Ile Cys Ala Ala Ile
705                 710                 715                 720

Val Thr Val Ser Val Ala Ala Ser Thr Trp Leu Phe Cys Lys Ser Arg
                725                 730                 735

Val Ser Cys Leu Thr Pro Tyr Arg Leu Thr Pro Asn Ala Arg Met Pro
            740                 745                 750

Leu Cys Leu Ala Val Leu Cys Cys Ala Arg Thr Ala Arg Ala Glu Thr
        755                 760                 765

Thr Trp Glu Ser Leu Asp His Leu Trp Asn Asn Asn Gln Gln Met Phe
    770                 775                 780
```

-continued

Trp Ile Gln Leu Leu Ile Pro Leu Ala Ala Leu Ile Val Val Thr Arg
785                 790                 795                 800

Leu Leu Lys Cys Val Cys Cys Val Val Pro Phe Leu Val Val Ala Gly
            805                 810                 815

Ala Ala Gly Ala Gly Ala Tyr Glu His Ala Thr Thr Met Pro Ser Gln
            820                 825                 830

Ala Gly Ile Ser Tyr Asn Thr Ile Val Asn Arg Ala Gly Tyr Ala Pro
            835                 840                 845

Leu Pro Ile Ser Ile Thr Pro Thr Lys Ile Lys Leu Ile Pro Thr Val
850                 855                 860

Asn Leu Glu Tyr Val Thr Cys His Tyr Lys Thr Gly Met Asp Ser Pro
865                 870                 875                 880

Ala Ile Lys Cys Cys Gly Ser Gln Glu Cys Thr Pro Thr Tyr Arg Pro
            885                 890                 895

Asp Glu Gln Cys Lys Val Phe Thr Gly Val Tyr Pro Phe Met Trp Gly
            900                 905                 910

Gly Ala Tyr Cys Phe Cys Asp Thr Glu Asn Thr Gln Val Ser Lys Ala
            915                 920                 925

Tyr Val Met Lys Ser Asp Asp Cys Leu Ala Asp His Ala Glu Ala Tyr
930                 935                 940

Lys Ala His Thr Ala Ser Val Gln Ala Phe Leu Asn Ile Thr Val Gly
945                 950                 955                 960

Glu His Ser Ile Val Thr Thr Val Tyr Val Asn Gly Glu Thr Pro Val
            965                 970                 975

Asn Phe Asn Gly Val Lys Leu Thr Ala Gly Pro Leu Ser Thr Ala Trp
            980                 985                 990

Thr Pro Phe Asp Arg Lys Ile Val Gln Tyr Ala Gly Glu Ile Tyr Asn
            995                 1000                1005

Tyr Asp Phe Pro Glu Tyr Gly Ala Gly Gln Pro Gly Ala Phe Gly
        1010                1015                1020

Asp Ile Gln Ser Arg Thr Val Ser Ser Ser Asp Leu Tyr Ala Asn
        1025                1030                1035

Thr Asn Leu Val Leu Gln Arg Pro Lys Ala Gly Ala Ile His Val
        1040                1045                1050

Pro Tyr Thr Gln Ala Pro Ser Gly Phe Glu Gln Trp Lys Lys Asp
        1055                1060                1065

Lys Ala Pro Ser Leu Lys Phe Thr Ala Pro Phe Gly Cys Glu Ile
        1070                1075                1080

Tyr Thr Asn Pro Ile Arg Ala Glu Asn Cys Ala Val Gly Ser Ile
        1085                1090                1095

Pro Leu Ala Phe Asp Ile Pro Asp Ala Leu Phe Thr Arg Val Ser
        1100                1105                1110

Glu Thr Pro Thr Leu Ser Ala Ala Glu Cys Thr Leu Asn Glu Cys
        1115                1120                1125

Val Tyr Ser Ser Asp Phe Gly Gly Ile Ala Thr Val Lys Tyr Ser
        1130                1135                1140

Ala Ser Lys Ser Gly Lys Cys Ala Val His Val Pro Ser Gly Thr
        1145                1150                1155

Ala Thr Leu Lys Glu Ala Ala Val Glu Leu Thr Glu Gln Gly Ser
        1160                1165                1170

Ala Thr Ile His Phe Ser Thr Ala Asn Ile His Pro Glu Phe Arg
        1175                1180                1185

-continued

```
Leu Gln Ile Cys Thr Ser Tyr Val Thr Cys Lys Gly Asp Cys His
    1190                1195                1200

Pro Pro Lys Asp His Ile Val Thr His Pro Gln Tyr His Ala Gln
    1205                1210                1215

Thr Phe Thr Ala Ala Val Ser Lys Thr Ala Trp Thr Trp Leu Thr
    1220                1225                1230

Ser Leu Leu Gly Gly Ser Ala Val Ile Ile Ile Gly Leu Val
    1235                1240                1245

Leu Ala Thr Ile Val Ala Met Tyr Val Leu Thr Asn Gln Lys His
    1250                1255                1260

Asn

<210> SEQ ID NO 2
<211> LENGTH: 1264
<212> TYPE: PRT
<213> ORGANISM: Artificial Sequence
<220> FEATURE:
<223> OTHER INFORMATION: Synthetic polypeptide

<400> SEQUENCE: 2

Met Asp Cys Asp Val Val Lys Ser Ala Glu Met Phe Pro Tyr Gln Pro
1               5                   10                  15

Met Tyr Pro Met Gln Pro Met Pro Phe Arg Asn Pro Phe Ala Thr Pro
            20                  25                  30

Arg Arg Pro Trp Phe Pro Arg Thr Asp Pro Phe Leu Ala Met Gln Val
        35                  40                  45

Gln Glu Leu Ala Arg Ser Met Ala Asn Leu Thr Phe Lys Gln Arg Arg
    50                  55                  60

Asp Val Pro Pro Glu Gly Pro Pro Ala Lys Lys Lys Lys Asp Asn
65                  70                  75                  80

Ser Gln Gln Gly Gly Arg Asn Gln Asn Gly Lys Lys Asn Lys Leu
                85                  90                  95

Val Lys Lys Lys Lys Thr Gly Pro Pro Pro Lys Asn Asn Gly
            100                 105                 110

Gly Lys Lys Lys Val Asn Arg Lys Pro Gly Lys Arg Gln Arg Met Val
        115                 120                 125

Met Lys Leu Glu Ser Asp Lys Thr Phe Pro Ile Met Leu Asp Gly Lys
    130                 135                 140

Val Asn Gly Tyr Ala Cys Val Val Gly Gly Lys Leu Phe Arg Pro Leu
145                 150                 155                 160

His Val Glu Gly Lys Ile Asp Asn Asp Val Leu Ser Ser Leu Lys Thr
                165                 170                 175

Lys Lys Ala Ser Lys Tyr Asp Leu Glu Tyr Ala Asp Val Pro Gln Ser
            180                 185                 190

Met Arg Ala Asp Thr Phe Lys Tyr Thr His Asp Lys Pro Gln Gly Tyr
        195                 200                 205

Tyr Asn Trp His His Gly Ala Val Gln Tyr Glu Asn Gly Arg Phe Thr
    210                 215                 220

Val Pro Arg Gly Val Gly Ala Arg Gly Asp Ser Gly Arg Pro Ile Leu
225                 230                 235                 240

Asp Asn Gln Gly Arg Val Val Ala Ile Val Leu Gly Gly Ala Asn Glu
                245                 250                 255

Gly Ser Arg Thr Ala Leu Ser Val Val Thr Trp Asn Glu Lys Gly Val
            260                 265                 270

Thr Val Lys Tyr Thr Pro Glu Asn Ser Glu Gln Trp Ser Leu Val Thr
```

```
                275                 280                 285
Thr Leu Cys Leu Leu Ala Asn Val Thr Phe Pro Cys Thr Gln Pro Pro
290                 295                 300
Ile Cys Tyr Asp Arg Lys Pro Ala Glu Thr Leu Ser Met Leu Ser His
305                 310                 315                 320
Asn Ile Asp Asn Pro Gly Tyr Asp Glu Leu Glu Ala Val Leu Lys
                325                 330                 335
Cys Pro Gly Arg Gly Lys Arg Ser Thr Glu Glu Leu Phe Lys Glu Tyr
                340                 345                 350
Lys Leu Thr Arg Pro Tyr Met Ala Lys Cys Val Arg Cys Ala Val Gly
                355                 360                 365
Ser Cys His Ser Pro Ile Ala Ile Glu Ala Val Arg Ser Glu Gly His
370                 375                 380
Asp Gly Tyr Val Arg Leu Gln Thr Ser Ser Gln Tyr Gly Leu Asp Pro
385                 390                 395                 400
Ser Gly Asn Leu Lys Gly Arg Thr Met Arg Tyr Asp Met His Gly Thr
                405                 410                 415
Ile Lys Glu Ile Pro Leu His Gln Val Ser Val His Thr Ser Arg Pro
                420                 425                 430
Cys His Ile Ile Asp Gly His Gly Tyr Phe Leu Leu Ala Arg Cys Pro
                435                 440                 445
Glu Gly Asp Ser Ile Thr Met Glu Phe Lys Lys Glu Ser Val Thr His
450                 455                 460
Ser Cys Ser Val Pro Tyr Glu Val Lys Phe Thr Pro Val Gly Arg Glu
465                 470                 475                 480
Leu Tyr Ser His Pro Pro Glu His Gly Ala Glu Gln Pro Cys His Val
                485                 490                 495
Tyr Ala His Asp Ala Gln Asn Arg Gly Ala Tyr Val Glu Met His Leu
                500                 505                 510
Pro Gly Ser Glu Val Asp Ser Thr Leu Leu Ser Met Ser Gly Ser Ser
                515                 520                 525
Val His Val Thr Pro Pro Ala Gly Gln Ser Val Gln Val Glu Cys Glu
                530                 535                 540
Cys Gly Gly Thr Lys Ile Ser Glu Thr Ile Asn Ser Ala Lys Gln Tyr
545                 550                 555                 560
Ser Gln Cys Ser Lys Thr Ser Gln Cys Arg Ala Tyr Arg Thr Gln Asn
                565                 570                 575
Asp Lys Trp Val Tyr Asn Ser Asp Lys Leu Pro Lys Ala Ser Gly Glu
                580                 585                 590
Thr Leu Lys Gly Lys Leu His Val Pro Phe Val Leu Thr Glu Ala Lys
                595                 600                 605
Cys Thr Val Pro Leu Ala Pro Glu Pro Ile Ile Thr Phe Gly Phe Arg
610                 615                 620
Ser Val Ser Leu Lys Leu His Pro Lys Asn Pro Thr Phe Leu Thr Thr
625                 630                 635                 640
Arg Gln Leu Asp Gly Glu Pro Ala Tyr Thr His Glu Leu Ile Thr His
                645                 650                 655
Pro Val Val Arg Asn Phe Ser Val Thr Glu Lys Gly Trp Glu Phe Val
                660                 665                 670
Trp Gly Asn His Pro Pro Gln Arg Tyr Trp Ser Gln Glu Thr Ala Pro
                675                 680                 685
Gly Asn Pro His Gly Leu Pro His Glu Val Ile Val His Tyr Tyr His
690                 695                 700
```

```
Arg Tyr Pro Met Ser Thr Ile Val Gly Leu Ser Ile Cys Ala Ala Ile
705                 710                 715                 720

Val Thr Thr Ser Ile Ala Ala Ser Val Trp Leu Phe Cys Lys Ser Arg
            725                 730                 735

Ile Ser Cys Leu Thr Pro Tyr Arg Leu Thr Pro Asn Ala Arg Ile Pro
            740                 745                 750

Phe Cys Leu Ala Val Leu Cys Cys Ala Arg Thr Ala Lys Ala Glu Thr
            755                 760                 765

Thr Trp Glu Ser Leu Asp His Leu Trp Asn His Asn Gln Gln Met Phe
            770                 775                 780

Trp Ser Gln Leu Leu Ile Pro Leu Ala Ala Leu Ile Val Ala Thr Arg
785                 790                 795                 800

Leu Leu Lys Cys Met Cys Cys Val Val Pro Phe Leu Val Val Ala Gly
                805                 810                 815

Ala Val Gly Ala Gly Ala Tyr Glu His Ala Thr Thr Met Pro Asn Gln
                820                 825                 830

Val Gly Ile Pro Tyr Asn Thr Ile Val Asn Arg Ala Gly Tyr Ala Pro
                835                 840                 845

Leu Pro Ile Ser Ile Val Pro Thr Lys Val Lys Leu Ile Pro Thr Val
850                 855                 860

Asn Leu Glu Tyr Ile Thr Cys His Tyr Lys Thr Gly Leu Asp Ser Pro
865                 870                 875                 880

Ala Ile Lys Cys Cys Gly Thr Gln Glu Cys Ser Pro Thr Tyr Arg Pro
                885                 890                 895

Asp Glu Gln Cys Lys Val Phe Ser Gly Val Tyr Pro Phe Met Trp Gly
                900                 905                 910

Gly Ala Tyr Cys Phe Cys Asp Thr Glu Asn Thr Gln Ile Ser Lys Ala
                915                 920                 925

Tyr Val Thr Lys Ser Glu Asp Cys Val Thr Asp His Ala Gln Ala Tyr
                930                 935                 940

Lys Ala His Thr Ala Ser Ile Gln Ala Phe Leu Asn Ile Thr Val Gly
945                 950                 955                 960

Gly His Ser Thr Thr Ala Val Val Tyr Val Asn Gly Glu Thr Pro Val
                965                 970                 975

Asn Phe Asn Gly Ile Lys Leu Val Ala Gly Pro Leu Ser Thr Ala Trp
                980                 985                 990

Ser Pro Phe Asp Lys Lys Ile Val Gln Tyr Ala Gly Glu Val Tyr Asn
            995                 1000                1005

Tyr Asp Phe Pro Glu Tyr Gly Ala Gly His Ala Gly Ala Phe Gly
    1010                1015                1020

Asp Ile Gln Ala Arg Thr Ile Ser Ser Ser Asp Val Tyr Ala Asn
    1025                1030                1035

Thr Asn Leu Val Leu Gln Arg Pro Asn Thr Gly Thr Ile His Val
    1040                1045                1050

Pro Tyr Thr Gln Ala Pro Ser Gly Tyr Glu Gln Trp Lys Lys Asp
    1055                1060                1065

Lys Pro Pro Ser Leu Lys Tyr Thr Ala Pro Phe Gly Cys Glu Ile
    1070                1075                1080

His Val Asn Pro Val Arg Ala Glu Asn Cys Ala Val Gly Phe Ile
    1085                1090                1095

Pro Leu Ala Phe Asp Ile Pro Asp Ala Leu Phe Thr Arg Val Ser
    1100                1105                1110
```

-continued

```
Glu Thr Pro Thr Leu Ser Ser Ala Glu Cys Ser Leu Asn Glu Cys
    1115                1120                1125

Thr Tyr Ser Thr Asp Phe Gly Gly Ile Ala Thr Val Lys Tyr Ser
    1130                1135                1140

Ala Ser Lys Ala Gly Lys Cys Ala Val His Ile Pro Ser Gly Thr
    1145                1150                1155

Ala Thr Leu Lys Glu Ala Ala Val Glu Leu Ala Glu Gln Gly Ser
    1160                1165                1170

Ala Thr Ile His Phe Ser Thr Ala Ser Ile His Pro Glu Phe Lys
    1175                1180                1185

Leu Gln Ile Cys Thr Lys Val Leu Thr Cys Lys Gly Asp Cys His
    1190                1195                1200

Pro Pro Arg Asp His Ile Val Thr His Pro Gln Tyr His Ala Gln
    1205                1210                1215

Ser Phe Thr Ala Ala Val Ser Lys Thr Ala Trp Thr Trp Ile Thr
    1220                1225                1230

Ser Leu Leu Gly Gly Ser Ala Ile Ile Ile Ile Ile Gly Leu Val
    1235                1240                1245

Leu Ala Thr Val Val Ala Met Tyr Val Leu Thr Asn Gln Arg His
    1250                1255                1260

Asn
```

<210> SEQ ID NO 3
<211> LENGTH: 1264
<212> TYPE: PRT
<213> ORGANISM: Artificial Sequence
<220> FEATURE:
<223> OTHER INFORMATION: Synthetic polypeptide

<400> SEQUENCE: 3

```
Met Asp Tyr Asp Ile Val Ser Ala Lys Met Phe Pro Phe Gln Pro Met
1               5                   10                  15

Tyr Pro Met Gln Pro Met Pro Tyr Arg Asn Pro Phe Ala Ala Pro Arg
                20                  25                  30

Arg Pro Trp Phe Pro Arg Thr Asp Pro Phe Leu Ala Met Gln Val Gln
            35                  40                  45

Glu Leu Thr Arg Ser Met Ala Asn Leu Thr Phe Lys Gln Arg Arg Asp
    50                  55                  60

Ala Pro Pro Glu Gly Pro Ala Lys Lys Pro Lys Arg Glu Ala Pro
65                  70                  75                  80

Gln Lys Gln Lys Gly Gly Gly Gln Gly Lys Lys Lys Asn Gln Gly
                85                  90                  95

Lys Lys Lys Ala Lys Thr Gly Pro Pro Asn Pro Lys Ala Gln Asn Gly
                100                 105                 110

Asn Lys Lys Lys Thr Asn Lys Lys Pro Gly Lys Arg Gln Arg Met Val
            115                 120                 125

Met Lys Leu Glu Ser Asp Lys Thr Phe Pro Ile Met Leu Glu Gly Lys
    130                 135                 140

Ile Asn Gly Tyr Ala Cys Val Val Gly Gly Lys Leu Phe Arg Pro Met
145                 150                 155                 160

His Val Glu Gly Lys Ile Asp Asn Asp Val Leu Ala Ala Leu Lys Thr
                165                 170                 175

Lys Lys Ala Ser Lys Tyr Asp Leu Glu Tyr Ala Asp Val Pro Gln Asn
                180                 185                 190

Met Arg Ala Asp Thr Phe Lys Tyr Thr His Glu Lys Pro Gln Gly Tyr
```

```
            195                 200                 205
Tyr Ser Trp His His Gly Ala Val Gln Tyr Glu Asn Gly Arg Phe Thr
210                 215                 220
Val Pro Lys Gly Val Gly Ala Lys Gly Asp Ser Gly Arg Pro Ile Leu
225                 230                 235                 240
Asp Asn Gln Gly Arg Val Val Ala Ile Val Leu Gly Gly Val Asn Glu
                    245                 250                 255
Gly Ser Arg Thr Ala Leu Ser Val Val Met Trp Asn Glu Lys Gly Val
                260                 265                 270
Thr Val Lys Tyr Thr Pro Glu Asn Cys Glu Gln Trp Ser Leu Val Thr
            275                 280                 285
Thr Met Cys Leu Leu Ala Asn Val Thr Phe Pro Cys Ala Gln Pro Pro
290                 295                 300
Ile Cys Tyr Asp Arg Lys Pro Ala Glu Thr Leu Ala Met Leu Ser Val
305                 310                 315                 320
Asn Val Asp Asn Pro Gly Tyr Asp Glu Leu Leu Glu Ala Ala Val Lys
                    325                 330                 335
Cys Pro Gly Arg Lys Arg Arg Ser Thr Glu Glu Leu Phe Lys Glu Tyr
                340                 345                 350
Lys Leu Thr Arg Pro Tyr Met Ala Arg Cys Ile Arg Cys Ala Val Gly
            355                 360                 365
Ser Cys His Ser Pro Ile Ala Ile Glu Ala Val Lys Ser Asp Gly His
370                 375                 380
Asp Gly Tyr Val Arg Leu Gln Thr Ser Ser Gln Tyr Gly Leu Asp Ser
385                 390                 395                 400
Ser Gly Asn Leu Lys Gly Arg Thr Met Arg Tyr Asp Met His Gly Thr
                    405                 410                 415
Ile Glu Glu Ile Pro Leu His Gln Val Ser Leu His Thr Ser Arg Pro
                420                 425                 430
Cys His Ile Val Asp Gly His Gly Tyr Phe Leu Leu Ala Arg Cys Pro
            435                 440                 445
Ala Gly Asp Ser Ile Thr Met Glu Phe Lys Lys Asp Ser Val Thr His
450                 455                 460
Ser Cys Ser Val Pro Tyr Glu Val Lys Phe Asn Pro Val Gly Arg Glu
465                 470                 475                 480
Leu Tyr Thr His Pro Pro Glu His Gly Ala Glu Gln Ala Cys Gln Val
                    485                 490                 495
Tyr Ala His Asp Ala Gln Asn Arg Gly Ala Tyr Val Glu Met His Leu
                500                 505                 510
Pro Gly Ser Glu Val Asp Ser Ser Leu Val Ser Leu Ser Gly Ser Ser
            515                 520                 525
Val Thr Val Thr Pro Pro Ala Gly Thr Ser Ala Leu Val Glu Cys Glu
530                 535                 540
Cys Gly Gly Thr Lys Ile Ser Glu Thr Ile Asn Thr Ala Lys Gln Phe
545                 550                 555                 560
Ser Gln Cys Thr Lys Lys Glu Gln Cys Arg Ala Tyr Arg Leu Gln Asn
                    565                 570                 575
Asp Lys Trp Val Tyr Asn Ser Asp Lys Leu Pro Lys Ala Ala Gly Ala
                580                 585                 590
Thr Leu Lys Gly Lys Leu His Val Pro Phe Leu Leu Ala Asp Gly Lys
            595                 600                 605
Cys Thr Val Pro Leu Ala Pro Glu Pro Met Ile Thr Phe Gly Phe Arg
610                 615                 620
```

```
Ser Val Ser Leu Lys Leu His Pro Lys Asn Pro Thr Tyr Leu Thr Thr
625                 630                 635                 640

Arg Gln Leu Ala Asp Glu Pro His Tyr Thr His Glu Leu Ile Ser Glu
            645                 650                 655

Pro Ala Val Arg Asn Phe Thr Val Thr Glu Lys Gly Trp Glu Phe Val
        660                 665                 670

Trp Gly Asn His Pro Pro Lys Arg Phe Trp Ala Gln Glu Thr Ala Pro
    675                 680                 685

Gly Asn Pro His Gly Leu Pro His Glu Val Ile Thr His Tyr Tyr His
690                 695                 700

Arg Tyr Pro Met Ser Thr Ile Leu Gly Leu Ser Ile Cys Ala Ala Ile
705                 710                 715                 720

Val Thr Val Ser Val Ala Ala Ser Thr Trp Leu Phe Cys Lys Ser Arg
                725                 730                 735

Val Ser Cys Leu Thr Pro Tyr Arg Leu Thr Pro Asn Ala Arg Met Pro
            740                 745                 750

Leu Cys Leu Ala Val Leu Cys Cys Ala Arg Thr Ala Arg Ala Glu Thr
        755                 760                 765

Thr Trp Glu Ser Leu Asp His Leu Trp Asn Asn Gln Gln Met Phe
770                 775                 780

Trp Ile Gln Leu Leu Ile Pro Leu Ala Ala Leu Ile Val Val Thr Arg
785                 790                 795                 800

Leu Leu Lys Cys Val Cys Val Val Pro Phe Leu Val Val Ala Gly
                805                 810                 815

Ala Ala Gly Ala Gly Ala Tyr Glu His Ala Thr Thr Met Pro Ser Gln
            820                 825                 830

Ala Gly Ile Ser Tyr Asn Thr Ile Val Asn Arg Ala Gly Tyr Ala Pro
        835                 840                 845

Leu Pro Ile Ser Ile Thr Pro Thr Lys Ile Lys Leu Ile Pro Thr Val
850                 855                 860

Asn Leu Glu Tyr Val Thr Cys His Tyr Lys Thr Gly Met Asp Ser Pro
865                 870                 875                 880

Ala Ile Lys Cys Cys Gly Ser Gln Glu Cys Thr Pro Thr Tyr Arg Pro
                885                 890                 895

Asp Glu Gln Cys Lys Val Phe Thr Gly Val Tyr Pro Phe Met Trp Gly
            900                 905                 910

Gly Ala Tyr Cys Phe Cys Asp Thr Glu Asn Thr Gln Val Ser Lys Ala
        915                 920                 925

Tyr Val Met Lys Ser Asp Asp Cys Leu Ala Asp His Ala Glu Ala Tyr
930                 935                 940

Lys Ala His Thr Ala Ser Val Gln Ala Phe Leu Asn Ile Thr Val Gly
945                 950                 955                 960

Glu His Ser Ile Val Thr Thr Val Tyr Val Asn Gly Glu Thr Pro Val
                965                 970                 975

Asn Phe Asn Gly Val Lys Leu Thr Ala Gly Pro Leu Ser Thr Ala Trp
            980                 985                 990

Thr Pro Phe Asp Arg Lys Ile Val  Gln Tyr Ala Gly Glu  Ile Tyr Asn
        995                 1000                1005

Tyr Asp  Phe Pro Glu Tyr Gly  Ala Gly Gln Pro Gly  Ala Phe Gly
        1010                1015                1020

Asp Ile  Gln Ser Arg Thr Val  Ser Ser Ser Asp Leu  Tyr Ala Asn
        1025                1030                1035
```

```
Thr Asn Leu Val Leu Gln Arg Pro Lys Ala Gly Ala Ile His Val
    1040                1045                1050

Pro Tyr Thr Gln Ala Pro Ser Gly Phe Glu Gln Trp Lys Lys Asp
    1055                1060                1065

Lys Ala Pro Ser Leu Lys Phe Thr Ala Pro Phe Gly Cys Glu Ile
    1070                1075                1080

Tyr Thr Asn Pro Ile Arg Ala Glu Asn Cys Ala Val Gly Ser Ile
    1085                1090                1095

Pro Leu Ala Phe Asp Ile Pro Asp Ala Leu Phe Thr Arg Val Ser
    1100                1105                1110

Glu Thr Pro Thr Leu Ser Ala Ala Glu Cys Thr Leu Asn Glu Cys
    1115                1120                1125

Val Tyr Ser Ser Asp Phe Gly Gly Ile Ala Thr Val Lys Tyr Ser
    1130                1135                1140

Ala Ser Lys Ser Gly Lys Cys Ala Val His Val Pro Ser Gly Thr
    1145                1150                1155

Ala Thr Leu Lys Glu Ala Ala Val Glu Leu Thr Glu Gln Gly Ser
    1160                1165                1170

Ala Thr Ile His Phe Ser Thr Ala Asn Ile His Pro Glu Phe Arg
    1175                1180                1185

Leu Gln Ile Cys Thr Ser Tyr Val Thr Cys Lys Gly Asp Cys His
    1190                1195                1200

Pro Pro Lys Asp His Ile Val Thr His Pro Gln Tyr His Ala Gln
    1205                1210                1215

Thr Phe Thr Ala Ala Val Ser Lys Thr Ala Trp Thr Trp Leu Thr
    1220                1225                1230

Ser Leu Leu Gly Gly Ser Ala Val Ile Ile Ile Gly Leu Val
    1235                1240                1245

Leu Ala Thr Ile Val Ala Met Tyr Val Leu Thr Asn Gln Lys His
    1250                1255                1260

Asn

<210> SEQ ID NO 4
<211> LENGTH: 1264
<212> TYPE: PRT
<213> ORGANISM: Artificial Sequence
<220> FEATURE:
<223> OTHER INFORMATION: Synthetic polypeptide

<400> SEQUENCE: 4

Met Asp Cys Asn Val Val Gln Ser Ala Thr Met Phe Pro Tyr Gln Ser
1               5                   10                  15

Pro Met Phe Pro Met Gln Pro Ala Pro Phe Arg Asn Pro Tyr Ala Pro
                    20                  25                  30

Pro Arg Arg Pro Trp Phe Pro Arg Thr Asp Pro Phe Leu Ala Met Gln
                35                  40                  45

Val Gln Glu Leu Thr Arg Ser Met Ala Asn Leu Thr Phe Lys Gln Arg
    50                  55                  60

Arg Glu Ala Pro Pro Glu Gly Pro Ala Lys Lys Arg Lys Glu
65                  70                  75                  80

Pro Gln Gln Gln Val Ala Gln Ala Gln Val Lys Lys Asn Gly Lys
                    85                  90                  95

Pro Lys Lys Lys Lys Ser Asn Gly Ala Pro Pro Lys Asn Gln Asn
                    100                 105                 110

Ser Thr Lys Lys Lys Pro Asn Lys Lys Pro Gly Lys Arg Gln Arg Met
```

```
            115                 120                 125
Val Met Lys Leu Glu Ser Asp Lys Thr Phe Pro Ile Met Leu Asp Gly
    130                 135                 140

Lys Val Asn Gly Tyr Ala Cys Val Val Gly Gly Lys Leu Phe Arg Pro
145                 150                 155                 160

Leu His Val Glu Gly Lys Ile Asp Asn Glu Thr Leu Ala Ser Leu Lys
                165                 170                 175

Thr Lys Lys Ala Ser Lys Tyr Asp Leu Glu Tyr Ala Asp Val Pro Gln
            180                 185                 190

Ser Met Arg Ala Asp Thr Phe Lys Tyr Thr His Asp Lys Pro Gln Gly
        195                 200                 205

Tyr Tyr Asn Trp His His Gly Ala Val Gln Tyr Glu Asn Gly Arg Phe
    210                 215                 220

Thr Val Pro Lys Gly Val Gly Ala Lys Gly Asp Ser Gly Arg Pro Ile
225                 230                 235                 240

Leu Asp Asn Gln Gly Arg Val Val Ala Ile Val Leu Gly Gly Val Asn
                245                 250                 255

Glu Gly Ser Arg Thr Ala Leu Ser Val Val Met Trp Thr Glu Lys Gly
            260                 265                 270

Val Thr Val Lys Tyr Thr Pro Glu Asn Cys Glu Gln Trp Ser Leu Val
        275                 280                 285

Thr Ala Val Cys Leu Leu Ala Asn Val Thr Phe Pro Cys Ser Thr Pro
    290                 295                 300

Pro Ile Cys Tyr Asp Arg Ala Pro Ala Glu Thr Leu Met Met Leu Ser
305                 310                 315                 320

Lys Asn Ile Asp Asn Pro Gly Tyr Asp Glu Leu Leu Glu Ala Val Leu
                325                 330                 335

Lys Cys Pro Gly Arg Gln Lys Arg Ser Thr Glu Glu Leu Phe Lys Glu
            340                 345                 350

Tyr Lys Leu Thr Lys Pro Tyr Met Ala Lys Cys Ile Arg Cys Ala Val
        355                 360                 365

Gly Ser Cys His Ser Pro Ile Ala Ile Glu Ala Val Arg Ser Glu Gly
    370                 375                 380

His Asp Gly Tyr Val Arg Leu Gln Thr Ser Ser Gln Tyr Gly Leu Asp
385                 390                 395                 400

Pro Ser Gly Asn Val Lys Ser Arg Val Met Arg Tyr Asn Met Tyr Gly
                405                 410                 415

Lys Ile Val Glu Val Pro Leu His Gln Val Ser Leu His Thr Ser Arg
            420                 425                 430

Pro Cys Gln Ile Val Asp Gly His Gly Tyr Phe Leu Leu Ala Arg Cys
        435                 440                 445

Pro Pro Gly Asp Ser Ile Thr Met Glu Phe Lys Lys Gly Ser Val Thr
    450                 455                 460

His Ser Cys Ser Val Pro Tyr Glu Val Lys Phe Thr Pro Val Gly Arg
465                 470                 475                 480

Glu Leu Tyr Ser His Pro Pro Glu His Gly Thr Glu His Pro Cys Arg
                485                 490                 495

Val Tyr Val His Asp Ala Gln Gln Lys Asp Ala Tyr Val Glu Met His
            500                 505                 510

Leu Pro Gly Ser Glu Val Asp Ser Ser Leu Leu Ser Met Ser Gly Ser
        515                 520                 525

Ala Val Arg Val Thr Pro Pro Ser Gly Gln Ser Val Leu Val Glu Cys
    530                 535                 540
```

```
Asn Cys Gly Ser Ala Val Ser Glu Thr Ile Asn Thr Ala Lys Ser Tyr
545                 550                 555                 560

Ser Gln Cys Thr Lys Thr Ser Gln Cys Arg Ala Tyr Arg Leu Gln Ser
                565                 570                 575

Asp Lys Trp Val Phe Asn Ser Asp Lys Leu Pro Lys Ala Ala Gly Glu
            580                 585                 590

Thr Leu Lys Gly Lys Leu His Val Pro Tyr Leu Leu Ser Glu Ala Lys
                595                 600                 605

Cys Thr Val Pro Leu Ala Pro Glu Pro Ile Val Thr Phe Gly Phe Arg
610                 615                 620

Phe Val Ser Leu Lys Leu His Pro Arg Asn Pro Thr Tyr Leu Thr Thr
625                 630                 635                 640

Arg Gln Leu Asp Gly Glu Pro Asn Tyr Thr His Glu Leu Ile Ser Glu
                645                 650                 655

Pro Thr Ile Arg Asn Phe Thr Val Thr Glu His Gly Trp Glu Tyr Val
                660                 665                 670

Trp Gly Asn His Pro Pro Gln Arg Tyr Trp Ala Gln Glu Thr Ala Pro
                675                 680                 685

Gly Asp Pro His Gly Leu Pro His Glu Val Ile Lys His Tyr Tyr His
690                 695                 700

Arg Tyr Pro Met Ser Thr Thr Leu Gly Leu Ser Ile Cys Ala Ala Val
705                 710                 715                 720

Val Thr Thr Ser Ile Ala Ala Ser Thr Trp Leu Leu Cys Lys Ser Arg
                725                 730                 735

Val Ser Cys Leu Thr Pro Tyr Arg Leu Thr Pro Asn Ala Gln Leu Pro
                740                 745                 750

Val Cys Leu Ala Phe Leu Cys Cys Ala Arg Thr Ala Arg Ala Glu Thr
                755                 760                 765

Ala Trp Glu Ser Leu Asp His Leu Trp Asn Asn Gln Gln Met Phe
770                 775                 780

Trp Thr Gln Leu Leu Ile Pro Leu Ala Ala Leu Ile Val Val Thr Arg
785                 790                 795                 800

Leu Leu Arg Cys Val Cys Cys Val Val Pro Phe Leu Val Leu Ala Gly
                805                 810                 815

Ala Ala Ser Val Gly Ala Tyr Glu His Ala Thr Thr Met Pro Ser Gln
                820                 825                 830

Val Gly Ile Pro Tyr Asn Thr Val Asn Arg Ala Gly Tyr Ala Pro
                835                 840                 845

Leu Ala Ile Ser Ile Ile Pro Thr Lys Ile Arg Leu Ile Pro Thr Leu
850                 855                 860

Asn Leu Glu Tyr Ile Thr Cys His Tyr Lys Thr Gly Leu Asp Ser Pro
865                 870                 875                 880

Ser Ile Lys Cys Cys Gly Thr Gln Glu Cys Pro Lys Val Asn Arg Pro
                885                 890                 895

Asp Glu Gln Cys Lys Val Phe Ala Gly Val Tyr Pro Phe Met Trp Gly
                900                 905                 910

Gly Ala Tyr Cys Phe Cys Asp Ser Glu Asn Thr Gln Ile Ser Arg Ala
                915                 920                 925

Tyr Val Met Lys Ser Asp Asp Cys Ser Ala Asp His Ala Leu Ala Tyr
                930                 935                 940

Lys Ala His Thr Ala Ser Ile Gln Ala Phe Leu Asn Ile Thr Val Gly
945                 950                 955                 960
```

```
Glu Gln Ser Thr Thr Ala Val Val Tyr Val Asn Gly Glu Thr Pro Ile
            965                 970                 975

Ser Phe Asn Gly Val Lys Leu Val Ala Gly Pro Leu Ser Thr Ala Trp
        980                 985                 990

Thr Pro Phe Asp Arg Lys Val Val Gln Tyr Ala Gly Glu Ile Tyr Asn
        995                 1000                1005

Tyr Asp Phe Pro Glu Tyr Gly Ala Gly His Ala Gly Ala Phe Gly
    1010                1015                1020

Asp Leu Gln Ala Arg Thr Ile Thr Ser Asn Asp Leu Tyr Ala Asn
    1025                1030                1035

Thr Asn Leu Val Leu Gln Arg Pro Lys Ser Gly Thr Val His Val
    1040                1045                1050

Pro Tyr Thr Gln Ala Pro Ser Gly Phe Glu Gln Trp Lys Lys Asp
    1055                1060                1065

Lys Pro Pro Ser Leu Lys Phe Thr Ala Pro Phe Gly Cys Glu Ile
    1070                1075                1080

Tyr Val Asn Pro Val Arg Ala Glu Asn Cys Ala Val Gly Ser Ile
    1085                1090                1095

Pro Leu Ser Phe Asp Ile Pro Asp Ala Leu Phe Thr Arg Val Ser
    1100                1105                1110

Asp Thr Pro Thr Leu Ser Thr Ala Glu Cys Thr Leu Asn Glu Cys
    1115                1120                1125

Val Tyr Ser Ser Asp Phe Gly Gly Ile Ala Ser Val Lys Tyr Ser
    1130                1135                1140

Ala Thr Lys Ala Gly Lys Cys Ala Val His Val Pro Ser Gly Thr
    1145                1150                1155

Ala Thr Leu Lys Glu Ser Leu Val Glu Val Val Glu Gln Gly Ser
    1160                1165                1170

Met Thr Leu His Phe Ser Thr Ala Ser Ile His Pro Glu Phe Arg
    1175                1180                1185

Leu Gln Ile Cys Thr Ser Phe Val Thr Cys Lys Gly Asp Cys His
    1190                1195                1200

Pro Pro Lys Asp His Ile Val Thr His Pro Gln His His Ala Gln
    1205                1210                1215

Thr Phe Thr Ala Ala Val Ser Lys Thr Ala Trp Thr Trp Leu Ser
    1220                1225                1230

Ser Leu Leu Gly Gly Ser Ala Ala Ile Ile Ile Gly Leu Val
    1235                1240                1245

Leu Ala Thr Leu Val Ala Met Tyr Val Leu Thr Asn Gln Lys Arg
    1250                1255                1260

Asn

<210> SEQ ID NO 5
<211> LENGTH: 1264
<212> TYPE: PRT
<213> ORGANISM: Artificial Sequence
<220> FEATURE:
<223> OTHER INFORMATION: Synthetic polypeptide

<400> SEQUENCE: 5

Met Asp Tyr Asp Ile Val Ser Ala Lys Met Phe Pro Phe Gln Pro Met
1               5                   10                  15

Tyr Pro Met Gln Pro Met Pro Tyr Arg Asn Pro Phe Ala Ala Pro Arg
            20                  25                  30

Arg Pro Trp Phe Pro Arg Thr Asp Pro Phe Leu Ala Met Gln Val Gln
```

```
                35                  40                  45
Glu Leu Ala Arg Ser Met Ala Asn Leu Thr Phe Lys Gln Arg Arg Asp
 50                  55                  60

Ala Pro Pro Glu Gly Pro Ala Lys Lys Pro Lys Arg Glu Ala Pro
 65                  70                  75                  80

Gln Lys Gln Lys Gly Gly Gln Gly Lys Lys Lys Asn Gln Gly
                 85                  90                  95

Lys Lys Lys Ala Lys Thr Gly Pro Pro Asn Pro Lys Ala Gln Asn Gly
                100                 105                 110

Asn Lys Lys Lys Thr Asn Lys Lys Pro Gly Lys Arg Gln Arg Met Val
                115                 120                 125

Met Lys Leu Glu Ser Asp Lys Thr Phe Pro Ile Met Leu Glu Gly Lys
     130                 135                 140

Ile Asn Gly Tyr Ala Cys Val Val Gly Lys Leu Phe Arg Pro Met
 145                 150                 155                 160

His Val Glu Gly Lys Ile Asp Asn Asp Val Leu Ala Ala Leu Lys Thr
                165                 170                 175

Lys Lys Ala Ser Lys Tyr Asp Leu Glu Tyr Ala Asp Val Pro Gln Asn
                180                 185                 190

Met Arg Ala Asp Thr Phe Lys Tyr Thr His Glu Lys Pro Gln Gly Tyr
     195                 200                 205

Tyr Ser Trp His His Gly Ala Val Gln Tyr Glu Asn Gly Arg Phe Thr
 210                 215                 220

Val Pro Arg Gly Val Gly Ala Arg Gly Asp Ser Gly Arg Pro Ile Leu
 225                 230                 235                 240

Asp Asn Gln Gly Arg Val Val Ala Ile Val Leu Gly Gly Ala Asn Glu
                245                 250                 255

Gly Ser Arg Thr Ala Leu Ser Val Val Met Trp Asn Glu Lys Gly Val
                260                 265                 270

Thr Val Lys Tyr Thr Pro Glu Asn Ser Glu Gln Trp Ser Leu Val Thr
     275                 280                 285

Thr Met Cys Leu Leu Ala Asn Val Thr Phe Pro Cys Ala Gln Pro Pro
     290                 295                 300

Ile Cys Tyr Asp Arg Lys Pro Ala Glu Thr Leu Ala Met Leu Ser Val
 305                 310                 315                 320

Asn Val Asp Asn Pro Gly Tyr Asp Glu Leu Leu Glu Ala Ala Val Lys
                325                 330                 335

Cys Pro Gly Arg Lys Arg Arg Ser Thr Glu Glu Leu Phe Lys Glu Tyr
                340                 345                 350

Lys Leu Thr Arg Pro Tyr Met Ala Arg Cys Ile Arg Cys Ala Val Gly
     355                 360                 365

Ser Cys His Ser Pro Ile Ala Ile Glu Ala Val Lys Ser Asp Gly His
     370                 375                 380

Asp Gly Tyr Val Arg Leu Gln Thr Ser Ser Gln Tyr Gly Leu Asp Ser
 385                 390                 395                 400

Ser Gly Asn Leu Lys Gly Arg Thr Met Arg Tyr Asp Met His Gly Thr
                405                 410                 415

Ile Glu Glu Ile Pro Leu His Gln Val Ser Val His Thr Ser Arg Pro
                420                 425                 430

Cys His Ile Ile Asp Gly His Gly Tyr Phe Leu Leu Ala Arg Cys Pro
     435                 440                 445

Ala Gly Asp Ser Ile Thr Met Glu Phe Lys Lys Asp Ser Val Thr His
 450                 455                 460
```

-continued

Ser Cys Ser Val Pro Tyr Glu Val Lys Phe Asn Pro Val Gly Arg Glu
465                 470                 475                 480

Leu Tyr Thr His Pro Glu His Gly Ala Glu Gln Ala Cys Gln Val
                    485                 490                 495

Tyr Ala His Asp Ala Gln Asn Arg Gly Ala Tyr Val Glu Met His Leu
                500                 505                 510

Pro Gly Ser Glu Val Asp Ser Ser Leu Val Ser Leu Ser Gly Ser Ser
            515                 520                 525

Val Thr Val Thr Pro Pro Ala Gly Thr Ser Ala Leu Val Glu Cys Glu
530                 535                 540

Cys Gly Gly Thr Lys Ile Ser Glu Thr Ile Asn Thr Ala Lys Gln Phe
545                 550                 555                 560

Ser Gln Cys Thr Lys Lys Glu Gln Cys Arg Ala Tyr Arg Leu Gln Asn
                565                 570                 575

Asp Lys Trp Val Tyr Asn Ser Asp Lys Leu Pro Lys Ala Ala Gly Ala
            580                 585                 590

Thr Leu Lys Gly Lys Leu His Val Pro Phe Leu Leu Ala Asp Gly Lys
            595                 600                 605

Cys Thr Val Pro Leu Ala Pro Glu Pro Met Ile Thr Phe Gly Phe Arg
610                 615                 620

Ser Val Ser Leu Lys Leu His Pro Lys Asn Pro Thr Tyr Leu Thr Thr
625                 630                 635                 640

Arg Gln Leu Ala Asp Glu Pro His Tyr Thr His Glu Leu Ile Ser Glu
                645                 650                 655

Pro Ala Val Arg Asn Phe Thr Val Glu Lys Gly Trp Glu Phe Val
                660                 665                 670

Trp Gly Asn His Pro Pro Lys Arg Phe Trp Ala Gln Glu Thr Ala Pro
            675                 680                 685

Gly Asn Pro His Gly Leu Pro His Glu Val Ile Thr His Tyr Tyr His
            690                 695                 700

Arg Tyr Pro Met Ser Thr Ile Leu Gly Leu Ser Ile Cys Ala Ala Ile
705                 710                 715                 720

Val Thr Thr Ser Ile Ala Ala Ser Val Trp Leu Phe Cys Lys Ser Arg
                725                 730                 735

Ile Ser Cys Leu Thr Pro Tyr Arg Leu Thr Pro Asn Ala Arg Met Pro
                740                 745                 750

Leu Cys Leu Ala Val Leu Cys Cys Ala Arg Thr Ala Arg Ala Glu Thr
            755                 760                 765

Thr Trp Glu Ser Leu Asp His Leu Trp Asn His Asn Gln Gln Met Phe
770                 775                 780

Trp Ser Gln Leu Leu Ile Pro Leu Ala Ala Leu Ile Val Ala Thr Arg
785                 790                 795                 800

Leu Leu Lys Cys Val Cys Cys Val Val Pro Phe Leu Val Val Ala Gly
                805                 810                 815

Ala Ala Gly Ala Gly Ala Tyr Glu His Ala Thr Thr Met Pro Asn Gln
            820                 825                 830

Val Gly Ile Pro Tyr Asn Thr Ile Val Asn Arg Ala Gly Tyr Ala Pro
            835                 840                 845

Leu Pro Ile Ser Ile Thr Pro Thr Lys Ile Lys Leu Ile Pro Thr Val
            850                 855                 860

Asn Leu Glu Tyr Val Thr Cys His Tyr Lys Thr Gly Met Asp Ser Pro
865                 870                 875                 880

Ala Ile Lys Cys Cys Gly Ser Gln Glu Cys Thr Pro Thr Tyr Arg Pro
                885                 890                 895

Asp Glu Gln Cys Lys Val Phe Thr Gly Val Tyr Pro Phe Met Trp Gly
            900                 905                 910

Gly Ala Tyr Cys Phe Cys Asp Thr Glu Asn Thr Gln Val Ser Lys Ala
            915                 920                 925

Tyr Val Met Lys Ser Asp Asp Cys Leu Ala Asp His Ala Glu Ala Tyr
        930                 935                 940

Lys Ala His Thr Ala Ser Val Gln Ala Phe Leu Asn Ile Thr Val Gly
945                 950                 955                 960

Glu His Ser Ile Val Thr Thr Val Tyr Val Asn Gly Glu Thr Pro Val
                965                 970                 975

Asn Phe Asn Gly Val Lys Leu Thr Ala Gly Pro Leu Ser Thr Ala Trp
            980                 985                 990

Thr Pro Phe Asp Arg Lys Ile Val Gln Tyr Ala Gly Glu Ile Tyr Asn
        995                 1000                1005

Tyr Asp Phe Pro Glu Tyr Gly Ala Gly Gln Pro Gly Ala Phe Gly
    1010                1015                1020

Asp Ile Gln Ser Arg Thr Val Ser Ser Ser Asp Leu Tyr Ala Asn
    1025                1030                1035

Thr Asn Leu Val Leu Gln Arg Pro Lys Ala Gly Ala Ile His Val
    1040                1045                1050

Pro Tyr Thr Gln Ala Pro Ser Gly Phe Glu Gln Trp Lys Lys Asp
    1055                1060                1065

Lys Ala Pro Ser Leu Lys Phe Thr Ala Pro Phe Gly Cys Glu Ile
    1070                1075                1080

Tyr Thr Asn Pro Ile Arg Ala Glu Asn Cys Ala Val Gly Ser Ile
    1085                1090                1095

Pro Leu Ala Phe Asp Ile Pro Asp Ala Leu Phe Thr Arg Val Ser
    1100                1105                1110

Glu Thr Pro Thr Leu Ser Ala Ala Glu Cys Thr Leu Asn Glu Cys
    1115                1120                1125

Val Tyr Ser Ser Asp Phe Gly Gly Ile Ala Thr Val Lys Tyr Ser
    1130                1135                1140

Ala Ser Lys Ser Gly Lys Cys Ala Val His Val Pro Ser Gly Thr
    1145                1150                1155

Ala Thr Leu Lys Glu Ala Ala Val Glu Leu Thr Glu Gln Gly Ser
    1160                1165                1170

Ala Thr Ile His Phe Ser Thr Ala Asn Ile His Pro Glu Phe Arg
    1175                1180                1185

Leu Gln Ile Cys Thr Ser Tyr Val Thr Cys Lys Gly Asp Cys His
    1190                1195                1200

Pro Pro Arg Asp His Ile Val Thr His Pro Gln Tyr His Ala Gln
    1205                1210                1215

Thr Phe Thr Ala Ala Val Ser Lys Thr Ala Trp Thr Trp Leu Thr
    1220                1225                1230

Ser Leu Leu Gly Gly Ser Ala Val Ile Ile Ile Gly Leu Val
    1235                1240                1245

Leu Ala Thr Ile Val Ala Met Tyr Val Leu Thr Asn Gln Lys His
    1250                1255                1260

Asn

<210> SEQ ID NO 6

```
<211> LENGTH: 1264
<212> TYPE: PRT
<213> ORGANISM: Artificial Sequence
<220> FEATURE:
<223> OTHER INFORMATION: Synthetic polypeptide

<400> SEQUENCE: 6

Met Asp Cys Asp Val Val Lys Ser Ala Glu Met Phe Pro Tyr Gln Pro
1               5                   10                  15

Met Tyr Pro Met Gln Pro Met Pro Phe Arg Asn Pro Phe Ala Thr Pro
            20                  25                  30

Arg Arg Pro Trp Phe Pro Arg Pro Asp Pro Tyr Leu Ala Leu Gln Val
            35                  40                  45

Gln Glu Leu Ala Arg Ser Met Ala Ser Leu Thr Phe Lys Gln Arg Arg
50                  55                  60

Asp Val Pro Pro Glu Gly Pro Pro Ala Lys Lys Lys Lys Lys Asp Asn
65                  70                  75                  80

Ser Gln Gln Gly Gly Arg Asn Gln Asn Gly Lys Lys Asn Lys Leu
                85                  90                  95

Val Lys Lys Lys Lys Thr Gly Pro Pro Pro Lys Asn Asn Gly
                100                 105                 110

Gly Lys Lys Lys Val Asn Arg Lys Pro Gly Lys Arg Gln Arg Met Val
            115                 120                 125

Met Lys Leu Glu Ser Asp Lys Thr Phe Pro Ile Leu Leu Asp Gly Lys
130                 135                 140

Ile Asn Gly Tyr Ala Cys Val Val Gly Gly Lys Leu Phe Arg Pro Met
145                 150                 155                 160

His Val Ala Gly Lys Ile Asp Asn Asp Val Leu Ser Ser Leu Lys Thr
                165                 170                 175

Lys Lys Ala Ser Lys Tyr Asp Leu Glu Tyr Ala Asp Val Pro Gln Asn
            180                 185                 190

Met Arg Ser Asp Thr Phe Lys Tyr Thr His Glu Lys Pro Arg Gly Tyr
        195                 200                 205

Tyr Ser Trp His His Gly Ala Val Gln Tyr Glu Asn Gly Arg Phe Thr
210                 215                 220

Val Pro Lys Gly Val Gly Ala Arg Gly Asp Ser Gly Arg Pro Ile Leu
225                 230                 235                 240

Asp Asn Gln Gly Arg Val Val Ala Ile Val Leu Gly Gly Met Asn Glu
                245                 250                 255

Gly Ser Arg Thr Ala Leu Ser Val Val Thr Trp Asn Glu Lys Gly Val
            260                 265                 270

Thr Val Lys Tyr Thr Pro Glu Asn Cys Glu Gln Trp Ser Leu Val Thr
        275                 280                 285

Thr Leu Cys Leu Leu Ala Asn Val Thr Phe Pro Cys Thr Gln Pro Pro
290                 295                 300

Ile Cys Tyr Asp Arg Lys Pro Ala Glu Thr Leu Ser Met Leu Ser His
305                 310                 315                 320

Asn Ile Asp Asn Pro Gly Tyr Asp Glu Leu Leu Glu Ala Val Leu Lys
                325                 330                 335

Cys Pro Gly Arg Gly Lys Arg Ser Thr Glu Glu Leu Phe Lys Glu Tyr
            340                 345                 350

Lys Leu Thr Arg Pro Tyr Met Ala Lys Cys Val Arg Cys Ala Val Gly
        355                 360                 365

Ser Cys His Ser Pro Ile Ala Ile Glu Ala Val Arg Ser Asp Gly His
370                 375                 380
```

```
Asp Gly Tyr Ile Arg Ile Gln Thr Ser Ser Gln Tyr Gly Leu Asp Pro
385                 390                 395                 400

Ser Gly Asn Leu Lys Gly Arg Thr Met Arg Tyr Asp Met His Gly Thr
            405                 410                 415

Ile Lys Glu Ile Pro Leu His Gln Val Ser Leu His Thr Ser Arg Pro
        420                 425                 430

Cys His Ile Val Asp Gly His Gly Tyr Phe Leu Leu Ala Arg Cys Pro
    435                 440                 445

Glu Gly Asp Ser Ile Thr Met Glu Phe Lys Lys Glu Ser Val Thr His
450                 455                 460

Ser Cys Ser Val Pro Tyr Glu Val Lys Phe Asn Pro Ala Gly Arg Glu
465                 470                 475                 480

Leu Tyr Thr His Pro Pro Glu His Gly Ala Glu Gln Pro Cys His Val
                485                 490                 495

Tyr Ala His Asp Ala Gln Asn Arg Gly Ala Tyr Val Glu Met His Leu
            500                 505                 510

Pro Gly Ser Glu Val Asp Ser Thr Leu Leu Ser Met Ser Gly Ser Ser
        515                 520                 525

Val His Val Thr Pro Pro Ala Gly Gln Ser Val Gln Val Glu Cys Glu
530                 535                 540

Cys Gly Gly Thr Lys Ile Ser Glu Thr Ile Asn Ser Ala Lys Gln Tyr
545                 550                 555                 560

Ser Gln Cys Ser Lys Thr Ser Gln Cys Arg Ala Tyr Arg Thr Gln Asn
                565                 570                 575

Asp Lys Trp Val Tyr Asn Ser Asp Lys Leu Pro Lys Ala Ser Gly Glu
            580                 585                 590

Thr Leu Lys Gly Lys Leu His Val Pro Phe Val Leu Thr Glu Ala Lys
        595                 600                 605

Cys Thr Val Pro Leu Ala Pro Glu Pro Ile Ile Thr Phe Gly Phe Arg
610                 615                 620

Ser Val Ser Leu Lys Leu His Pro Lys Asn Pro Thr Phe Leu Thr Thr
625                 630                 635                 640

Arg Gln Leu Asp Gly Glu Pro Ala Tyr Thr His Glu Leu Ile Thr His
                645                 650                 655

Pro Val Val Arg Asn Phe Ser Val Thr Glu Lys Gly Trp Glu Phe Val
            660                 665                 670

Trp Gly Asn His Pro Pro Gln Arg Tyr Trp Ser Gln Glu Thr Ala Pro
        675                 680                 685

Gly Asn Pro His Gly Leu Pro His Glu Val Ile Val His Tyr Tyr His
690                 695                 700

Arg Tyr Pro Met Ser Thr Ile Val Gly Leu Ser Ile Cys Ala Ala Ile
705                 710                 715                 720

Val Thr Val Ser Val Ala Ala Ser Thr Trp Leu Phe Cys Arg Ser Arg
                725                 730                 735

Val Ala Cys Leu Thr Pro Tyr Arg Leu Thr Pro Asn Ala Arg Ile Pro
            740                 745                 750

Phe Cys Leu Ala Val Leu Cys Cys Ala Arg Thr Ala Lys Ala Glu Thr
        755                 760                 765

Thr Trp Glu Ser Leu Asp His Leu Trp Asn Asn Asn Gln Gln Met Phe
770                 775                 780

Trp Ile Gln Leu Leu Ile Pro Leu Ala Ala Leu Ile Val Val Thr Arg
785                 790                 795                 800
```

-continued

```
Leu Leu Lys Cys Met Cys Cys Val Val Pro Phe Leu Val Val Ala Gly
                805                 810                 815

Ala Val Gly Ala Gly Ala Tyr Glu His Ala Thr Thr Met Pro Ser Gln
            820                 825                 830

Ala Gly Ile Ser Tyr Asn Thr Ile Val Asn Arg Ala Gly Tyr Ala Pro
            835                 840                 845

Leu Pro Ile Ser Ile Val Pro Thr Lys Val Lys Leu Ile Pro Thr Val
        850                 855                 860

Asn Leu Glu Tyr Ile Thr Cys His Tyr Lys Thr Gly Met Asp Ser Pro
865                 870                 875                 880

Ala Ile Lys Cys Cys Gly Thr Gln Glu Cys Ser Pro Thr Tyr Arg Pro
                885                 890                 895

Asp Glu Gln Cys Lys Val Phe Ser Gly Val Tyr Pro Phe Met Trp Gly
            900                 905                 910

Gly Ala Tyr Cys Phe Cys Asp Thr Glu Asn Thr Gln Ile Ser Lys Ala
            915                 920                 925

Tyr Val Thr Lys Ser Glu Asp Cys Val Thr Asp His Ala Gln Ala Tyr
        930                 935                 940

Lys Ala His Thr Ala Ser Ile Gln Ala Phe Leu Asn Ile Thr Val Gly
945                 950                 955                 960

Gly His Ser Thr Thr Ala Val Val Tyr Val Asn Gly Glu Thr Pro Val
                965                 970                 975

Asn Phe Asn Gly Ile Lys Leu Val Ala Gly Pro Leu Ser Thr Ala Trp
            980                 985                 990

Ser Pro Phe Asp Lys Lys Ile Val  Gln Tyr Ala Gly Glu  Val Tyr Asn
            995                 1000                 1005

Tyr Asp  Phe Pro Glu Tyr Gly  Ala Gly His Ala Gly  Ala Phe Gly
        1010                 1015                 1020

Asp Ile  Gln Ala Arg Thr Ile  Ser Ser Ser Asp Val  Tyr Ala Asn
        1025                 1030                 1035

Thr Asn  Leu Val Leu Gln Arg  Pro Asn Thr Gly Thr  Ile His Val
        1040                 1045                 1050

Pro Tyr  Thr Gln Ala Pro Ser  Gly Tyr Glu Gln Trp  Lys Lys Asp
        1055                 1060                 1065

Lys Pro  Pro Ser Leu Lys Tyr  Thr Ala Pro Phe Gly  Cys Glu Ile
        1070                 1075                 1080

His Val  Asn Pro Val Arg Ala  Glu Asn Cys Ala Val  Gly Phe Ile
        1085                 1090                 1095

Pro Leu  Ala Phe Asp Ile Pro  Asp Ala Leu Phe Thr  Arg Val Ser
        1100                 1105                 1110

Glu Thr  Pro Thr Leu Ser Ser  Ala Glu Cys Ser Leu  Asn Glu Cys
        1115                 1120                 1125

Thr Tyr  Ser Thr Asp Phe Gly  Gly Ile Ala Thr Val  Lys Tyr Ser
        1130                 1135                 1140

Ala Ser  Lys Ala Gly Lys Cys  Ala Val His Ile Pro  Ser Gly Thr
        1145                 1150                 1155

Ala Thr  Leu Lys Glu Ala Ala  Val Glu Leu Ala Glu  Gln Gly Ser
        1160                 1165                 1170

Ala Thr  Ile His Phe Ser Thr  Ala Ser Ile His Pro  Glu Phe Lys
        1175                 1180                 1185

Leu Gln  Ile Cys Thr Lys Val  Leu Thr Cys Lys Gly  Asp Cys His
        1190                 1195                 1200

Pro Pro  Lys Asp His Ile Val  Thr His Pro Gln Tyr  His Ala Gln
```

```
                1205                1210                1215

Ser Phe Thr Ala Ala Val Ser Lys Thr Ala Trp Thr Trp Ile Thr
    1220                1225                1230

Ser Leu Leu Gly Gly Ser Ala Ile Ile Ile Ile Ile Gly Leu Val
    1235                1240                1245

Leu Ala Thr Val Val Ala Met Tyr Val Leu Thr Asn Gln Arg His
    1250                1255                1260

Asn

<210> SEQ ID NO 7
<211> LENGTH: 1236
<212> TYPE: PRT
<213> ORGANISM: Artificial Sequence
<220> FEATURE:
<223> OTHER INFORMATION: Synthetic polypeptide

<400> SEQUENCE: 7

Met Phe Pro Tyr Pro Gln Leu Asn Phe Pro Pro Val Tyr Pro Thr Asn
1               5                   10                  15

Pro Met Ala Tyr Arg Asp Pro Asn Pro Pro Arg Arg Arg Trp Arg Pro
            20                  25                  30

Phe Arg Pro Pro Leu Ala Ala Gln Ile Glu Asp Leu Arg Arg Ser Ile
        35                  40                  45

Ala Asn Leu Thr Phe Lys Gln Arg Ser Pro Asn Pro Pro Pro Gly Pro
    50                  55                  60

Pro Pro Lys Lys Lys Lys Ser Ala Pro Lys Pro Lys Pro Thr Gln Pro
65                  70                  75                  80

Lys Lys Lys Lys Gln Gln Ala Lys Lys Thr Lys Arg Lys Pro Lys Pro
                85                  90                  95

Gly Lys Arg Gln Arg Met Cys Met Lys Leu Glu Ser Asp Lys Thr Phe
            100                 105                 110

Pro Ile Met Leu Asn Gly Gln Val Asn Gly Tyr Ala Cys Val Val Gly
        115                 120                 125

Gly Arg Leu Met Lys Pro Leu His Val Glu Gly Lys Ile Asp Asn Glu
    130                 135                 140

Gln Leu Ala Ala Val Lys Leu Lys Lys Ala Ser Met Tyr Asp Leu Glu
145                 150                 155                 160

Tyr Gly Asp Val Pro Gln Asn Met Lys Ser Asp Thr Leu Gln Tyr Thr
                165                 170                 175

Ser Asp Lys Pro Pro Gly Phe Tyr Asn Trp His His Gly Ala Val Gln
            180                 185                 190

Tyr Glu Asn Gly Arg Phe Thr Val Pro Arg Gly Val Gly Gly Lys Gly
        195                 200                 205

Asp Ser Gly Arg Pro Ile Leu Asp Asn Arg Gly Arg Val Val Ala Ile
    210                 215                 220

Val Leu Gly Gly Ala Asn Glu Gly Thr Arg Thr Ala Leu Ser Val Val
225                 230                 235                 240

Thr Trp Asn Gln Lys Gly Val Thr Ile Lys Asp Thr Pro Glu Gly Ser
                245                 250                 255

Glu Pro Trp Ser Leu Val Thr Ala Leu Cys Val Leu Ser Asn Val Thr
            260                 265                 270

Phe Pro Cys Asp Lys Pro Pro Val Cys Tyr Ser Leu Ala Pro Glu Arg
        275                 280                 285

Thr Leu Asp Val Leu Glu Glu Asn Val Asp Asn Pro Asn Tyr Asp Thr
    290                 295                 300
```

```
Leu Leu Glu Asn Val Leu Lys Cys Pro Ser Arg Arg Pro Lys Arg Ser
305                 310                 315                 320

Ile Thr Asp Asp Phe Thr Leu Thr Ser Pro Tyr Leu Gly Phe Cys Pro
                325                 330                 335

Tyr Cys Arg His Ser Thr Pro Cys Phe Ser Pro Ile Lys Ile Glu Asn
                340                 345                 350

Val Trp Asp Glu Ser Asp Asp Gly Ser Ile Arg Ile Gln Val Ser Ala
                355                 360                 365

Gln Phe Gly Tyr Asn Gln Ala Gly Thr Ala Asp Val Thr Lys Phe Arg
370                 375                 380

Tyr Met Ser Phe Asp His Asp His Asp Ile Lys Glu Asp Ser Met Glu
385                 390                 395                 400

Lys Ile Ala Ile Ser Thr Ser Gly Pro Cys Arg Arg Leu Gly His Lys
                405                 410                 415

Gly Tyr Phe Leu Leu Ala Gln Cys Pro Pro Gly Asp Ser Val Thr Val
                420                 425                 430

Ser Ile Thr Ser Gly Ala Ser Glu Asn Ser Cys Thr Val Glu Lys Lys
                435                 440                 445

Ile Arg Arg Lys Phe Val Gly Arg Glu Glu Tyr Leu Phe Pro Pro Val
450                 455                 460

His Gly Lys Leu Val Lys Cys His Val Tyr Asp His Leu Lys Glu Thr
465                 470                 475                 480

Ser Ala Gly Tyr Ile Thr Met His Arg Pro Gly Pro His Ala Tyr Lys
                485                 490                 495

Ser Tyr Leu Glu Glu Ala Ser Gly Glu Val Tyr Ile Lys Pro Pro Ser
                500                 505                 510

Gly Lys Asn Val Thr Tyr Glu Cys Lys Cys Gly Asp Tyr Ser Thr Gly
                515                 520                 525

Ile Val Ser Thr Arg Thr Lys Met Asn Gly Cys Thr Lys Ala Lys Gln
                530                 535                 540

Cys Ile Ala Tyr Lys Ser Asp Gln Thr Lys Trp Val Phe Asn Ser Pro
545                 550                 555                 560

Asp Leu Ile Arg His Thr Asp His Ser Val Gln Gly Lys Leu His Ile
                565                 570                 575

Pro Phe Arg Leu Thr Pro Thr Val Cys Pro Val Pro Leu Ala His Thr
                580                 585                 590

Pro Thr Val Thr Lys Trp Phe Lys Gly Ile Thr Leu His Leu Thr Ala
                595                 600                 605

Thr Arg Pro Thr Leu Leu Thr Thr Arg Lys Leu Gly Leu Arg Ala Asp
                610                 615                 620

Ala Thr Ala Glu Trp Ile Thr Gly Thr Thr Ser Arg Asn Phe Ser Val
625                 630                 635                 640

Gly Arg Glu Gly Leu Glu Tyr Val Trp Gly Asn His Glu Pro Val Arg
                645                 650                 655

Val Trp Ala Gln Glu Ser Ala Pro Gly Asp Pro His Gly Trp Pro His
                660                 665                 670

Glu Ile Ile Ile His Tyr Tyr His Arg His Pro Val Tyr Thr Val Ile
                675                 680                 685

Val Leu Cys Gly Val Ala Leu Ala Ile Leu Val Gly Thr Ala Ser Ser
                690                 695                 700

Ala Ala Cys Ile Ala Lys Ala Arg Arg Asp Cys Leu Thr Pro Tyr Ala
705                 710                 715                 720
```

-continued

Leu Ala Pro Asn Ala Thr Val Pro Thr Ala Leu Ala Val Leu Cys Cys
            725                 730                 735

Ile Arg Pro Thr Asn Ala Glu Thr Phe Gly Glu Thr Leu Asn His Leu
            740                 745                 750

Trp Phe Asn Asn Gln Pro Phe Leu Trp Ala Gln Leu Cys Ile Pro Leu
            755                 760                 765

Ala Ala Leu Val Ile Leu Phe Arg Cys Phe Ser Cys Cys Met Pro Phe
            770                 775                 780

Leu Leu Val Ala Gly Val Cys Leu Gly Lys Val Asp Ala Phe Glu His
785                 790                 795                 800

Ala Thr Thr Val Pro Asn Val Pro Gly Ile Pro Tyr Lys Ala Leu Val
            805                 810                 815

Glu Arg Ala Gly Tyr Ala Pro Leu Asn Leu Glu Ile Thr Val Val Ser
            820                 825                 830

Ser Glu Leu Thr Pro Ser Thr Asn Lys Glu Tyr Val Thr Cys Lys Phe
            835                 840                 845

His Thr Val Ile Pro Ser Pro Gln Val Lys Cys Cys Gly Ser Leu Glu
            850                 855                 860

Cys Lys Ala Ser Ser Lys Ala Asp Tyr Thr Cys Arg Val Phe Gly Gly
865                 870                 875                 880

Val Tyr Pro Phe Met Trp Gly Gly Ala Gln Cys Phe Cys Asp Ser Glu
            885                 890                 895

Asn Thr Gln Leu Ser Glu Ala Tyr Val Glu Phe Ala Pro Asp Cys Thr
            900                 905                 910

Ile Asp His Ala Val Ala Leu Lys Val His Thr Ala Ala Leu Lys Val
            915                 920                 925

Gly Leu Arg Ile Val Tyr Gly Asn Thr Thr Ala His Leu Asp Thr Phe
            930                 935                 940

Val Asn Gly Val Thr Pro Gly Ser Ser Arg Asp Leu Lys Val Ile Ala
945                 950                 955                 960

Gly Pro Ile Ser Ala Ala Phe Ser Pro Phe Asp His Lys Val Val Ile
            965                 970                 975

Arg Lys Gly Leu Val Tyr Asn Tyr Asp Phe Pro Glu Tyr Gly Ala Met
            980                 985                 990

Lys Pro Gly Ala Phe Gly Asp Ile Gln Ala Ser Ser Leu Asp Ala Thr
            995                 1000                1005

Asp Ile Val Ala Arg Thr Asp Ile Arg Leu Leu Lys Pro Ser Val
            1010                1015                1020

Lys Asn Ile His Val Pro Tyr Thr Gln Ala Val Ser Gly Tyr Glu
            1025                1030                1035

Met Trp Lys Asn Asn Ser Gly Arg Pro Leu Gln Glu Thr Ala Pro
            1040                1045                1050

Phe Gly Cys Lys Ile Glu Val Glu Pro Leu Arg Ala Ser Asn Cys
            1055                1060                1065

Ala Tyr Gly His Ile Pro Ile Ser Ile Asp Ile Pro Asp Ala Ala
            1070                1075                1080

Phe Val Arg Ser Ser Glu Ser Pro Thr Ile Leu Glu Val Ser Cys
            1085                1090                1095

Thr Val Ala Asp Cys Ile Tyr Ser Ala Asp Phe Gly Gly Ser Leu
            1100                1105                1110

Thr Leu Gln Tyr Lys Ala Asp Arg Glu Gly His Cys Pro Val His
            1115                1120                1125

Ser His Ser Thr Thr Ala Val Leu Lys Glu Ala Thr Thr His Val

```
                    1130                1135                1140

Thr Ala Val Gly Ser Ile Thr Leu His Phe Ser Thr Ser Ser Pro
            1145                1150                1155

Gln Ala Asn Phe Ile Val Ser Leu Cys Gly Lys Lys Thr Thr Cys
    1160                1165                1170

Asn Ala Glu Cys Lys Pro Pro Ala Asp His Ile Ile Gly Glu Pro
    1175                1180                1185

His Lys Val Asp Gln Glu Phe Gln Ala Ala Val Ser Lys Thr Ser
    1190                1195                1200

Trp Asn Trp Leu Leu Ala Leu Phe Gly Gly Ala Ser Ser Leu Ile
    1205                1210                1215

Val Val Gly Leu Ile Val Leu Val Cys Ser Ser Met Leu Ile Asn
    1220                1225                1230

Thr Arg Arg
    1235

<210> SEQ ID NO 8
<211> LENGTH: 1236
<212> TYPE: PRT
<213> ORGANISM: Artificial Sequence
<220> FEATURE:
<223> OTHER INFORMATION: Synthetic polypeptide

<400> SEQUENCE: 8

Met Phe Pro Tyr Pro Gln Leu Thr Phe Pro Pro Met Tyr Gln Pro Asn
1               5                   10                  15

Pro Met Ala Tyr Arg Asp Pro Asn Pro Pro Arg Arg Arg Trp Arg Pro
            20                  25                  30

Phe Arg Val Pro Leu Ala Ala Gln Ile Glu Glu Leu Arg Arg Ser Ile
        35                  40                  45

Ala Asn Leu Thr Leu Lys Gln Arg Ala Pro Asn Pro Pro Ala Gly Pro
    50                  55                  60

Pro Ala Lys Lys Lys Thr Gln Pro Lys Pro Lys Ala Thr Pro Pro
65                  70                  75                  80

Lys Lys Lys Lys Gln Gln Val Lys Lys Gln Lys Arg Lys Pro Lys Pro
                85                  90                  95

Gly Lys Arg Gln Arg Leu Cys Met Lys Leu Glu Ser Asp Lys Thr Phe
            100                 105                 110

Pro Ile Leu Leu Asn Gly Gln Val Asn Gly Tyr Ala Cys Val Val Gly
        115                 120                 125

Gly Arg Leu Met Lys Pro Leu His Val Glu Gly Lys Ile Asp Asn Glu
    130                 135                 140

Gln Leu Ala Ala Ile Lys Leu Lys Lys Ala Ser Met Tyr Asp Leu Glu
145                 150                 155                 160

Tyr Gly Asp Val Pro Gln Asn Met Lys Ser Asp Thr Leu Gln Tyr Thr
                165                 170                 175

Ser Glu Lys Pro Pro Gly Phe Tyr Asn Trp His His Gly Thr Val Gln
            180                 185                 190

Tyr Glu Asn Gly Arg Phe Ser Val Pro Arg Gly Val Gly Gly Lys Gly
        195                 200                 205

Asp Ser Gly Arg Pro Ile Leu Asp Asn Lys Gly Arg Val Val Ala Ile
    210                 215                 220

Val Leu Gly Gly Ala Asn Glu Gly Ser Arg Thr Ala Leu Ser Val Val
225                 230                 235                 240

Thr Trp Asn Gln Lys Gly Val Thr Ile Lys Asp Thr Pro Glu Gly Thr
```

-continued

```
            245                 250                 255
Glu Gln Trp Ser Leu Ile Thr Ala Met Cys Val Leu Ala Asn Val Thr
            260                 265                 270

Phe Pro Cys Asp Lys Pro Pro Val Cys Tyr Ser Leu Thr Pro Glu Arg
            275                 280                 285

Thr Leu Asp Val Leu Glu Glu Asn Val Asp Asn Pro Gly Tyr Asp Thr
            290                 295                 300

Leu Leu Glu Asn Val Leu Lys Cys Pro Ser Arg Arg Gln Lys Arg Ser
305                 310                 315                 320

Ile Thr Asp Asp Phe Thr Leu Thr Ser Pro Tyr Leu Gly His Cys Pro
                    325                 330                 335

Tyr Cys Leu His Ala Thr Pro Cys Phe Ser Pro Ile Lys Ile Glu Lys
                340                 345                 350

Val Trp Asp Glu Ser Asp Asp Gly Thr Ile Arg Ile Gln Val Ser Ala
                355                 360                 365

Gln Leu Gly Tyr Asn Gln Ala Gly Thr Ala Asp Pro Thr Lys Phe Arg
            370                 375                 380

Tyr Met Ser Tyr Glu Gln Asp His Asp Ile Lys Glu Ala Ser Met Asp
385                 390                 395                 400

Lys Ile Ala Ile Ser Thr Ser Gly Pro Cys Ser Arg Leu Gly His Lys
                    405                 410                 415

Gly Tyr Phe Leu Leu Ala Arg Cys Pro Pro Gly Asp Ser Val Thr Val
                420                 425                 430

Ser Ile Thr Ser Gly Thr Ser Glu Asn Ser Cys Thr Val Glu Arg Lys
                435                 440                 445

Ile Arg Arg Lys Phe Val Gly Arg Glu Glu Tyr Leu Leu Pro Pro Val
            450                 455                 460

His Gly Lys Leu Ile Lys Cys His Val Tyr Asp His Leu Lys Glu Thr
465                 470                 475                 480

Thr Ala Gly Tyr Ile Thr Met His Arg Pro Gly Pro His Ala Tyr Ala
                    485                 490                 495

Thr Tyr Val Glu Glu Ser Ser Gly Glu Val Tyr Ile Arg Pro Pro Ser
                500                 505                 510

Gly Lys Asn Val Thr Tyr Glu Cys Lys Cys Gly Asp Tyr Ser Thr Gly
                515                 520                 525

Thr Val Asn Thr Arg Thr Lys Met Pro Gly Cys Thr Lys Lys Lys Gln
            530                 535                 540

Cys Ile Ala Tyr Lys His Asp Gln Thr Lys Trp Val Phe Asn Ser Pro
545                 550                 555                 560

Asp Leu Ile Arg His Ser Asp His Ala Val Gln Gly Lys Leu His Ile
                    565                 570                 575

Pro Phe Lys Leu Thr Ala Thr Ala Cys Pro Val Pro Leu Ala His Thr
                580                 585                 590

Pro Thr Val Glu Lys Trp Phe Lys Gly Val Thr Leu His Leu Thr Ala
                595                 600                 605

Ser His Pro Thr Leu Leu Thr Thr Arg Lys Leu Gly Pro Arg Ala Glu
            610                 615                 620

Pro Thr Ser Glu Trp Ile Val Gly Thr Val Ser Arg Asn Phe Ser Val
625                 630                 635                 640

Gly Arg Glu Gly Leu Glu Tyr Thr Trp Gly Asn His Asp Pro Val Arg
                    645                 650                 655

Val Trp Ser Gln Glu Ser Ala Pro Gly Asp Pro His Gly Trp Pro His
                660                 665                 670
```

```
Glu Ile Ile Val His Tyr Tyr His Arg His Pro Leu Tyr Thr Ile Ala
        675                 680                 685

Val Leu Cys Gly Leu Val Leu Ile Thr Val Ile Gly Ile Ala Ser Ala
    690                 695                 700

Ala Ala Cys Ile Ser Lys Ala Arg Arg Asp Cys Leu Thr Pro Tyr Ala
705                 710                 715                 720

Leu Ala Pro Asn Ala Ala Val Pro Thr Leu Leu Ala Val Leu Cys Cys
            725                 730                 735

Ile Arg Pro Thr His Ala Glu Thr Leu Gly Glu Ser Leu Gly His Leu
        740                 745                 750

Trp Leu Asn Asn Gln Pro Leu Trp Ala Gln Leu Cys Leu Pro Leu
        755                 760                 765

Ala Ala Leu Ile Ile Leu Phe Arg Phe Phe Ser Cys Cys Leu Pro Phe
    770                 775                 780

Leu Leu Val Ala Gly Val Cys Leu Gly Lys Ala Asp Ala Tyr Glu His
785                 790                 795                 800

Ala Thr Thr Val Pro Asn Val Pro Gly Val Pro Tyr Lys Ala Leu Val
            805                 810                 815

Glu Arg Ser Gly Tyr Ala Pro Leu Asn Leu Glu Val Thr Val Val Ser
        820                 825                 830

Ser Glu Leu Ile Pro Ser Thr Asn Lys Glu Tyr Val Thr Cys Lys Phe
835                 840                 845

His Thr Ile Ile Pro Ser Pro Gln Val Lys Cys Cys Gly Ser Leu Glu
    850                 855                 860

Cys Gln Ala Ser Arg Lys Ala Asp Tyr Thr Cys Arg Val Phe Gly Gly
865                 870                 875                 880

Val Tyr Pro Phe Met Trp Gly Gly Ala Gln Cys Ser Cys Asp Ser Glu
            885                 890                 895

Asn Thr Gln Leu Ser Glu Ala Tyr Val Glu Phe Ala Pro Asp Cys Thr
        900                 905                 910

Ala Asp His Ala Val Ala Leu Lys Val His Thr Ala Ala Leu Lys Val
    915                 920                 925

Gly Leu Gln Ile Val Tyr Gly Asn Thr Ser Thr Arg Leu Asp Thr Phe
930                 935                 940

Val Asn Gly Val Thr Pro Gly Ile Ser Gly Ala Leu Lys Val Ile Ala
945                 950                 955                 960

Gly Pro Ile Ser Ala Ala Phe Thr Pro Phe Asp His Lys Val Val Ile
            965                 970                 975

Arg Lys Gly Lys Val Tyr Asn Tyr Asp Phe Pro Glu Tyr Gly Ala Met
        980                 985                 990

Lys Pro Gly Val Phe Gly Asp Ile Gln Ala Ser Ser Leu Asp Ser Thr
    995                 1000                1005

Asp Ile Val Ala Arg Thr Asp Val Arg Leu Leu Lys Pro Ser Val
    1010                1015                1020

Lys Ser Ile His Val Pro Tyr Thr Gln Ala Ala Ser Gly Tyr Glu
    1025                1030                1035

Met Trp Lys Asn Asn Ser Gly Arg Pro Leu Gln Asp Thr Ala Pro
    1040                1045                1050

Phe Gly Cys Lys Ile Glu Val Asp Pro Leu Arg Ala Val Asp Cys
    1055                1060                1065

Ala Tyr Gly His Ile Pro Leu Ser Ile Asp Ile Pro Asp Ala Ala
    1070                1075                1080
```

```
Phe Val Arg Thr Ser Glu Ala Pro Thr Val Leu Glu Met Ser Cys
1085                1090                1095

Thr Val Thr Ala Cys Ile Tyr Ser Ala Asp Phe Gly Gly Ser Leu
1100                1105                1110

Thr Leu Gln Tyr Lys Ala Asp Lys Glu Gly Asn Cys Pro Val His
1115                1120                1125

Ser His Ser Ser Thr Ala Val Leu Lys Glu Ala Thr Thr His Val
1130                1135                1140

Val His Ser Gly Ser Val Thr Leu His Phe Ser Thr Ser Ser Pro
1145                1150                1155

Gln Val Asn Phe Ile Val Ser Leu Cys Gly Lys Lys Thr Thr Cys
1160                1165                1170

Asp Ala Glu Cys Lys Pro Pro Ser Asp His Ile Ile Gly Glu Pro
1175                1180                1185

His Lys Val Asn Gln Glu Phe Gln Ala Ala Val Ser Lys Thr Ser
1190                1195                1200

Trp Asn Trp Leu Phe Ala Met Leu Gly Gly Ala Ser Ser Leu Ile
1205                1210                1215

Val Val Gly Leu Leu Val Leu Ala Cys Ser Ser Met Ile Ile Asn
1220                1225                1230

Thr Arg Arg
1235

<210> SEQ ID NO 9
<211> LENGTH: 1236
<212> TYPE: PRT
<213> ORGANISM: Artificial Sequence
<220> FEATURE:
<223> OTHER INFORMATION: Synthetic polypeptide

<400> SEQUENCE: 9

Met Phe Pro Tyr Pro Gln Leu Asn Phe Pro Pro Val Tyr Pro Thr Asn
1               5                   10                  15

Pro Met Ala Tyr Arg Asp Pro Asn Pro Pro Arg Arg Arg Trp Arg Pro
                20                  25                  30

Phe Arg Pro Pro Leu Ala Ala Gln Ile Glu Asp Leu Arg Arg Ser Ile
            35                  40                  45

Ala Asn Leu Thr Phe Lys Gln Arg Ser Pro Asn Pro Pro Pro Gly Pro
    50                  55                  60

Pro Pro Lys Lys Lys Lys Ser Ala Pro Lys Pro Lys Pro Thr Gln Pro
65                  70                  75                  80

Lys Lys Lys Lys Gln Gln Ala Lys Lys Thr Lys Arg Lys Pro Lys Pro
                85                  90                  95

Gly Lys Arg Gln Arg Met Cys Met Lys Leu Glu Ser Asp Lys Thr Phe
            100                 105                 110

Pro Ile Met Leu Asn Gly Gln Val Asn Gly Tyr Ala Cys Val Val Gly
        115                 120                 125

Gly Arg Leu Met Lys Pro Leu His Val Glu Gly Lys Ile Asp Asn Glu
    130                 135                 140

Gln Leu Ala Ala Val Lys Leu Lys Lys Ala Ser Lys Tyr Asp Leu Glu
145                 150                 155                 160

Tyr Gly Asp Val Pro Gln Asn Met Lys Ser Asp Thr Leu Gln Tyr Thr
                165                 170                 175

Ser Asp Lys Pro Pro Gly Phe Tyr Asn Trp His His Gly Ala Val Gln
            180                 185                 190
```

```
Tyr Glu Asn Gly Arg Phe Thr Val Pro Arg Gly Val Gly Lys Gly
            195                 200                 205
Asp Ser Gly Arg Pro Ile Leu Asp Asn Arg Gly Arg Val Val Ala Ile
        210                 215                 220
Val Leu Gly Gly Ala Asn Glu Gly Thr Arg Thr Ala Leu Ser Val Val
225                 230                 235                 240
Thr Trp Asn Gln Lys Gly Val Thr Ile Arg Asp Thr Pro Glu Gly Ser
                245                 250                 255
Glu Pro Trp Ser Leu Val Thr Ala Leu Cys Val Leu Ser Asn Val Thr
            260                 265                 270
Phe Pro Cys Asp Lys Pro Pro Val Cys Tyr Ser Leu Ala Pro Glu Arg
        275                 280                 285
Thr Leu Asp Val Leu Glu Glu Asn Val Asp Asn Pro Asn Tyr Asp Thr
    290                 295                 300
Leu Leu Glu Asn Val Leu Lys Cys Pro Ser Arg Arg Pro Lys Arg Ser
305                 310                 315                 320
Ile Thr Asp Asp Phe Thr Leu Thr Ser Pro Tyr Leu Gly Phe Cys Pro
                325                 330                 335
Tyr Cys Arg His Ser Thr Pro Cys Phe Ser Pro Ile Lys Ile Glu Asn
            340                 345                 350
Val Trp Asp Glu Ser Asp Gly Ser Ile Arg Ile Gln Val Ser Ala
        355                 360                 365
Gln Phe Gly Tyr Asn Gln Ala Gly Thr Ala Asp Val Thr Lys Phe Arg
    370                 375                 380
Tyr Met Ser Phe Asp His Asp His Asp Ile Lys Glu Asp Ser Met Glu
385                 390                 395                 400
Lys Ile Ala Ile Ser Thr Ser Gly Pro Cys Arg Arg Leu Gly His Lys
                405                 410                 415
Gly Tyr Phe Leu Leu Ala Gln Cys Pro Pro Gly Asp Ser Val Thr Val
            420                 425                 430
Ser Ile Thr Ser Gly Ala Ser Glu Asn Ser Cys Thr Val Glu Lys Lys
        435                 440                 445
Ile Arg Arg Lys Phe Val Gly Arg Glu Glu Tyr Leu Phe Pro Pro Val
    450                 455                 460
His Gly Lys Leu Val Lys Cys His Val Tyr Asp His Leu Lys Glu Thr
465                 470                 475                 480
Ser Ala Gly Tyr Ile Thr Met His Arg Pro Gly Pro His Ala Tyr Lys
                485                 490                 495
Ser Tyr Leu Glu Glu Ala Ser Gly Glu Val Tyr Ile Lys Pro Pro Ser
            500                 505                 510
Gly Lys Asn Val Thr Tyr Glu Cys Lys Cys Gly Asp Tyr Ser Thr Gly
        515                 520                 525
Ile Val Ser Thr Arg Thr Lys Met Asn Gly Cys Thr Lys Ala Lys Gln
    530                 535                 540
Cys Ile Ala Tyr Lys Ser Asp Gln Thr Lys Trp Val Phe Asn Ser Pro
545                 550                 555                 560
Asp Leu Ile Arg His Thr Asp His Ser Val Gln Gly Lys Leu His Ile
                565                 570                 575
Pro Phe Arg Leu Thr Pro Thr Val Cys Pro Val Pro Leu Ala His Thr
            580                 585                 590
Pro Thr Val Thr Lys Trp Phe Lys Gly Ile Thr Leu His Leu Thr Ala
        595                 600                 605
Thr Arg Pro Thr Leu Leu Thr Thr Arg Lys Leu Gly Leu Arg Ala Asp
```

```
                610             615             620
Ala Thr Ala Glu Trp Ile Thr Gly Thr Thr Ser Arg Asn Phe Ser Val
625             630             635             640

Gly Arg Glu Gly Leu Glu Tyr Val Trp Gly Asn His Glu Pro Val Arg
                645             650             655

Val Trp Ala Gln Glu Ser Ala Pro Gly Asp Pro His Gly Trp Pro His
            660             665             670

Glu Ile Ile Ile His Tyr Tyr His Arg His Pro Val Tyr Thr Val Ile
                675             680             685

Val Leu Cys Gly Val Ala Leu Ala Ile Leu Val Gly Thr Ala Ser Ser
690             695             700

Ala Ala Cys Ile Ala Lys Ala Arg Arg Asp Cys Leu Thr Pro Tyr Ala
705             710             715             720

Leu Ala Pro Asn Ala Thr Val Pro Thr Ala Leu Ala Val Leu Cys Cys
                725             730             735

Ile Arg Pro Thr Asn Ala Glu Thr Phe Gly Glu Thr Leu Asn His Leu
            740             745             750

Trp Phe Asn Asn Gln Pro Phe Leu Trp Ala Gln Leu Cys Ile Pro Leu
                755             760             765

Ala Ala Leu Val Ile Leu Phe Arg Cys Phe Ser Cys Met Pro Phe
770             775             780

Leu Leu Val Ala Gly Val Cys Leu Gly Lys Val Asp Ala Phe Glu His
785             790             795             800

Ala Thr Thr Val Pro Asn Val Pro Gly Ile Pro Tyr Lys Ala Leu Val
                805             810             815

Glu Arg Ala Gly Tyr Ala Pro Leu Asn Leu Glu Ile Thr Val Val Ser
            820             825             830

Ser Glu Leu Thr Pro Ser Thr Asn Lys Glu Tyr Val Thr Cys Lys Phe
        835             840             845

His Thr Val Ile Pro Ser Pro Gln Val Lys Cys Cys Gly Ser Leu Glu
850             855             860

Cys Lys Ala Ser Ser Lys Ala Asp Tyr Thr Cys Arg Val Phe Gly Gly
865             870             875             880

Val Tyr Pro Phe Met Trp Gly Gly Ala Gln Cys Phe Cys Asp Ser Glu
            885             890             895

Asn Thr Gln Leu Ser Glu Ala Tyr Val Glu Phe Ala Pro Asp Cys Thr
        900             905             910

Ile Asp His Ala Val Ala Leu Lys Val His Thr Ala Ala Leu Lys Val
            915             920             925

Gly Leu Arg Ile Val Tyr Gly Asn Thr Thr Ala His Leu Asp Thr Phe
930             935             940

Val Asn Gly Val Thr Pro Gly Ser Ser Arg Asp Leu Lys Val Ile Ala
945             950             955             960

Gly Pro Ile Ser Ala Ala Phe Ser Pro Phe Asp His Lys Val Val Ile
            965             970             975

Arg Lys Gly Leu Val Tyr Asn Tyr Asp Phe Pro Glu Tyr Gly Ala Met
        980             985             990

Lys Pro Gly Ala Phe Gly Asp Ile Gln Ala Ser Ser Leu Asp Ala Thr
    995             1000            1005

Asp Ile Val Ala Arg Thr Asp Ile Arg Leu Leu Lys Pro Ser Val
    1010            1015            1020

Lys Asn Ile His Val Pro Tyr Thr Gln Ala Val Ser Gly Tyr Glu
    1025            1030            1035
```

-continued

```
Met Trp Lys Asn Asn Ser Gly Arg Pro Leu Gln Glu Thr Ala Pro
1040                1045                1050

Phe Gly Cys Lys Ile Glu Val Glu Pro Leu Arg Ala Ser Asn Cys
1055                1060                1065

Ala Tyr Gly His Ile Pro Ile Ser Ile Asp Ile Pro Asp Ala Ala
1070                1075                1080

Phe Val Arg Ser Ser Glu Ser Pro Thr Ile Leu Glu Val Ser Cys
1085                1090                1095

Thr Val Ala Asp Cys Ile Tyr Ser Ala Asp Phe Gly Gly Ser Leu
1100                1105                1110

Thr Leu Gln Tyr Lys Ala Asp Arg Glu Gly His Cys Pro Val His
1115                1120                1125

Ser His Ser Thr Thr Ala Val Leu Lys Glu Ala Thr Thr His Val
1130                1135                1140

Thr Ala Val Gly Ser Ile Thr Leu His Phe Ser Thr Ser Ser Pro
1145                1150                1155

Gln Ala Asn Phe Ile Val Ser Leu Cys Gly Lys Lys Ser Thr Cys
1160                1165                1170

Asn Ala Glu Cys Lys Pro Pro Ala Asp His Ile Ile Gly Glu Pro
1175                1180                1185

His Lys Val Asp Gln Glu Phe Gln Ala Ala Val Ser Lys Thr Ser
1190                1195                1200

Trp Asn Trp Leu Leu Ala Leu Phe Gly Gly Ala Ser Ser Leu Ile
1205                1210                1215

Val Val Gly Leu Ile Val Leu Val Cys Ser Ser Met Leu Ile Asn
1220                1225                1230

Thr Arg Arg
1235

<210> SEQ ID NO 10
<211> LENGTH: 1242
<212> TYPE: PRT
<213> ORGANISM: Artificial Sequence
<220> FEATURE:
<223> OTHER INFORMATION: Synthetic polypeptide

<400> SEQUENCE: 10

Met Phe Pro Tyr Pro Thr Leu Asn Tyr Pro Pro Met Ala Pro Ile Asn
1                 5                   10                  15

Pro Met Ala Tyr Arg Asp Pro Asn Pro Arg Arg Arg Trp Arg Pro
                20                  25                  30

Phe Arg Pro Pro Leu Ala Ala Gln Ile Glu Asp Leu Arg Arg Ser Ile
            35                  40                  45

Ala Asn Leu Thr Leu Lys Gln Arg Ala Pro Asn Pro Pro Ala Gly Pro
        50                  55                  60

Pro Ala Lys Arg Lys Lys Pro Ala Pro Lys Pro Ala Gln Ala
65                  70                  75                  80

Lys Lys Lys Arg Pro Pro Pro Ala Lys Lys Gln Lys Arg Lys Pro
                85                  90                  95

Lys Pro Gly Lys Arg Gln Arg Met Cys Met Lys Leu Glu Ser Asp Lys
            100                 105                 110

Thr Phe Pro Ile Met Leu Asn Gly Gln Val Asn Gly Tyr Ala Cys Val
        115                 120                 125

Val Gly Gly Arg Val Phe Lys Pro Leu His Val Glu Gly Arg Ile Asp
    130                 135                 140
```

-continued

```
Asn Glu Gln Leu Ala Ala Ile Lys Leu Lys Lys Ala Ser Ile Tyr Asp
145                 150                 155                 160
Leu Glu Tyr Gly Asp Val Pro Gln Cys Met Lys Ser Asp Thr Leu Gln
            165                 170                 175
Tyr Thr Ser Asp Lys Pro Pro Gly Phe Tyr Asn Trp His His Gly Ala
            180                 185                 190
Val Gln Tyr Glu Asn Asn Arg Phe Thr Val Pro Arg Gly Val Gly Gly
        195                 200                 205
Lys Gly Asp Ser Gly Arg Pro Ile Leu Asp Asn Lys Gly Arg Val Val
        210                 215                 220
Ala Ile Val Leu Gly Gly Val Asn Glu Gly Ser Arg Thr Ala Leu Ser
225                 230                 235                 240
Val Val Thr Trp Asn Gln Lys Gly Val Thr Val Lys Asp Thr Pro Glu
            245                 250                 255
Gly Ser Glu Pro Trp Ser Leu Ala Thr Val Met Cys Val Leu Ala Asn
            260                 265                 270
Ile Thr Phe Pro Cys Asp Gln Pro Pro Cys Met Pro Cys Cys Tyr Glu
            275                 280                 285
Lys Asn Pro His Glu Thr Leu Thr Met Leu Glu Gln Asn Tyr Asp Ser
        290                 295                 300
Arg Ala Tyr Asp Gln Leu Leu Asp Ala Ala Val Lys Cys Asn Ala Arg
305                 310                 315                 320
Arg Thr Arg Arg Asp Leu Asp Thr His Phe Thr Gln Tyr Lys Leu Ala
            325                 330                 335
Arg Pro Tyr Ile Ala Asp Cys Pro Asn Cys Gly His Ser Arg Cys Asp
            340                 345                 350
Ser Pro Ile Ala Ile Glu Glu Val Arg Gly Asp Ala His Ala Gly Val
            355                 360                 365
Ile Arg Ile Gln Thr Ser Ala Met Phe Gly Leu Lys Thr Asp Gly Val
        370                 375                 380
Asp Leu Ala Tyr Met Ser Phe Met Asn Gly Lys Thr Gln Lys Ser Ile
385                 390                 395                 400
Lys Ile Asp Asn Leu His Val Arg Thr Ser Ala Pro Cys Ser Leu Val
            405                 410                 415
Ser His His Gly Tyr Tyr Ile Leu Ala Gln Cys Pro Pro Gly Asp Thr
            420                 425                 430
Val Thr Val Gly Phe His Asp Gly Pro Asn Arg His Thr Cys Thr Val
            435                 440                 445
Ala His Lys Val Glu Phe Arg Pro Val Gly Arg Glu Lys Tyr Arg His
        450                 455                 460
Pro Pro Glu His Gly Val Glu Leu Pro Cys Asn Arg Tyr Thr His Lys
465                 470                 475                 480
Arg Ala Asp Gln Gly His Tyr Val Glu Met His Gln Pro Gly Leu Val
            485                 490                 495
Ala Asp His Ser Leu Leu Ser Ile His Ser Ala Lys Val Lys Ile Thr
            500                 505                 510
Val Pro Ser Gly Ala Gln Val Lys Tyr Tyr Cys Lys Cys Pro Asp Val
            515                 520                 525
Arg Glu Gly Ile Thr Ser Ser Asp His Thr Thr Thr Cys Thr Asp Val
        530                 535                 540
Lys Gln Cys Arg Ala Tyr Leu Ile Asp Asn Lys Lys Trp Val Tyr Asn
545                 550                 555                 560
```

```
Ser Gly Arg Leu Pro Arg Gly Glu Gly Asp Thr Phe Lys Gly Lys Leu
                565                 570                 575

His Val Pro Phe Val Pro Val Lys Ala Lys Cys Ile Ala Thr Leu Ala
            580                 585                 590

Pro Glu Pro Leu Val Glu His Lys His Arg Thr Leu Ile Leu His Leu
        595                 600                 605

His Pro Asp His Pro Thr Leu Leu Thr Thr Arg Ser Leu Gly Ser Asp
610                 615                 620

Ala Asn Pro Thr Arg Gln Trp Ile Glu Arg Thr Thr Val Asn Phe
625                 630                 635                 640

Thr Val Thr Gly Glu Gly Leu Glu Tyr Thr Trp Gly Asn His Pro Pro
                645                 650                 655

Lys Arg Val Trp Ala Gln Glu Ser Gly Glu Gly Asn Pro His Gly Trp
            660                 665                 670

Pro His Glu Val Val Val Tyr Tyr Tyr Asn Arg Tyr Pro Leu Thr Thr
        675                 680                 685

Ile Ile Gly Leu Cys Thr Cys Val Ala Ile Met Val Ser Cys Val
    690                 695                 700

Thr Ser Val Trp Leu Leu Cys Arg Thr Arg Asn Leu Cys Ile Thr Pro
705                 710                 715                 720

Tyr Lys Leu Ala Pro Asn Ala Gln Val Pro Ile Leu Ala Leu Leu
                725                 730                 735

Cys Cys Ile Lys Pro Thr Arg Ala Asp Asp Thr Leu Gln Val Leu Asn
            740                 745                 750

Tyr Leu Trp Asn Asn Asn Gln Asn Phe Phe Trp Met Gln Thr Leu Ile
        755                 760                 765

Pro Leu Ala Ala Leu Ile Val Cys Met Arg Met Leu Arg Cys Leu Phe
770                 775                 780

Cys Cys Gly Pro Ala Phe Leu Leu Val Cys Gly Ala Leu Gly Ala Ala
785                 790                 795                 800

Ala Tyr Glu His Thr Ala Val Met Pro Asn Lys Val Gly Ile Pro Tyr
                805                 810                 815

Lys Ala Leu Val Glu Arg Pro Gly Tyr Ala Pro Val His Leu Gln Ile
            820                 825                 830

Gln Leu Val Asn Thr Arg Ile Ile Pro Ser Thr Asn Leu Glu Tyr Ile
        835                 840                 845

Thr Cys Lys Tyr Lys Thr Lys Val Pro Ser Pro Val Val Lys Cys Cys
850                 855                 860

Gly Ala Thr Gln Cys Thr Ser Lys Pro His Pro Asp Tyr Gln Cys Gln
865                 870                 875                 880

Val Phe Thr Gly Val Tyr Pro Phe Met Trp Gly Gly Ala Tyr Cys Phe
                885                 890                 895

Cys Asp Thr Glu Asn Thr Gln Met Ser Glu Ala Tyr Val Glu Arg Ser
            900                 905                 910

Glu Glu Cys Ser Ile Asp His Ala Lys Ala Tyr Lys Val His Thr Gly
        915                 920                 925

Thr Val Gln Ala Met Val Asn Ile Thr Tyr Gly Ser Val Ser Trp Arg
930                 935                 940

Ser Ala Asp Val Tyr Val Asn Gly Glu Thr Pro Ala Lys Ile Gly Asp
945                 950                 955                 960

Ala Lys Leu Ile Ile Gly Pro Leu Ser Ser Ala Trp Ser Pro Phe Asp
                965                 970                 975

Asn Lys Val Val Val Tyr Gly His Glu Val Tyr Asn Tyr Asp Phe Pro
```

```
                980            985            990
Glu Tyr Gly Thr Gly Lys Ala Gly  Ser Phe Gly Asp Leu Gln Ser Arg
            995               1000              1005
Thr Ser Thr Ser Asn Asp Leu  Tyr Ala Asn Thr Asn Leu Lys Leu
    1010              1015              1020
Gln Arg Pro Gln Ala Gly Ile Val His Thr Pro Phe Thr Gln Ala
    1025              1030              1035
Pro Ser Gly Phe Glu Arg Trp Lys Arg Asp Lys Gly Ala Pro Leu
    1040              1045              1050
Asn Asp Val Ala Pro Phe Gly Cys Ser Ile Ala Leu Glu Pro Leu
    1055              1060              1065
Arg Ala Glu Asn Cys Ala Val Gly Ser Ile Pro Ile Ser Ile Asp
    1070              1075              1080
Ile Pro Asp Ala Ala Phe Thr Arg Ile Ser Glu Thr Pro Thr Val
    1085              1090              1095
Ser Asp Leu Glu Cys Lys Ile Thr Glu Cys Thr Tyr Ala Ser Asp
    1100              1105              1110
Phe Gly Gly Ile Ala Thr Val Ala Tyr Lys Ser Lys Ala Gly
    1115              1120              1125
Asn Cys Pro Ile His Ser Pro Ser Gly Val Ala Val Ile Lys Glu
    1130              1135              1140
Asn Asp Val Thr Leu Ala Glu Ser Gly Ser Phe Thr Phe His Phe
    1145              1150              1155
Ser Thr Ala Asn Ile His Pro Ala Phe Lys Leu Gln Val Cys Thr
    1160              1165              1170
Ser Ala Val Thr Cys Lys Gly Asp Cys Lys Pro Pro Lys Asp His
    1175              1180              1185
Ile Val Asp Tyr Pro Ala Gln His Thr Glu Ser Phe Thr Ser Ala
    1190              1195              1200
Ile Ser Ala Thr Ala Trp Ser Trp Leu Lys Val Leu Val Gly Gly
    1205              1210              1215
Thr Ser Ala Phe Ile Val Leu Gly Leu Ile Ala Thr Ala Val Val
    1220              1225              1230
Ala Leu Val Leu Phe Phe His Arg His
    1235              1240

<210> SEQ ID NO 11
<211> LENGTH: 1240
<212> TYPE: PRT
<213> ORGANISM: Artificial Sequence
<220> FEATURE:
<223> OTHER INFORMATION: Synthetic polypeptide

<400> SEQUENCE: 11

Met Phe Pro Tyr Pro Ile Leu Asn Tyr Pro Pro Met Ala Pro Val Asn
1               5                   10                  15
Pro Met Ala Tyr Arg Asp Pro Asn Pro Arg Gln Val Ala Pro Phe
            20                  25                  30
Arg Pro Pro Leu Ala Ala Arg Ile Glu Asp Leu Arg Arg Ser Ile Ala
        35                  40                  45
Asn Leu Thr Phe Lys Gln Arg Ala Pro Asn Pro Pro Gly Pro Pro
        50                  55                  60
Ala Lys Arg Lys Lys Pro Ala Pro Lys Pro Lys Pro Ala Ala Pro Lys
65                  70                  75                  80
Lys Lys Arg Gln Pro Pro Pro Ala Lys Lys Gln Lys Arg Lys Gln Lys
```

```
                        85                  90                  95
        Pro Gly Lys Arg Gln Arg Met Cys Ile Lys Leu Glu Ser Asp Lys Thr
                        100                 105                 110

Phe Pro Ile Leu Leu Asn Gly Gln Val Asn Gly Tyr Ala Cys Val Phe
                        115                 120                 125

Gly Gly Arg Val Phe Lys Pro Leu His Val Glu Gly Lys Ile Asp Asn
                        130                 135                 140

Glu Gln Leu Ala Ala Ile Lys Leu Lys Lys Ala Ser Ile Tyr Asp Leu
        145                 150                 155                 160

Glu Tyr Gly Asp Val Pro Gln Cys Met Lys Ser Asp Thr Leu Gln Tyr
                        165                 170                 175

Thr Ser Glu Lys Pro Pro Gly Phe Tyr Asn Trp His His Gly Ala Val
                        180                 185                 190

Gln Tyr Asp Asn Asn Arg Phe Thr Val Pro Arg Gly Val Gly Gly Glu
                        195                 200                 205

Gly Asp Ser Gly Arg Pro Ile Leu Asp Asn Arg Gly Arg Val Val Ala
                        210                 215                 220

Ile Val Leu Gly Gly Ala Asn Glu Gly Ser Arg Thr Ala Leu Ser Val
        225                 230                 235                 240

Val Thr Trp Asn Gln Lys Gly Val Thr Ile Lys Asp Thr Pro Glu Gly
                        245                 250                 255

Ser Glu Pro Trp Ser Leu Thr Thr Val Met Cys Val Leu Ala Asn Ile
                        260                 265                 270

Thr Phe Pro Cys Glu Gln Pro Pro Cys Met Pro Cys Cys Tyr Glu Lys
                        275                 280                 285

Asn Pro His Glu Thr Leu Ser Met Leu Glu Gln Asn Tyr Asp Ser Gln
                        290                 295                 300

Ala Tyr Asp Gln Leu Leu Glu Ala Ala Val Lys Cys Asn Gly Arg Arg
        305                 310                 315                 320

Thr Arg Arg Asp Leu Glu Thr His Phe Thr Gln Tyr Lys Leu Ala Arg
                        325                 330                 335

Pro Tyr Ile Ala Asp Cys Ser Asn Cys Gly His Gly Arg Cys Asp Ser
                        340                 345                 350

Pro Ile Ala Ile Glu Asp Val Arg Gly Asp Ala His Ala Gly Tyr Ile
                        355                 360                 365

Arg Ile Gln Thr Ser Ala Met Phe Gly Leu Lys Ser Asp Gly Val Asp
                        370                 375                 380

Leu Ala Tyr Met Ser Phe Met Asn Gly Lys Thr Leu Lys Ala Ile Lys
        385                 390                 395                 400

Ile Glu His Leu Tyr Ala Arg Thr Ser Ala Pro Cys Ser Leu Val Ser
                        405                 410                 415

Tyr His Gly Tyr Tyr Leu Leu Ala Gln Cys Pro Pro Gly Asp Thr Val
                        420                 425                 430

Thr Val Gly Phe Gln Asp Gly Ala Asn Lys His Met Cys Thr Ile Ala
                        435                 440                 445

His Lys Val Glu Phe Lys Pro Val Gly Arg Glu Lys Tyr Arg His Pro
        450                 455                 460

Pro Ala His Gly Val Glu Leu Pro Cys Asn Lys Tyr Thr His Lys Arg
        465                 470                 475                 480

Ala Asp Gln Gly Tyr Tyr Val Glu Met His Gln Pro Gly Val Val Ala
                        485                 490                 495

Asp His Ser Leu Leu Ser Leu Ser Ser Thr Lys Val Lys Ile Thr Val
                        500                 505                 510
```

```
Pro Ser Gly Ser Gln Val Lys Tyr Tyr Cys Lys Cys Pro Asp Val Gln
            515                 520                 525

Glu Gly Thr Thr Ser Gly Asp His Thr Thr Thr Cys Thr Asp Leu Lys
    530                 535                 540

Gln Cys Arg Ala Tyr Leu Ile Asp Asn Lys Lys Trp Val Phe Asn Ser
545                 550                 555                 560

Gly Lys Leu Pro Arg Gly Glu Gly Thr Phe Lys Gly Lys Leu His
                565                 570                 575

Val Pro Phe Val Pro Val Thr Ser Lys Cys Thr Ala Thr Leu Ala Pro
            580                 585                 590

Glu Pro Leu Val Glu His Lys His Arg Ser Leu Ile Leu His Leu His
            595                 600                 605

Pro Glu His Pro Thr Leu Leu Thr Thr Arg Ala Leu Gly Asn Asp Ala
            610                 615                 620

Arg Pro Thr Arg Gln Trp Val Asp Gln Pro Thr Thr Val Asn Phe Thr
625                 630                 635                 640

Val Thr Gly Glu Gly Phe Glu Tyr Thr Trp Gly Asn His Pro Pro Lys
                645                 650                 655

Lys Ile Trp Ala Gln Glu Ser Gly Glu Gly Asn Pro His Gly Trp Pro
            660                 665                 670

His Glu Val Val Ile Tyr Tyr Tyr Asn Arg Tyr Pro Met Thr Thr Ile
            675                 680                 685

Val Gly Leu Cys Thr Cys Ala Ala Ile Ile Met Val Ser Cys Ile Thr
            690                 695                 700

Ser Val Trp Leu Leu Cys Arg Ala Arg Asn Leu Cys Ile Thr Pro Tyr
705                 710                 715                 720

Arg Leu Ala Pro Asn Ala Gln Val Pro Ile Leu Leu Ala Val Leu Cys
                725                 730                 735

Cys Val Lys Pro Thr Arg Ala Asp Asp Thr Leu Gln Val Leu Gly Tyr
            740                 745                 750

Leu Trp Asn His Asn Gln Asn Phe Phe Trp Met Gln Thr Leu Leu Pro
            755                 760                 765

Leu Ala Ala Leu Ile Val Cys Met Arg Met Leu Arg Cys Leu Leu Cys
770                 775                 780

Cys Gly Pro Ala Phe Leu Leu Val Cys Gly Ala Trp Ala Ala Ala Tyr
785                 790                 795                 800

Glu His Thr Ala Val Met Ser Asn Lys Val Gly Ile Pro Tyr Lys Ala
                805                 810                 815

Leu Val Glu Arg Pro Ser Tyr Ala Pro Val His Leu Gln Ile Gln Leu
            820                 825                 830

Val Thr Thr Lys Ile Ile Pro Ser Ala Asn Leu Glu Tyr Ile Thr Cys
            835                 840                 845

Lys Tyr Lys Thr Lys Val Leu Ser Pro Val Val Lys Cys Cys Gly Ala
850                 855                 860

Thr Gln Cys Thr Ser Lys Gln His Pro Asp Tyr Gln Cys Gln Val Phe
865                 870                 875                 880

Ala Gly Val Tyr Pro Phe Met Trp Gly Gly Ala Tyr Cys Phe Cys Asp
                885                 890                 895

Thr Glu Asn Thr Gln Met Ser Glu Ala Tyr Ile Glu Arg Ala Glu Glu
            900                 905                 910

Cys Ser Val Asp Gln Ala Lys Ala Tyr Lys Val His Thr Gly Thr Val
            915                 920                 925
```

```
Gln Ala Val Val Asn Ile Thr Tyr Gly Ser Val Thr Trp Arg Ser Ala
        930                 935                 940

Asp Val Tyr Val Asn Gly Glu Thr Pro Ala Lys Ile Gly Asp Ala Lys
945                 950                 955                 960

Leu Thr Ile Gly Pro Leu Ser Ser Ala Trp Thr Pro Phe Asp Ser Lys
                965                 970                 975

Val Val Val Tyr Gly His Glu Val His Asn Tyr Asp Phe Pro Glu Tyr
            980                 985                 990

Gly Thr Gly Arg Ala Gly Ser Phe Gly Asp Leu Gln Ser Arg Thr Leu
        995                 1000                1005

Thr Ser Asn Asp Leu Tyr Ala Asn Thr Asn Leu Lys Leu Gln Arg
    1010                1015                1020

Pro Gln Pro Gly Val Val His Thr Pro Tyr Thr Gln Ala Pro Ser
    1025                1030                1035

Gly Phe Glu Arg Trp Lys Lys Asp Arg Gly Ala Pro Leu Asn Asp
    1040                1045                1050

Ile Ala Pro Phe Gly Cys Thr Ile Ala Leu Asp Pro Leu Arg Ala
    1055                1060                1065

Glu Asn Cys Ala Val Gly Asn Ile Pro Leu Ser Ile Asp Ile Pro
    1070                1075                1080

Asp Ala Ala Phe Thr Arg Ile Ala Glu Thr Pro Thr Val Ser Asp
    1085                1090                1095

Leu Glu Cys Lys Val Thr Glu Cys Thr Tyr Ala Ser Asp Phe Gly
    1100                1105                1110

Gly Ile Ala Thr Val Ala Tyr Lys Ala Ser Lys Ala Gly Asn Cys
    1115                1120                1125

Pro Ile His Ser Pro Ser Gly Ile Ala Val Ile Lys Glu Asn Asp
    1130                1135                1140

Val Thr Leu Ala Asp Ser Gly Ser Phe Thr Phe His Phe Ser Thr
    1145                1150                1155

Ala Ser Ile His Pro Ala Phe Lys Met Gln Val Cys Thr Ser Val
    1160                1165                1170

Val Thr Cys Lys Gly Asp Cys Lys Pro Pro Lys Asp His Ile Leu
    1175                1180                1185

Asp Tyr Pro Ala Gln His Thr Glu Thr Phe Thr Ser Ala Val Ser
    1190                1195                1200

Ala Thr Ala Trp Ser Trp Leu Lys Val Leu Val Gly Ser Thr Ser
    1205                1210                1215

Ala Phe Ile Val Leu Gly Ile Ile Ala Thr Ala Val Val Ala Leu
    1220                1225                1230

Val Leu Phe Thr His Lys His
    1235                1240

<210> SEQ ID NO 12
<211> LENGTH: 1242
<212> TYPE: PRT
<213> ORGANISM: Artificial Sequence
<220> FEATURE:
<223> OTHER INFORMATION: Synthetic polypeptide

<400> SEQUENCE: 12

Met Phe Pro Tyr Pro Thr Leu Asn Tyr Pro Pro Met Ala Pro Ile Asn
1               5                   10                  15

Pro Met Ala Tyr Arg Asp Pro Asn Pro Pro Arg Arg Trp Arg Pro
                20                  25                  30
```

-continued

```
Phe Arg Pro Pro Leu Ala Ala Gln Ile Glu Asp Leu Arg Ser Ile
     35                   40                  45
Ala Asn Leu Thr Leu Lys Gln Arg Ala Pro Asn Pro Ala Gly Pro
 50                  55                  60
Pro Ala Lys Arg Lys Lys Pro Ala Pro Lys Pro Lys Pro Ala Gln Ala
 65                  70                  75                  80
Lys Lys Lys Arg Pro Pro Pro Ala Lys Gln Lys Arg Lys Pro
                 85                  90                  95
Lys Pro Gly Lys Arg Gln Arg Met Cys Met Lys Leu Glu Ser Asp Lys
                100                 105                 110
Thr Phe Pro Ile Met Leu Asn Gly Gln Val Asn Gly Tyr Ala Cys Val
            115                 120                 125
Val Gly Gly Arg Val Phe Lys Pro Leu His Val Glu Gly Arg Ile Asp
    130                 135                 140
Asn Glu Gln Leu Ala Ala Ile Lys Leu Lys Lys Ala Ser Ile Tyr Asp
145                 150                 155                 160
Leu Glu Tyr Gly Asp Val Pro Gln Cys Met Lys Ser Asp Thr Leu Gln
                165                 170                 175
Tyr Thr Ser Asp Lys Pro Pro Gly Phe Tyr Asn Trp His His Gly Ala
            180                 185                 190
Val Gln Tyr Glu Asn Asn Arg Phe Thr Val Pro Arg Gly Val Gly Gly
    195                 200                 205
Lys Gly Asp Ser Gly Arg Pro Ile Leu Asp Asn Lys Gly Arg Val Val
    210                 215                 220
Ala Ile Val Leu Gly Gly Val Asn Glu Gly Ser Arg Thr Ala Leu Ser
225                 230                 235                 240
Val Val Thr Trp Asn Gln Lys Gly Val Thr Val Lys Asp Thr Pro Glu
                245                 250                 255
Gly Ser Glu Pro Trp Ser Leu Ala Thr Val Met Cys Val Leu Ala Asn
            260                 265                 270
Ile Thr Phe Pro Cys Asp Gln Pro Pro Cys Met Pro Cys Cys Tyr Glu
    275                 280                 285
Lys Asn Pro His Glu Thr Leu Thr Met Leu Glu Gln Asn Tyr Asp Ser
290                 295                 300
Arg Ala Tyr Asp Gln Leu Leu Asp Ala Ala Val Lys Cys Asn Ala Arg
305                 310                 315                 320
Arg Thr Arg Arg Asp Leu Asp Thr His Phe Thr Gln Tyr Lys Leu Ala
                325                 330                 335
Arg Pro Tyr Ile Ala Asp Cys Pro Asn Cys Gly His Ser Arg Cys Asp
            340                 345                 350
Ser Pro Ile Ala Ile Glu Glu Val Arg Gly Asp Ala His Ala Gly Val
    355                 360                 365
Ile Arg Ile Gln Thr Ser Ala Met Phe Gly Leu Lys Thr Asp Gly Val
    370                 375                 380
Asp Leu Ala Tyr Met Ser Phe Met Asn Gly Lys Thr Gln Lys Ser Ile
385                 390                 395                 400
Lys Ile Asp Asn Leu His Val Arg Thr Ser Ala Pro Cys Ser Leu Val
                405                 410                 415
Ser His His Gly Tyr Tyr Ile Leu Ala Gln Cys Pro Pro Gly Asp Thr
            420                 425                 430
Val Thr Val Gly Phe His Asp Gly Pro Asn Arg His Thr Cys Thr Val
    435                 440                 445
Ala His Lys Val Glu Phe Arg Pro Val Gly Arg Glu Lys Tyr Arg His
```

```
              450             455             460
Pro Pro Glu His Gly Val Glu Leu Pro Cys Asn Arg Tyr Thr His Lys
465                 470                 475                 480

Arg Ala Asp Gln Gly His Tyr Val Glu Met His Gln Pro Gly Leu Val
                485                 490                 495

Ala Asp His Ser Leu Leu Ser Ile His Ser Ala Lys Val Lys Ile Thr
            500                 505                 510

Val Pro Ser Gly Ala Gln Val Lys Tyr Tyr Cys Lys Cys Pro Asp Val
        515                 520                 525

Arg Glu Gly Ile Thr Ser Ser Asp His Thr Thr Cys Thr Asp Val
    530                 535                 540

Lys Gln Cys Arg Ala Tyr Leu Ile Asp Asn Lys Lys Trp Val Tyr Asn
545                 550                 555                 560

Ser Gly Arg Leu Pro Arg Gly Glu Gly Asp Thr Phe Lys Gly Lys Leu
                565                 570                 575

His Val Pro Phe Val Pro Val Lys Ala Lys Cys Ile Ala Thr Leu Ala
            580                 585                 590

Pro Glu Pro Leu Val Glu His Lys His Arg Thr Leu Ile Leu His Leu
        595                 600                 605

His Pro Asp His Pro Thr Leu Leu Thr Thr Arg Ser Leu Gly Ser Asp
    610                 615                 620

Ala Asn Pro Thr Arg Gln Trp Ile Glu Arg Pro Thr Thr Val Asn Phe
625                 630                 635                 640

Thr Val Thr Gly Glu Gly Leu Glu Tyr Thr Trp Gly Asn His Pro Pro
                645                 650                 655

Lys Arg Val Trp Ala Gln Glu Ser Gly Glu Gly Asn Pro His Gly Trp
            660                 665                 670

Pro His Glu Val Val Tyr Tyr Tyr Asn Arg Tyr Pro Leu Thr Thr
        675                 680                 685

Ile Ile Gly Leu Cys Thr Cys Val Ala Ile Ile Met Val Ser Cys Val
    690                 695                 700

Thr Ser Val Trp Leu Leu Cys Arg Thr Arg Asn Leu Cys Ile Thr Pro
705                 710                 715                 720

Tyr Lys Leu Ala Pro Asn Ala Gln Val Pro Ile Leu Leu Ala Leu Leu
                725                 730                 735

Cys Cys Ile Lys Pro Thr Arg Ala Asp Asp Thr Leu Gln Val Leu Asn
            740                 745                 750

Tyr Leu Trp Asn Asn Asn Gln Asn Phe Phe Trp Met Gln Thr Leu Ile
        755                 760                 765

Pro Leu Ala Ala Leu Ile Val Cys Met Arg Met Leu Arg Cys Leu Phe
    770                 775                 780

Cys Cys Gly Pro Ala Phe Leu Leu Val Cys Gly Ala Leu Gly Ala Ala
785                 790                 795                 800

Ala Tyr Glu His Thr Ala Val Met Pro Asn Lys Val Gly Ile Pro Tyr
                805                 810                 815

Lys Ala Leu Val Glu Arg Pro Gly Tyr Ala Pro Val His Leu Gln Ile
            820                 825                 830

Gln Leu Val Asn Thr Arg Ile Ile Pro Ser Thr Asn Leu Glu Tyr Ile
        835                 840                 845

Thr Cys Lys Tyr Lys Thr Lys Val Pro Ser Pro Val Val Lys Cys Cys
    850                 855                 860

Gly Ala Thr Gln Cys Thr Ser Lys Pro His Pro Asp Tyr Gln Cys Gln
865                 870                 875                 880
```

-continued

```
Val Phe Thr Gly Val Tyr Pro Phe Met Trp Gly Gly Ala Tyr Cys Phe
                885                 890                 895

Cys Asp Thr Glu Asn Thr Gln Met Ser Glu Ala Tyr Val Glu Arg Ser
            900                 905                 910

Glu Glu Cys Ser Ile Asp His Ala Lys Ala Tyr Lys Val His Thr Gly
        915                 920                 925

Thr Val Gln Ala Met Val Asn Ile Thr Tyr Gly Ser Val Ser Trp Arg
    930                 935                 940

Ser Ala Asp Val Tyr Val Asn Gly Glu Thr Pro Ala Lys Ile Gly Asp
945                 950                 955                 960

Ala Lys Leu Ile Ile Gly Pro Leu Ser Ser Ala Trp Ser Pro Phe Asp
                965                 970                 975

Asn Lys Val Val Val Tyr Gly His Glu Val Tyr Asn Tyr Asp Phe Pro
            980                 985                 990

Glu Tyr Gly Thr Gly Lys Ala Gly  Ser Phe Gly Asp Leu  Gln Ser Arg
        995                 1000                1005

Thr Ser  Thr Ser Asn Asp Leu  Tyr Ala Asn Thr Asn  Leu Lys Leu
    1010                1015                1020

Gln Arg  Pro Gln Ala Gly Ile  Val His Thr Pro Phe  Thr Gln Ala
    1025                1030                1035

Pro Ser  Gly Phe Glu Arg Trp  Lys Arg Asp Lys Gly  Ala Pro Leu
    1040                1045                1050

Asn Asp  Val Ala Pro Phe Gly  Cys Ser Ile Ala Leu  Glu Pro Leu
    1055                1060                1065

Arg Ala  Glu Asn Cys Ala Val  Gly Ser Ile Pro Ile  Ser Ile Asp
    1070                1075                1080

Ile Pro  Asp Ala Ala Phe Thr  Arg Ile Ser Glu Thr  Pro Thr Val
    1085                1090                1095

Ser Asp  Leu Glu Cys Lys Ile  Thr Glu Cys Thr Tyr  Ala Ser Asp
    1100                1105                1110

Phe Gly  Gly Ile Ala Thr Val  Ala Tyr Lys Ser Ser  Lys Ala Gly
    1115                1120                1125

Asn Cys  Pro Ile His Ser Pro  Ser Gly Val Ala Val  Ile Lys Glu
    1130                1135                1140

Asn Asp  Val Thr Leu Ala Glu  Ser Gly Ser Phe Thr  Phe His Phe
    1145                1150                1155

Ser Thr  Ala Asn Ile His Pro  Ala Phe Lys Leu Gln  Val Cys Thr
    1160                1165                1170

Ser Ala  Val Thr Cys Lys Gly  Asp Cys Lys Pro Pro  Lys Asp His
    1175                1180                1185

Ile Val  Asp Tyr Pro Ala Gln  His Thr Glu Ser Phe  Thr Ser Ala
    1190                1195                1200

Ile Ser  Ala Thr Ala Trp Ser  Trp Leu Lys Val Leu  Val Gly Gly
    1205                1210                1215

Thr Ser  Ala Phe Ile Val Leu  Gly Leu Ile Ala Thr  Ala Val Val
    1220                1225                1230

Ala Leu  Val Leu Phe Phe His  Arg His
    1235                1240

<210> SEQ ID NO 13
<211> LENGTH: 1248
<212> TYPE: PRT
<213> ORGANISM: Artificial Sequence
<220> FEATURE:
```

<223> OTHER INFORMATION: Synthetic polypeptide

<400> SEQUENCE: 13

```
Met Glu Phe Ile Pro Thr Gln Thr Phe Tyr Asn Arg Arg Tyr Gln Pro
  1               5                  10                  15

Arg Pro Trp Thr Pro Arg Pro Thr Ile Gln Val Ile Arg Pro Arg Pro
                 20                  25                  30

Arg Pro Gln Arg Gln Ala Gly Gln Leu Ala Gln Leu Ile Ser Ala Val
             35                  40                  45

Asn Lys Leu Thr Met Arg Ala Val Pro Gln Lys Pro Arg Arg Asn
 50                  55                  60

Arg Lys Asn Lys Lys Gln Lys Gln Ala Pro Gln Asn Asn
 65                  70                  75                  80

Thr Asn Gln Lys Lys Gln Pro Pro Lys Lys Pro Ala Gln Lys Lys
                 85                  90                  95

Lys Lys Pro Gly Arg Arg Glu Arg Met Cys Met Lys Ile Glu Asn Asp
                100                 105                 110

Cys Ile Phe Glu Val Lys His Glu Gly Lys Val Thr Gly Tyr Ala Cys
            115                 120                 125

Leu Val Gly Asp Lys Val Met Lys Pro Ala His Val Lys Gly Thr Ile
        130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Ile Pro Val Met Cys Leu Leu Ala
            260                 265                 270

Asn Thr Thr Phe Pro Cys Ser Gln Pro Pro Cys Thr Pro Cys Cys Tyr
        275                 280                 285

Glu Lys Glu Pro Glu Lys Thr Leu Arg Met Leu Glu Asp Asn Val Met
290                 295                 300

Arg Pro Gly Tyr Tyr Gln Leu Leu Gln Ala Ser Leu Thr Cys Ser Pro
305                 310                 315                 320

His Arg Gln Arg Arg Ser Thr Lys Asp Asn Phe Asn Val Tyr Lys Ala
                325                 330                 335

Thr Arg Pro Tyr Leu Ala His Cys Pro Asp Cys Gly Glu Gly His Ser
            340                 345                 350

Cys His Ser Pro Val Ala Leu Glu Arg Ile Arg Asn Glu Ala Thr Asp
        355                 360                 365

Gly Thr Leu Lys Ile Gln Val Ser Leu Gln Ile Gly Ile Lys Thr Asp
    370                 375                 380

Asp Ser His Asp Trp Thr Lys Leu Arg Tyr Met Asp Asn His Met Pro
385                 390                 395                 400
```

```
Ala Asp Ala Glu Arg Ala Gly Leu Phe Val Arg Thr Ser Ala Pro Cys
                405                 410                 415

Thr Ile Thr Gly Thr Met Gly His Phe Ile Leu Ala Arg Cys Pro Lys
            420                 425                 430

Gly Glu Thr Leu Thr Val Gly Phe Thr Asp Ser Arg Lys Ile Ser His
            435                 440                 445

Ser Cys Thr His Pro Phe His His Asp Pro Val Ile Gly Arg Glu
450                 455                 460

Lys Phe His Ser Arg Pro Gln His Gly Lys Glu Leu Pro Cys Ser Thr
465                 470                 475                 480

Tyr Val Gln Ser Thr Ala Ala Thr Thr Glu Glu Ile Glu Val His Met
                485                 490                 495

Pro Pro Asp Thr Pro Asp Arg Thr Leu Met Ser Gln Gln Ser Gly Asn
            500                 505                 510

Val Lys Ile Thr Val Asn Gly Gln Thr Val Arg Tyr Lys Cys Asn Cys
            515                 520                 525

Gly Gly Ser Asn Glu Gly Leu Thr Thr Thr Asp Lys Val Ile Asn Asn
            530                 535                 540

Cys Lys Val Asp Gln Cys His Ala Ala Val Thr Asn His Lys Lys Trp
545                 550                 555                 560

Gln Tyr Asn Ser Pro Leu Val Pro Arg Asn Ala Glu Leu Gly Asp Arg
                565                 570                 575

Lys Gly Lys Ile His Ile Pro Phe Pro Leu Ala Asn Val Thr Cys Arg
            580                 585                 590

Val Pro Lys Ala Arg Asn Pro Thr Val Thr Tyr Gly Lys Asn Gln Val
            595                 600                 605

Ile Met Leu Leu Tyr Pro Asp His Pro Thr Leu Leu Ser Tyr Arg Asn
            610                 615                 620

Met Gly Glu Glu Pro Asn Tyr Gln Glu Glu Trp Val Thr His Lys Lys
625                 630                 635                 640

Glu Ile Arg Leu Thr Val Pro Thr Glu Gly Leu Glu Val Thr Trp Gly
                645                 650                 655

Asn Asn Glu Pro Tyr Lys Tyr Trp Pro Gln Leu Ser Thr Asn Gly Thr
            660                 665                 670

Ala His Gly His Pro His Glu Ile Ile Leu Tyr Tyr Tyr Glu Leu Tyr
            675                 680                 685

Pro Thr Met Thr Val Val Val Ser Val Ala Thr Phe Ile Leu Leu
            690                 695                 700

Ser Met Val Gly Val Ala Val Gly Met Cys Met Cys Ala Arg Arg Arg
705                 710                 715                 720

Cys Ile Thr Pro Tyr Glu Leu Thr Pro Gly Ala Thr Val Pro Phe Leu
                725                 730                 735

Leu Ser Leu Ile Cys Cys Ile Arg Thr Ala Lys Ala Ala Thr Tyr Gln
            740                 745                 750

Glu Ala Val Tyr Leu Trp Asn Glu Gln Gln Pro Leu Phe Trp Leu
            755                 760                 765

Gln Ala Leu Ile Pro Leu Ala Ala Leu Ile Val Leu Cys Asn Cys Leu
770                 775                 780

Arg Leu Leu Pro Cys Cys Cys Lys Thr Leu Ala Phe Leu Ala Val Met
785                 790                 795                 800

Ser Val Gly Ala His Thr Val Ser Ala Tyr Glu His Val Thr Val Ile
                805                 810                 815

Pro Asn Thr Val Gly Val Pro Tyr Lys Thr Leu Val Asn Arg Pro Gly
```

```
                820                 825                 830
Tyr Ser Pro Met Val Leu Glu Met Glu Leu Leu Ser Val Thr Leu Glu
            835                 840                 845
Pro Thr Leu Ser Leu Asp Tyr Ile Thr Cys Glu Tyr Lys Thr Val Ile
            850                 855                 860
Pro Ser Pro Tyr Val Lys Cys Cys Gly Thr Ala Glu Cys Lys Asp Lys
865                 870                 875                 880
Ser Leu Pro Asp Tyr Ser Cys Lys Val Phe Thr Gly Val Tyr Pro Phe
            885                 890                 895
Met Trp Gly Gly Ala Tyr Cys Phe Cys Asp Ala Glu Asn Thr Gln Leu
            900                 905                 910
Ser Glu Ala His Val Glu Lys Ser Glu Ser Cys Lys Thr Glu Phe Ala
            915                 920                 925
Ser Ala Tyr Arg Ala His Thr Ala Ser Ala Ser Ala Lys Leu Arg Val
            930                 935                 940
Leu Tyr Gln Gly Asn Asn Ile Thr Val Thr Ala Tyr Ala Asn Gly Asp
945                 950                 955                 960
His Ala Val Thr Val Lys Asp Ala Lys Phe Ile Val Gly Pro Met Ser
            965                 970                 975
Ser Ala Trp Thr Pro Phe Asp Asn Lys Ile Val Val Tyr Lys Gly Asp
            980                 985                 990
Val Tyr Asn Met Asp Tyr Pro Pro Phe Gly Ala Gly Arg Pro Gly Gln
            995                 1000                1005
Phe Gly Asp Ile Gln Ser Arg Thr Pro Glu Ser Glu Asp Val Tyr
        1010                1015                1020
Ala Asn Thr Gln Leu Val Leu Gln Arg Pro Ser Ala Gly Thr Val
        1025                1030                1035
His Val Pro Tyr Ser Gln Ala Pro Ser Gly Phe Lys Tyr Trp Leu
        1040                1045                1050
Lys Glu Arg Gly Ala Ser Leu Gln His Thr Ala Pro Phe Gly Cys
        1055                1060                1065
Gln Ile Ala Thr Asn Pro Val Arg Ala Met Asn Cys Ala Val Gly
        1070                1075                1080
Asn Met Pro Ile Ser Ile Asp Ile Pro Asp Ala Ala Phe Thr Arg
        1085                1090                1095
Val Val Asp Ala Pro Ser Leu Thr Asp Met Ser Cys Glu Val Pro
        1100                1105                1110
Ala Cys Thr His Ser Ser Asp Phe Gly Gly Val Ala Ile Ile Lys
        1115                1120                1125
Tyr Ala Ala Ser Lys Lys Gly Lys Cys Ala Val His Ser Met Thr
        1130                1135                1140
Asn Ala Val Thr Ile Arg Glu Ala Glu Ile Glu Val Glu Gly Asn
        1145                1150                1155
Ser Gln Leu Gln Ile Ser Phe Ser Thr Ala Leu Ala Ser Ala Glu
        1160                1165                1170
Phe Arg Val Gln Val Cys Ser Thr Gln Val His Cys Ala Ala Glu
        1175                1180                1185
Cys His Pro Pro Lys Asp His Ile Val Asn Tyr Pro Ala Ser His
        1190                1195                1200
Thr Thr Leu Gly Val Gln Asp Ile Ser Ala Thr Ala Met Ser Trp
        1205                1210                1215
Val Gln Lys Ile Thr Gly Gly Val Gly Leu Val Val Ala Val Ala
        1220                1225                1230
```

-continued

```
Ala Leu Ile Leu Ile Val Val Leu Cys Val Ser Phe Ser Arg His
    1235                1240                1245

<210> SEQ ID NO 14
<211> LENGTH: 977
<212> TYPE: PRT
<213> ORGANISM: Artificial Sequence
<220> FEATURE:
<223> OTHER INFORMATION: Synthetic polypeptide

<400> SEQUENCE: 14

Thr Thr Met Cys Leu Leu Ala Asn Val Thr Phe Pro Cys Ala Gln Pro
1               5                   10                  15

Pro Ile Cys Tyr Asp Arg Lys Pro Ala Glu Thr Leu Ala Met Leu Ser
            20                  25                  30

Val Asn Val Asp Asn Pro Gly Tyr Asp Glu Leu Leu Glu Ala Ala Val
        35                  40                  45

Lys Cys Pro Gly Arg Lys Arg Arg Ser Thr Glu Glu Leu Phe Lys Glu
50                  55                  60

Tyr Lys Leu Thr Arg Pro Tyr Met Ala Arg Cys Ile Arg Cys Ala Val
65                  70                  75                  80

Gly Ser Cys His Ser Pro Ile Ala Ile Glu Ala Val Lys Ser Asp Gly
                85                  90                  95

His Asp Gly Tyr Val Arg Leu Gln Thr Ser Ser Gln Tyr Gly Leu Asp
            100                 105                 110

Ser Ser Gly Asn Leu Lys Gly Arg Thr Met Arg Tyr Asp Met His Gly
        115                 120                 125

Thr Ile Glu Glu Ile Pro Leu His Gln Val Ser Leu His Thr Ser Arg
130                 135                 140

Pro Cys His Ile Val Asp Gly His Gly Tyr Phe Leu Leu Ala Arg Cys
145                 150                 155                 160

Pro Ala Gly Asp Ser Ile Thr Met Glu Phe Lys Lys Asp Ser Val Thr
                165                 170                 175

His Ser Cys Ser Val Pro Tyr Glu Val Lys Phe Asn Pro Val Gly Arg
            180                 185                 190

Glu Leu Tyr Thr His Pro Pro Glu His Gly Ala Glu Gln Ala Cys Gln
        195                 200                 205

Val Tyr Ala His Asp Ala Gln Asn Arg Gly Ala Tyr Val Glu Met His
210                 215                 220

Leu Pro Gly Ser Glu Val Asp Ser Ser Leu Val Ser Leu Ser Gly Ser
225                 230                 235                 240

Ser Val Thr Val Thr Pro Pro Ala Gly Thr Ser Ala Leu Val Glu Cys
                245                 250                 255

Glu Cys Gly Gly Thr Lys Ile Ser Glu Thr Ile Asn Thr Ala Lys Gln
            260                 265                 270

Phe Ser Gln Cys Thr Lys Glu Gln Cys Arg Ala Tyr Arg Leu Gln
        275                 280                 285

Asn Asp Lys Trp Val Tyr Asn Ser Asp Lys Leu Pro Lys Ala Ala Gly
290                 295                 300

Ala Thr Leu Lys Gly Lys Leu His Val Pro Phe Leu Leu Ala Asp Gly
305                 310                 315                 320

Lys Cys Thr Val Pro Leu Ala Pro Glu Pro Met Ile Thr Phe Gly Phe
                325                 330                 335

Arg Ser Val Ser Leu Lys Leu His Pro Lys Asn Pro Thr Tyr Leu Thr
            340                 345                 350
```

```
Thr Arg Gln Leu Ala Asp Glu Pro His Tyr Thr His Glu Leu Ile Ser
        355                 360                 365

Glu Pro Ala Val Arg Asn Phe Thr Val Thr Glu Lys Gly Trp Glu Phe
370                 375                 380

Val Trp Gly Asn His Pro Pro Lys Arg Phe Trp Ala Gln Glu Thr Ala
385                 390                 395                 400

Pro Gly Asn Pro His Gly Leu Pro His Glu Val Ile Thr His Tyr Tyr
                405                 410                 415

His Arg Tyr Pro Met Ser Thr Ile Leu Gly Leu Ser Ile Cys Ala Ala
            420                 425                 430

Ile Val Thr Val Ser Val Ala Ala Ser Thr Trp Leu Phe Cys Lys Ser
        435                 440                 445

Arg Val Ser Cys Leu Thr Pro Tyr Arg Leu Thr Pro Asn Ala Arg Met
450                 455                 460

Pro Leu Cys Leu Ala Val Leu Cys Cys Ala Arg Thr Ala Arg Ala Glu
465                 470                 475                 480

Thr Thr Trp Glu Ser Leu Asp His Leu Trp Asn Asn Gln Gln Met
                485                 490                 495

Phe Trp Ile Gln Leu Leu Ile Pro Leu Ala Ala Leu Ile Val Val Thr
            500                 505                 510

Arg Leu Leu Lys Cys Val Cys Cys Val Val Pro Phe Leu Val Val Ala
        515                 520                 525

Gly Ala Ala Gly Ala Gly Ala Tyr Glu His Ala Thr Thr Met Pro Ser
530                 535                 540

Gln Ala Gly Ile Ser Tyr Asn Thr Ile Val Asn Arg Ala Gly Tyr Ala
545                 550                 555                 560

Pro Leu Pro Ile Ser Ile Thr Pro Thr Lys Ile Lys Leu Ile Pro Thr
                565                 570                 575

Val Asn Leu Glu Tyr Val Thr Cys His Tyr Lys Thr Gly Met Asp Ser
            580                 585                 590

Pro Ala Ile Lys Cys Cys Gly Ser Gln Glu Cys Thr Pro Thr Tyr Arg
        595                 600                 605

Pro Asp Glu Gln Cys Lys Val Phe Thr Gly Val Tyr Pro Phe Met Trp
610                 615                 620

Gly Gly Ala Tyr Cys Phe Cys Asp Thr Glu Asn Thr Gln Val Ser Lys
625                 630                 635                 640

Ala Tyr Val Met Lys Ser Asp Asp Cys Leu Ala Asp His Ala Glu Ala
                645                 650                 655

Tyr Lys Ala His Thr Ala Ser Val Gln Ala Phe Leu Asn Ile Thr Val
            660                 665                 670

Gly Glu His Ser Ile Val Thr Thr Val Tyr Val Asn Gly Glu Thr Pro
        675                 680                 685

Val Asn Phe Asn Gly Val Lys Leu Thr Ala Gly Pro Leu Ser Thr Ala
690                 695                 700

Trp Thr Pro Phe Asp Arg Lys Ile Val Gln Tyr Ala Gly Glu Ile Tyr
705                 710                 715                 720

Asn Tyr Asp Phe Pro Glu Tyr Gly Ala Gly Gln Pro Gly Ala Phe Gly
                725                 730                 735

Asp Ile Gln Ser Arg Thr Val Ser Ser Ser Asp Leu Tyr Ala Asn Thr
            740                 745                 750

Asn Leu Val Leu Gln Arg Pro Lys Ala Gly Ala Ile His Val Pro Tyr
        755                 760                 765
```

Thr Gln Ala Pro Ser Gly Phe Glu Gln Trp Lys Lys Asp Lys Ala Pro
        770                 775                 780

Ser Leu Lys Phe Thr Ala Pro Phe Gly Cys Glu Ile Tyr Thr Asn Pro
785                 790                 795                 800

Ile Arg Ala Glu Asn Cys Ala Val Gly Ser Ile Pro Leu Ala Phe Asp
                805                 810                 815

Ile Pro Asp Ala Leu Phe Thr Arg Val Ser Glu Thr Pro Thr Leu Ser
            820                 825                 830

Ala Ala Glu Cys Thr Leu Asn Glu Cys Val Tyr Ser Ser Asp Phe Gly
        835                 840                 845

Gly Ile Ala Thr Val Lys Tyr Ser Ala Ser Lys Ser Gly Lys Cys Ala
    850                 855                 860

Val His Val Pro Ser Gly Thr Ala Thr Leu Lys Glu Ala Ala Val Glu
865                 870                 875                 880

Leu Thr Glu Gln Gly Ser Ala Thr Ile His Phe Ser Thr Ala Asn Ile
                885                 890                 895

His Pro Glu Phe Arg Leu Gln Ile Cys Thr Ser Tyr Val Thr Cys Lys
            900                 905                 910

Gly Asp Cys His Pro Pro Lys Asp His Ile Val Thr His Pro Gln Tyr
        915                 920                 925

His Ala Gln Thr Phe Thr Ala Ala Val Ser Lys Thr Ala Trp Thr Trp
    930                 935                 940

Leu Thr Ser Leu Leu Gly Gly Ser Ala Val Ile Ile Ile Gly Leu
945                 950                 955                 960

Val Leu Ala Thr Ile Val Ala Met Tyr Val Leu Thr Asn Gln Lys His
                965                 970                 975

Asn

<210> SEQ ID NO 15
<211> LENGTH: 977
<212> TYPE: PRT
<213> ORGANISM: Artificial Sequence
<220> FEATURE:
<223> OTHER INFORMATION: Synthetic polypeptide

<400> SEQUENCE: 15

Thr Thr Leu Cys Leu Leu Ala Asn Val Thr Phe Pro Cys Thr Gln Pro
1               5                   10                  15

Pro Ile Cys Tyr Asp Arg Lys Pro Ala Glu Thr Leu Ser Met Leu Ser
                20                  25                  30

His Asn Ile Asp Asn Pro Gly Tyr Asp Glu Leu Leu Glu Ala Val Leu
            35                  40                  45

Lys Cys Pro Gly Arg Gly Lys Arg Ser Thr Glu Glu Leu Phe Lys Glu
    50                  55                  60

Tyr Lys Leu Thr Arg Pro Tyr Met Ala Lys Cys Val Arg Cys Ala Val
65                  70                  75                  80

Gly Ser Cys His Ser Pro Ile Ala Ile Glu Ala Val Arg Ser Glu Gly
                85                  90                  95

His Asp Gly Tyr Val Arg Leu Gln Thr Ser Ser Gln Tyr Gly Leu Asp
            100                 105                 110

Pro Ser Gly Asn Leu Lys Gly Arg Thr Met Arg Tyr Asp Met His Gly
    115                 120                 125

Thr Ile Lys Glu Ile Pro Leu His Gln Val Ser Val His Thr Ser Arg
130                 135                 140

Pro Cys His Ile Ile Asp Gly His Gly Tyr Phe Leu Leu Ala Arg Cys

```
                145                 150                 155                 160
        Pro Glu Gly Asp Ser Ile Thr Met Glu Phe Lys Lys Glu Ser Val Thr
                        165                 170                 175
        His Ser Cys Ser Val Pro Tyr Glu Val Lys Phe Thr Pro Val Gly Arg
                        180                 185                 190
        Glu Leu Tyr Ser His Pro Pro Glu His Gly Ala Glu Gln Pro Cys His
                        195                 200                 205
        Val Tyr Ala His Asp Ala Gln Asn Arg Gly Ala Tyr Val Glu Met His
                210                 215                 220
        Leu Pro Gly Ser Glu Val Asp Ser Thr Leu Leu Ser Met Ser Gly Ser
        225                 230                 235                 240
        Ser Val His Val Thr Pro Pro Ala Gly Gln Ser Val Gln Val Glu Cys
                        245                 250                 255
        Glu Cys Gly Gly Thr Lys Ile Ser Glu Thr Ile Asn Ser Ala Lys Gln
                        260                 265                 270
        Tyr Ser Gln Cys Ser Lys Thr Ser Gln Cys Arg Ala Tyr Arg Thr Gln
                        275                 280                 285
        Asn Asp Lys Trp Val Tyr Asn Ser Asp Lys Leu Pro Lys Ala Ser Gly
                290                 295                 300
        Glu Thr Leu Lys Gly Lys Leu His Val Pro Phe Val Leu Thr Glu Ala
        305                 310                 315                 320
        Lys Cys Thr Val Pro Leu Ala Pro Glu Pro Ile Ile Thr Phe Gly Phe
                        325                 330                 335
        Arg Ser Val Ser Leu Lys Leu His Pro Lys Asn Pro Thr Phe Leu Thr
                        340                 345                 350
        Thr Arg Gln Leu Asp Gly Glu Pro Ala Tyr Thr His Glu Leu Ile Thr
                        355                 360                 365
        His Pro Val Val Arg Asn Phe Ser Val Thr Glu Lys Gly Trp Glu Phe
                        370                 375                 380
        Val Trp Gly Asn His Pro Pro Gln Arg Tyr Trp Ser Gln Glu Thr Ala
        385                 390                 395                 400
        Pro Gly Asn Pro His Gly Leu Pro His Glu Val Ile Val His Tyr Tyr
                        405                 410                 415
        His Arg Tyr Pro Met Ser Thr Ile Val Gly Leu Ser Ile Cys Ala Ala
                        420                 425                 430
        Ile Val Thr Thr Ser Ile Ala Ala Ser Val Trp Leu Phe Cys Lys Ser
                        435                 440                 445
        Arg Ile Ser Cys Leu Thr Pro Tyr Arg Leu Thr Pro Asn Ala Arg Ile
                        450                 455                 460
        Pro Phe Cys Leu Ala Val Leu Cys Cys Ala Arg Thr Ala Lys Ala Glu
        465                 470                 475                 480
        Thr Thr Trp Glu Ser Leu Asp His Leu Trp Asn His Asn Gln Gln Met
                        485                 490                 495
        Phe Trp Ser Gln Leu Leu Ile Pro Leu Ala Ala Leu Ile Val Ala Thr
                        500                 505                 510
        Arg Leu Leu Lys Cys Met Cys Cys Val Val Pro Phe Leu Val Val Ala
                        515                 520                 525
        Gly Ala Val Gly Ala Gly Ala Tyr Glu His Ala Thr Thr Met Pro Asn
                        530                 535                 540
        Gln Val Gly Ile Pro Tyr Asn Thr Ile Val Asn Arg Ala Gly Tyr Ala
        545                 550                 555                 560
        Pro Leu Pro Ile Ser Ile Val Pro Thr Lys Val Lys Leu Ile Pro Thr
                        565                 570                 575
```

```
Val Asn Leu Glu Tyr Ile Thr Cys His Tyr Lys Thr Gly Leu Asp Ser
                580                 585                 590

Pro Ala Ile Lys Cys Cys Gly Thr Gln Glu Cys Ser Pro Thr Tyr Arg
            595                 600                 605

Pro Asp Glu Gln Cys Lys Val Phe Ser Gly Val Tyr Pro Phe Met Trp
        610                 615                 620

Gly Gly Ala Tyr Cys Phe Cys Asp Thr Glu Asn Thr Gln Ile Ser Lys
625                 630                 635                 640

Ala Tyr Val Thr Lys Ser Glu Asp Cys Val Thr Asp His Ala Gln Ala
                645                 650                 655

Tyr Lys Ala His Thr Ala Ser Ile Gln Ala Phe Leu Asn Ile Thr Val
            660                 665                 670

Gly Gly His Ser Thr Thr Ala Val Val Tyr Val Asn Gly Glu Thr Pro
        675                 680                 685

Val Asn Phe Asn Gly Ile Lys Leu Val Ala Gly Pro Leu Ser Thr Ala
    690                 695                 700

Trp Ser Pro Phe Asp Lys Lys Ile Val Gln Tyr Ala Gly Glu Val Tyr
705                 710                 715                 720

Asn Tyr Asp Phe Pro Glu Tyr Gly Ala Gly His Ala Gly Ala Phe Gly
                725                 730                 735

Asp Ile Gln Ala Arg Thr Ile Ser Ser Ser Asp Val Tyr Ala Asn Thr
            740                 745                 750

Asn Leu Val Leu Gln Arg Pro Asn Thr Gly Thr Ile His Val Pro Tyr
        755                 760                 765

Thr Gln Ala Pro Ser Gly Tyr Glu Gln Trp Lys Lys Asp Lys Pro Pro
    770                 775                 780

Ser Leu Lys Tyr Thr Ala Pro Phe Gly Cys Glu Ile His Val Asn Pro
785                 790                 795                 800

Val Arg Ala Glu Asn Cys Ala Val Gly Phe Ile Pro Leu Ala Phe Asp
                805                 810                 815

Ile Pro Asp Ala Leu Phe Thr Arg Val Ser Glu Thr Pro Thr Leu Ser
            820                 825                 830

Ser Ala Glu Cys Ser Leu Asn Glu Cys Thr Tyr Ser Asp Phe Gly
        835                 840                 845

Gly Ile Ala Thr Val Lys Tyr Ser Ala Ser Lys Ala Gly Lys Cys Ala
850                 855                 860

Val His Ile Pro Ser Gly Thr Ala Thr Leu Lys Glu Ala Ala Val Glu
865                 870                 875                 880

Leu Ala Glu Gln Gly Ser Ala Thr Ile His Phe Ser Thr Ala Ser Ile
                885                 890                 895

His Pro Glu Phe Lys Leu Gln Ile Cys Thr Lys Val Leu Thr Cys Lys
            900                 905                 910

Gly Asp Cys His Pro Pro Arg Asp His Ile Val Thr His Pro Gln Tyr
        915                 920                 925

His Ala Gln Ser Phe Thr Ala Ala Val Ser Lys Thr Ala Trp Thr Trp
    930                 935                 940

Ile Thr Ser Leu Leu Gly Gly Ser Ala Ile Ile Ile Ile Gly Leu
945                 950                 955                 960

Val Leu Ala Thr Val Val Ala Met Tyr Val Leu Thr Asn Gln Arg His
                965                 970                 975

Asn
```

```
<210> SEQ ID NO 16
<211> LENGTH: 977
<212> TYPE: PRT
<213> ORGANISM: Artificial Sequence
<220> FEATURE:
<223> OTHER INFORMATION: Synthetic polypeptide

<400> SEQUENCE: 16

Thr Thr Met Cys Leu Leu Ala Asn Val Thr Phe Pro Cys Ala Gln Pro
1               5                   10                  15

Pro Ile Cys Tyr Asp Arg Lys Pro Ala Glu Thr Leu Ala Met Leu Ser
                20                  25                  30

Val Asn Val Asp Asn Pro Gly Tyr Asp Glu Leu Leu Glu Ala Ala Val
            35                  40                  45

Lys Cys Pro Gly Arg Lys Arg Arg Ser Thr Glu Glu Leu Phe Lys Glu
        50                  55                  60

Tyr Lys Leu Thr Arg Pro Tyr Met Ala Arg Cys Ile Arg Cys Ala Val
65                  70                  75                  80

Gly Ser Cys His Ser Pro Ile Ala Ile Glu Ala Val Lys Ser Asp Gly
                85                  90                  95

His Asp Gly Tyr Val Arg Leu Gln Thr Ser Ser Gln Tyr Gly Leu Asp
                100                 105                 110

Ser Ser Gly Asn Leu Lys Gly Arg Thr Met Arg Tyr Asp Met His Gly
            115                 120                 125

Thr Ile Glu Glu Ile Pro Leu His Gln Val Ser Leu His Thr Ser Arg
130                 135                 140

Pro Cys His Ile Val Asp Gly His Gly Tyr Phe Leu Leu Ala Arg Cys
145                 150                 155                 160

Pro Ala Gly Asp Ser Ile Thr Met Glu Phe Lys Lys Asp Ser Val Thr
                165                 170                 175

His Ser Cys Ser Val Pro Tyr Glu Val Lys Phe Asn Pro Val Gly Arg
            180                 185                 190

Glu Leu Tyr Thr His Pro Pro Glu His Gly Ala Glu Gln Ala Cys Gln
        195                 200                 205

Val Tyr Ala His Asp Ala Gln Asn Arg Gly Ala Tyr Val Glu Met His
210                 215                 220

Leu Pro Gly Ser Glu Val Asp Ser Ser Leu Val Ser Leu Ser Gly Ser
225                 230                 235                 240

Ser Val Thr Val Thr Pro Pro Ala Gly Thr Ser Ala Leu Val Glu Cys
                245                 250                 255

Glu Cys Gly Gly Thr Lys Ile Ser Glu Thr Ile Asn Thr Ala Lys Gln
            260                 265                 270

Phe Ser Gln Cys Thr Lys Lys Glu Gln Cys Arg Ala Tyr Arg Leu Gln
        275                 280                 285

Asn Asp Lys Trp Val Tyr Asn Ser Asp Lys Leu Pro Lys Ala Ala Gly
290                 295                 300

Ala Thr Leu Lys Gly Lys Leu His Val Pro Phe Leu Leu Ala Asp Gly
305                 310                 315                 320

Lys Cys Thr Val Pro Leu Ala Pro Glu Pro Met Ile Thr Phe Gly Phe
                325                 330                 335

Arg Ser Val Ser Leu Lys Leu His Pro Lys Asn Pro Thr Tyr Leu Thr
            340                 345                 350

Thr Arg Gln Leu Ala Asp Glu Pro His Tyr Thr His Glu Leu Ile Ser
        355                 360                 365

Glu Pro Ala Val Arg Asn Phe Thr Val Thr Glu Lys Gly Trp Glu Phe
```

-continued

```
                370                 375                 380
Val Trp Gly Asn His Pro Pro Lys Arg Phe Trp Ala Gln Glu Thr Ala
385                 390                 395                 400

Pro Gly Asn Pro His Gly Leu Pro His Glu Val Ile Thr His Tyr Tyr
                405                 410                 415

His Arg Tyr Pro Met Ser Thr Ile Leu Gly Leu Ser Ile Cys Ala Ala
                420                 425                 430

Ile Val Thr Val Ser Val Ala Ala Ser Thr Trp Leu Phe Cys Lys Ser
                435                 440                 445

Arg Val Ser Cys Leu Thr Pro Tyr Arg Leu Thr Pro Asn Ala Arg Met
                450                 455                 460

Pro Leu Cys Leu Ala Val Leu Cys Cys Ala Arg Thr Ala Arg Ala Glu
465                 470                 475                 480

Thr Thr Trp Glu Ser Leu Asp His Leu Trp Asn Asn Asn Gln Gln Met
                485                 490                 495

Phe Trp Ile Gln Leu Leu Ile Pro Leu Ala Ala Leu Ile Val Val Thr
                500                 505                 510

Arg Leu Leu Lys Cys Val Cys Cys Val Val Pro Phe Leu Val Val Ala
                515                 520                 525

Gly Ala Ala Gly Ala Gly Ala Tyr Glu His Ala Thr Thr Met Pro Ser
530                 535                 540

Gln Ala Gly Ile Ser Tyr Asn Thr Ile Val Asn Arg Ala Gly Tyr Ala
545                 550                 555                 560

Pro Leu Pro Ile Ser Ile Thr Pro Thr Lys Ile Lys Leu Ile Pro Thr
                565                 570                 575

Val Asn Leu Glu Tyr Val Thr Cys His Tyr Lys Thr Gly Met Asp Ser
                580                 585                 590

Pro Ala Ile Lys Cys Cys Gly Ser Gln Glu Cys Thr Pro Thr Tyr Arg
                595                 600                 605

Pro Asp Glu Gln Cys Lys Val Phe Thr Gly Val Tyr Pro Phe Met Trp
                610                 615                 620

Gly Gly Ala Tyr Cys Phe Cys Asp Thr Glu Asn Thr Gln Val Ser Lys
625                 630                 635                 640

Ala Tyr Val Met Lys Ser Asp Asp Cys Leu Ala Asp His Ala Glu Ala
                645                 650                 655

Tyr Lys Ala His Thr Ala Ser Val Gln Ala Phe Leu Asn Ile Thr Val
                660                 665                 670

Gly Glu His Ser Ile Val Thr Thr Val Tyr Val Asn Gly Glu Thr Pro
                675                 680                 685

Val Asn Phe Asn Gly Val Lys Leu Thr Ala Gly Pro Leu Ser Thr Ala
690                 695                 700

Trp Thr Pro Phe Asp Arg Lys Ile Val Gln Tyr Ala Gly Glu Ile Tyr
705                 710                 715                 720

Asn Tyr Asp Phe Pro Glu Tyr Gly Ala Gly Gln Pro Gly Ala Phe Gly
                725                 730                 735

Asp Ile Gln Ser Arg Thr Val Ser Ser Ser Asp Leu Tyr Ala Asn Thr
                740                 745                 750

Asn Leu Val Leu Gln Arg Pro Lys Ala Gly Ala Ile His Val Pro Tyr
                755                 760                 765

Thr Gln Ala Pro Ser Gly Phe Glu Gln Trp Lys Lys Asp Lys Ala Pro
                770                 775                 780

Ser Leu Lys Phe Thr Ala Pro Phe Gly Cys Glu Ile Tyr Thr Asn Pro
785                 790                 795                 800
```

-continued

```
Ile Arg Ala Glu Asn Cys Ala Val Gly Ser Ile Pro Leu Ala Phe Asp
                805                 810                 815
Ile Pro Asp Ala Leu Phe Thr Arg Val Ser Glu Thr Pro Thr Leu Ser
            820                 825                 830
Ala Ala Glu Cys Thr Leu Asn Glu Cys Val Tyr Ser Ser Asp Phe Gly
        835                 840                 845
Gly Ile Ala Thr Val Lys Tyr Ser Ala Ser Lys Ser Gly Lys Cys Ala
    850                 855                 860
Val His Val Pro Ser Gly Thr Ala Thr Leu Lys Glu Ala Ala Val Glu
865                 870                 875                 880
Leu Thr Glu Gln Gly Ser Ala Thr Ile His Phe Ser Thr Ala Asn Ile
                885                 890                 895
His Pro Glu Phe Arg Leu Gln Ile Cys Thr Ser Tyr Val Thr Cys Lys
            900                 905                 910
Gly Asp Cys His Pro Pro Lys Asp His Ile Val Thr His Pro Gln Tyr
        915                 920                 925
His Ala Gln Thr Phe Thr Ala Ala Val Ser Lys Thr Ala Trp Thr Trp
    930                 935                 940
Leu Thr Ser Leu Leu Gly Gly Ser Ala Val Ile Ile Ile Ile Gly Leu
945                 950                 955                 960
Val Leu Ala Thr Ile Val Ala Met Tyr Val Leu Thr Asn Gln Lys His
                965                 970                 975
Asn
```

<210> SEQ ID NO 17
<211> LENGTH: 976
<212> TYPE: PRT
<213> ORGANISM: Artificial Sequence
<220> FEATURE:
<223> OTHER INFORMATION: Synthetic polypeptide

<400> SEQUENCE: 17

```
Thr Ala Val Cys Leu Leu Ala Asn Val Thr Phe Pro Cys Ser Thr Pro
1               5                   10                  15
Pro Ile Cys Tyr Asp Arg Ala Pro Ala Glu Thr Leu Met Met Leu Ser
            20                  25                  30
Lys Asn Ile Asp Asn Pro Gly Tyr Asp Glu Leu Leu Glu Ala Val Leu
        35                  40                  45
Lys Cys Pro Gly Arg Gln Lys Arg Ser Thr Glu Glu Leu Phe Lys Glu
    50                  55                  60
Tyr Lys Leu Thr Lys Pro Tyr Met Ala Lys Cys Ile Arg Cys Ala Val
65                  70                  75                  80
Gly Ser Cys His Ser Pro Ile Ala Ile Glu Ala Val Arg Ser Glu Gly
                85                  90                  95
His Asp Gly Tyr Val Arg Leu Gln Thr Ser Ser Gln Tyr Gly Leu Asp
            100                 105                 110
Pro Ser Gly Asn Val Lys Ser Arg Val Met Arg Tyr Asn Met Tyr Gly
        115                 120                 125
Lys Ile Val Glu Val Pro Leu His Gln Val Ser Leu His Thr Ser Arg
    130                 135                 140
Pro Cys Gln Ile Val Asp Gly His Gly Tyr Phe Leu Leu Ala Arg Cys
145                 150                 155                 160
Pro Pro Gly Asp Ser Ile Thr Met Glu Phe Lys Lys Gly Ser Val Thr
                165                 170                 175
```

His Ser Cys Ser Val Pro Tyr Glu Val Lys Phe Thr Pro Val Gly Arg
            180                 185                 190

Glu Leu Tyr Ser His Pro Glu His Gly Thr Glu His Pro Cys Arg
        195                 200                 205

Val Tyr Val His Asp Ala Gln Gln Lys Asp Ala Tyr Val Glu Met His
        210                 215                 220

Leu Pro Gly Ser Glu Val Asp Ser Ser Leu Ser Met Ser Gly Ser
225                 230                 235                 240

Ala Val Arg Val Thr Pro Pro Ser Gly Gln Ser Val Leu Val Glu Cys
                245                 250                 255

Asn Cys Gly Ser Ala Val Ser Glu Thr Ile Asn Thr Ala Lys Ser Tyr
            260                 265                 270

Ser Gln Cys Thr Lys Thr Ser Gln Cys Arg Ala Tyr Arg Leu Gln Ser
        275                 280                 285

Asp Lys Trp Val Phe Asn Ser Asp Lys Leu Pro Lys Ala Ala Gly Glu
        290                 295                 300

Thr Leu Lys Gly Lys Leu His Val Pro Tyr Leu Leu Ser Glu Ala Lys
305                 310                 315                 320

Cys Thr Val Pro Leu Ala Pro Glu Pro Ile Val Thr Phe Gly Phe Arg
                325                 330                 335

Phe Val Ser Leu Lys Leu His Pro Arg Asn Pro Thr Tyr Leu Thr Thr
            340                 345                 350

Arg Gln Leu Asp Gly Glu Pro Asn Tyr Thr His Glu Leu Ile Ser Glu
        355                 360                 365

Pro Thr Ile Arg Asn Phe Thr Val Thr Glu His Gly Trp Glu Tyr Val
        370                 375                 380

Trp Gly Asn His Pro Pro Gln Arg Tyr Trp Ala Gln Glu Thr Ala Pro
385                 390                 395                 400

Gly Asp Pro His Gly Leu Pro His Glu Val Ile Lys His Tyr Tyr His
                405                 410                 415

Arg Tyr Pro Met Ser Thr Thr Leu Gly Leu Ser Ile Cys Ala Ala Val
            420                 425                 430

Val Thr Thr Ser Ile Ala Ala Ser Thr Trp Leu Leu Cys Lys Ser Arg
        435                 440                 445

Val Ser Cys Leu Thr Pro Tyr Arg Leu Thr Pro Asn Ala Gln Leu Pro
        450                 455                 460

Val Cys Leu Ala Phe Leu Cys Cys Ala Arg Thr Ala Arg Ala Glu Thr
465                 470                 475                 480

Ala Trp Glu Ser Leu Asp His Leu Trp Asn Asn Asn Gln Gln Met Phe
                485                 490                 495

Trp Thr Gln Leu Leu Ile Pro Leu Ala Ala Leu Ile Val Val Thr Arg
            500                 505                 510

Leu Leu Arg Cys Val Cys Cys Val Val Pro Phe Leu Val Leu Ala Gly
        515                 520                 525

Ala Ala Ser Val Gly Ala Tyr Glu His Ala Thr Thr Met Pro Ser Gln
        530                 535                 540

Val Gly Ile Pro Tyr Asn Thr Val Val Asn Arg Ala Gly Tyr Ala Pro
545                 550                 555                 560

Leu Ala Ile Ser Ile Ile Pro Thr Lys Ile Arg Leu Ile Pro Thr Leu
                565                 570                 575

Asn Leu Glu Tyr Ile Thr Cys His Tyr Lys Thr Gly Leu Asp Ser Pro
            580                 585                 590

Ser Ile Lys Cys Cys Gly Thr Gln Glu Cys Pro Lys Val Asn Arg Pro 595                 600                 605
Asp Glu Gln Cys Lys Val Phe Ala Gly Val Tyr Pro Phe Met Trp Gly
            610                 615                 620

Gly Ala Tyr Cys Phe Cys Asp Ser Glu Asn Thr Gln Ile Ser Arg Ala
625                 630                 635                 640

Tyr Val Met Lys Ser Asp Asp Cys Ser Ala Asp His Ala Leu Ala Tyr
                645                 650                 655

Lys Ala His Thr Ala Ser Ile Gln Ala Phe Leu Asn Ile Thr Val Gly
            660                 665                 670

Glu Gln Ser Thr Thr Ala Val Val Tyr Val Asn Gly Glu Thr Pro Ile
        675                 680                 685

Ser Phe Asn Gly Val Lys Leu Val Ala Gly Pro Leu Ser Thr Ala Trp
        690                 695                 700

Thr Pro Phe Asp Arg Lys Val Val Gln Tyr Ala Gly Glu Ile Tyr Asn
705                 710                 715                 720

Tyr Asp Phe Pro Glu Tyr Gly Ala Gly His Ala Gly Ala Phe Gly Asp
                725                 730                 735

Leu Gln Ala Arg Thr Ile Thr Ser Asn Asp Leu Tyr Ala Asn Thr Asn
            740                 745                 750

Leu Val Leu Gln Arg Pro Lys Ser Gly Thr Val His Val Pro Tyr Thr
        755                 760                 765

Gln Ala Pro Ser Gly Phe Glu Gln Trp Lys Lys Asp Lys Pro Pro Ser
770                 775                 780

Leu Lys Phe Thr Ala Pro Phe Gly Cys Glu Ile Tyr Val Asn Pro Val
785                 790                 795                 800

Arg Ala Glu Asn Cys Ala Val Gly Ser Ile Pro Leu Ser Phe Asp Ile
                805                 810                 815

Pro Asp Ala Leu Phe Thr Arg Val Ser Asp Thr Pro Thr Leu Ser Thr
            820                 825                 830

Ala Glu Cys Thr Leu Asn Glu Cys Val Tyr Ser Ser Asp Phe Gly Gly
        835                 840                 845

Ile Ala Ser Val Lys Tyr Ser Ala Thr Lys Ala Gly Lys Cys Ala Val
        850                 855                 860

His Val Pro Ser Gly Thr Ala Thr Leu Lys Glu Ser Leu Val Glu Val
865                 870                 875                 880

Val Glu Gln Gly Ser Met Thr Leu His Phe Ser Thr Ala Ser Ile His
                885                 890                 895

Pro Glu Phe Arg Leu Gln Ile Cys Thr Ser Phe Val Thr Cys Lys Gly
            900                 905                 910

Asp Cys His Pro Pro Lys Asp His Ile Val Thr His Pro Gln His His
        915                 920                 925

Ala Gln Thr Phe Thr Ala Ala Val Ser Lys Thr Ala Trp Thr Trp Leu
        930                 935                 940

Ser Ser Leu Leu Gly Gly Ser Ala Ala Ile Ile Ile Ile Gly Leu Val
945                 950                 955                 960

Leu Ala Thr Leu Val Ala Met Tyr Val Leu Thr Asn Gln Lys Arg Asn
                965                 970                 975

<210> SEQ ID NO 18
<211> LENGTH: 977
<212> TYPE: PRT
<213> ORGANISM: Artificial Sequence
<220> FEATURE:
<223> OTHER INFORMATION: Synthetic polypeptide

<400> SEQUENCE: 18

Thr Thr Met Cys Leu Leu Ala Asn Val Thr Phe Pro Cys Ala Gln Pro
1               5                   10                  15
Pro Ile Cys Tyr Asp Arg Lys Pro Ala Glu Thr Leu Ala Met Leu Ser
            20                  25                  30
Val Asn Val Asp Asn Pro Gly Tyr Asp Glu Leu Leu Glu Ala Ala Val
        35                  40                  45
Lys Cys Pro Gly Arg Lys Arg Arg Ser Thr Glu Glu Leu Phe Lys Glu
    50                  55                  60
Tyr Lys Leu Thr Arg Pro Tyr Met Ala Arg Cys Ile Arg Cys Ala Val
65                  70                  75                  80
Gly Ser Cys His Ser Pro Ile Ala Ile Glu Ala Val Lys Ser Asp Gly
                85                  90                  95
His Asp Gly Tyr Val Arg Leu Gln Thr Ser Ser Gln Tyr Gly Leu Asp
            100                 105                 110
Ser Ser Gly Asn Leu Lys Gly Arg Thr Met Arg Tyr Asp Met His Gly
        115                 120                 125
Thr Ile Glu Glu Ile Pro Leu His Gln Val Ser Val His Thr Ser Arg
    130                 135                 140
Pro Cys His Ile Ile Asp Gly His Gly Tyr Phe Leu Leu Ala Arg Cys
145                 150                 155                 160
Pro Ala Gly Asp Ser Ile Thr Met Glu Phe Lys Lys Asp Ser Val Thr
                165                 170                 175
His Ser Cys Ser Val Pro Tyr Glu Val Lys Phe Asn Pro Val Gly Arg
            180                 185                 190
Glu Leu Tyr Thr His Pro Pro Glu His Gly Ala Glu Gln Ala Cys Gln
        195                 200                 205
Val Tyr Ala His Asp Ala Gln Asn Arg Gly Ala Tyr Val Glu Met His
    210                 215                 220
Leu Pro Gly Ser Glu Val Asp Ser Ser Leu Val Ser Leu Ser Gly Ser
225                 230                 235                 240
Ser Val Thr Val Thr Pro Pro Ala Gly Thr Ser Ala Leu Val Glu Cys
                245                 250                 255
Glu Cys Gly Gly Thr Lys Ile Ser Glu Thr Ile Asn Thr Ala Lys Gln
            260                 265                 270
Phe Ser Gln Cys Thr Lys Lys Glu Gln Cys Arg Ala Tyr Arg Leu Gln
        275                 280                 285
Asn Asp Lys Trp Val Tyr Asn Ser Asp Lys Leu Pro Lys Ala Ala Gly
    290                 295                 300
Ala Thr Leu Lys Gly Lys Leu His Val Pro Phe Leu Leu Ala Asp Gly
305                 310                 315                 320
Lys Cys Thr Val Pro Leu Ala Pro Glu Pro Met Ile Thr Phe Gly Phe
                325                 330                 335
Arg Ser Val Ser Leu Lys Leu His Pro Lys Asn Pro Thr Tyr Leu Thr
            340                 345                 350
Thr Arg Gln Leu Ala Asp Glu Pro His Tyr Thr His Glu Leu Ile Ser
        355                 360                 365
Glu Pro Ala Val Arg Asn Phe Thr Val Thr Glu Lys Gly Trp Glu Phe
    370                 375                 380
Val Trp Gly Asn His Pro Pro Lys Arg Phe Trp Ala Gln Glu Thr Ala
385                 390                 395                 400
Pro Gly Asn Pro His Gly Leu Pro His Glu Val Ile Thr His Tyr Tyr
                405                 410                 415

```
His Arg Tyr Pro Met Ser Thr Ile Leu Gly Leu Ser Ile Cys Ala Ala
            420                 425                 430

Ile Val Thr Thr Ser Ile Ala Ala Ser Val Trp Leu Phe Cys Lys Ser
            435                 440                 445

Arg Ile Ser Cys Leu Thr Pro Tyr Arg Leu Thr Pro Asn Ala Arg Met
450                     455                 460

Pro Leu Cys Leu Ala Val Leu Cys Cys Ala Arg Thr Ala Arg Ala Glu
465                 470                 475                 480

Thr Thr Trp Glu Ser Leu Asp His Leu Trp Asn His Asn Gln Gln Met
                485                 490                 495

Phe Trp Ser Gln Leu Leu Ile Pro Leu Ala Ala Leu Ile Val Ala Thr
                500                 505                 510

Arg Leu Leu Lys Cys Val Cys Cys Val Val Pro Phe Leu Val Val Ala
            515                 520                 525

Gly Ala Ala Gly Ala Gly Ala Tyr Glu His Ala Thr Thr Met Pro Asn
530                 535                 540

Gln Val Gly Ile Pro Tyr Asn Thr Ile Val Asn Arg Ala Gly Tyr Ala
545                 550                 555                 560

Pro Leu Pro Ile Ser Ile Thr Pro Thr Lys Ile Lys Leu Ile Pro Thr
                565                 570                 575

Val Asn Leu Glu Tyr Val Thr Cys His Tyr Lys Thr Gly Met Asp Ser
            580                 585                 590

Pro Ala Ile Lys Cys Cys Gly Ser Gln Glu Cys Thr Pro Thr Tyr Arg
            595                 600                 605

Pro Asp Glu Gln Cys Lys Val Phe Thr Gly Val Tyr Pro Phe Met Trp
610                 615                 620

Gly Gly Ala Tyr Cys Phe Cys Asp Thr Glu Asn Thr Gln Val Ser Lys
625                 630                 635                 640

Ala Tyr Val Met Lys Ser Asp Asp Cys Leu Ala Asp His Ala Glu Ala
                645                 650                 655

Tyr Lys Ala His Thr Ala Ser Val Gln Ala Phe Leu Asn Ile Thr Val
                660                 665                 670

Gly Glu His Ser Ile Val Thr Thr Val Tyr Val Asn Gly Glu Thr Pro
            675                 680                 685

Val Asn Phe Asn Gly Val Lys Leu Thr Ala Gly Pro Leu Ser Thr Ala
            690                 695                 700

Trp Thr Pro Phe Asp Arg Lys Ile Val Gln Tyr Ala Gly Glu Ile Tyr
705                 710                 715                 720

Asn Tyr Asp Phe Pro Glu Tyr Gly Ala Gly Gln Pro Gly Ala Phe Gly
                725                 730                 735

Asp Ile Gln Ser Arg Thr Val Ser Ser Asp Leu Tyr Ala Asn Thr
                740                 745                 750

Asn Leu Val Leu Gln Arg Pro Lys Ala Gly Ala Ile His Val Pro Tyr
            755                 760                 765

Thr Gln Ala Pro Ser Gly Phe Glu Gln Trp Lys Lys Asp Lys Ala Pro
            770                 775                 780

Ser Leu Lys Phe Thr Ala Pro Phe Gly Cys Glu Ile Tyr Thr Asn Pro
785                 790                 795                 800

Ile Arg Ala Glu Asn Cys Ala Val Gly Ser Ile Pro Leu Ala Phe Asp
                805                 810                 815

Ile Pro Asp Ala Leu Phe Thr Arg Val Ser Glu Thr Pro Thr Leu Ser
            820                 825                 830
```

Ala Ala Glu Cys Thr Leu Asn Glu Cys Val Tyr Ser Ser Asp Phe Gly
            835                 840                 845

Gly Ile Ala Thr Val Lys Tyr Ser Ala Ser Lys Ser Gly Lys Cys Ala
850                 855                 860

Val His Val Pro Ser Gly Thr Ala Thr Leu Lys Glu Ala Ala Val Glu
865                 870                 875                 880

Leu Thr Glu Gln Gly Ser Ala Thr Ile His Phe Ser Thr Ala Asn Ile
            885                 890                 895

His Pro Glu Phe Arg Leu Gln Ile Cys Thr Ser Tyr Val Thr Cys Lys
            900                 905                 910

Gly Asp Cys His Pro Pro Arg Asp His Ile Val Thr His Pro Gln Tyr
        915                 920                 925

His Ala Gln Thr Phe Thr Ala Ala Val Ser Lys Thr Ala Trp Thr Trp
        930                 935                 940

Leu Thr Ser Leu Leu Gly Gly Ser Ala Val Ile Ile Ile Gly Leu
945                 950                 955                 960

Val Leu Ala Thr Ile Val Ala Met Tyr Val Leu Thr Asn Gln Lys His
                965                 970                 975

Asn

<210> SEQ ID NO 19
<211> LENGTH: 977
<212> TYPE: PRT
<213> ORGANISM: Artificial Sequence
<220> FEATURE:
<223> OTHER INFORMATION: Synthetic polypeptide

<400> SEQUENCE: 19

Thr Thr Leu Cys Leu Leu Ala Asn Val Thr Phe Pro Cys Thr Gln Pro
1               5                   10                  15

Pro Ile Cys Tyr Asp Arg Lys Pro Ala Glu Thr Leu Ser Met Leu Ser
                20                  25                  30

His Asn Ile Asp Asn Pro Gly Tyr Asp Glu Leu Leu Glu Ala Val Leu
            35                  40                  45

Lys Cys Pro Gly Arg Gly Lys Arg Ser Thr Glu Glu Leu Phe Lys Glu
50                  55                  60

Tyr Lys Leu Thr Arg Pro Tyr Met Ala Lys Cys Val Arg Cys Ala Val
65                  70                  75                  80

Gly Ser Cys His Ser Pro Ile Ala Ile Glu Ala Val Arg Ser Asp Gly
                85                  90                  95

His Asp Gly Tyr Ile Arg Ile Gln Thr Ser Ser Gln Tyr Gly Leu Asp
            100                 105                 110

Pro Ser Gly Asn Leu Lys Gly Arg Thr Met Arg Tyr Asp Met His Gly
        115                 120                 125

Thr Ile Lys Glu Ile Pro Leu His Gln Val Ser Leu His Thr Ser Arg
130                 135                 140

Pro Cys His Ile Val Asp Gly His Gly Tyr Phe Leu Leu Ala Arg Cys
145                 150                 155                 160

Pro Glu Gly Asp Ser Ile Thr Met Glu Phe Lys Lys Glu Ser Val Thr
                165                 170                 175

His Ser Cys Ser Val Pro Tyr Glu Val Lys Phe Asn Pro Ala Gly Arg
            180                 185                 190

Glu Leu Tyr Thr His Pro Pro Glu His Gly Ala Glu Gln Pro Cys His
        195                 200                 205

Val Tyr Ala His Asp Ala Gln Asn Arg Gly Ala Tyr Val Glu Met His

```
                210                 215                 220
Leu Pro Gly Ser Glu Val Asp Ser Thr Leu Leu Ser Met Ser Gly Ser
225                 230                 235                 240

Ser Val His Val Thr Pro Pro Ala Gly Gln Ser Val Gln Val Glu Cys
                    245                 250                 255

Glu Cys Gly Gly Thr Lys Ile Ser Glu Thr Ile Asn Ser Ala Lys Gln
                260                 265                 270

Tyr Ser Gln Cys Ser Lys Thr Ser Gln Cys Arg Ala Tyr Arg Thr Gln
                275                 280                 285

Asn Asp Lys Trp Val Tyr Asn Ser Asp Lys Leu Pro Lys Ala Ser Gly
        290                 295                 300

Glu Thr Leu Lys Gly Lys Leu His Val Pro Phe Val Leu Thr Glu Ala
305                 310                 315                 320

Lys Cys Thr Val Pro Leu Ala Pro Glu Pro Ile Ile Thr Phe Gly Phe
                    325                 330                 335

Arg Ser Val Ser Leu Lys Leu His Pro Lys Asn Pro Thr Phe Leu Thr
                340                 345                 350

Thr Arg Gln Leu Asp Gly Glu Pro Ala Tyr Thr His Glu Leu Ile Thr
            355                 360                 365

His Pro Val Val Arg Asn Phe Ser Val Thr Glu Lys Gly Trp Glu Phe
        370                 375                 380

Val Trp Gly Asn His Pro Pro Gln Arg Tyr Trp Ser Gln Glu Thr Ala
385                 390                 395                 400

Pro Gly Asn Pro His Gly Leu Pro His Glu Val Ile Val His Tyr Tyr
                    405                 410                 415

His Arg Tyr Pro Met Ser Thr Ile Val Gly Leu Ser Ile Cys Ala Ala
                420                 425                 430

Ile Val Thr Val Ser Val Ala Ala Ser Thr Trp Leu Phe Cys Arg Ser
                435                 440                 445

Arg Val Ala Cys Leu Thr Pro Tyr Arg Leu Thr Pro Asn Ala Arg Ile
        450                 455                 460

Pro Phe Cys Leu Ala Val Leu Cys Cys Ala Arg Thr Ala Lys Ala Glu
465                 470                 475                 480

Thr Thr Trp Glu Ser Leu Asp His Leu Trp Asn Asn Gln Gln Met
                    485                 490                 495

Phe Trp Ile Gln Leu Leu Ile Pro Leu Ala Ala Leu Ile Val Val Thr
                500                 505                 510

Arg Leu Leu Lys Cys Met Cys Cys Val Val Pro Phe Leu Val Val Ala
                515                 520                 525

Gly Ala Val Gly Ala Gly Ala Tyr Glu His Ala Thr Thr Met Pro Ser
        530                 535                 540

Gln Ala Gly Ile Ser Tyr Asn Thr Ile Val Asn Arg Ala Gly Tyr Ala
545                 550                 555                 560

Pro Leu Pro Ile Ser Ile Val Pro Thr Lys Val Lys Leu Ile Pro Thr
                    565                 570                 575

Val Asn Leu Glu Tyr Ile Thr Cys His Tyr Lys Thr Gly Met Asp Ser
                580                 585                 590

Pro Ala Ile Lys Cys Cys Gly Thr Gln Glu Cys Ser Pro Thr Tyr Arg
                595                 600                 605

Pro Asp Glu Gln Cys Lys Val Phe Ser Gly Val Tyr Pro Phe Met Trp
        610                 615                 620

Gly Gly Ala Tyr Cys Phe Cys Asp Thr Glu Asn Thr Gln Ile Ser Lys
625                 630                 635                 640
```

Ala Tyr Val Thr Lys Ser Glu Asp Cys Val Thr Asp His Ala Gln Ala
            645                 650                 655

Tyr Lys Ala His Thr Ala Ser Ile Gln Ala Phe Leu Asn Ile Thr Val
        660                 665                 670

Gly Gly His Ser Thr Thr Ala Val Val Tyr Val Asn Gly Glu Thr Pro
            675                 680                 685

Val Asn Phe Asn Gly Ile Lys Leu Val Ala Gly Pro Leu Ser Thr Ala
690                 695                 700

Trp Ser Pro Phe Asp Lys Lys Ile Val Gln Tyr Ala Gly Glu Val Tyr
705                 710                 715                 720

Asn Tyr Asp Phe Pro Glu Tyr Gly Ala Gly His Ala Gly Ala Phe Gly
                725                 730                 735

Asp Ile Gln Ala Arg Thr Ile Ser Ser Ser Asp Val Tyr Ala Asn Thr
            740                 745                 750

Asn Leu Val Leu Gln Arg Pro Asn Thr Gly Thr Ile His Val Pro Tyr
        755                 760                 765

Thr Gln Ala Pro Ser Gly Tyr Glu Gln Trp Lys Lys Asp Lys Pro Pro
    770                 775                 780

Ser Leu Lys Tyr Thr Ala Pro Phe Gly Cys Glu Ile His Val Asn Pro
785                 790                 795                 800

Val Arg Ala Glu Asn Cys Ala Val Gly Phe Ile Pro Leu Ala Phe Asp
                805                 810                 815

Ile Pro Asp Ala Leu Phe Thr Arg Val Ser Glu Thr Pro Thr Leu Ser
            820                 825                 830

Ser Ala Glu Cys Ser Leu Asn Glu Cys Thr Tyr Ser Thr Asp Phe Gly
        835                 840                 845

Gly Ile Ala Thr Val Lys Tyr Ser Ala Ser Lys Ala Gly Lys Cys Ala
    850                 855                 860

Val His Ile Pro Ser Gly Thr Ala Thr Leu Lys Glu Ala Ala Val Glu
865                 870                 875                 880

Leu Ala Glu Gln Gly Ser Ala Thr Ile His Phe Ser Thr Ala Ser Ile
                885                 890                 895

His Pro Glu Phe Lys Leu Gln Ile Cys Thr Lys Val Leu Thr Cys Lys
            900                 905                 910

Gly Asp Cys His Pro Pro Lys Asp His Ile Val Thr His Pro Gln Tyr
        915                 920                 925

His Ala Gln Ser Phe Thr Ala Ala Val Ser Lys Thr Ala Trp Thr Trp
    930                 935                 940

Ile Thr Ser Leu Leu Gly Gly Ser Ala Ile Ile Ile Ile Gly Leu
945                 950                 955                 960

Val Leu Ala Thr Val Val Ala Met Tyr Val Leu Thr Asn Gln Arg His
                965                 970                 975

Asn

<210> SEQ ID NO 20
<211> LENGTH: 974
<212> TYPE: PRT
<213> ORGANISM: Artificial Sequence
<220> FEATURE:
<223> OTHER INFORMATION: Synthetic polypeptide

<400> SEQUENCE: 20

Thr Ala Leu Cys Val Leu Ser Asn Val Thr Phe Pro Cys Asp Lys Pro
1               5                   10                  15

-continued

```
Pro Val Cys Tyr Ser Leu Ala Pro Glu Arg Thr Leu Asp Val Leu Glu
                20                  25                  30

Glu Asn Val Asp Asn Pro Asn Tyr Asp Thr Leu Leu Glu Asn Val Leu
            35                  40                  45

Lys Cys Pro Ser Arg Arg Pro Lys Arg Ser Ile Thr Asp Asp Phe Thr
50                  55                  60

Leu Thr Ser Pro Tyr Leu Gly Phe Cys Pro Tyr Cys Arg His Ser Thr
65                  70                  75                  80

Pro Cys Phe Ser Pro Ile Lys Ile Glu Asn Val Trp Asp Glu Ser Asp
                85                  90                  95

Asp Gly Ser Ile Arg Ile Gln Val Ser Ala Gln Phe Gly Tyr Asn Gln
                100                 105                 110

Ala Gly Thr Ala Asp Val Thr Lys Phe Arg Tyr Met Ser Phe Asp His
            115                 120                 125

Asp His Asp Ile Lys Glu Asp Ser Met Glu Lys Ile Ala Ile Ser Thr
130                 135                 140

Ser Gly Pro Cys Arg Arg Leu Gly His Lys Gly Tyr Phe Leu Leu Ala
145                 150                 155                 160

Gln Cys Pro Pro Gly Asp Ser Val Thr Val Ser Ile Thr Ser Gly Ala
                165                 170                 175

Ser Glu Asn Ser Cys Thr Val Glu Lys Lys Ile Arg Arg Lys Phe Val
            180                 185                 190

Gly Arg Glu Glu Tyr Leu Phe Pro Pro Val His Gly Lys Leu Val Lys
            195                 200                 205

Cys His Val Tyr Asp His Leu Lys Glu Thr Ser Ala Gly Tyr Ile Thr
210                 215                 220

Met His Arg Pro Gly Pro His Ala Tyr Lys Ser Tyr Leu Glu Glu Ala
225                 230                 235                 240

Ser Gly Glu Val Tyr Ile Lys Pro Pro Ser Gly Lys Asn Val Thr Tyr
                245                 250                 255

Glu Cys Lys Cys Gly Asp Tyr Ser Thr Gly Ile Val Ser Thr Arg Thr
            260                 265                 270

Lys Met Asn Gly Cys Thr Lys Ala Lys Gln Cys Ile Ala Tyr Lys Ser
            275                 280                 285

Asp Gln Thr Lys Trp Val Phe Asn Ser Pro Asp Leu Ile Arg His Thr
290                 295                 300

Asp His Ser Val Gln Gly Lys Leu His Ile Pro Phe Arg Leu Thr Pro
305                 310                 315                 320

Thr Val Cys Pro Val Pro Leu Ala His Thr Pro Thr Val Thr Lys Trp
                325                 330                 335

Phe Lys Gly Ile Thr Leu His Leu Thr Ala Thr Arg Pro Thr Leu Leu
            340                 345                 350

Thr Thr Arg Lys Leu Gly Leu Arg Ala Asp Ala Thr Ala Glu Trp Ile
            355                 360                 365

Thr Gly Thr Thr Ser Arg Asn Phe Ser Val Gly Arg Glu Gly Leu Glu
            370                 375                 380

Tyr Val Trp Gly Asn His Glu Pro Val Arg Val Trp Ala Gln Glu Ser
385                 390                 395                 400

Ala Pro Gly Asp Pro His Gly Trp Pro His Glu Ile Ile Ile His Tyr
                405                 410                 415

Tyr His Arg His Pro Val Tyr Thr Val Ile Val Leu Cys Gly Val Ala
            420                 425                 430

Leu Ala Ile Leu Val Gly Thr Ala Ser Ser Ala Ala Cys Ile Ala Lys
```

-continued

```
              435                 440                 445
Ala Arg Arg Asp Cys Leu Thr Pro Tyr Ala Leu Ala Pro Asn Ala Thr
450                 455                 460
Val Pro Thr Ala Leu Ala Val Leu Cys Cys Ile Arg Pro Thr Asn Ala
465                 470                 475                 480
Glu Thr Phe Gly Glu Thr Leu Asn His Leu Trp Phe Asn Asn Gln Pro
                    485                 490                 495
Phe Leu Trp Ala Gln Leu Cys Ile Pro Leu Ala Leu Val Ile Leu
                500                 505                 510
Phe Arg Cys Phe Ser Cys Cys Met Pro Phe Leu Leu Val Ala Gly Val
            515                 520                 525
Cys Leu Gly Lys Val Asp Ala Phe Glu His Ala Thr Thr Val Pro Asn
530                 535                 540
Val Pro Gly Ile Pro Tyr Lys Ala Leu Val Arg Ala Gly Tyr Ala
545                 550                 555                 560
Pro Leu Asn Leu Glu Ile Thr Val Val Ser Ser Glu Leu Thr Pro Ser
                565                 570                 575
Thr Asn Lys Glu Tyr Val Thr Cys Lys Phe His Thr Val Ile Pro Ser
                580                 585                 590
Pro Gln Val Lys Cys Cys Gly Ser Leu Glu Cys Lys Ala Ser Ser Lys
            595                 600                 605
Ala Asp Tyr Thr Cys Arg Val Phe Gly Gly Val Tyr Pro Phe Met Trp
610                 615                 620
Gly Gly Ala Gln Cys Phe Cys Asp Ser Glu Asn Thr Gln Leu Ser Glu
625                 630                 635                 640
Ala Tyr Val Glu Phe Ala Pro Asp Cys Thr Ile Asp His Ala Val Ala
                645                 650                 655
Leu Lys Val His Thr Ala Ala Leu Lys Val Gly Leu Arg Ile Val Tyr
                660                 665                 670
Gly Asn Thr Thr Ala His Leu Asp Thr Phe Val Asn Gly Val Thr Pro
                675                 680                 685
Gly Ser Ser Arg Asp Leu Lys Val Ile Ala Gly Pro Ile Ser Ala Ala
            690                 695                 700
Phe Ser Pro Phe Asp His Lys Val Val Ile Arg Lys Gly Leu Val Tyr
705                 710                 715                 720
Asn Tyr Asp Phe Pro Glu Tyr Gly Ala Met Lys Pro Gly Ala Phe Gly
                725                 730                 735
Asp Ile Gln Ala Ser Ser Leu Asp Ala Thr Asp Ile Val Ala Arg Thr
                740                 745                 750
Asp Ile Arg Leu Leu Lys Pro Ser Val Lys Asn Ile His Val Pro Tyr
            755                 760                 765
Thr Gln Ala Val Ser Gly Tyr Glu Met Trp Lys Asn Asn Ser Gly Arg
770                 775                 780
Pro Leu Gln Glu Thr Ala Pro Phe Gly Cys Lys Ile Glu Val Glu Pro
785                 790                 795                 800
Leu Arg Ala Ser Asn Cys Ala Tyr Gly His Ile Pro Ile Ser Ile Asp
                805                 810                 815
Ile Pro Asp Ala Ala Phe Val Arg Ser Ser Glu Ser Pro Thr Ile Leu
                820                 825                 830
Glu Val Ser Cys Thr Val Ala Asp Cys Ile Tyr Ser Ala Asp Phe Gly
            835                 840                 845
Gly Ser Leu Thr Leu Gln Tyr Lys Ala Asp Arg Glu Gly His Cys Pro
            850                 855                 860
```

```
Val His Ser His Ser Thr Thr Ala Val Leu Lys Glu Ala Thr Thr His
865                 870                 875                 880

Val Thr Ala Val Gly Ser Ile Thr Leu His Phe Ser Thr Ser Ser Pro
            885                 890                 895

Gln Ala Asn Phe Ile Val Ser Leu Cys Gly Lys Lys Thr Thr Cys Asn
        900                 905                 910

Ala Glu Cys Lys Pro Pro Ala Asp His Ile Ile Gly Glu Pro His Lys
        915                 920                 925

Val Asp Gln Glu Phe Gln Ala Val Ser Lys Thr Ser Trp Asn Trp
930                 935                 940

Leu Leu Ala Leu Phe Gly Gly Ala Ser Ser Leu Ile Val Val Gly Leu
945                 950                 955                 960

Ile Val Leu Val Cys Ser Ser Met Leu Ile Asn Thr Arg Arg
                965                 970

<210> SEQ ID NO 21
<211> LENGTH: 974
<212> TYPE: PRT
<213> ORGANISM: Artificial Sequence
<220> FEATURE:
<223> OTHER INFORMATION: Synthetic polypeptide

<400> SEQUENCE: 21

Thr Ala Met Cys Val Leu Ala Asn Val Thr Phe Pro Cys Asp Lys Pro
1               5                   10                  15

Pro Val Cys Tyr Ser Leu Thr Pro Glu Arg Thr Leu Asp Val Leu Glu
            20                  25                  30

Glu Asn Val Asp Asn Pro Gly Tyr Asp Thr Leu Leu Glu Asn Val Leu
        35                  40                  45

Lys Cys Pro Ser Arg Arg Gln Lys Arg Ser Ile Thr Asp Phe Thr
50                  55                  60

Leu Thr Ser Pro Tyr Leu Gly His Cys Pro Tyr Cys Leu His Ala Thr
65                  70                  75                  80

Pro Cys Phe Ser Pro Ile Lys Ile Glu Lys Val Trp Asp Glu Ser Asp
                85                  90                  95

Asp Gly Thr Ile Arg Ile Gln Val Ser Ala Gln Leu Gly Tyr Asn Gln
            100                 105                 110

Ala Gly Thr Ala Asp Pro Thr Lys Phe Arg Tyr Met Ser Tyr Glu Gln
        115                 120                 125

Asp His Asp Ile Lys Glu Ala Ser Met Asp Lys Ile Ala Ile Ser Thr
    130                 135                 140

Ser Gly Pro Cys Ser Arg Leu Gly His Lys Gly Tyr Phe Leu Leu Ala
145                 150                 155                 160

Arg Cys Pro Pro Gly Asp Ser Val Thr Val Ser Ile Thr Ser Gly Thr
                165                 170                 175

Ser Glu Asn Ser Cys Thr Val Glu Arg Lys Ile Arg Arg Lys Phe Val
            180                 185                 190

Gly Arg Glu Glu Tyr Leu Leu Pro Pro Val His Gly Lys Leu Ile Lys
        195                 200                 205

Cys His Val Tyr Asp His Leu Lys Glu Thr Thr Ala Gly Tyr Ile Thr
    210                 215                 220

Met His Arg Pro Gly Pro His Ala Tyr Ala Thr Tyr Val Glu Glu Ser
225                 230                 235                 240

Ser Gly Glu Val Tyr Ile Arg Pro Pro Ser Gly Lys Asn Val Thr Tyr
                245                 250                 255
```

Glu Cys Lys Cys Gly Asp Tyr Ser Thr Gly Thr Val Asn Thr Arg Thr
            260                 265                 270

Lys Met Pro Gly Cys Thr Lys Lys Gln Cys Ile Ala Tyr Lys His
        275                 280                 285

Asp Gln Thr Lys Trp Val Phe Asn Ser Pro Asp Leu Ile Arg His Ser
            290                 295                 300

Asp His Ala Val Gln Gly Lys Leu His Ile Pro Phe Lys Leu Thr Ala
305                 310                 315                 320

Thr Ala Cys Pro Val Pro Leu Ala His Thr Pro Thr Val Glu Lys Trp
                325                 330                 335

Phe Lys Gly Val Thr Leu His Leu Thr Ala Ser His Pro Thr Leu Leu
            340                 345                 350

Thr Thr Arg Lys Leu Gly Pro Arg Ala Glu Pro Thr Ser Glu Trp Ile
            355                 360                 365

Val Gly Thr Val Ser Arg Asn Phe Ser Val Gly Arg Glu Gly Leu Glu
370                 375                 380

Tyr Thr Trp Gly Asn His Asp Pro Val Arg Val Trp Ser Gln Glu Ser
385                 390                 395                 400

Ala Pro Gly Asp Pro His Gly Trp Pro His Glu Ile Ile Val His Tyr
                405                 410                 415

Tyr His Arg His Pro Leu Tyr Thr Ile Ala Val Leu Cys Gly Leu Val
                420                 425                 430

Leu Ile Thr Val Ile Gly Ile Ala Ser Ala Ala Ala Cys Ile Ser Lys
            435                 440                 445

Ala Arg Arg Asp Cys Leu Thr Pro Tyr Ala Leu Ala Pro Asn Ala Ala
            450                 455                 460

Val Pro Thr Leu Leu Ala Val Leu Cys Cys Ile Arg Pro Thr His Ala
465                 470                 475                 480

Glu Thr Leu Gly Glu Ser Leu Gly His Leu Trp Leu Asn Asn Gln Pro
                485                 490                 495

Leu Leu Trp Ala Gln Leu Cys Leu Pro Leu Ala Ala Leu Ile Ile Leu
            500                 505                 510

Phe Arg Phe Phe Ser Cys Cys Leu Pro Phe Leu Leu Val Ala Gly Val
            515                 520                 525

Cys Leu Gly Lys Ala Asp Ala Tyr Glu His Ala Thr Thr Val Pro Asn
530                 535                 540

Val Pro Gly Val Pro Tyr Lys Ala Leu Val Glu Arg Ser Gly Tyr Ala
545                 550                 555                 560

Pro Leu Asn Leu Glu Val Thr Val Val Ser Ser Glu Leu Ile Pro Ser
                565                 570                 575

Thr Asn Lys Glu Tyr Val Thr Cys Lys Phe His Thr Ile Ile Pro Ser
            580                 585                 590

Pro Gln Val Lys Cys Cys Gly Ser Leu Glu Cys Gln Ala Ser Arg Lys
            595                 600                 605

Ala Asp Tyr Thr Cys Arg Val Phe Gly Gly Val Tyr Pro Phe Met Trp
            610                 615                 620

Gly Gly Ala Gln Cys Ser Cys Asp Ser Glu Asn Thr Gln Leu Ser Glu
625                 630                 635                 640

Ala Tyr Val Glu Phe Ala Pro Asp Cys Thr Ala Asp His Ala Val Ala
                645                 650                 655

Leu Lys Val His Thr Ala Ala Leu Lys Val Gly Leu Gln Ile Val Tyr
            660                 665                 670

```
Gly Asn Thr Ser Thr Arg Leu Asp Thr Phe Val Asn Gly Val Thr Pro
            675                 680                 685
Gly Ile Ser Gly Ala Leu Lys Val Ile Ala Gly Pro Ile Ser Ala Ala
690                 695                 700
Phe Thr Pro Phe Asp His Lys Val Val Ile Arg Lys Gly Lys Val Tyr
705                 710                 715                 720
Asn Tyr Asp Phe Pro Glu Tyr Gly Ala Met Lys Pro Gly Val Phe Gly
                725                 730                 735
Asp Ile Gln Ala Ser Ser Leu Asp Ser Thr Asp Ile Val Ala Arg Thr
            740                 745                 750
Asp Val Arg Leu Leu Lys Pro Ser Val Lys Ser Ile His Val Pro Tyr
            755                 760                 765
Thr Gln Ala Ala Ser Gly Tyr Glu Met Trp Lys Asn Asn Ser Gly Arg
            770                 775                 780
Pro Leu Gln Asp Thr Ala Pro Phe Gly Cys Lys Ile Glu Val Asp Pro
785                 790                 795                 800
Leu Arg Ala Val Asp Cys Ala Tyr Gly His Ile Pro Leu Ser Ile Asp
                805                 810                 815
Ile Pro Asp Ala Ala Phe Val Arg Thr Ser Glu Ala Pro Thr Val Leu
            820                 825                 830
Glu Met Ser Cys Thr Val Thr Ala Cys Ile Tyr Ser Ala Asp Phe Gly
            835                 840                 845
Gly Ser Leu Thr Leu Gln Tyr Lys Ala Asp Lys Glu Gly Asn Cys Pro
            850                 855                 860
Val His Ser His Ser Ser Thr Ala Val Leu Lys Glu Ala Thr Thr His
865                 870                 875                 880
Val Val His Ser Gly Ser Val Thr Leu His Phe Ser Thr Ser Ser Pro
                885                 890                 895
Gln Val Asn Phe Ile Val Ser Leu Cys Gly Lys Lys Thr Thr Cys Asp
            900                 905                 910
Ala Glu Cys Lys Pro Pro Ser Asp His Ile Ile Gly Glu Pro His Lys
            915                 920                 925
Val Asn Gln Glu Phe Gln Ala Ala Val Ser Lys Thr Ser Trp Asn Trp
930                 935                 940
Leu Phe Ala Met Leu Gly Gly Ala Ser Ser Leu Ile Val Val Gly Leu
945                 950                 955                 960
Leu Val Leu Ala Cys Ser Ser Met Ile Ile Asn Thr Arg Arg
                965                 970

<210> SEQ ID NO 22
<211> LENGTH: 974
<212> TYPE: PRT
<213> ORGANISM: Artificial Sequence
<220> FEATURE:
<223> OTHER INFORMATION: Synthetic polypeptide

<400> SEQUENCE: 22

Thr Ala Leu Cys Val Leu Ser Asn Val Thr Phe Pro Cys Asp Lys Pro
1               5                   10                  15
Pro Val Cys Tyr Ser Leu Ala Pro Glu Arg Thr Leu Asp Val Leu Glu
            20                  25                  30
Glu Asn Val Asp Asn Pro Asn Tyr Asp Thr Leu Leu Glu Asn Val Leu
        35                  40                  45
Lys Cys Pro Ser Arg Arg Pro Lys Arg Ser Ile Thr Asp Asp Phe Thr
    50                  55                  60
```

-continued

Leu Thr Ser Pro Tyr Leu Gly Phe Cys Pro Tyr Cys Arg His Ser Thr
65              70                  75                  80

Pro Cys Phe Ser Pro Ile Lys Ile Glu Asn Val Trp Asp Glu Ser Asp
            85                  90                  95

Asp Gly Ser Ile Arg Ile Gln Val Ser Ala Gln Phe Gly Tyr Asn Gln
            100                 105                 110

Ala Gly Thr Ala Asp Val Thr Lys Phe Arg Tyr Met Ser Phe Asp His
            115                 120                 125

Asp His Asp Ile Lys Glu Asp Ser Met Glu Lys Ile Ala Ile Ser Thr
            130                 135                 140

Ser Gly Pro Cys Arg Arg Leu Gly His Lys Gly Tyr Phe Leu Leu Ala
145                 150                 155                 160

Gln Cys Pro Pro Gly Asp Ser Val Thr Val Ser Ile Thr Ser Gly Ala
                165                 170                 175

Ser Glu Asn Ser Cys Thr Val Glu Lys Lys Ile Arg Arg Lys Phe Val
            180                 185                 190

Gly Arg Glu Glu Tyr Leu Phe Pro Pro Val His Gly Lys Leu Val Lys
            195                 200                 205

Cys His Val Tyr Asp His Leu Lys Glu Thr Ser Ala Gly Tyr Ile Thr
            210                 215                 220

Met His Arg Pro Gly Pro His Ala Tyr Lys Ser Tyr Leu Glu Glu Ala
225                 230                 235                 240

Ser Gly Glu Val Tyr Ile Lys Pro Pro Ser Gly Lys Asn Val Thr Tyr
                245                 250                 255

Glu Cys Lys Cys Gly Asp Tyr Ser Thr Gly Ile Val Ser Thr Arg Thr
            260                 265                 270

Lys Met Asn Gly Cys Thr Lys Ala Lys Gln Cys Ile Ala Tyr Lys Ser
            275                 280                 285

Asp Gln Thr Lys Trp Val Phe Asn Ser Pro Asp Leu Ile Arg His Thr
            290                 295                 300

Asp His Ser Val Gln Gly Lys Leu His Ile Pro Phe Arg Leu Thr Pro
305                 310                 315                 320

Thr Val Cys Pro Val Pro Leu Ala His Thr Pro Thr Val Thr Lys Trp
                325                 330                 335

Phe Lys Gly Ile Thr Leu His Leu Thr Ala Thr Arg Pro Thr Leu Leu
            340                 345                 350

Thr Thr Arg Lys Leu Gly Leu Arg Ala Asp Ala Thr Ala Glu Trp Ile
            355                 360                 365

Thr Gly Thr Thr Ser Arg Asn Phe Ser Val Gly Arg Glu Gly Leu Glu
            370                 375                 380

Tyr Val Trp Gly Asn His Glu Pro Val Arg Val Trp Ala Gln Glu Ser
385                 390                 395                 400

Ala Pro Gly Asp Pro His Gly Trp Pro His Glu Ile Ile His Tyr
                405                 410                 415

Tyr His Arg His Pro Val Tyr Thr Val Ile Val Leu Cys Gly Val Ala
            420                 425                 430

Leu Ala Ile Leu Val Gly Thr Ala Ser Ser Ala Ala Cys Ile Ala Lys
            435                 440                 445

Ala Arg Arg Asp Cys Leu Thr Pro Tyr Ala Leu Ala Pro Asn Ala Thr
            450                 455                 460

Val Pro Thr Ala Leu Ala Val Leu Cys Cys Ile Arg Pro Thr Asn Ala
465                 470                 475                 480

Glu Thr Phe Gly Glu Thr Leu Asn His Leu Trp Phe Asn Asn Gln Pro

```
            485             490              495
Phe Leu Trp Ala Gln Leu Cys Ile Pro Leu Ala Ala Leu Val Ile Leu
            500             505              510

Phe Arg Cys Phe Ser Cys Cys Met Pro Phe Leu Leu Val Ala Gly Val
            515             520              525

Cys Leu Gly Lys Val Asp Ala Phe Glu His Ala Thr Thr Val Pro Asn
530             535             540

Val Pro Gly Ile Pro Tyr Lys Ala Leu Val Glu Arg Ala Gly Tyr Ala
545             550             555              560

Pro Leu Asn Leu Glu Ile Thr Val Val Ser Ser Glu Leu Thr Pro Ser
            565             570              575

Thr Asn Lys Glu Tyr Val Thr Cys Lys Phe His Thr Val Ile Pro Ser
            580             585              590

Pro Gln Val Lys Cys Cys Gly Ser Leu Glu Cys Lys Ala Ser Ser Lys
            595             600              605

Ala Asp Tyr Thr Cys Arg Val Phe Gly Gly Val Tyr Pro Phe Met Trp
            610             615              620

Gly Gly Ala Gln Cys Phe Cys Asp Ser Glu Asn Thr Gln Leu Ser Glu
625             630             635              640

Ala Tyr Val Glu Phe Ala Pro Asp Cys Thr Ile Asp His Ala Val Ala
            645             650              655

Leu Lys Val His Thr Ala Ala Leu Lys Val Gly Leu Arg Ile Val Tyr
            660             665              670

Gly Asn Thr Thr Ala His Leu Asp Thr Phe Val Asn Gly Val Thr Pro
            675             680              685

Gly Ser Ser Arg Asp Leu Lys Val Ile Ala Gly Pro Ile Ser Ala Ala
690             695             700

Phe Ser Pro Phe Asp His Lys Val Val Ile Arg Lys Gly Leu Val Tyr
705             710             715              720

Asn Tyr Asp Phe Pro Glu Tyr Gly Ala Met Lys Pro Gly Ala Phe Gly
            725             730              735

Asp Ile Gln Ala Ser Ser Leu Asp Ala Thr Asp Ile Val Ala Arg Thr
            740             745              750

Asp Ile Arg Leu Leu Lys Pro Ser Val Lys Asn Ile His Val Pro Tyr
            755             760              765

Thr Gln Ala Val Ser Gly Tyr Glu Met Trp Lys Asn Asn Ser Gly Arg
            770             775              780

Pro Leu Gln Glu Thr Ala Pro Phe Gly Cys Lys Ile Glu Val Glu Pro
785             790             795              800

Leu Arg Ala Ser Asn Cys Ala Tyr Gly His Ile Pro Ile Ser Ile Asp
            805             810              815

Ile Pro Asp Ala Ala Phe Val Arg Ser Ser Glu Ser Pro Thr Ile Leu
            820             825              830

Glu Val Ser Cys Thr Val Ala Asp Cys Ile Tyr Ser Ala Asp Phe Gly
            835             840              845

Gly Ser Leu Thr Leu Gln Tyr Lys Ala Asp Arg Glu Gly His Cys Pro
            850             855              860

Val His Ser His Ser Thr Thr Ala Val Leu Lys Glu Ala Thr Thr His
865             870             875              880

Val Thr Ala Val Gly Ser Ile Thr Leu His Phe Ser Thr Ser Ser Pro
            885             890              895

Gln Ala Asn Phe Ile Val Ser Leu Cys Gly Lys Lys Ser Thr Cys Asn
            900             905              910
```

-continued

```
Ala Glu Cys Lys Pro Pro Ala Asp His Ile Ile Gly Glu Pro His Lys
            915                 920                 925

Val Asp Gln Glu Phe Gln Ala Val Ser Lys Thr Ser Trp Asn Trp
    930                 935                 940

Leu Leu Ala Leu Phe Gly Gly Ala Ser Ser Leu Ile Val Val Gly Leu
945                 950                 955                 960

Ile Val Leu Val Cys Ser Ser Met Leu Ile Asn Thr Arg Arg
                965                 970

<210> SEQ ID NO 23
<211> LENGTH: 978
<212> TYPE: PRT
<213> ORGANISM: Artificial Sequence
<220> FEATURE:
<223> OTHER INFORMATION: Synthetic polypeptide

<400> SEQUENCE: 23

Thr Val Met Cys Val Leu Ala Asn Ile Thr Phe Pro Cys Asp Gln Pro
1               5                   10                  15

Pro Cys Met Pro Cys Cys Tyr Glu Lys Asn Pro His Glu Thr Leu Thr
                20                  25                  30

Met Leu Glu Gln Asn Tyr Asp Ser Arg Ala Tyr Asp Gln Leu Leu Asp
            35                  40                  45

Ala Ala Val Lys Cys Asn Ala Arg Arg Thr Arg Arg Asp Leu Asp Thr
        50                  55                  60

His Phe Thr Gln Tyr Lys Leu Ala Arg Pro Tyr Ile Ala Asp Cys Pro
65                  70                  75                  80

Asn Cys Gly His Ser Arg Cys Asp Ser Pro Ile Ala Ile Glu Glu Val
                85                  90                  95

Arg Gly Asp Ala His Ala Gly Val Ile Arg Ile Gln Thr Ser Ala Met
            100                 105                 110

Phe Gly Leu Lys Thr Asp Gly Val Asp Leu Ala Tyr Met Ser Phe Met
        115                 120                 125

Asn Gly Lys Thr Gln Lys Ser Ile Lys Ile Asp Asn Leu His Val Arg
    130                 135                 140

Thr Ser Ala Pro Cys Ser Leu Val Ser His His Gly Tyr Tyr Ile Leu
145                 150                 155                 160

Ala Gln Cys Pro Pro Gly Asp Thr Val Thr Val Gly Phe His Asp Gly
                165                 170                 175

Pro Asn Arg His Thr Cys Thr Val Ala His Lys Val Glu Phe Arg Pro
            180                 185                 190

Val Gly Arg Glu Lys Tyr Arg His Pro Pro Glu His Gly Val Glu Leu
        195                 200                 205

Pro Cys Asn Arg Tyr Thr His Lys Arg Ala Asp Gln Gly His Tyr Val
    210                 215                 220

Glu Met His Gln Pro Gly Leu Val Ala Asp His Ser Leu Leu Ser Ile
225                 230                 235                 240

His Ser Ala Lys Val Lys Ile Thr Val Pro Ser Gly Ala Gln Val Lys
                245                 250                 255

Tyr Tyr Cys Lys Cys Pro Asp Val Arg Glu Gly Ile Thr Ser Ser Asp
            260                 265                 270

His Thr Thr Thr Cys Thr Asp Val Lys Gln Cys Arg Ala Tyr Leu Ile
        275                 280                 285

Asp Asn Lys Lys Trp Val Tyr Asn Ser Gly Arg Leu Pro Arg Gly Glu
    290                 295                 300
```

```
Gly Asp Thr Phe Lys Gly Lys Leu His Val Pro Phe Val Pro Val Lys
305                 310                 315                 320

Ala Lys Cys Ile Ala Thr Leu Ala Pro Glu Pro Leu Val Glu His Lys
            325                 330                 335

His Arg Thr Leu Ile Leu His Leu His Pro Asp His Pro Thr Leu Leu
        340                 345                 350

Thr Thr Arg Ser Leu Gly Ser Asp Ala Asn Pro Thr Arg Gln Trp Ile
    355                 360                 365

Glu Arg Pro Thr Thr Val Asn Phe Thr Val Thr Gly Glu Gly Leu Glu
370                 375                 380

Tyr Thr Trp Gly Asn His Pro Pro Lys Arg Val Trp Ala Gln Glu Ser
385                 390                 395                 400

Gly Glu Gly Asn Pro His Gly Trp Pro His Glu Val Val Val Tyr Tyr
            405                 410                 415

Tyr Asn Arg Tyr Pro Leu Thr Thr Ile Ile Gly Leu Cys Thr Cys Val
        420                 425                 430

Ala Ile Ile Met Val Ser Cys Val Thr Ser Val Trp Leu Leu Cys Arg
            435                 440                 445

Thr Arg Asn Leu Cys Ile Thr Pro Tyr Lys Leu Ala Pro Asn Ala Gln
    450                 455                 460

Val Pro Ile Leu Leu Ala Leu Leu Cys Cys Ile Lys Pro Thr Arg Ala
465                 470                 475                 480

Asp Asp Thr Leu Gln Val Leu Asn Tyr Leu Trp Asn Asn Asn Gln Asn
            485                 490                 495

Phe Phe Trp Met Gln Thr Leu Ile Pro Leu Ala Ala Leu Ile Val Cys
            500                 505                 510

Met Arg Met Leu Arg Cys Leu Phe Cys Cys Gly Pro Ala Phe Leu Leu
        515                 520                 525

Val Cys Gly Ala Leu Gly Ala Ala Ala Tyr Glu His Thr Ala Val Met
    530                 535                 540

Pro Asn Lys Val Gly Ile Pro Tyr Lys Ala Leu Val Glu Arg Pro Gly
545                 550                 555                 560

Tyr Ala Pro Val His Leu Gln Ile Gln Leu Val Asn Thr Arg Ile Ile
            565                 570                 575

Pro Ser Thr Asn Leu Glu Tyr Ile Thr Cys Lys Tyr Lys Thr Lys Val
        580                 585                 590

Pro Ser Pro Val Val Lys Cys Cys Gly Ala Thr Gln Cys Thr Ser Lys
    595                 600                 605

Pro His Pro Asp Tyr Gln Cys Gln Val Phe Thr Gly Val Tyr Pro Phe
610                 615                 620

Met Trp Gly Gly Ala Tyr Cys Phe Cys Asp Thr Glu Asn Thr Gln Met
625                 630                 635                 640

Ser Glu Ala Tyr Val Glu Arg Ser Glu Glu Cys Ser Ile Asp His Ala
            645                 650                 655

Lys Ala Tyr Lys Val His Thr Gly Thr Val Gln Ala Met Val Asn Ile
        660                 665                 670

Thr Tyr Gly Ser Val Ser Trp Arg Ser Ala Asp Val Tyr Val Asn Gly
    675                 680                 685

Glu Thr Pro Ala Lys Ile Gly Asp Ala Lys Leu Ile Ile Gly Pro Leu
690                 695                 700

Ser Ser Ala Trp Ser Pro Phe Asp Asn Lys Val Val Tyr Gly His
705                 710                 715                 720
```

Glu Val Tyr Asn Tyr Asp Phe Pro Glu Tyr Gly Thr Gly Lys Ala Gly
            725                 730                 735

Ser Phe Gly Asp Leu Gln Ser Arg Thr Ser Thr Ser Asn Asp Leu Tyr
            740                 745                 750

Ala Asn Thr Asn Leu Lys Leu Gln Arg Pro Gln Ala Gly Ile Val His
            755                 760                 765

Thr Pro Phe Thr Gln Ala Pro Ser Gly Phe Glu Arg Trp Lys Arg Asp
            770                 775                 780

Lys Gly Ala Pro Leu Asn Asp Val Ala Pro Phe Gly Cys Ser Ile Ala
785                 790                 795                 800

Leu Glu Pro Leu Arg Ala Glu Asn Cys Ala Val Gly Ser Ile Pro Ile
            805                 810                 815

Ser Ile Asp Ile Pro Asp Ala Ala Phe Thr Arg Ile Ser Glu Thr Pro
            820                 825                 830

Thr Val Ser Asp Leu Glu Cys Lys Ile Thr Glu Cys Thr Tyr Ala Ser
            835                 840                 845

Asp Phe Gly Gly Ile Ala Thr Val Ala Tyr Lys Ser Ser Lys Ala Gly
            850                 855                 860

Asn Cys Pro Ile His Ser Pro Ser Gly Val Ala Val Ile Lys Glu Asn
865                 870                 875                 880

Asp Val Thr Leu Ala Glu Ser Gly Ser Phe Thr Phe His Phe Ser Thr
            885                 890                 895

Ala Asn Ile His Pro Ala Phe Lys Leu Gln Val Cys Thr Ser Ala Val
            900                 905                 910

Thr Cys Lys Gly Asp Cys Lys Pro Pro Lys Asp His Ile Val Asp Tyr
            915                 920                 925

Pro Ala Gln His Thr Glu Ser Phe Thr Ser Ala Ile Ser Ala Thr Ala
            930                 935                 940

Trp Ser Trp Leu Lys Val Leu Val Gly Gly Thr Ser Ala Phe Ile Val
945                 950                 955                 960

Leu Gly Leu Ile Ala Thr Ala Val Val Ala Leu Val Leu Phe Phe His
            965                 970                 975

Arg His

<210> SEQ ID NO 24
<211> LENGTH: 977
<212> TYPE: PRT
<213> ORGANISM: Artificial Sequence
<220> FEATURE:
<223> OTHER INFORMATION: Synthetic polypeptide

<400> SEQUENCE: 24

Thr Val Met Cys Val Leu Ala Asn Ile Thr Phe Pro Cys Glu Gln Pro
1               5                   10                  15

Pro Cys Met Pro Cys Cys Tyr Glu Lys Asn Pro His Glu Thr Leu Ser
                20                  25                  30

Met Leu Glu Gln Asn Tyr Asp Ser Gln Ala Tyr Asp Gln Leu Leu Glu
            35                  40                  45

Ala Ala Val Lys Cys Asn Gly Arg Arg Thr Arg Asp Leu Glu Thr
        50                  55                  60

His Phe Thr Gln Tyr Lys Leu Ala Arg Pro Tyr Ile Ala Asp Cys Ser
65                  70                  75                  80

Asn Cys Gly His Gly Arg Cys Asp Ser Pro Ile Ala Ile Glu Asp Val
                85                  90                  95

Arg Gly Asp Ala His Ala Gly Tyr Ile Arg Ile Gln Thr Ser Ala Met

-continued

```
                100             105                 110
Phe Gly Leu Lys Ser Asp Gly Val Asp Leu Ala Tyr Met Ser Phe Met
            115                 120             125
Asn Gly Lys Thr Leu Lys Ala Ile Lys Ile Glu His Leu Tyr Ala Arg
        130                 135             140
Thr Ser Ala Pro Cys Ser Leu Val Ser Tyr His Gly Tyr Tyr Leu Leu
145                 150                 155                 160
Ala Gln Cys Pro Pro Gly Asp Thr Val Thr Val Gly Phe Gln Asp Gly
                165                 170                 175
Ala Asn Lys His Met Cys Thr Ile Ala His Lys Val Glu Phe Lys Pro
            180                 185             190
Val Gly Arg Glu Lys Tyr Arg His Pro Ala His Gly Val Glu Leu
        195                 200             205
Pro Cys Asn Lys Tyr Thr His Lys Arg Ala Asp Gln Gly Tyr Tyr Val
        210                 215             220
Glu Met His Gln Pro Gly Val Val Ala Asp His Ser Leu Leu Ser Leu
225                 230                 235                 240
Ser Ser Thr Lys Val Lys Ile Thr Val Pro Ser Gly Ser Gln Val Lys
                245                 250                 255
Tyr Tyr Cys Lys Cys Pro Asp Val Gln Glu Gly Thr Thr Ser Gly Asp
                260                 265                 270
His Thr Thr Thr Cys Thr Asp Leu Lys Gln Cys Arg Ala Tyr Leu Ile
            275                 280                 285
Asp Asn Lys Lys Trp Val Phe Asn Ser Gly Lys Leu Pro Arg Gly Glu
        290                 295                 300
Gly Glu Thr Phe Lys Gly Lys Leu His Val Pro Phe Val Pro Val Thr
305                 310                 315                 320
Ser Lys Cys Thr Ala Thr Leu Ala Pro Glu Pro Leu Val Glu His Lys
                325                 330                 335
His Arg Ser Leu Ile Leu His Leu His Pro Glu His Pro Thr Leu Leu
            340                 345                 350
Thr Thr Arg Ala Leu Gly Asn Asp Ala Arg Pro Thr Arg Gln Trp Val
            355                 360                 365
Asp Gln Pro Thr Thr Val Asn Phe Thr Val Thr Gly Glu Gly Phe Glu
        370                 375                 380
Tyr Thr Trp Gly Asn His Pro Pro Lys Lys Ile Trp Ala Gln Glu Ser
385                 390                 395                 400
Gly Glu Gly Asn Pro His Gly Trp Pro His Glu Val Val Ile Tyr Tyr
                405                 410                 415
Tyr Asn Arg Tyr Pro Met Thr Thr Ile Val Gly Leu Cys Thr Cys Ala
                420                 425                 430
Ala Ile Ile Met Val Ser Cys Ile Thr Ser Val Trp Leu Leu Cys Arg
            435                 440                 445
Ala Arg Asn Leu Cys Ile Thr Pro Tyr Arg Leu Ala Pro Asn Ala Gln
        450                 455                 460
Val Pro Ile Leu Leu Ala Val Leu Cys Cys Val Lys Pro Thr Arg Ala
465                 470                 475                 480
Asp Asp Thr Leu Gln Val Leu Gly Tyr Leu Trp Asn His Asn Gln Asn
                485                 490                 495
Phe Phe Trp Met Gln Thr Leu Leu Pro Leu Ala Ala Leu Ile Val Cys
            500                 505                 510
Met Arg Met Leu Arg Cys Leu Leu Cys Cys Gly Pro Ala Phe Leu Leu
            515                 520                 525
```

-continued

```
Val Cys Gly Ala Trp Ala Ala Tyr Glu His Thr Ala Val Met Ser
            530                 535                 540
Asn Lys Val Gly Ile Pro Tyr Lys Ala Leu Val Glu Arg Pro Ser Tyr
545                 550                 555                 560
Ala Pro Val His Leu Gln Ile Gln Leu Val Thr Thr Lys Ile Ile Pro
                565                 570                 575
Ser Ala Asn Leu Glu Tyr Ile Thr Cys Lys Tyr Lys Thr Lys Val Leu
            580                 585                 590
Ser Pro Val Val Lys Cys Cys Gly Ala Thr Gln Cys Thr Ser Lys Gln
        595                 600                 605
His Pro Asp Tyr Gln Cys Gln Val Phe Ala Gly Val Tyr Pro Phe Met
    610                 615                 620
Trp Gly Gly Ala Tyr Cys Phe Cys Asp Thr Glu Asn Thr Gln Met Ser
625                 630                 635                 640
Glu Ala Tyr Ile Glu Arg Ala Glu Glu Cys Ser Val Asp Gln Ala Lys
                645                 650                 655
Ala Tyr Lys Val His Thr Gly Thr Val Gln Ala Val Val Asn Ile Thr
            660                 665                 670
Tyr Gly Ser Val Thr Trp Arg Ser Ala Asp Val Tyr Val Asn Gly Glu
        675                 680                 685
Thr Pro Ala Lys Ile Gly Asp Ala Lys Leu Thr Ile Gly Pro Leu Ser
    690                 695                 700
Ser Ala Trp Thr Pro Phe Asp Ser Lys Val Val Val Tyr Gly His Glu
705                 710                 715                 720
Val His Asn Tyr Asp Phe Pro Glu Tyr Gly Thr Gly Arg Ala Gly Ser
                725                 730                 735
Phe Gly Asp Leu Gln Ser Arg Thr Leu Thr Ser Asn Asp Leu Tyr Ala
            740                 745                 750
Asn Thr Asn Leu Lys Leu Gln Arg Pro Gln Pro Gly Val Val His Thr
        755                 760                 765
Pro Tyr Thr Gln Ala Pro Ser Gly Phe Glu Arg Trp Lys Lys Asp Arg
    770                 775                 780
Gly Ala Pro Leu Asn Asp Ile Ala Pro Phe Gly Cys Thr Ile Ala Leu
785                 790                 795                 800
Asp Pro Leu Arg Ala Glu Asn Cys Ala Val Gly Asn Ile Pro Leu Ser
                805                 810                 815
Ile Asp Ile Pro Asp Ala Ala Phe Thr Arg Ile Ala Glu Thr Pro Thr
            820                 825                 830
Val Ser Asp Leu Glu Cys Lys Val Thr Glu Cys Thr Tyr Ala Ser Asp
        835                 840                 845
Phe Gly Gly Ile Ala Thr Val Ala Tyr Lys Ala Ser Lys Ala Gly Asn
    850                 855                 860
Cys Pro Ile His Ser Pro Ser Gly Ile Ala Val Ile Lys Glu Asn Asp
865                 870                 875                 880
Val Thr Leu Ala Asp Ser Gly Ser Phe Thr Phe His Phe Ser Thr Ala
                885                 890                 895
Ser Ile His Pro Ala Phe Lys Met Gln Val Cys Thr Ser Val Val Thr
            900                 905                 910
Cys Lys Gly Asp Cys Lys Pro Pro Lys Asp His Ile Leu Asp Tyr Pro
        915                 920                 925
Ala Gln His Thr Glu Thr Phe Ser Ala Val Ser Ala Thr Ala Trp
    930                 935                 940
```

-continued

```
Ser Trp Leu Lys Val Leu Val Gly Ser Thr Ser Ala Phe Ile Val Leu
945                 950                 955                 960

Gly Ile Ile Ala Thr Ala Val Val Ala Leu Val Leu Phe Thr His Lys
                965                 970                 975

His

<210> SEQ ID NO 25
<211> LENGTH: 978
<212> TYPE: PRT
<213> ORGANISM: Artificial Sequence
<220> FEATURE:
<223> OTHER INFORMATION: Synthetic polypeptide

<400> SEQUENCE: 25

Thr Val Met Cys Val Leu Ala Asn Ile Thr Phe Pro Cys Asp Gln Pro
1               5                   10                  15

Pro Cys Met Pro Cys Cys Tyr Glu Lys Asn Pro His Glu Thr Leu Thr
                20                  25                  30

Met Leu Glu Gln Asn Tyr Asp Ser Arg Ala Tyr Asp Gln Leu Leu Asp
            35                  40                  45

Ala Ala Val Lys Cys Asn Ala Arg Arg Thr Arg Arg Asp Leu Asp Thr
50                  55                  60

His Phe Thr Gln Tyr Lys Leu Ala Arg Pro Tyr Ile Ala Asp Cys Pro
65                  70                  75                  80

Asn Cys Gly His Ser Arg Cys Asp Ser Pro Ile Ala Ile Glu Glu Val
                85                  90                  95

Arg Gly Asp Ala His Ala Gly Val Ile Arg Ile Gln Thr Ser Ala Met
            100                 105                 110

Phe Gly Leu Lys Thr Asp Gly Val Asp Leu Ala Tyr Met Ser Phe Met
        115                 120                 125

Asn Gly Lys Thr Gln Lys Ser Ile Lys Ile Asp Asn Leu His Val Arg
130                 135                 140

Thr Ser Ala Pro Cys Ser Leu Val Ser His His Gly Tyr Tyr Ile Leu
145                 150                 155                 160

Ala Gln Cys Pro Pro Gly Asp Thr Val Thr Val Gly Phe His Asp Gly
                165                 170                 175

Pro Asn Arg His Thr Cys Thr Val Ala His Lys Val Glu Phe Arg Pro
            180                 185                 190

Val Gly Arg Glu Lys Tyr Arg His Pro Pro Glu His Gly Val Glu Leu
        195                 200                 205

Pro Cys Asn Arg Tyr Thr His Lys Arg Ala Asp Gln Gly His Tyr Val
210                 215                 220

Glu Met His Gln Pro Gly Leu Val Ala Asp His Ser Leu Leu Ser Ile
225                 230                 235                 240

His Ser Ala Lys Val Lys Ile Thr Val Pro Ser Gly Ala Gln Val Lys
                245                 250                 255

Tyr Tyr Cys Lys Cys Pro Asp Val Arg Glu Gly Ile Thr Ser Ser Asp
            260                 265                 270

His Thr Thr Thr Cys Thr Asp Val Lys Gln Cys Arg Ala Tyr Leu Ile
        275                 280                 285

Asp Asn Lys Lys Trp Val Tyr Asn Ser Gly Arg Leu Pro Arg Gly Glu
290                 295                 300

Gly Asp Thr Phe Lys Gly Lys Leu His Val Pro Phe Val Pro Val Lys
305                 310                 315                 320

Ala Lys Cys Ile Ala Thr Leu Ala Pro Glu Pro Leu Val Glu His Lys
```

```
                    325                 330                 335
His Arg Thr Leu Ile Leu His Leu His Pro Asp His Pro Thr Leu Leu
                340                 345                 350

Thr Thr Arg Ser Leu Gly Ser Asp Ala Asn Pro Thr Arg Gln Trp Ile
                355                 360                 365

Glu Arg Pro Thr Thr Val Asn Phe Thr Val Thr Gly Glu Gly Leu Glu
            370                 375                 380

Tyr Thr Trp Gly Asn His Pro Pro Lys Arg Val Trp Ala Gln Glu Ser
385                 390                 395                 400

Gly Glu Gly Asn Pro His Gly Trp Pro His Glu Val Val Tyr Tyr
                    405                 410                 415

Tyr Asn Arg Tyr Pro Leu Thr Thr Ile Ile Gly Leu Cys Thr Cys Val
                420                 425                 430

Ala Ile Ile Met Val Ser Cys Val Thr Ser Val Trp Leu Leu Cys Arg
                435                 440                 445

Thr Arg Asn Leu Cys Ile Thr Pro Tyr Lys Leu Ala Pro Asn Ala Gln
                450                 455                 460

Val Pro Ile Leu Leu Ala Leu Leu Cys Cys Ile Lys Pro Thr Arg Ala
465                 470                 475                 480

Asp Asp Thr Leu Gln Val Leu Asn Tyr Leu Trp Asn Asn Gln Asn
                    485                 490                 495

Phe Phe Trp Met Gln Thr Leu Ile Pro Leu Ala Leu Ile Val Cys
                500                 505                 510

Met Arg Met Leu Arg Cys Leu Phe Cys Cys Gly Pro Ala Phe Leu Leu
                515                 520                 525

Val Cys Gly Ala Leu Gly Ala Ala Tyr Glu His Thr Ala Val Met
            530                 535                 540

Pro Asn Lys Val Gly Ile Pro Tyr Lys Ala Leu Val Glu Arg Pro Gly
545                 550                 555                 560

Tyr Ala Pro Val His Leu Gln Ile Gln Leu Val Asn Thr Arg Ile Ile
                565                 570                 575

Pro Ser Thr Asn Leu Glu Tyr Ile Thr Cys Lys Tyr Lys Thr Lys Val
                580                 585                 590

Pro Ser Pro Val Val Lys Cys Cys Gly Ala Thr Gln Cys Thr Ser Lys
            595                 600                 605

Pro His Pro Asp Tyr Gln Cys Gln Val Phe Thr Gly Val Tyr Pro Phe
    610                 615                 620

Met Trp Gly Gly Ala Tyr Cys Phe Cys Asp Thr Glu Asn Thr Gln Met
625                 630                 635                 640

Ser Glu Ala Tyr Val Glu Arg Ser Glu Glu Cys Ser Ile Asp His Ala
                645                 650                 655

Lys Ala Tyr Lys Val His Thr Gly Thr Val Gln Ala Met Val Asn Ile
                660                 665                 670

Thr Tyr Gly Ser Val Ser Trp Arg Ser Ala Asp Val Tyr Val Asn Gly
            675                 680                 685

Glu Thr Pro Ala Lys Ile Gly Asp Ala Lys Leu Ile Ile Gly Pro Leu
    690                 695                 700

Ser Ser Ala Trp Ser Pro Phe Asp Asn Lys Val Val Tyr Gly His
705                 710                 715                 720

Glu Val Tyr Asn Tyr Asp Phe Pro Glu Tyr Gly Thr Gly Lys Ala Gly
                725                 730                 735

Ser Phe Gly Asp Leu Gln Ser Arg Thr Ser Thr Ser Asn Asp Leu Tyr
            740                 745                 750
```

-continued

Ala Asn Thr Asn Leu Lys Leu Gln Arg Pro Gln Ala Gly Ile Val His
        755                 760                 765

Thr Pro Phe Thr Gln Ala Pro Ser Gly Phe Glu Arg Trp Lys Arg Asp
    770                 775                 780

Lys Gly Ala Pro Leu Asn Asp Val Ala Pro Phe Gly Cys Ser Ile Ala
785                 790                 795                 800

Leu Glu Pro Leu Arg Ala Glu Asn Cys Ala Val Gly Ser Ile Pro Ile
                805                 810                 815

Ser Ile Asp Ile Pro Asp Ala Ala Phe Thr Arg Ile Ser Glu Thr Pro
                820                 825                 830

Thr Val Ser Asp Leu Glu Cys Lys Ile Thr Glu Cys Thr Tyr Ala Ser
        835                 840                 845

Asp Phe Gly Gly Ile Ala Thr Val Ala Tyr Lys Ser Ser Lys Ala Gly
    850                 855                 860

Asn Cys Pro Ile His Ser Pro Ser Gly Val Ala Val Ile Lys Glu Asn
865                 870                 875                 880

Asp Val Thr Leu Ala Glu Ser Gly Ser Phe Thr Phe His Phe Ser Thr
                885                 890                 895

Ala Asn Ile His Pro Ala Phe Lys Leu Gln Val Cys Thr Ser Ala Val
                900                 905                 910

Thr Cys Lys Gly Asp Cys Lys Pro Pro Lys Asp His Ile Val Asp Tyr
        915                 920                 925

Pro Ala Gln His Thr Glu Ser Phe Thr Ser Ala Ile Ser Ala Thr Ala
    930                 935                 940

Trp Ser Trp Leu Lys Val Leu Val Gly Gly Thr Ser Ala Phe Ile Val
945                 950                 955                 960

Leu Gly Leu Ile Ala Thr Ala Val Val Ala Leu Val Leu Phe His
                965                 970                 975

Arg His

<210> SEQ ID NO 26
<211> LENGTH: 964
<212> TYPE: PRT
<213> ORGANISM: Artificial Sequence
<220> FEATURE:
<223> OTHER INFORMATION: Synthetic polypeptide

<400> SEQUENCE: 26

Val Met Cys Leu Leu Ala Asn Thr Thr Phe Pro Cys Ser Gln Pro Pro
1               5                   10                  15

Cys Thr Pro Cys Cys Tyr Glu Lys Glu Pro Glu Lys Thr Leu Arg Met
            20                  25                  30

Leu Glu Asp Asn Val Met Arg Pro Gly Tyr Tyr Gln Leu Leu Gln Ala
        35                  40                  45

Ser Leu Thr Cys Ser Pro His Arg Gln Arg Ser Thr Lys Asp Asn
    50                  55                  60

Phe Asn Val Tyr Lys Ala Thr Arg Pro Tyr Leu Ala His Cys Pro Asp
65                  70                  75                  80

Cys Gly Glu Gly His Ser Cys His Ser Pro Val Ala Leu Glu Arg Ile
                85                  90                  95

Arg Asn Glu Ala Thr Asp Gly Thr Leu Lys Ile Gln Val Ser Leu Gln
                100                 105                 110

Ile Gly Ile Lys Thr Asp Asp Ser His Asp Trp Thr Lys Leu Arg Tyr
            115                 120                 125

```
Met Asp Asn His Met Pro Ala Asp Ala Glu Arg Ala Gly Leu Phe Val
130                 135                 140

Arg Thr Ser Ala Pro Cys Thr Ile Thr Gly Thr Met Gly His Phe Ile
145                 150                 155                 160

Leu Ala Arg Cys Pro Lys Gly Glu Thr Leu Thr Val Gly Phe Thr Asp
                165                 170                 175

Ser Arg Lys Ile Ser His Ser Cys Thr His Pro Phe His His Asp Pro
                180                 185                 190

Pro Val Ile Gly Arg Glu Lys Phe His Ser Arg Pro Gln His Gly Lys
            195                 200                 205

Glu Leu Pro Cys Ser Thr Tyr Val Gln Ser Thr Ala Ala Thr Thr Glu
210                 215                 220

Glu Ile Glu Val His Met Pro Pro Asp Thr Pro Asp Arg Thr Leu Met
225                 230                 235                 240

Ser Gln Gln Ser Gly Asn Val Lys Ile Thr Val Asn Gly Gln Thr Val
                245                 250                 255

Arg Tyr Lys Cys Asn Cys Gly Gly Ser Asn Glu Gly Leu Thr Thr Thr
                260                 265                 270

Asp Lys Val Ile Asn Asn Cys Lys Val Asp Gln Cys His Ala Ala Val
            275                 280                 285

Thr Asn His Lys Lys Trp Gln Tyr Asn Ser Pro Leu Val Pro Arg Asn
290                 295                 300

Ala Glu Leu Gly Asp Arg Lys Gly Lys Ile His Ile Pro Phe Pro Leu
305                 310                 315                 320

Ala Asn Val Thr Cys Arg Val Pro Lys Ala Arg Asn Pro Thr Val Thr
                325                 330                 335

Tyr Gly Lys Asn Gln Val Ile Met Leu Leu Tyr Pro Asp His Pro Thr
                340                 345                 350

Leu Leu Ser Tyr Arg Asn Met Gly Glu Glu Pro Asn Tyr Gln Glu Glu
            355                 360                 365

Trp Val Thr His Lys Lys Glu Ile Arg Leu Thr Val Pro Thr Glu Gly
370                 375                 380

Leu Glu Val Thr Trp Gly Asn Asn Glu Pro Tyr Lys Tyr Trp Pro Gln
385                 390                 395                 400

Leu Ser Thr Asn Gly Thr Ala His Gly His Pro His Glu Ile Ile Leu
                405                 410                 415

Tyr Tyr Tyr Glu Leu Tyr Pro Thr Met Thr Val Val Val Ser Val
                420                 425                 430

Ala Thr Phe Ile Leu Leu Ser Met Val Gly Val Ala Val Gly Met Cys
                435                 440                 445

Met Cys Ala Arg Arg Arg Cys Ile Thr Pro Tyr Glu Leu Thr Pro Gly
450                 455                 460

Ala Thr Val Pro Phe Leu Leu Ser Leu Ile Cys Cys Ile Arg Thr Ala
465                 470                 475                 480

Lys Ala Ala Thr Tyr Gln Glu Ala Ala Val Tyr Leu Trp Asn Glu Gln
                485                 490                 495

Gln Pro Leu Phe Trp Leu Gln Ala Leu Ile Pro Leu Ala Ala Leu Ile
            500                 505                 510

Val Leu Cys Asn Cys Leu Arg Leu Leu Pro Cys Cys Cys Lys Thr Leu
            515                 520                 525

Ala Phe Leu Ala Val Met Ser Val Gly Ala His Thr Val Ser Ala Tyr
530                 535                 540

Glu His Val Thr Val Ile Pro Asn Thr Val Gly Val Pro Tyr Lys Thr
```

-continued

```
545                 550                 555                 560
Leu Val Asn Arg Pro Gly Tyr Ser Pro Met Val Leu Glu Met Glu Leu
                565                 570                 575
Leu Ser Val Thr Leu Glu Pro Thr Leu Ser Leu Asp Tyr Ile Thr Cys
                580                 585                 590
Glu Tyr Lys Thr Val Ile Pro Ser Pro Tyr Val Lys Cys Gly Thr
                595                 600                 605
Ala Glu Cys Lys Asp Lys Ser Leu Pro Asp Tyr Ser Cys Lys Val Phe
    610                 615                 620
Thr Gly Val Tyr Pro Phe Met Trp Gly Gly Ala Tyr Cys Phe Cys Asp
625                 630                 635                 640
Ala Glu Asn Thr Gln Leu Ser Glu Ala His Val Glu Lys Ser Glu Ser
                645                 650                 655
Cys Lys Thr Glu Phe Ala Ser Ala Tyr Arg Ala His Thr Ala Ser Ala
                660                 665                 670
Ser Ala Lys Leu Arg Val Leu Tyr Gln Gly Asn Asn Ile Thr Val Thr
                675                 680                 685
Ala Tyr Ala Asn Gly Asp His Ala Val Thr Val Lys Asp Ala Lys Phe
    690                 695                 700
Ile Val Gly Pro Met Ser Ser Ala Trp Thr Pro Phe Asp Asn Lys Ile
705                 710                 715                 720
Val Val Tyr Lys Gly Asp Val Tyr Asn Met Asp Tyr Pro Pro Phe Gly
                725                 730                 735
Ala Gly Arg Pro Gly Gln Phe Gly Asp Ile Gln Ser Arg Thr Pro Glu
                740                 745                 750
Ser Glu Asp Val Tyr Ala Asn Thr Gln Leu Val Leu Gln Arg Pro Ser
                755                 760                 765
Ala Gly Thr Val His Val Pro Tyr Ser Gln Ala Pro Ser Gly Phe Lys
                770                 775                 780
Tyr Trp Leu Lys Glu Arg Gly Ala Ser Leu Gln His Thr Ala Pro Phe
785                 790                 795                 800
Gly Cys Gln Ile Ala Thr Asn Pro Val Arg Ala Met Asn Cys Ala Val
                805                 810                 815
Gly Asn Met Pro Ile Ser Ile Asp Ile Pro Asp Ala Ala Phe Thr Arg
                820                 825                 830
Val Val Asp Ala Pro Ser Leu Thr Asp Met Ser Cys Glu Val Pro Ala
                835                 840                 845
Cys Thr His Ser Ser Asp Phe Gly Gly Val Ala Ile Ile Lys Tyr Ala
850                 855                 860
Ala Ser Lys Lys Gly Lys Cys Ala Val His Ser Met Thr Asn Ala Val
865                 870                 875                 880
Thr Ile Arg Glu Ala Glu Ile Glu Val Glu Gly Asn Ser Gln Leu Gln
                885                 890                 895
Ile Ser Phe Ser Thr Ala Leu Ala Ser Ala Glu Phe Arg Val Gln Val
                900                 905                 910
Cys Ser Thr Gln Val His Cys Ala Ala Glu Cys His Pro Pro Lys Asp
                915                 920                 925
His Ile Val Asn Tyr Pro Ala Ser His Thr Thr Leu Gly Val Gln Asp
                930                 935                 940
Ile Ser Ala Thr Ala Met Ser Trp Val Gln Lys Ile Thr Gly Gly Val
945                 950                 955                 960
Gly Leu Val Val
```

ALPHAVIRUS IMMUNOGENS AND METHODS OF USE

CROSS REFERENCE TO RELATED APPLICATIONS

This application claims the benefit of U.S. Provisional Application No. 63/144,551, filed Feb. 2, 2021, which is herein incorporated by reference in its entirety.

ACKNOWLEDGMENT OF GOVERNMENT SUPPORT

This invention was made with government support under Contract No. 89233218CNA000001 awarded by the U.S. Department of Energy/National Nuclear Security Administration and Funded Proposal FRCALL16-BR-TA7-G14-2-0002 awarded by the U.S. Department of Defense/Defense Threat Reduction Agency. The government has certain rights in the invention.

FIELD

This disclosure concerns synthetic alphavirus polypeptides, and sets of polypeptides, designed to maximize the number of potential immunogenic epitopes from wild-type virus. This disclosure further concerns compositions that include a cocktail of the synthetic polypeptides, or nucleic acid molecules encoding the polypeptides, and their use to elicit an immune response against alphaviruses in a subject.

BACKGROUND

Three encephalitic alphaviruses, Eastern, Western, and Venezuelan equine encephalitis viruses (i.e., EEEV, WEEV, and VEEV, respectively) present episodic public health risks. Chikungunya virus (CHIKV), another alphavirus, also causes disease in humans characterized by high fever and severe joint pain. A single vaccine that induces protective immunity against not only individual isolates of these viruses, but against all known variant strains, would be a significant contribution to public health.

SUMMARY

Disclosed herein are synthetic immunogenic polypeptides, and cocktails thereof, derived from members of the alphavirus genus. These immunogens are based on natural alphavirus proteins, but have improved coverage of potential epitopes. The disclosed immunogenic compositions, which include multiple synthetic polypeptide immunogens, or nucleic acid molecules encoding the synthetic polypeptide immunogens, are capable of inducing broader protection against alphavirus infection than conventionally designed vaccines.

Provided herein are synthetic immunogenic polypeptides having an amino acid sequence at least 95% identical to any one of SEQ ID NOs: 1-26, or an immunogenic portion thereof. In some embodiments, the immunogenic polypeptides are at least 99% identical to any one of SEQ ID NOs: 1-26, or an immunogenic portion thereof. In some examples, the synthetic immunogenic polypeptides have an amino acid sequence comprising or consisting of any one of SEQ ID NOs: 1-26, or an immunogenic portion thereof, such as an immunogenic portion that is at least 18 amino acids in length.

Further provided are sets of synthetic immunogenic polypeptides that include two more polypeptides disclosed herein. In some embodiments, the set of immunogenic polypeptides includes three or more, four or more, five or more, six or more, or seven or more polypeptides disclosed herein. In some examples, the set includes at least three polypeptides, wherein at least one polypeptide is derived from Venezuelan equine encephalitis virus (VEEV), at least one polypeptide is derived from Western equine encephalitis virus (WEEV), and at least one polypeptide is derived from Eastern equine encephalitis virus (EEEV). In particular examples, the set further includes at least one polypeptide derived from Chikungunya virus (CHIKV).

Also provided herein are isolated nucleic acid molecules (such as DNA, cDNA, RNA or mRNA) encoding the synthetic immunogenic polypeptides, as well as sets of nucleic acid molecules encoding the sets of immunogenic polypeptides disclosed herein. Vectors containing the isolated nucleic acid molecules are further provided. In some embodiments, each isolated nucleic acid molecule is contained in a separate vector. In other embodiments, two or more of the isolated nucleic acid molecules are contained in a single vector.

Further provided herein are compositions that include a synthetic immunogenic polypeptide, a set of synthetic immunogenic polypeptides, a nucleic acid molecule, a set of nucleic acid molecules, or a vector disclosed herein.

Methods of inducing an immune response against one or more alphaviruses by administering any of the compositions disclosed herein is also provided. In some examples, the alphavirus is VEEV, WEEV, EEEV and/or CHIKV.

The foregoing and other objects and features of the disclosure will become more apparent from the following detailed description, which proceeds with reference to the accompanying figures.

BRIEF DESCRIPTION OF THE DRAWINGS

FIGS. 1A-1B: Coverage of a natural alphavirus sequence set by candidate mosaic/epigraph immunogenic compositions (FIG. 1A) and conventional vaccine candidates (FIG. 1B). For each natural sequence, the 9-mer coverage was computed (the fraction of the 9-mers present in that sequence that are included in each composition). Sequences are plotted left-to-right in descending rank order of coverage. For example, for the 6K protein, the 04.SIN:ZPC and VEEV single-mosaic compositions both cover 56% of VEEV isolates at a level of 62% of 9-mers or better, and 78% of isolates at a level of at least 37% of 9-mers.

SEQUENCE LISTING

The amino acid sequences listed in the accompanying sequence listing are shown using standard three letter code for amino acids, as defined in 37 C.F.R. 1.822. The Sequence Listing is submitted as an ASCII text file, created on Jan. 20, 2022, 250,879 bytes, which is incorporated by reference herein. In the accompanying sequence listing:

SEQ ID NO: 1 is the amino acid sequence of synthetic polypeptide VEEVs+.structPs.uniq.EG-1.1.

SEQ ID NO: 2 is the amino acid sequence of synthetic polypeptide VEEVs+.structPs.uniq.EG-2.1.

SEQ ID NO: 3 is the amino acid sequence of synthetic polypeptide VEEVs+.structPs.uniq.EG-2.2.

SEQ ID NO: 4 is the amino acid sequence of synthetic polypeptide VEEVs+.structPs.uniq.EG-3.1.

SEQ ID NO: 5 is the amino acid sequence of synthetic polypeptide VEEVs+.structPs.uniq.EG-3.2.

SEQ ID NO: 6 is the amino acid sequence of synthetic polypeptide VEEVs+.structPs.uniq.EG-3.3.

SEQ ID NO: 7 is the amino acid sequence of synthetic polypeptide WEEVs+.structPs.uniq.EG-1.1.

SEQ ID NO: 8 is the amino acid sequence of synthetic polypeptide WEEVs+.structPs.uniq.EG-2.1.

SEQ ID NO: 9 is the amino acid sequence of synthetic polypeptide WEEVs+.structPs.uniq.EG-2.2.

SEQ ID NO: 10 is the amino acid sequence of synthetic polypeptide EEEVs+.structPs.uniq.EG-1.1.

SEQ ID NO: 11 is the amino acid sequence of synthetic polypeptide EEEVs+.structPs.uniq.EG-2.1.

SEQ ID NO: 12 is the amino acid sequence of synthetic polypeptide EEEVs+.structPs.uniq.EG-2.2.

SEQ ID NO: 13 is the amino acid sequence of synthetic polypeptide CHKs+.structPs.uniq.EG-1.1.

SEQ ID NO: 14 is the amino acid sequence of synthetic polypeptide VEEVs+.structPs.uniq.EG-1.1-noCP.

SEQ ID NO: 15 is the amino acid sequence of synthetic polypeptide VEEVs+.structPs.uniq.EG-2.1-noCP.

SEQ ID NO: 16 is the amino acid sequence of synthetic polypeptide VEEVs+.structPs.uniq.EG-2.2-noCP.

SEQ ID NO: 17 is the amino acid sequence of synthetic polypeptide VEEVs+.structPs.uniq.EG-3.1-noCP.

SEQ ID NO: 18 is the amino acid sequence of synthetic polypeptide VEEVs+.structPs.uniq.EG-3.2-noCP.

SEQ ID NO: 19 is the amino acid sequence of synthetic polypeptide VEEVs+.structPs.uniq.EG-3.3-noCP.

SEQ ID NO: 20 is the amino acid sequence of synthetic polypeptide WEEVs+.structPs.uniq.EG-1.1-noCP.

SEQ ID NO: 21 is the amino acid sequence of synthetic polypeptide WEEVs+.structPs.uniq.EG-2.1-noCP.

SEQ ID NO: 22 is the amino acid sequence of synthetic polypeptide WEEVs+.structPs.uniq.EG-2.2-noCP.

SEQ ID NO: 23 is the amino acid sequence of synthetic polypeptide EEEVs+.structPs.uniq.EG-1.1-noCP.

SEQ ID NO: 24 is the amino acid sequence of synthetic polypeptide EEEVs+.structPs.uniq.EG-2.1-noCP.

SEQ ID NO: 25 is the amino acid sequence of synthetic polypeptide EEEVs+.structPs.uniq.EG-2.2-noCP.

SEQ ID NO: 26 is the amino acid sequence of synthetic polypeptide CHKs+.structPs.uniq.EG-1.1-noCP.

DETAILED DESCRIPTION

I. Abbreviations

CHKV chikungunya virus
CP capsid protein
EEEV Eastern equine encephalitis viruses
WEEV Western equine encephalitis viruses
VEEV Venezuelan equine encephalitis viruses II. Terms and Methods Unless otherwise noted, technical terms are used according to conventional usage. Definitions of common terms in molecular biology may be found in Benjamin Lewin, Genes X, published by Jones & Bartlett Publishers, 2009; and Meyers et al. (eds.), *The Encyclopedia of Cell Biology and Molecular Medicine*, published by Wiley-VCH in 16 volumes, 2008; and other similar references.

As used herein, the singular forms "a," "an," and "the," refer to both the singular as well as plural, unless the context clearly indicates otherwise. For example, the term "an antigen" includes single or plural antigens and can be considered equivalent to the phrase "at least one antigen." As used herein, the term "comprises" means "includes." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described herein. In case of conflict, the present specification, including explanations of terms, will control. In addition, the materials, methods, and examples are illustrative only and not intended to be limiting.

To facilitate review of the various embodiments, the following explanations of terms are provided:

Adjuvant: A substance or vehicle that non-specifically enhances the immune response to an antigen. Adjuvants can include a suspension of minerals (alum, aluminum hydroxide, or phosphate) on which antigen is adsorbed; or water-in-oil emulsion in which antigen solution is emulsified in mineral oil (for example, Freund's incomplete adjuvant), sometimes with the inclusion of killed mycobacteria (Freund's complete adjuvant) to further enhance antigenicity. Immunostimulatory oligonucleotides (such as those including a CpG motif) can also be used as adjuvants (for example, see U.S. Pat. Nos. 6,194,388; 6,207,646; 6,214,806; 6,218,371; 6,239,116; 6,339,068; 6,406,705; and 6,429,199). Adjuvants also include biological molecules, such as costimulatory molecules. Exemplary biological adjuvants include IL-2, RANTES, GM-CSF, TNF-α, IFN-7, G-CSF, LFA-3, CD72, B7-1, B7-2, OX-40L and 41 BBL. In some embodiments herein, the adjuvant is a liposome-based adjuvant, such as Army Liposome Formulation (ALF; see Alving et al., *Expert Rev Vaccines* 19(3): 279-292, 2020). Adjuvants can be used in combination with the disclosed immunogenic polypeptides, nucleic acid molecules, vectors and compositions.

Administration: To provide or give a subject an agent, such as a therapeutic agent (e.g. an immunogenic composition), by any effective route. Exemplary routes of administration include, but are not limited to, injection (such as subcutaneous, intramuscular, intradermal, intraperitoneal, and intravenous), oral, intraductal, sublingual, rectal, transdermal, intranasal, vaginal and inhalation routes.

Alphavirus: A genus of small, positive-sense, single-stranded RNA viruses belonging to the Togaviridae family. These viruses are transmitted by arthropods (typically mosquitoes) and can cause disease in both humans and animals. The alphaviruses express a structural polyprotein composed of the capsid, E3, E2, 6K and E1 proteins. Alphaviruses include, for example, Chikungunya virus (CHIKV), Venezuelan equine encephalitis virus (VEEV), Western equine encephalitis virus (WEEV), Eastern equine encephalitis virus (EEEV), Sindbis virus, Semliki Forest virus and Ross River virus.

Antibody: An immunoglobulin molecule produced by B lymphoid cells with a specific amino acid sequence. Antibodies are evoked in humans or other animals by a specific antigen (immunogen). Antibodies are characterized by reacting specifically with the antigen in some demonstrable way, antibody and antigen each being defined in terms of the other. "Eliciting an antibody response" refers to the ability of an antigen or other molecule to induce the production of antibodies.

Antigen: A compound, composition, or substance that can stimulate the production of antibodies or a T cell response in a subject, including compositions that are injected or absorbed into a subject. An antigen reacts with the products of specific humoral or cellular immunity, including those induced by heterologous antigens, such as the disclosed polypeptides. "Epitope" or "antigenic determinant" refers to the region of an antigen to which B and/or T cells respond. In one embodiment, T cells respond to the epitope, when the epitope is presented in conjunction with an MHC molecule. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, about 8-10, or about 6-22 amino acids in a unique spatial conformation. Methods of determining spatial conformation of epitopes include, for example, x-ray crystallography and nuclear magnetic resonance.

Examples of antigens include, but are not limited to, peptides, lipids, polysaccharides, and nucleic acids containing antigenic determinants, such as those recognized by an immune cell. In some examples, antigens include peptides derived from a pathogen of interest. Exemplary pathogens include bacteria, fungi, viruses and parasites. In specific examples, an antigen is derived from an alphavirus, such as a structural protein from VEEV, WEEV, EEEV or CHIKV.

Chikungunya virus (CHIKV): A member of the alphavirus genus. CHIKV is generally transmitted from mosquitoes to humans and causes symptoms including fever, joint pain and swelling, headache and rash.

EEEV: A member of the alphavirus genus. EEEV can infect a wide range of animals, including mammals, birds, reptiles and amphibians. Transmission to humans occurs through the bite of an infected mosquito. Symptoms of EEEV infection include high fever, muscle pain, altered mental status, headache, encephalitis, photophobia and seizures.

Fusion protein: A protein containing amino acid sequence from at least two different (heterologous) proteins or peptides. Fusion proteins can be generated, for example, by expression of a nucleic acid sequence engineered from nucleic acid sequences encoding at least a portion of two different (heterologous) proteins. To create a fusion protein, the nucleic acid sequences must be in the same reading frame and contain no internal stop codons. Fusion proteins, particularly short fusion proteins, can also be generated by chemical synthesis. In some examples herein, the fusion protein includes an immunogenic polypeptide disclosed herein fused to a heterologous protein.

Heterologous: A heterologous protein, polypeptide or nucleic acid refers to a protein, polypeptide or nucleic acid derived from a different source or species. A heterologous protein or polypeptide may also refer to a protein or polypeptide with an amino acid sequence that differs from a naturally occurring protein or polypeptide. Similarly, a heterologous nucleic acid refer to a nucleic acid with a nucleotide sequence that differs from a naturally occurring nucleic acid molecule.

Immune response: A response of a cell of the immune system, such as a B-cell, T-cell, macrophage or polymorphonucleocyte, to a stimulus such as an antigen or vaccine. An immune response can include any cell of the body involved in a host defense response, including for example, an epithelial cell that secretes an interferon or a cytokine. An immune response includes, but is not limited to, an innate immune response or inflammation. As used herein, a protective immune response refers to an immune response that protects a subject from infection (prevents infection or prevents the development of disease associated with infection). Methods of measuring immune responses are well known in the art and include, for example, measuring proliferation and/or activity of lymphocytes (such as B or T cells), secretion of cytokines or chemokines, inflammation, antibody production and the like.

Immunogen: A compound, composition, or substance which is capable, under appropriate conditions, of stimulating an immune response, such as the production of antibodies or a T-cell response in an animal, including compositions that are injected or absorbed into an animal.

Immunogenic polypeptide: A protein or a portion thereof that is capable of inducing an immune response in a subject, such as a subject infected with, or at risk of infection with, a pathogen. Administration of an immunogenic polypeptide derived from a pathogen of interest can elicit an immune response against the pathogen. Administration of an immunogenic polypeptide can lead to protective immunity against a pathogen of interest (such as an alphavirus). In the context of the present disclosure, "an immunogenic portion" of an immunogenic polypeptide (such as an immunogenic portion of a polypeptide of any one of SEQ ID NOs: 1-26), is a fragment of the polypeptide that retains immunogenicity (the ability to induce an immune response). In some examples, the immunogenic portion is at least 18 amino acids in length.

Immunogenic composition: A composition comprising an immunogenic polypeptide or a nucleic acid encoding an immunogenic polypeptide that induces a measurable CTL response against virus expressing the immunogenic polypeptide or a portion thereof, induces a measurable helper T cell response, or induces a measurable B cell response (such as production of antibodies) against the immunogenic polypeptide or a portion thereof. In one example, an "immunogenic composition" is composition including one or more polypeptides from an alphavirus, such as one or more of the immunogenic polypeptides disclosed herein. It further refers to isolated nucleic acids encoding an immunogenic polypeptide, such as a nucleic acid that can be used to express the immunogenic polypeptide (and thus be used to elicit an immune response against this polypeptide or a portion thereof).

For in vitro use, an immunogenic composition may consist of at least one (such as two or more) isolated polypeptides, peptide epitopes, or nucleic acids encoding the polypeptide or peptide epitope. For in vivo use, the immunogenic composition will typically include at least one (such as one, two, three, or more) polypeptide, peptide, or nucleic acid in pharmaceutically acceptable carriers, and/or other agents. Any particular peptide, such as a disclosed polypeptide or a nucleic acid encoding the polypeptide, can be readily tested for its ability to induce a CTL, helper T cell, or B cell response by art-recognized assays. Immunogenic compositions can include adjuvants, which are well known to one of skill in the art.

Immunize: To render a subject protected from an infectious disease, such as by vaccination.

Isolated: An "isolated" biological component (such as a nucleic acid molecule, protein, virus or cell) has been substantially separated or purified away from other biological components in the cell or tissue of an organism, or the organism itself, in which the component naturally occurs, such as other chromosomal and extra-chromosomal DNA and RNA, proteins and cells. Nucleic acid molecules and proteins that have been "isolated" include those purified by standard purification methods. The term also embraces nucleic acid molecules and proteins prepared by recombinant expression in a host cell as well as chemically synthesized nucleic acid molecules and proteins. Isolated does not require absolute purity, and can include protein, peptide, or nucleic acid molecules that are at least 50% isolated, such as at least 75%, 80%, 90%, 95%, 98%, 99%, or even 99.9% isolated.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable carrier: The pharmaceutically acceptable carriers (vehicles) useful in this disclosure are conventional. *Remington: The Science and Practice of Pharmacy*, The University of the Sciences in Philadelphia, Editor, Lippincott, Williams, & Wilkins, Philadelphia, PA, 21$^{st}$ Edition (2005), describes compositions and formulations suitable for pharmaceutical delivery of one or more therapeutic compounds, molecules or agents (e.g. immunogenic polypeptides).

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide, peptide or protein: A polymer in which the monomers are amino acid residues which are joined together through amide bonds. When the amino acids are alpha-amino acids, either the L-optical isomer or the D-optical isomer can be used. The terms "polypeptide," "peptide" and "protein" are used interchangeably herein. These terms apply to amino acid polymers in which one or more amino acid residue is an artificial chemical mimetic of a corresponding naturally occurring amino acid, as well as to naturally occurring amino acid polymers and non-naturally occurring amino acid polymers. The term "residue" or "amino acid residue" includes reference to an amino acid that is incorporated into a protein, polypeptide, or peptide.

A conservative substitution in a polypeptide is a substitution of one amino acid residue in a protein sequence for a different amino acid residue having similar biochemical properties. Typically, conservative substitutions have little to no impact on the activity of a resulting polypeptide. For example, a protein or peptide including one or more conservative substitutions (for example no more than 1, 2, 3, 4 or 5 substitutions) retains the structure and function of the wild-type protein or peptide. A polypeptide can be produced to contain one or more conservative substitutions by manipulating the nucleotide sequence that encodes that polypeptide using, for example, standard procedures such as site-directed mutagenesis or PCR. In one example, such variants can be readily selected by testing antibody cross-reactivity or its ability to induce an immune response. Examples of conservative substitutions are shown below.

| Original Residue | Conservative Substitutions |
| --- | --- |
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain.

The substitutions which in general are expected to produce the greatest changes in protein properties will be non-conservative, for instance changes in which (a) a hydrophilic residue, for example, seryl or threonyl, is substituted for (or by) a hydrophobic residue, for example, leucyl, isoleucyl, phenylalanyl, valyl or alanyl; (b) a cysteine or proline is substituted for (or by) any other residue; (c) a residue having an electropositive side chain, for example, lysyl, arginyl, or histadyl, is substituted for (or by) an electronegative residue, for example, glutamyl or aspartyl; or (d) a residue having a bulky side chain, for example, phenylalanine, is substituted for (or by) one not having a side chain, for example, glycine.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Recombinant: A recombinant nucleic acid molecule, protein or virus is one that has a sequence that is not naturally occurring or has a sequence that is made by an artificial combination of two otherwise separated segments of sequence. This artificial combination can be accomplished by chemical synthesis or by the artificial manipulation of isolated segments of nucleic acid molecules, such as by genetic engineering techniques. The term "recombinant" also includes nucleic acids, proteins and viruses that have been altered solely by addition, substitution, or deletion of a portion of the natural nucleic acid molecule, protein or virus.

Subject: Living multi-cellular vertebrate organisms, a category that includes human and non-human mammals. In some embodiments herein, the subject is a human or veterinary subject, such as an equine species, for example a horse.

Synthetic: Produced by artificial means in a laboratory, for example a synthetic nucleic acid or protein can be chemically synthesized in a laboratory.

Therapeutically effective amount or effective amount: The amount of an agent, such as a nucleic acid, polypeptide, or other therapeutic agent, that is sufficient to prevent, treat (including prophylaxis), reduce and/or ameliorate the symptoms and/or underlying causes of a disorder or disease, for example to prevent, inhibit, and/or treat an alphavirus infection, such as a VEEV, WEEV, EEEV or CHIKV infection. In some embodiments, an "effective amount" is an amount necessary to induce an immune response sufficient to prevent or inhibit infection by an alphavirus. For instance, this can be the amount necessary to inhibit viral replication or to measurably alter outward symptoms of the viral infection, such as an increase of T cell counts antigen-specific antibodies. In general, this amount will be sufficient to measurably inhibit virus (for example, alphavirus) replication or infectivity, such as by about 20%, about 30%, about 40%, about 50%, about 60%, at least 70%, about 80%, about 90% or about 100% compared to replication or infectivity in the absence of treatment.

Vaccine: A preparation of immunogenic material capable of stimulating an immune response, administered for the prevention, amelioration, or treatment of disease, such as an infectious disease. The immunogenic material may include, for example, attenuated or killed microorganisms (such as attenuated viruses), or antigenic proteins, peptides or DNA derived from an infectious microorganism. Vaccines may elicit both prophylactic (preventative) and therapeutic responses. Methods of administration vary according to the vaccine, but may include inoculation, ingestion, inhalation or other forms of administration. Inoculations can be delivered by any of a number of routes, including parenteral, such as intravenous, subcutaneous or intramuscular. Vaccines may be administered with an adjuvant to boost the immune response.

Vector: A vector is a nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. A vector can also include one or more selectable marker genes and other genetic elements. An expression vector is a vector that contains the necessary regulatory sequences to allow transcription and translation of inserted gene or genes.

VEEV: A member of the alphavirus genus. VEEV can infect all equine species (including horses, donkeys and zebras) as well as humans. This virus is transmitted by a variety of arthropod vectors including several different species of mosquito. In humans, symptoms of infection include fever, headache, encephalitis, malaise, tremor, myalgia, nausea and vomiting.

WEEV: A member of the alphavirus genus. WEEV is transmitted by mosquitoes, but also circulates in birds and other animals. WEEV can cause disease in humans and equine species. In humans, WEEV infection is often asymptomatic, but in severe cases can cause encephalitis, delirium, coma, paralysis and death.

III. Description of Several Embodiments

Research into vaccines against human immunodeficiency virus (HIV), a highly variable virus, has led to the development of methods for optimizing immunological coverage of diverse pathogens (Fischer et al., *Nat Med* 13, 100-106, 2007; Thurmond et al., *Bioinformatics* 24, 1639-1640, 2008; Theiler and Korber, *Stat Med* doi:10.1002/sim.7203, 2017). Vaccines generated by these methods include long protein sequences that strongly resemble natural proteins throughout their length, typically delivered as a cocktail of 2-4 distinct proteins, which are engineered to have minimal "rare" epitopes, and to be mutually non-redundant (e.g., a given cocktail will include all common variants of a given potential epitope, up to the limits of the common variants and the number of proteins in the cocktail).

The present disclosure describes the design of synthetic immunogens, and combinations thereof, targeting the encephalitic alphaviruses. These immunogens are based on natural proteins, but have improved coverage of potential epitopes. The disclosed immunogenic compositions, which include multiple synthetic immunogens, are capable of inducing broader protection than conventionally designed vaccines.

Disclosed herein are a series of synthetic amino acid sequences, and their combinations, for use as immunogens (e.g., for use as vaccines), deliverable either as polypeptides, or as nucleic acid sequences that encode the disclosed immunogens. Two sets of sequences are described: one set includes the capsid (CP) protein (full-length sequences; SEQ ID NOs: 1-13), and the other set excludes the capsid protein (SEQ ID NOs: 14-26).

Provided are synthetic immunogenic polypeptides based on, but not identical to, natural alphavirus polypeptide sequences. In some embodiments, the immunogenic polypeptides have an amino acid sequence at least 95%, at least 96%, at least 97%, at least 98% or at least 99% identical to any one of SEQ ID NOs: 1-26. In some examples, the synthetic immunogenic polypeptide has an amino acid sequence comprising or consisting of any one of SEQ ID NOs: 1-26.

In other embodiments, the immunogenic polypeptides have an amino acid sequence at least 95%, at least 96%, at least 97%, at least 98% or at least 99% identical to an immunogenic portion of any one of SEQ ID NOs: 1-26, wherein the immunogenic portion is at least 18, at least 27, at least 36, at least 45, at least 54, at least 63, at least 72, at least 81, at least 90, at least 99, at least 108, at least 117, at least 126, at least 135, at least 144, at least 153, at least 162, at least 171, at least 180, at least 189, at least 198, at least 207, at least 216, at least 225, at least 234, at least 243, at least 252, at least 261, at least 270, at least 279, at least 288, at least 297, at least 306, at least 315, at least 324, at least 333, at least 342, at least 351, at least 360, at least 369, at least 378, at least 387, at least 396, at least 405, at least 414, at least 423, at least 432, at least 441, at least 450, at least 459, at least 468, at least 477, at least 486, at least 495, at least 504, at least 513, at least 522, at least 531, at least 540, at least 549, at least 558, at least 567, at least 576, at least 585, at least 594, at least 603, at least 612, at least 621, at least 630, at least 639, at least 648, at least 657, at least 666, at least 675, at least 684, at least 693, at least 702, at least 711, at least 720, at least 729, at least 738, at least 747, at least 756, at least 765, at least 774, at least 783, at least 792, at least 801, at least 810, at least 819, at least 828, at least 837,at least 846, at least 855, at least 864, at least 873, at least 882, at least 891, at least 900, at least 909, at least 918, at least 927, at least 936, at least 945, at least 954, at least 963, at least 972, at least 981, at least 990, at least 999, at least 1008, at least 1017, at least 1026, at least 1035, at least 1044, at least 1053, at least 1062, at least 1071, at least 1080, at least 1089, at least 1098, at least 1107, at least 1116, at least 1125, at least 1134, at least 1143, at least 1152, at least 1161, at least 1170, at least 1179, at least 1188, at least 1197, at least 1206, at least 1215, at least 1224, at least 1233, at least 1242, at least 1251 or at least 1260 amino acids in length, and wherein the immunogenic portion is synthetic. In some examples, the synthetic immunogenic polypeptide has an amino acid sequence comprising or consisting of an immunogenic portion of any one of SEQ ID NOs: 1-26, wherein the immunogenic portion is at least 18, at least 27, at least 36, at least 45, at least 54, at least 63, at least 72, at least 81, at least 90, at least 99, at least 108, at least 117, at least 126, at least 135, at least 144, at least 153, at least 162, at least 171, at least 180, at least 189, at least 198, at least 207, at least 216, at least 225, at least 234, at least 243, at least 252, at least 261, at least 270, at least 279, at least 288, at least 297, at least 306, at least 315, at least 324, at least 333, at least 342, at least 351, at least 360, at least 369, at least 378, at least 387, at least 396, at least 405, at least 414, at least 423, at least 432, at least 441, at least 450, at least 459, at least 468, at least 477, at least 486, at least 495, at least 504, at least 513, at least 522, at least 531, at least 540, at least 549, at least 558, at least 567, at least 576, at least 585, at least 594, at least 603, at least 612, at least 621, at least 630, at least 639, at least 648, at least 657, at least 666, at least 675, at least 684, at least 693, at least 702, at least 711, at least 720, at least 729, at least 738, at least 747, at least 756, at least 765, at least 774, at least 783, at least 792, at least 801, at least 810, at least 819, at least 828, at least 837, at least 846, at least 855, at least 864, at least 873, at least 882, at least 891, at least 900, at least 909, at least 918, at least 927, at least 936, at least 945, at least 954, at least 963, at least 972, at least 981, at least 990, at least 999, at least 1008, at least 1017, at least 1026, at least 1035, at least 1044, at least 1053, at least 1062, at least 1071, at least 1080, at least 1089, at least 1098, at least 1107, at least 1116, at least 1125, at least 1134, at least 1143, at least 1152, at least 1161, at least 1170, at least 1179, at least 1188, at least 1197, at least 1206, at least 1215, at least 1224, at least 1233, at least 1242, at least 1251 or at least 1260 amino acids in length, and wherein the immunogenic portion is synthetic.

In some embodiments, provided are fusion proteins that include an immunogenic polypeptide disclosed herein fused to a heterologous protein. For example, the heterologous protein can be a protein tag (for example an affinity tag), such as a His tag, FLAG tag, myc tag, chitin binding protein (CBP), maltose binding protein (MBP) or glutathione-S-transferase (GST). In other examples, the heterologous protein is a carrier protein, such as keyhole limpet hemocyanin (KLH), bovine serum albumin (BSA) or ovalbumin (OVA).

Also provided are sets of synthetic immunogenic polypeptides, or fusion proteins thereof. In some embodiments, the set includes two or more, three or more, four or more, five or more, six or more, or seven or more polypeptides selected from polypeptides having at least 95%, at least 96%, at least 97%, at least 98% or at least 99% identity to any one of SEQ ID NOs: 1-26, or an immunogenic portion thereof. In some examples, the set includes two or more, three or more, four or more, five or more, six or more, or seven or more polypeptides selected from polypeptides having an amino acid sequence set forth as any one of SEQ ID NOs: 1-26, or an immunogenic portion thereof. In specific examples, the two or more, three or more, four or more, five or more, six or more, or seven or more polypeptides are selected from polypeptides having an amino acid sequence consisting of the amino acid sequences set forth as any one of SEQ ID NOs: 1-26, or an immunogenic portion thereof.

In some embodiments, the set of synthetic immunogenic polypeptides includes at least three polypeptides, wherein at least one polypeptide is derived from Venezuelan equine encephalitis virus (VEEV), at least one polypeptide is derived from Western equine encephalitis virus (WEEV), and at least one polypeptide is derived from Eastern equine encephalitis virus (EEEV). In some examples, the set further includes at least one polypeptide derived from Chikungunya virus (CHIKV).

In some examples, the set of synthetic immunogenic polypeptides includes a first polypeptide, a second polypeptide and a third polypeptide, wherein: the amino acid sequence of the first polypeptide comprises or consists of SEQ ID NO: 1, SEQ ID NO: 2, SEQ ID NO: 3, SEQ ID NO: 4, SEQ ID NO: 5, SEQ ID NO: 6, SEQ ID NO: 14, SEQ ID NO: 15, SEQ ID NO: 16, SEQ ID NO: 17, SEQ ID NO: 18 or SEQ ID NO: 19, or an immunogenic portion thereof; the amino acid sequence of the second polypeptide comprises or consists of SEQ ID NO: 7, SEQ ID NO: 8, SEQ ID NO: 9, SEQ ID NO: 20, SEQ ID NO: 21 or SEQ ID NO: 22, or an immunogenic portion thereof; and the amino acid sequence of the third polypeptide comprises or consists of SEQ ID NO: 10, SEQ ID NO: 11, SEQ ID NO: 12, SEQ ID NO: 23, SEQ ID NO: 24 or SEQ ID NO: 25, or an immunogenic portion thereof. In specific examples, the set of polypeptides further includes a fourth polypeptide, wherein the amino acid sequence of the fourth polypeptide comprises or consists of SEQ ID NO: 13 or SEQ ID NO: 26, or an immunogenic portion thereof.

In other examples, the set of synthetic immunogenic polypeptides includes a first polypeptide, a second polypeptide and a third polypeptide, wherein: the amino acid sequence of the first polypeptide comprises or consists of an immunogenic portion of SEQ ID NO: 1, SEQ ID NO: 2, SEQ ID NO: 3, SEQ ID NO: 4, SEQ ID NO: 5, SEQ ID NO: 6, SEQ ID NO: 14, SEQ ID NO: 15, SEQ ID NO: 16, SEQ ID NO: 17, SEQ ID NO: 18 or SEQ ID NO: 19; the amino acid sequence of the second polypeptide comprises or consists of an immunogenic portion of SEQ ID NO: 7, SEQ ID NO: 8, SEQ ID NO: 9, SEQ ID NO: 20, SEQ ID NO: 21 or SEQ ID NO: 22; and the amino acid sequence of the third polypeptide comprises or consists of an immunogenic portion of SEQ ID NO: 10, SEQ ID NO: 11, SEQ ID NO: 12, SEQ ID NO: 23, SEQ ID NO: 24 or SEQ ID NO: 25. In specific examples, the set of polypeptides further includes a fourth polypeptide, wherein the amino acid sequence of the fourth polypeptide comprises or consists of an immunogenic portion of SEQ ID NO: 13 or SEQ ID NO: 26. In these examples, the immunogenic portion of the polypeptide is at least 18, at least 27, at least 36, at least 45, at least 54, at least 63, at least 72, at least 81, at least 90, at least 99, at least 108, at least 117, at least 126, at least 135, at least 144, at least 153, at least 162, at least 171, at least 180, at least 189, at least 198, at least 207, at least 216, at least 225, at least 234, at least 243, at least 252, at least 261, at least 270, at least 279, at least 288, at least 297, at least 306, at least 315, at least 324, at least 333, at least 342, at least 351, at least 360, at least 369, at least 378, at least 387, at least 396, at least 405, at least 414, at least 423, at least 432, at least 441, at least 450, at least 459, at least 468, at least 477, at least 486, at least 495, at least 504, at least 513, at least 522, at least 531, at least 540, at least 549, at least 558, at least 567, at least 576, at least 585, at least 594, at least 603, at least 612, at least 621, at least 630, at least 639, at least 648, at least 657, at least 666, at least 675, at least 684, at least 693, at least 702, at least 711, at least 720, at least 729, at least 738, at least 747, at least 756, at least 765, at least 774, at least 783, at least 792, at least 801, at least 810, at least 819, at least 828, at least 837, at least 846, at least 855, at least 864, at least 873, at least 882, at least 891, at least 900, at least 909, at least 918, at least 927, at least 936, at least 945, at least 954, at least 963, at least 972, at least 981, at least 990, at least 999, at least 1008, at least 1017, at least 1026, at least 1035, at least 1044, at least 1053, at least 1062, at least 1071, at least 1080, at least 1089, at least 1098, at least 1107, at least 1116, at least 1125, at least 1134, at least 1143, at least 1152, at least 1161, at least 1170, at least 1179, at least 1188, at least 1197, at least 1206, at least 1215, at least 1224, at least 1233, at least 1242, at least 1251 or at least 1260 amino acids in length.

In one non-limiting example, the set of synthetic immunogenic polypeptides includes three synthetic polypeptides having amino acid sequences comprising or consisting of the amino acid sequences of SEQ ID NO: 1, SEQ ID NO: 7 and SEQ ID NO: 10.

In another non-limiting example, the set of synthetic immunogenic polypeptides includes six synthetic polypeptides having amino acid sequences comprising or consisting of the amino acid sequences of SEQ ID NO: 2, SEQ ID NO: 3, SEQ ID NO: 8, SEQ ID NO: 9, SEQ ID NO: 10 and SEQ ID NO: 13.

In another non-limiting example, the set of synthetic immunogenic polypeptides includes five synthetic polypeptides having amino acid sequences comprising or consisting of the amino acid sequences of SEQ ID NO: 2, SEQ ID NO: 3, SEQ ID NO: 8, SEQ ID NO: 9 and SEQ ID NO: 10.

In another non-limiting example, the set of synthetic immunogenic polypeptides includes six synthetic polypeptides having amino acid sequences comprising or consisting of the amino acid sequences of SEQ ID NO: 2, SEQ ID NO: 3, SEQ ID NO: 8, SEQ ID NO: 9, SEQ ID NO: 11 and SEQ ID NO: 12.

In another non-limiting example, the set of synthetic immunogenic polypeptides includes six synthetic polypeptides having amino acid sequences comprising or consisting of the amino acid sequences of SEQ ID NO: 4, SEQ ID NO; 5, SEQ ID NO: 6, SEQ ID NO: 7, SEQ ID NO: 10 and SEQ ID NO: 13.

In another non-limiting example, the set of synthetic immunogenic polypeptides includes five synthetic polypeptides having amino acid sequences comprising or consisting of the amino acid sequences of SEQ ID NO: 4, SEQ ID NO; 5, SEQ ID NO: 6, SEQ ID NO: 7 and SEQ ID NO: 10.

In another non-limiting example, the set of synthetic immunogenic polypeptides includes seven synthetic polypeptides having amino acid sequences comprising or consisting of the amino acid sequences of SEQ ID NO: 4, SEQ ID NO; 5, SEQ ID NO: 6, SEQ ID NO: 7, SEQ ID NO: 11, SEQ ID NO: 12 and SEQ ID NO: 13.

In another non-limiting example, the set of synthetic immunogenic polypeptides includes six synthetic polypeptides having amino acid sequences comprising or consisting of the amino acid sequences of SEQ ID NO: 4, SEQ ID NO; 5, SEQ ID NO: 6, SEQ ID NO: 7, SEQ ID NO: 11 and SEQ ID NO: 12.

In another non-limiting example, the set of synthetic immunogenic polypeptides includes seven synthetic polypeptide having amino acid sequences comprising or consisting of the amino acid sequence of SEQ ID NO: 4, SEQ ID NO; 5, SEQ ID NO: 6, SEQ ID NO: 8, SEQ ID NO: 9, SEQ ID NO: 11 and SEQ ID NO: 12.

Further provided are nucleic acid molecules (e.g., DNA, cDNA, RNA or mRNA) encoding the synthetic immunogenic polypeptides disclosed herein. Vectors that include the isolated nucleic acid molecule or molecules are also provided.

Also provided are sets of isolated nucleic acid molecules that include two or more, three or more, four or more, five or more, six or more, or seven or more nucleic acid molecules, wherein each nucleic acid molecule encodes an immunogenic polypeptide (or a fusion protein thereof). In some embodiments, each nucleic acid molecule encodes an immunogenic polypeptide having an amino acid sequence that is at least 95%, at least 96%, at least 97%, at least 98% or at least 99% identical to an amino acid sequence set forth as any one of SEQ ID NOs: 1-26, or an immunogenic portion thereof. In some examples, each nucleic acid molecule encodes an immunogenic polypeptide comprising an amino acid sequence set forth as any one of SEQ ID NOs: 1-26, or an immunogenic portion thereof. In specific non-limiting examples, the two or more, three or more, four or more, five or more, six or more, or seven or more nucleic acid molecules each encode an immunogenic polypeptide selected from polypeptides having an amino acid sequence consisting of the amino acid sequences set forth as any one of SEQ ID NOs: 1-26, or an immunogenic portion thereof.

In some embodiments, the set of isolated nucleic acid molecules includes at least three nucleic acid molecules, wherein at least one nucleic acid molecule encodes a polypeptide derived from Venezuelan equine encephalitis virus (VEEV), at least one nucleic acid molecule encodes a polypeptide derived from Western equine encephalitis virus (WEEV), and at least one nucleic acid molecule encodes a polypeptide derived from Eastern equine encephalitis virus (EEEV). In some examples, the set further includes at least one nucleic acid molecule encoding a polypeptide derived from Chikungunya virus (CHIKV).

In some examples, the set of isolated nucleic acid molecules includes a first nucleic acid molecule, a second nucleic acid molecule and a third nucleic acid molecule, wherein: the first nucleic acid molecule encodes a polypeptide having an amino acid sequence comprising or consisting of SEQ ID NO: 1, SEQ ID NO: 2, SEQ ID NO: 3, SEQ ID NO: 4, SEQ ID NO: 5, SEQ ID NO: 6, SEQ ID NO: 14, SEQ ID NO: 15, SEQ ID NO: 16, SEQ ID NO: 17, SEQ ID NO: 18 or SEQ ID NO: 19; the second nucleic acid molecule encodes a polypeptide having an amino acid sequence comprising or consisting of SEQ ID NO: 7, SEQ ID NO: 8, SEQ ID NO: 9, SEQ ID NO: 20, SEQ ID NO: 21 or SEQ ID NO: 22; and the third nucleic acid molecule encodes a polypeptide having an amino acid sequence comprising or consisting of SEQ ID NO: 10, SEQ ID NO: 11, SEQ ID NO: 12, SEQ ID NO: 23, SEQ ID NO: 24 or SEQ ID NO: 25. In specific examples, the set of isolated nucleic acid molecules further includes a fourth nucleic acid molecule, wherein the fourth nucleic acid molecule encodes a polypeptide having an amino acid sequence comprising or consisting of SEQ ID NO: 13 or SEQ ID NO: 26.

In other examples, the set of isolated nucleic acid molecules includes a first nucleic acid molecule, a second nucleic acid molecule and a third nucleic acid molecule, wherein: the first nucleic acid molecule encodes a polypeptide having an amino acid sequence comprising or consisting of an immunogenic portion of SEQ ID NO: 1, SEQ ID NO: 2, SEQ ID NO: 3, SEQ ID NO: 4, SEQ ID NO: 5, SEQ ID NO: 6, SEQ ID NO: 14, SEQ ID NO: 15, SEQ ID NO: 16, SEQ ID NO: 17, SEQ ID NO: 18 or SEQ ID NO: 19; the second nucleic acid molecule encodes a polypeptide having an amino acid sequence comprising or consisting of an immunogenic portion of SEQ ID NO: 7, SEQ ID NO: 8, SEQ ID NO: 9, SEQ ID NO: 20, SEQ ID NO: 21 or SEQ ID NO: 22; and the third nucleic acid molecule encodes a polypeptide having an amino acid sequence comprising or consisting of an immunogenic portion of SEQ ID NO: 10, SEQ ID NO: 11, SEQ ID NO: 12, SEQ ID NO: 23, SEQ ID NO: 24 or SEQ ID NO: 25. In specific examples, the set of isolated nucleic acid molecules further includes a fourth nucleic acid molecule, wherein the fourth nucleic acid molecule encodes a polypeptide having an amino acid sequence comprising or consisting of an immunogenic portion of SEQ ID NO: 13 or SEQ ID NO: 26. In these examples, the immunogenic portion of the polypeptide is at least 18, at least 27, at least 36, at least 45, at least 54, at least 63, at least 72, at least 81, at least 90, at least 99, at least 108, at least 117, at least 126, at least 135, at least 144, at least 153, at least 162, at least 171, at least 180, at least 189, at least 198, at least 207, at least 216, at least 225, at least 234, at least 243, at least 252, at least 261, at least 270, at least 279, at least 288, at least 297, at least 306, at least 315, at least 324, at least 333, at least 342, at least 351, at least 360, at least 369, at least 378, at least 387, at least 396, at least 405, at least 414, at least 423, at least 432, at least 441, at least 450, at least 459, at least 468, at least 477, at least 486, at least 495, at least 504, at least 513, at least 522, at least 531, at least 540, at least 549, at least 558, at least 567, at least 576, at least 585, at least 594, at least 603, at least 612, at least 621, at least 630, at least 639, at least 648, at least 657, at least 666, at least 675, at least 684, at least 693, at least 702, at least 711, at least 720, at least 729, at least 738, at least 747, at least 756, at least 765, at least 774, at least 783, at least 792, at least 801, at least 810, at least 819, at least 828, at least 837, at least 846, at least 855, at least 864, at least 873, at least 882, at least 891, at least 900, at least 909, at least 918, at least 927, at least 936, at least 945, at least 954, at least 963, at least 972, at least 981, at least 990, at least 999, at least 1008, at least 1017, at least 1026, at least 1035, at least 1044, at least 1053, at least 1062, at least 1071, at least 1080, at least 1089, at least 1098, at least 1107, at least 1116, at least 1125, at least 1134, at least 1143, at least 1152, at least 1161, at least 1170, at least 1179, at least 1188, at least 1197, at least 1206, at least 1215, at least 1224, at least 1233, at least 1242, at least 1251 or at least 1260 amino acids in length.

In one non-limiting example, the set of isolated nucleic acid molecules includes three nucleic acid molecules encoding polypeptides having amino acid sequences comprising or consisting of the amino acid sequences of SEQ ID NO: 1, SEQ ID NO: 7 and SEQ ID NO: 10.

In another non-limiting example, the set of isolated nucleic acid molecules includes six nucleic acid molecules encoding polypeptides having amino acid sequences comprising or consisting of the amino acid sequences of SEQ ID NO: 2, SEQ ID NO: 3, SEQ ID NO: 8, SEQ ID NO: 9, SEQ ID NO: 10 and SEQ ID NO: 13.

In another non-limiting example, the set of isolated nucleic acid molecules includes five nucleic acid molecules encoding polypeptides having amino acid sequences comprising or consisting of the amino acid sequences of SEQ ID NO: 2, SEQ ID NO: 3, SEQ ID NO: 8, SEQ ID NO: 9 and SEQ ID NO: 10.

In another non-limiting example, the set of isolated nucleic acid molecules includes six nucleic acid molecules encoding polypeptides having amino acid sequences comprising or consisting of the amino acid sequences of SEQ ID NO: 2, SEQ ID NO: 3, SEQ ID NO: 8, SEQ ID NO: 9, SEQ ID NO: 11 and SEQ ID NO: 12.

In another non-limiting example, the set of isolated nucleic acid molecules includes six nucleic acid molecules encoding polypeptides having amino acid sequences comprising or consisting of the amino acid sequences of SEQ ID NO: 4, SEQ ID NO; 5, SEQ ID NO: 6, SEQ ID NO: 7, SEQ ID NO: 10 and SEQ ID NO: 13.

In another non-limiting example, the set of isolated nucleic acid molecules includes five nucleic acid molecules encoding polypeptides having amino acid sequences comprising or consisting of the amino acid sequences of SEQ ID NO: 4, SEQ ID NO; 5, SEQ ID NO: 6, SEQ ID NO: 7 and SEQ ID NO: 10.

In another non-limiting example, the set of isolated nucleic acid molecules includes seven nucleic acid molecules encoding polypeptides having amino acid sequences comprising or consisting of the amino acid sequences of SEQ ID NO: 4, SEQ ID NO; 5, SEQ ID NO: 6, SEQ ID NO: 7, SEQ ID NO: 11, SEQ ID NO: 12 and SEQ ID NO: 13.

In another non-limiting example, the set of isolated nucleic acid molecules includes six nucleic acid molecules encoding polypeptides having amino acid sequences comprising or consisting of the amino acid sequences of SEQ ID NO: 4, SEQ ID NO; 5, SEQ ID NO: 6, SEQ ID NO: 7, SEQ ID NO: 11 and SEQ ID NO: 12.

In another non-limiting example, the set of isolated nucleic acid molecules includes seven nucleic acid molecules encoding polypeptides having amino acid sequences comprising or consisting of the amino acid sequence of SEQ ID NO: 4, SEQ ID NO; 5, SEQ ID NO: 6, SEQ ID NO: 8, SEQ ID NO: 9, SEQ ID NO: 11 and SEQ ID NO: 12.

Further provided is a vector or plurality of vectors that include the set of isolated nucleic acid molecules disclosed herein. In some embodiments, each isolated nucleic acid molecule is contained in a separate vector. In other embodiments, two or more (such as three or more, four or more, five or more, six or more, or seven or more) of the isolated nucleic acid molecules are contained in a single vector. In some examples, all of the isolated nucleic acid molecules of the set are contained in a single vector.

Also provided are compositions that include a synthetic immunogenic polypeptide, a set of synthetic immunogenic polypeptides, a nucleic acid molecule, a set of isolated nucleic acid molecules, or a vector or plurality of vectors. In some embodiments, the composition includes a pharmaceutically acceptable carrier, an adjuvant, or both. In some examples, the adjuvant is a liposome-based adjuvant. In specific non-limiting examples, the liposome-based adjuvant comprises ALF, such as ALF adsorbed to aluminum hydroxide (ALFA), ALF containing QS21 saponin (ALFQ), or ALFQ adsorbed to aluminum hydroxide (ALFQA).

Methods of eliciting an immune response against one or more alphaviruses in a subject are also provided. In some embodiments, the method includes administering to the subject an effective amount of a synthetic immunogenic polypeptide, a set of synthetic immunogenic polypeptides, a nucleic acid molecule, a set of isolated nucleic acid molecules, a vector or plurality of vectors, or composition disclosed herein. In some examples, the one or more alphaviruses include Venezuelan equine encephalitis virus, Western equine encephalitis virus, Eastern equine encephalitis virus, Chikungunya virus, or any combination thereof.

In some embodiments, the subject is administered the set of immunogenic polypeptides and the polypeptides in the set are administered to the subject simultaneously, substantially simultaneously, or sequentially.

In other embodiments, the subject is administered the set of nucleic acid molecules and the nucleic acid molecules in the set are administered to the subject simultaneously, substantially simultaneously, or sequentially.

In other embodiments, the subject is administered the plurality of vectors and the vectors are administered to the subject simultaneously, substantially simultaneously, or sequentially.

IV. Immunogenic Polypeptide Sequences

Exemplary immunogenic polypeptide sequences generated as described in Example 1 are provided below. In some embodiments, the disclosed immunogenic polypeptides include, consist essentially of, or consist of an amino acid sequence at least 95% identical to the amino acid sequence set forth as one of SEQ ID NOs: 1-26 (or an immunogenic portion thereof), such as at least 95% identical, at least 96% identical, at least 97% identical, at least 98% identical, at least 99% identical, or even 100% identical to the sequence set forth as one of SEQ ID NOs: 1-26 (or an immunogenic portion thereof). In some embodiments, the disclosed synthetic polypeptides are utilized in combination, for example as sets of immunogenic polypeptides. In some examples, the set of immunogenic polypeptides includes 2, 3, 4, 5, 6, 7, or 8 of the disclosed polypeptides. Exemplary sets of polypeptides are shown in Example 1. However, additional combinations of the disclosed immunogenic polypeptides can also be selected to produce additional sets.

A. Venezuelan Equine Encephalitis Virus (VEEV)—Full Length Sequences

```
VEEVs + .structPs.uniq.EG-1.1
                                                          (SEQ ID NO: 1)
MDYDIVSAKMFPFQPMYPMQPMPYRNPFAAPRRPWFPRTDPFLAMQVQELTRSMANL

TFKQRRDAPPEGPPAKKPKREAPQKQKGGGQGKKKKNQGKKKAKTGPPNPKAQNGNK

KKTNKKPGKRQRMVMKLESDKTFPIMLEGKINGYACVVGGKLFRPMHVEGKIDNDVL

AALKTKKASKYDLEYADVPQNMRADTFKYTHEKPQGYYSWHHGAVQYENGRFTVPK

GVGAKGDSGRPILDNQGRVVAIVLGGVNEGSRTALSVVMWNEKGVTVKYTPENCEQW

SLVTTMCLLANVTFPCAQPPICYDRKPAETLAMLSVNVDNPGYDELLEAAVKCPGRKR

RSTEELFKEYKLTRPYMARCIRCAVGSCHSPIAIEAVKSDGHDGYVRLQTSSQYGLDSSG

NLKGRTMRYDMHGTIEEIPLHQVSLHTSRPCHIVDGHGYFLLARCPAGDSITMEFKKDS

VTHSCSVPYEVKFNPVGRELYTHPPEHGAEQACQVYAHDAQNRGAYVEMHLPGSEVD

SSLVSLSGSSVTVTPPAGTSALVECECGGTKISETINTAKQFSQCTKKEQCRAYRLQNDK

WVYNSDKLPKAAGATLKGKLHVPFLLADGKCTVPLAPEPMITGFRSVSLKLHPKNPTY

LTTRQLADEPHYTHELISEPAVRNFTVTEKGWEFVWGNHPPKRFWAQETAPGNPHGLP

HEVITHYYHRYPMSTILGLSICAAIVTVSVAASTWLFCKSRVSCLTPYRLTPNARMPLCL

AVLCCARTARAETTWESLDHLWNNNQQMFWIQLLIPLAALIVVTRLLKCVCCVVPFLV

VAGAAGAGAYEHATTMPSQAGISYNTIVNRAGYAPLPISITPTKIKLIPTVNLEYVTCHY

KTGMDSPAIKCCGSQECTPTYRPDEQCKVFTGVYPFMWGGAYCFCDTENTQVSKAYV

MKSDDCLADHAEAYKAHTASVQAFLNITVGEHSIVTTVYVNGETPVNFNGVKLTAGPL

STAWTPFDRKIVQYAGEIYNYDFPEYGAGQPGAFGDIQSRTVSSSDLYANTNLVLQRPK

AGAIHVPYTQAPSGFEQWKKDKAPSLKFTAPFGCEIYTNPIRAENCAVGSIPLAFDIPDAL

FTRVSETPTLSAAECTLNECVYSSDFGGIATVKYSASKSGKCAVHVPSGTATLKEAAVEL

TEQGSATIHFSTANIHPEFRLQICTSYVTCKGDCHPPKDHIVTHPQYHAQTFTAAVSKTA

WTWLTSLLGGSAVIIIGLVLATIVAMYVLTNQKHN

VEEVs + .structPs.uniq.EG-2.1
                                                          (SEQ ID NO: 2)
MDCDVVKSAEMFPYQPMYPMQPMPFRNPFATPRRPWFPRTDPFLAMQVQELARSMAN

LTFKQRRDVPPEGPPAKKKKKDNSQQGGRNQNGKKKNKLVKKKKKTGPPPPKNNGGK

KKVNRKPGKRQRMVMKLESDKTFPIMLDGKVNGYACVVGGKLFRPLHVEGKIDNDVL

SSLKTKKASKYDLEYADVPQSMRADTFKYTHDKPQGYYNWHHGAVQYENGRFTVPR

GVGARGDSGRPILDNQGRVVAIVLGGANEGSRTALSVVTWNEKGVTVKYTPENSEQWS

LVTTLCLLANVTFPCTQPPICYDRKPAETLSMLSHNIDNPGYDELLEAVLKCPGRGKRST

EELFKEYKLTRPYMAKCVRCAVGSCHSPIAIEAVRSEGHDGYVRLQTSSQYGLDPSGNL

KGRTMRYDMHGTIKEIPLHQVSVHTSRPCHIIDGHGYFLLARCPEGDSITMEFKKESVTH

SCSVPYEVKFTPVGRELYSHPPEHGAEQPCHVYAHDAQNRGAYVEMHLPGSEVDSTLL
```

-continued

SMSGSSVHVTPPAGQSVQVECECGGTKISETINSAKQYSQCSKTSQCRAYRTQNDKWV

YNSDKLPKASGETLKGKLHVPFVLTEAKCTVPLAPEPIITFGFRSVSLKLHPKNPTFLTTR

QLDGEPAYTHELITHPVVRNFSVTEKGWEFVWGNHPPQRYWSQETAPGNPHGLPHEVI

VHYYHRYPMSTIVGLSICAAIVTTSIAASVWLFCKSRISCLTPYRLTPNARIPFCLAVLCC

ARTAKAETTWESLDHLWNHNQQMFWSQLLIPLAALIVATRLLKCMCCVVPFLVVAGA

VGAGAYEHATTMPNQVGIPYNTIVNRAGYAPLPISIVPTKVKLIPTVNLEYITCHYKTGL

DSPAIKCCGTQECSPTYRPDEQCKVFSGVYPFMWGGAYCFCDTENTQISKAYVTKSEDC

VTDHAQAYKAHTASIQAFLNITVGGHSTTAVVYVNGETPVNFNGIKLVAGPLSTAWSPF

DKKIVQYAGEVYNYDFPEYGAGHAGAFGDIQARTISSSDVYANTNLVLQRPNTGTIHVP

YTQAPSGYEQWKKDKPPSLKYTAPFGCEIHVNPVRAENCAVGFIPLAFDIPDALFTRVSE

TPTLSSAECSLNECTYSTDFGGIATVKYSASKAGKCAVHIPSGTATLKEAAVELAEQGSA

TIHFSTASIHPEFKLQICTKVLTCKGDCHPPRDHIVTHPQYHAQSFTAAVSKTAWTWITSL

LGGSAIIIIGLVLATVVAMYVLTNQRHN

VEEVs + .structPs.uniq.EG-2.2
(SEQ ID NO: 3)
MDYDIVSAKMFPFQPMYPMQPMPYRNPFAAPRRPWFPRTDPFLAMQVQELTRSMANL

TFKQRRDAPPEGPPAKKPKREAPQKQKGGGQGKKKKNQGKKKAKTGPPNPKAQNGNK

KKTNKKPGKRQRMVMKLESDKTFPIMLEGKINGYACVVGGKLFRPMHVEGKIDNDVL

AALKTKKASKYDLEYADVPQNMRADTFKYTHEKPQGYYSWHHGAVQYENGRFTVPK

GVGAKGDSGRPILDNQGRVVAIVLGGVNEGSRTALSVVMWNEKGVTVKYTPENCEQW

SLVTTMCLLANVTFPCAQPPICYDRKPAETLAMLSVNVDNPGYDELLEAAVKCPGRKR

RSTEELFKEYKLTRPYMARCIRCAVGSCHSPIAIEAVKSDGHDGYVRLQTSSQYGLDSSG

NLKGRTMRYDMHGTIEEIPLHQVSLHTSRPCHIVDGHGYFLLARCPAGDSITMEFKKDS

VTHSCSVPYEVKFNPVGRELYTHPPEHGAEQACQVYAHDAQNRGAYVEMHLPGSEVD

SSLVSLSGSSVTVTPPAGTSALVECECGGTKISETINTAKQFSQCTKKEQCRAYRLQNDK

WVYNSDKLPKAAGATLKGKLHVPFLLADGKCTVPLAPEPMITFGFRSVSLKLHPKNPTY

LTTRQLADEPHYTHELISEPAVRNFTVTEKGWEFVWGNHPPKRFWAQETAPGNPHGLP

HEVITHYYHRYPMSTILGLSICAAIVTVSVAASTWLFCKSRVSCLTPYRLTPNARMPLCL

AVLCCARTARAETTWESLDHLWNNNQQMFWIQLLIPLAALIVVTRLLKCVCCVVPFLV

VAGAAGAGAYEHATTMPSQAGISYNTIVNRAGYAPLPISITPTKIKLIPTVNLEYVTCHY

KTGMDSPAIKCCGSQECTPTYRPDEQCKVFTGVYPFMWGGAYCFCDTENTQVSKAYV

MKSDDCLADHAEAYKAHTASVQAFLNITVGEHSIVTTVYVNGETPVNFNGVKLTAGPL

STAWTPFDRKIVQYAGEIYNYDFPEYGAGQPGAFGDIQSRTVSSSDLYANTNLVLQRPK

AGAIHVPYTQAPSGFEQWKKDKAPSLKFTAPFGCEIYTNPIRAENCAVGSIPLAFDIPDAL

FTRVSETPTLSAAECTLNECVYSSDFGGIATVKYSASKSGKCAVHVPSGTATLKEAAVEL

TEQGSATIHFSTANIHPEFRLQICTSYVTCKGDCHPPKDHIVTHPQYHAQTFTAAVSKTA

WTWLTSLLGGSAVIIIGLVLATIVAMYVLTNQKHN

VEEVs + .structPs.uniq.EG-3.1
(SEQ ID NO: 4)
MDCNVVQSATMFPYQSPMFPMQPAPFRNPYAPPRRPWFPRTDPFLAMQVQELTRSMAN

LTFKQRREAPPEGPPAKKKRKEPQQQVAQAQVKKKNGKPKKKKSNGAPPPKNQNSTK

KKPNKKPGKRQRMVMKLESDKTFPIMLDGKVNGYACVVGGKLFRPLHVEGKIDNETL

ASLKTKKASKYDLEYADVPQSMRADTFKYTHDKPQGYYNWHHGAVQYENGRFTVPK

-continued

GVGAKGDSGRPILDNQGRVVAIVLGGVNEGSRTALSVVMWTEKGVTVKYTPENCEQW

SLVTAVCLLANVTFPCSTPPICYDRAPAETLMMLSKNIDNPGYDELLEAVLKCPGRQKR

STEELFKEYKLTKPYMAKCIRCAVGSCHSPIAIEAVRSEGHDGYVRLQTSSQYGLDPSGN

VKSRVMRYNMYGKIVEVPLHQVSLHTSRPCQIVDGHGYFLLARCPPGDSITMEFKKGSV

THSCSVPYEVKFTPVGRELYSHPPEHGTEHPCRVYVHDAQQKDAYVEMHLPGSEVDSS

LLSMSGSAVRVTPPSGQSVLVECNCGSAVSETINTAKSYSQCTKTSQCRAYRLQSDKWV

FNSDKLPKAAGETLKGKLHVPYLLSEAKCTVPLAPEPIVTFGFRFVSLKLHPRNPTYLTT

RQLDGEPNYTHELISEPTIRNFTVTEHGWEYVWGNHPPQRYWAQETAPGDPHGLPHEVI

KHYYHRYPMSTTLGLSICAAVVTTSIAASTWLLCKSRVSCLTPYRLTPNAQLPVCLAFLC

CARTARAETAWESLDHLWNNNQQMFWTQLLIPLAALIVVTRLLRCVCCVVPFLVLAGA

ASVGAYEHATTMPSQVGIPYNTVVNRAGYAPLAISIIPTKIRLIPTLNLEYITCHYKTGLDS

PSIKCCGTQECPKVNRPDEQCKVFAGVYPFMWGGAYCFCDSENTQISRAYVMKSDDCS

ADHALAYKAHTASIQAFLNITVGEQSTTAVVYVNGETPISFNGVKLVAGPLSTAWTPFD

RKVVQYAGEIYNYDFPEYGAGHAGAFGDLQARTITSNDLYANTNLVLQRPKSGTVHVP

YTQAPSGFEQWKKDKPPSLKFTAPFGCEIYVNPVRAENCAVGSIPLSFDIPDALFTRVSDT

PTLSTAECTLNECVYSSDFGGIASVKYSATKAGKCAVHVPSGTATLKESLVEVVEQGSM

TLHFSTASIHPEFRLQICTSFVTCKGDCHPPKDHIVTHPQHHAQTFTAAVSKTAWTWLSS

LLGGSAAIIIGLVLATLVAMYVLTNQKRN

VEEVs+.structPs.uniq.EG-3.2
(SEQ ID NO: 5)
MDYDIVSAKMFPFQPMYPMQPMPYRNPFAAPRRPWFPRTDPFLAMQVQELARSMANL

TFKQRRDAPPEGPPAKKPKREAPQKQKGGGQGKKKKNQGKKKAKTGPPNPKAQNGNK

KKTNKKPGKRQRMVMKLESDKTFPIMLEGKINGYACVVGGKLFRPMHVEGKIDNDVL

AALKTKKASKYDLEYADVPQNMRADTFKYTHEKPQGYYSWHHGAVQYENGRFTVPR

GVGARGDSGRPILDNQGRVVAIVLGGANEGSRTALSVVMWNEKGVTVKYTPENSEQW

SLVTTMCLLANVTFPCAQPPICYDRKPAETLAMLSVNVDNPGYDELLEAAVKCPGRKR

RSTEELFKEYKLTRPYMARCIRCAVGSCHSPIAIEAVKSDGHDGYVRLQTSSQYGLDSSG

NLKGRTMRYDMHGTIEEIPLHQVSVHTSRPCHIIDGHGYFLLARCPAGDSITMEFKKDSV

THSCSVPYEVKFNPVGRELYTHPPEHGAEQACQVYAHDAQNRGAYVEMHLPGSEVDSS

LVSLSGSSVTVTPPAGTSALVECECGGTKISETINTAKQFSQCTKKEQCRAYRLQNDKW

VYNSDKLPKAAGATLKGKLHVPFLLADGKCTVPLAPEPMITFGFRSVSLKLHPKNPTYL

TTRQLADEPHYTHELISEPAVRNFTVTEKGWEFVWGNHPPKRFWAQETAPGNPHGLPH

EVITHYYHRYPMSTILGLSICAAIVTTSIAASVWLFCKSRISCLTPYRLTPNARMPLCLAV

LCCARTARAETTWESLDHLWNHNQQMFWSQLLIPLAALIVATRLLKCVCCVVPFLVVA

GAAGAGAYEHATTMPNQVGIPYNTIVNRAGYAPLPISITPTKIKLIPTVNLEYVTCHYKT

GMDSPAIKCCGSQECTPTYRPDEQCKVFTGVYPFMWGGAYCFCDTENTQVSKAYVMK

SDDCLADHAEAYKAHTASVQAFLNITVGEHSIVTTVYVNGETPVNFNGVKLTAGPLSTA

WTPFDRKIVQYAGEIYNYDFPEYGAGQPGAFGDIQSRTVSSSDLYANTNLVLQRPKAGA

IHVPYTQAPSGFEQWKKDKAPSLKFTAPFGCEIYTNPIRAENCAVGSIPLAFDIPDALFTR

VSETPTLSAAECTLNECVYSSDFGGIATVKYSASKSGKCAVHVPSGTATLKEAAVELTE

```
QGSATIHFSTANIHPEFRLQICTSYVTCKGDCHPPRDHIVTHPQYHAQTFTAAVSKTAWT

WLTSLLGGSAVIIIGLVLATIVAMYVLTNQKHN
```

VEEVs + .structPs.uniq.EG-3.3

(SEQ ID NO: 6)

```
MDCDVVKSAEMFPYQPMYPMQPMPFRNPFATPRRPWFPRPDPYLALQVQELARSMAS

LTFKQRRDVPPEGPPAKKKKKDNSQQGGRNQNGKKKNKLVKKKKKTGPPPPKNNGGK

KKVNRKPGKRQRMVMKLESDKTFPILLDGKINGYACVVGGKLFRPMHVAGKIDNDVL

SSLKTKKASKYDLEYADVPQNMRSDTFKYTHEKPRGYYSWHHGAVQYENGRFTVPKG

VGARGDSGRPILDNQGRVVAIVLGGMNEGSRTALSVVTWNEKGVTVKYTPENCEQWS

LVTTLCLLANVTFPCTQPPICYDRKPAETLSMLSHNIDNPGYDELLEAVLKCPGRGKRST

EELFKEYKLTRPYMAKCVRCAVGSCHSPIAIEAVRSDGHDGYIRIQTSSQYGLDPSGNLK

GRTMRYDMHGTIKEIPLHQVSLHTSRPCHIVDGHGYFLLARCPEGDSITMEFKKESVTHS

CSVPYEVKFNPAGRELYTHPPEHGAEQPCHVYAHDAQNRGAYVEMHLPGSEVDSTLLS

MSGSSVHVTPPAGQSVQVECECGGTKISETINSAKQYSQCSKTSQCRAYRTQNDKWVY

NSDKLPKASGETLKGKLHVPFVLTEAKCTVPLAPEPIITFGFRSVSLKLHPKNPTFLTTRQ

LDGEPAYTHELITHPVVRNFSVTEKGWEFVWGNHPPQRYWSQETAPGNPHGLPHEVIV

HYYHRYPMSTIVGLSICAAIVTVSVAASTWLFCRSRVACLTPYRLTPNARIPFCLAVLCC

ARTAKAETTWESLDHLWNNNQQMFWIQLLIPLAALIVVTRLLKCMCCVVPFLVVAGAV

GAGAYEHATTMPSQAGISYNTIVNRAGYAPLPISIVPTKVKLIPTVNLEYITCHYKTGMD

SPAIKCCGTQECSPTYRPDEQCKVFSGVYPFMWGGAYCFCDTENTQISKAYVTKSEDCV

TDHAQAYKAHTASIQAFLNITVGGHSTTAVVYVNGETPVNFNGIKLVAGPLSTAWSPFD

KKIVQYAGEVYNYDFPEYGAGHAGAFGDIQARTISSSDVYANTNLVLQRPNTGTIHVPY

TQAPSGYEQWKKDKPPSLKYTAPFGCEIHVNPVRAENCAVGFIPLAFDIPDALFTRVSET

PTLSSAECSLNECTYSTDFGGIATVKYSASKAGKCAVHIPSGTATLKEAAVELAEQGSAT

IHFSTASIHPEFKLQICTKVLTCKGDCHPPKDHIVTHPQYHAQSFTAAVSKTAWTWITSLL

GGSAIIIIGLVLATVVAMYVLTNQRHN
```

B. Western Equine Encephalitis Virus (WEEV)—Full Length Sequences

WEEVs + .structPs.uniq.EG-1.1

(SEQ ID NO: 7)

```
MFPYPQLNFPPVYPTNPMAYRDPNPPRRRWRPFRPPLAAQIEDLRRSIANLTFKQRSPNP

PPGPPPKKKKSAPKPKPTQPKKKKQQAKKTKRKPKPGKRQRMCMKLESDKTFPIMLNG

QVNGYACVVGGRLMKPLHVEGKIDNEQLAAVKLKKASMYDLEYGDVPQNMKSDTLQ

YTSDKPPGFYNWHHGAVQYENGRFTVPRGVGGKGDSGRPILDNRGRVVAIVLGGANE

GTRTALSVVTWNQKGVTIKDTPEGSEPWSLVTALCVLSNVTFPCDKPPVCYSLAPERTL

DVLEENVDNPNYDTLLENVLKCPSRRPKRSITDDFTLTSPYLGFCPYCRHSTPCFSPIKIE

NVWDESDDGSIRIQVSAQFGYNQAGTADVTKFRYMSFDHDHDIKEDSMEKIAISTSGPC

RRLGHKGYFLLAQCPPGDSVTVSITGASENSCTVEKKIRRKFVGREEYLFPPVHGKLVK

CHVYDHLKETSAGYITMHRPGPHAYKSYLEEASGEVYIKPPSGKNVTYECKCGDYSTGI

VSTRTKMNGCTKAKQCIAYKSDQTKWVFNSPDLIRHTDHSVQGKLHIPFRLTPTVCPVP

LAHTPTVTKWFKGITLHLTATRPTLLTTRKLGLRADATAEWITGTTSRNFSVGREGLEY
```

-continued

VWGNHEPVRVWAQESAPGDPHGWPHEIIIHYYHRHPVYTVIVLCGVALAILVGTASSAA

CIAKARRDCLTPYALAPNATVPTALAVLCCIRPTNAETFGETLNHLWFNNQPFLWAQLC

IPLAALVILFRCFSCCMPFLLVAGVCLGKVDAFEHATTVPNVPGIPYKALVERAGYAPLN

LEITVVSSELTPSTNKEYVTCKFHTVIPSPQVKCCGSLECKASSKADYTCRVFGGVYPFM

WGGAQCFCDSENTQLSEAYVEFAPDCTIDHAVALKVHTAALKVGLRIVYGNTTAHLDT

FVNGVTPGSSRDLKVIAGPISAAFSPFDHKVVIRKGLVYNYDFPEYGAMKPGAFGDIQAS

SLDATDIVARTDIRLLKPSVKNIHVPYTQAVSGYEMWKNNSGRPLQETAPFGCKIEVEPL

RASNCAYGHIPISIDIPDAAFVRSSESPTILEVSCTVADCIYSADFGGSLTLQYKADREGHC

PVHSHSTTAVLKEATTHVTAVGSITLHESTSSPQANFIVSLCGKKTTCNAECKPPADHIIG

EPHKVDQEFQAAVSKTSWNWLLALFGGASSLIVVGLIVLVCSSMLINTRR

WEEVs + .structPs.uniq.EG-2.1

(SEQ ID NO: 8)

MFPYPQLTFPPMYQPNPMAYRDPNPPRRRWRPFRVPLAAQIEELRRSIANLTLKQRAPNP

PAGPPAKKKKTQPKPKATPPKKKKQQVKKQKRKPKPGKRQRLCMKLESDKTFPILLNG

QVNGYACVVGGRLMKPLHVEGKIDNEQLAAIKLKKASMYDLEYGDVPQNMKSDTLQY

TSEKPPGFYNWHHGTVQYENGRFSVPRGVGGKGDSGRPILDNKGRVVAIVLGGANEGS

RTALSVVTWNQKGVTIKDTPEGTEQWSLITAMCVLANVTFPCDKPPVCYSLTPERTLDV

LEENVDNPGYDTLLENVLKCPSRRQKRSITDDFTLTSPYLGHCPYCLHATPCFSPIKIEKV

WDESDDGTIRIQVSAQLGYNQAGTADPTKFRYMSYEQDHDIKEASMDKIAISTSGPCSR

LGHKGYFLLARCPPGDSVTVSITSGTSENSCTVERKIRRKFVGREEYLLPPVHGKLIKCH

VYDHLKETTAGYITMHRPGPHAYATYVEESSGEVYIRPPSGKNVTYECKCGDYSTGTV

NTRTKMPGCTKKKQCIAYKHDQTKWVFNSPDLIRHSDHAVQGKLHIPFKLTATACPVPL

AHTPTVEKWFKGVTLHLTASHPTLLTTRKLGPRAEPTSEWIVGTVSRNFSVGREGLEYT

WGNHDPVRVWSQESAPGDPHGWPHEIIVHYYHRHPLYTIAVLCGLVLITVIGIASAAACI

SKARRDCLTPYALAPNAAVPTLLAVLCCIRPTHAETLGESLGHLWLNNQPLLWAQLCLP

LAALIILFRFFSCCLPFLLVAGVCLGKADAYEHATTVPNVPGVPYKALVERSGYAPLNLE

VTVVSSELIPSTNKEYVTCKFHTIIPSPQVKCCGSLECQASRKADYTCRVFGGVYPFMWG

GAQCSCDSENTQLSEAYVEFAPDCTADHAVALKVHTAALKVGLQIVYGNTSTRLDTFV

NGVTPGISGALKVIAGPISAAFTPFDHKVVIRKGKVYNYDFPEYGAMKPGVFGDIQASSL

DSTDIVARTDVRLLKPSVKSIHVPYTQAASGYEMWKNNSGRPLQDTAPFGCKIEVDPLR

AVDCAYGHIPLSIDIPDAAFVRTSEAPTVLEMSCTVTACIYSADFGGSLTLQYKADKEGN

CPVHSHSSTAVLKEATTHVVHSGSVTLHFSTSSPQVNFIVSLCGKKTTCDAECKPPSDHII

GEPHKVNQEFQAAVSKTSWNWLFAMLGGASSLIVVGLLVLACSSMIINTRR

WEEVs + .structPs.uniq.EG-2.2

(SEQ ID NO: 9)

MFPYPQLNFPPVYPTNPMAYRDPNPPRRRWRPFRPPLAAQIEDLRRSIANLTFKQRSPNP

PPGPPPKKKKSAPKPKPTQPKKKKQQAKKTKRKPKPGKRQRMCMKLESDKTFPIMLNG

QVNGYACVVGGRLMKPLHVEGKIDNEQLAAVKLKKASKYDLEYGDVPQNMKSDTLQ

YTSDKPPGFYNWHHGAVQYENGRFTVPRGVGGKGDSGRPILDNRGRVVAIVLGGANE

GTRTALSVVTWNQKGVTIRDTPEGSEPWSLVTALCVLSNVTFPCDKPPVCYSLAPERTL

DVLEENVDNPNYDTLLENVLKCPSRRPKRSITDDFTLTSPYLGFCPYCRHSTPCFSPIKIE

NVWDESDDGSIRIQVSAQFGYNQAGTADVTKFRYMSFDHDHDIKEDSMEKIAISTSGPC

RRLGHKGYFLLAQCPPGDSVTVSITSGASENSCTVEKKIRRKFVGREEYLFPPVHGKLVK

-continued

CHVYDHLKETSAGYITMHRPGPHAYKSYLEEASGEVYIKPPSGKNVTYECKCGDYSTGI

VSTRTKMNGCTKAKQCIAYKSDQTKWVFNSPDLIRHTDHSVQGKLHIPFRLTPTVCPVP

LAHTPTVTKWFKGITLHLTATRPTLLTTRKLGLRADATAEWITGTTSRNFSVGREGLEY

VWGNHEPVRVWAQESAPGDPHGWPHEIIIHYYHRHPVYTVIVLCGVALAILVGTASSAA

CIAKARRDCLTPYALAPNATVPTALAVLCCIRPTNAETFGETLNHLWFNNQPFLWAQLC

IPLAALVILFRCFSCCMPFLLVAGVCLGKVDAFEHATTVPNVPGIPYKALVERAGYAPLN

LEITVVSSELTPSTNKEYVTCKFHTVIPSPQVKCCGSLECKASSKADYTCRVFGGVYPFM

WGGAQCFCDSENTQLSEAYVEFAPDCTIDHAVALKVHTAALKVGLRIVYGNTTAHLDT

FVNGVTPGSSRDLKVIAGPISAAFSPFDHKVVIRKGLVYNYDFPEYGAMKPGAFGDIQAS

SLDATDIVARTDIRLLKPSVKNIHVPYTQAVSGYEMWKNNSGRPLQETAPFGCKIEVEPL

RASNCAYGHIPISIDIPDAAFVRSSESPTILEVSCTVADCIYSADFGGSLTLQYKADREGHC

PVHSHSTTAVLKEATTHVTAVGSITLHFSTSSPQANFIVSLCGKKSTCNAECKPPADHIIG

EPHKVDQEFQAAVSKTSWNWLLALFGGASSLIVVGLIVLVCSSMLINTRR

C. Eastern Equine Encephalitis Virus (EEEV)—Full Length Sequences

EEEVs + .structPs.uniq.EG-1.1
(SEQ ID NO: 10)
MFPYPTLNYPPMAPINPMAYRDPNPPRRRWRPFRPPLAAQIEDLRRSIANLTLKQRAPNP

PAGPPAKRKKPAPKPKPAQAKKKRPPPPAKKQKRKPKPGKRQRMCMKLESDKTFPIML

NGQVNGYACVVGGRVFKPLHVEGRIDNEQLAAIKLKKASIYDLEYGDVPQCMKSDTLQ

YTSDKPPGFYNWHHGAVQYENNRFTVPRGVGGKGDSGRPILDNKGRVVAIVLGGVNE

GSRTALSVVTWNQKGVTVKDTPEGSEPWSLATVMCVLANITFPCDQPPCMPCCYEKNP

HETLTMLEQNYDSRAYDQLLDAAVKCNARRTRRDLDTHFTQYKLARPYIADCPNCGHS

RCDSPIAIEEVRGDAHAGVIRIQTSAMFGLKTDGVDLAYMSFMNGKTQKSIKIDNLHVR

TSAPCSLVSHHGYYILAQCPPGDTVTVGFHDGPNRHTCTVAHKVEFRPVGREKYRHPPE

HGVELPCNRYTHKRADQGHYVEMHQPGLVADHSLLSIHSAKVKITVPSGAQVKYYCKC

PDVREGITSSDHTTTCTDVKQCRAYLIDNKKWVYNSGRLPRGEGDTFKGKLHVPFVPV

KAKCIATLAPEPLVEHKHRTLILHLHPDHPTLLTTRSLGSDANPTRQWIERPTTVNFTVTG

EGLEYTWGNHPPKRVWAQESGEGNPHGWPHEVVVYYYNRYPLTTIIGLCTCVAIIMVS

CVTSVWLLCRTRNLCITPYKLAPNAQVPILLALLCCIKPTRADDTLQVLNYLWNNNQNF

FWMQTLIPLAALIVCMRMLRCLFCCGPAFLLVCGALGAAAYEHTAVMPNKVGIPYKAL

VERPGYAPVHLQIQLVNTRIIPSTNLEYITCKYKTKVPSPVVKCCGATQCTSKPHPDYQC

QVFTGVYPFMWGGAYCFCDTENTQMSEAYVERSEECSIDHAKAYKVHTGTVQAMVNI

TYGSVSWRSADVYVNGETPAKIGDAKLIIGPLSSAWSPFDNKVVVYGHEVYNYDFPEY

GTGKAGSFGDLQSRTSTSNDLYANTNLKLQRPQAGIVHTPFTQAPSGFERWKRDKGAPL

NDVAPFGCSIALEPLRAENCAVGSIPISIDIPDAAFTRISETPTVSDLECKITECTYASDFGG

IATVAYKSSKAGNCPIHSPSGVAVIKENDVTLAESGSFTFHFSTANIHPAFKLQVCTSAVT

CKGDCKPPKDHIVDYPAQHTESFTSAISATAWSWLKVLVGGTSAFIVLGLIATAVVALV

LFFHRH

EEEVs + .structPs.uniq.EG-2.1

(SEQ ID NO: 11)

MFPYPILNYPPMAPVNPMAYRDPNPPRQVAPFRPPLAARIEDLRRSIANLTFKQRAPNPP

PGPPAKRKKPAPKPKPAAPKKKRQPPPAKKQKRKQPGKRQRMCIKLESDKTFPILLNG

QVNGYACVFGGRVFKPLHVEGKIDNEQLAAIKLKKASIYDLEYGDVPQCMKSDTLQYT

SEKPPGFYNWHHGAVQYDNNRFTVPRGVGGEGDSGRPILDNRGRVVAIVLGGANEGSR

TALSVVTWNQKGVTIKDTPEGSEPWSLTTVMCVLANITFPCEQPPCMPCCYEKNPHETL

SMLEQNYDSQAYDQLLEAAVKCNGRRTRRDLETHFTQYKLARPYIADCSNCGHGRCDS

PIAIEDVRGDAHAGYIRIQTSAMFGLKSDGVDLAYMSFMNGKTLKAIKIEHLYARTSAPC

SLVSYHGYYLLAQCPPGDTVTVGFQDGANKHMCTIAHKVEFKPVGREKYRHPPAHGVE

LPCNKYTHKRADQGYYVEMHQPGVVADHSLLSLSSTKVKITVPSGSQVKYYCKCPDVQ

EGTTSGDHTTTCTDLKQCRAYLIDNKKWVFNSGKLPRGEGETFKGKLHVPFVPVTSKCT

ATLAPEPLVEHKHRSLILHLHPEHPTLLTTRALGNDARPTRQWVDQPTTVNFTVTGEGFE

YTWGNHPPKKIWAQESGEGNPHGWPHEVVIYYYNRYPMTTIVGLCTCAAIIMVSCITSV

WLLCRARNLCITPYRLAPNAQVPILLAVLCCVKPTRADDTLQVLGYLWNHNQNFFWM

QTLLLPLAALIVCMRMLRCLLCCGPAFLLVCGAWAAAYEHTAVMSNKVGIPYKALVERP

SYAPVHLQIQLVTTKIIPSANLEYITCKYKTKVLSPVVKCCGATQCTSKQHPDYQCQVFA

GVYPFMWGGAYCFCDTENTQMSEAYIERAEECSVDQAKAYKVHTGTVQAVVNITYGS

VTWRSADVYVNGETPAKIGDAKLTIGPLSSAWTPFDSKVVVYGHEVHNYDFPEYGTGR

AGSFGDLQSRTLTSNDLYANTNLKLQRPQPGVVHTPYTQAPSGFERWKKDRGAPLNDI

APFGCTIALDPLRAENCAVGNIPLSIDIPDAAFTRIAETPTVSDLECKVTECTYASDFGGIA

TVAYKASKAGNCPIHSPSGIAVIKENDVTLADSGSFTFHFSTASIHPAFKMQVCTSVVTC

KGDCKPPKDHILDYPAQHTETFTSAVSATAWSWLKVLVGSTSAFIVLGIIATAVVALVLF

THKH

EEEVs + .structPs.uniq.EG-2.2

(SEQ ID NO: 12)

MFPYPTLNYPPMAPINPMAYRDPNPPRRRWRPFRPPLAAQIEDLRRSIANLTLKQRAPNP

PAGPPAKRKKPAPKPKPAQAKKKRPPPPAKKQKRKPKPGKRQRMCMKLESDKTFPIML

NGQVNGYACVVGGRVFKPLHVEGRIDNEQLAAIKLKKASIYDLEYGDVPQCMKSDTLQ

YTSDKPPGFYNWHHGAVQYENNRFTVPRGVGGKGDSGRPILDNKGRVVAIVLGGVNE

GSRTALSVVTWNQKGVTVKDTPEGSEPWSLATVMCVLANITFPCDQPPCMPCCYEKNP

HETLTMLEQNYDSRAYDQLLDAAVKCNARRTRRDLDTHFTQYKLARPYIADCPNCGHS

RCDSPIAIEEVRGDAHAGVIRIQTSAMFGLKTDGVDLAYMSFMNGKTQKSIKIDNLHVR

TSAPCSLVSHHGYYILAQCPPGDTVTVGFHDGPNRHTCTVAHKVEFRPVGREKYRHPPE

HGVELPCNRYTHKRADQGHYVEMHQPGLVADHSLLSIHSAKVKITVPSGAQVKYYCKC

PDVREGITSSDHTTTCTDVKQCRAYLIDNKKWVYNSGRLPRGEGDTFKGKLHVPFVPV

KAKCIATLAPEPLVEHKHRTLILHLHPDHPTLLTTRSLGSDANPTRQWIERPTTVNFTVTG

EGLEYTWGNHPPKRVWAQESGEGNPHGWPHEVVVYYYNRYPLTTIIGLCTCVAIIMVS

CVTSVWLLCRTRNLCITPYKLAPNAQVPILLALLCCIKPTRADDTLQVLNYLWNNNQNF

FWMQTLIPLAALIVCMRMLRCLFCCGPAFLLVCGALGAAAYEHTAVMPNKVGIPYKAL

VERPGYAPVHLQIQLVNTRIIPSTNLEYITCKYKTKVPSPVVKCCGATQCTSKPHPDYQC

QVFTGVYPFMWGGAYCFCDTENTQMSEAYVERSEECSIDHAKAYKVHTGTVQAMVNI

-continued

TYGSVSWRSADVYVNGETPAKIGDAKLIIGPLSSAWSPFDNKVVVYGHEVYNYDFPEY

GTGKAGSFGDLQSRTSTSNDLYANTNLKLQRPQAGIVHTPFTQAPSGFERWKRDKGAPL

NDVAPFGCSIALEPLRAENCAVGSIPISIDIPDAAFTRISETPTVSDLECKITECTYASDFGG

IATVAYKSSKAGNCPIHSPSGVAVIKENDVTLAESGSFTFHFSTANIHPAFKLQVCTSAVT

CKGDCKPPKDHIVDYPAQHTESFTSAISATAWSWLKVLVGGTSAFIVLGLIATAVVALV

LFFHRH

D. Chikungunya virus (CHKV)—Full Length Sequence

CHKs + .structPs.uniq.EG-1.1
(SEQ ID NO: 13)

MEFIPTQTFYNRRYQPRPWTPRPTIQVIRPRPRPQRQAGQLAQLISAVNK

LTMRAVPQQKPRRNRKNKKQKQKQQAPQNNTNQKKQPPKKKPAQKKKKPG

RRERMCMKIENDCIFEVKHEGKVTGYACLVGDKVMKPAHVKGTIDNADLA

KLAFKRSSKYDLECAQIPVHMKSDASKFTHEKPEGYYNWHHGAVQYSGGR

FTIPTGAGKPGDSGRPIFDNKGRVVAIVLGGANEGARTALSVVTWNKDIV

TKITPEGAEEWSLAIPVMCLLANTTFPCSQPPCTPCCYEKEPEKTLRMLE

DNVMRPGYYQLLQASLTCSPHRQRRSTKDNFNVYKATRPYLAHCPDCGEG

HSCHSPVALERIRNEATDGTLKIQVSLQIGIKTDDSHDWTKLRYMDNHMP

ADAERAGLFVRTSAPCTITGTMGHFILARCPKGETLTVGFTDSRKISHSC

THPFHHDPPVIGREKFHSRPQHGKELPCSTYVQSTAATTEEIEVHMPPDT

PDRTLMSQQSGNVKITVNGQTVRYKCNCGGSNEGLTTTDKVINNCKVDQC

HAAVTNHKKWQYNSPLVPRNAELGDRKGKIHIPFPLANVTCRVPKARNPT

-continued

VTYGKNQVIMLLYPDHPTLLSYRNMGEEPNYQEEWVTHKKEIRLTVPTEG

LEVTWGNNEPYKYWPQLSTNGTAHGHPHEIILYYYELYPTMTVVVVSVAT

FILLSMVGVAVGMCMCARRRCITPYELTPGATVPFLLSLICCIRTAKAAT

YQEAAVYLWNEQQPLFWLQALIPLAALIVLCNCLRLLPCCCKTLAFLAVM

SVGAHTVSAYEHVTVIPNTVGVPYKTLVNRPGYSPMVLEMELLSVTLEPT

LSLDYITCEYKTVIPSPYVKCCGTAECKDKSLPDYSCKVFTGVYPFMWGG

AYCFCDAENTQLSEAHVEKSESCKTEFASAYRAHTASASAKLRVLYQGNN

ITVTAYANGDHAVTVKDAKFIVGPMSSAWTPFDNKIVVYKGDVYNMDYPP

FGAGRPGQFGDIQSRTPESEDVYANTQLVLQRPSAGTVHVPYSQAPSGFK

YWLKERGASLQHTAPFGCQIATNPVRAMNCAVGNMPISIDIPDAAFTRVV

DAPSLTDMSCEVPACTHSSDFGGVAIIKYAASKKGKCAVHSMTNAVTIRE

AEIEVEGNSQLQISFSTALASAEFRVQVCSTQVHCAAECHPPKDHIVNYP

ASHTTLGVQDISATAMSWVQKITGGVGLVVAVAALILIVVLCVSFSRH

E. VEEV—Sequences without CP Gene

VEEVs + .structPs.uniq.EG-1.1-noCP
(SEQ ID NO: 14)

TTMCLLANVTFPCAQPPICYDRKPAETLAMLSVNVDNPGYDELLEAAVKCPGRKRRSTE

ELFKEYKLTRPYMARCIRCAVGSCHSPIAIEAVKSDGHDGYVRLQTSSQYGLDSSGNLK

GRTMRYDMHGTIEEIPLHQVSLHTSRPCHIVDGHGYFLLARCPAGDSITMEFKKDSVTHS

CSVPYEVKFNPVGRELYTHPPEHGAEQACQVYAHDAQNRGAYVEMHLPGSEVDSSLVS

LSGSSVTVTPPAGTSALVECECGGTKISETINTAKQFSQCTKKEQCRAYRLQNDKWVYN

SDKLPKAAGATLKGKLHVPFLLADGKCTVPLAPEPMITFGFRSVSLKLHPKNPTYLTTR

QLADEPHYTHELISEPAVRNFTVTEKGWEFVWGNHPPKRFWAQETAPGNPHGLPHEVIT

HYYHRYPMSTILGLSICAAIVTVSVAASTWLFCKSRVSCLTPYRLTPNARMPLCLAVLCC

ARTARAETTWESLDHLWNNNQQMFWIQLLIPLAALIVVTRLLKCVCCVVPFLVVAGAA

GAGAYEHATTMPSQAGISYNTIVNRAGYAPLPISITPTKIKLIPTVNLEYVTCHYKTGMDS

PAIKCCGSQECTPTYRPDEQCKVFTGVYPFMWGGAYCFCDTENTQVSKAYVMKSDDCL

ADHAEAYKAHTASVQAFLNITVGEHSIVTTVYVNGETPVNFNGVKLTAGPLSTAWTPFD

RKIVQYAGEIYNYDFPEYGAGQPGAFGDIQSRTVSSSDLYANTNLVLQRPKAGAIHVPY

TQAPSGFEQWKKDKAPSLKFTAPFGCEIYTNPIRAENCAVGSIPLAFDIPDALFTRVSETP

TLSAAECTLNECVYSSDFGGIATVKYSASKSGKCAVHVPSGTATLKEAAVELTEQGSATI

HFSTANIHPEFRLQICTSYVTCKGDCHPPKDHIVTHPQYHAQTFTAAVSKTAWTWLTSL

LGGSAVIIIGLVLATIVAMYVLTNQKHN

-continued

VEEVs+.structPs.uniq.EG-2.1-noCP
(SEQ ID NO: 15)
TTLCLLANVTFPCTQPPICYDRKPAETLSMLSHNIDNPGYDELLEAVLKCPGRGKRSTEE

LFKEYKLTRPYMAKCVRCAVGSCHSPIAIEAVRSEGHDGYVRLQTSSQYGLDPSGNLKG

RTMRYDMHGTIKEIPLHQVSVHTSRPCHIIDGHGYFLLARCPEGDSITMEFKKESVTHSC

SVPYEVKFTPVGRELYSHPPEHGAEQPCHVYAHDAQNRGAYVEMHLPGSEVDSTLLSM

SGSSVHVTPPAGQSVQVECECGGTKISETINSAKQYSQCSKTSQCRAYRTQNDKWVYNS

DKLPKASGETLKGKLHVPFVLTEAKCTVPLAPEPIITFGFRSVSLKLHPKNPTFLTTRQLD

GEPAYTHELITHPVVRNFSVTEKGWEFVWGNHPPQRYWSQETAPGNPHGLPHEVIVHY

YHRYPMSTIVGLSICAAIVTTSIAASVWLFCKSRISCLTPYRLTPNARIPFCLAVLCCARTA

KAETTWESLDHLWNHNQQMFWSQLLIPLAALIVATRLLKCMCCVVPFLVVAGAVGAG

AYEHATTMPNQVGIPYNTIVNRAGYAPLPISIVPTKVKLIPTVNLEYITCHYKTGLDSPAI

KCCGTQECSPTYRPDEQCKVFSGVYPFMWGGAYCFCDTENTQISKAYVTKSEDCVTDH

AQAYKAHTASIQAFLNITVGGHSTTAVVYVNGETPVNFNGIKLVAGPLSTAWSPFDKKI

VQYAGEVYNYDFPEYGAGHAGAFGDIQARTISSSDVYANTNLVLQRPNTGTIHVPYTQA

PSGYEQWKKDKPPSLKYTAPFGCEIHVNPVRAENCAVGFIPLAFDIPDALFTRVSETPTLS

SAECSLNECTYSTDFGGIATVKYSASKAGKCAVHIPSGTATLKEAAVELAEQGSATIHFS

TASIHPEFKLQICTKVLTCKGDCHPPRDHIVTHPQYHAQSFTAAVSKTAWTWITSLLGGS

AIIIIGLVLATVVAMYVLTNQRHN

VEEVs+.structPs.uniq.EG-2.2-noCP
(SEQ ID NO: 16)
TTMCLLANVTFPCAQPPICYDRKPAETLAMLSVNVDNPGYDELLEAAVKCPGRKRRSTE

ELFKEYKLTRPYMARCIRCAVGSCHSPIAIEAVKSDGHDGYVRLQTSSQYGLDSSGNLK

GRTMRYDMHGTIEEIPLHQVSLHTSRPCHIVDGHGYFLLARCPAGDSITMEFKKDSVTHS

CSVPYEVKFNPVGRELYTHPPEHGAEQACQVYAHDAQNRGAYVEMHLPGSEVDSSLVS

LSGSSVTVTPPAGTSALVECECGGTKISETINTAKQFSQCTKKEQCRAYRLQNDKWVYN

SDKLPKAAGATLKGKLHVPFLLADGKCTVPLAPEPMITFGFRSVSLKLHPKNPTYLTTR

QLADEPHYTHELISEPAVRNFTVTEKGWEFVWGNHPPKRFWAQETAPGNPHGLPHEVIT

HYYHRYPMSTILGLSICAAIVTVSVAASTWLFCKSRVSCLTPYRLTPNARMPLCLAVLCC

ARTARAETTWESLDHLWNNNQQMFWIQLLIPLAALIVVTRLLKCVCCVVPFLVVAGAA

GAGAYEHATTMPSQAGISYNTIVNRAGYAPLPISITPTKIKLIPTVNLEYVTCHYKTGMDS

PAIKCCGSQECTPTYRPDEQCKVFTGVYPFMWGGAYCFCDTENTQVSKAYVMKSDDCL

ADHAEAYKAHTASVQAFLNITVGEHSIVTTVYVNGETPVNFNGVKLTAGPLSTAWTPFD

RKIVQYAGEIYNYDFPEYGAGQPGAFGDIQSRTVSSSDLYANTNLVLQRPKAGAIHVPY

TQAPSGFEQWKKDKAPSLKFTAPFGCEIYTNPIRAENCAVGSIPLAFDIPDALFTRVSETP

TLSAAECTLNECVYSSDFGGIATVKYSASKSGKCAVHVPSGTATLKEAAVELTEQGSATI

HFSTANIHPEFRLQICTSYVTCKGDCHPPKDHIVTHPQYHAQTFTAAVSKTAWTWLTSL

LGGSAVIIIGLVLATIVAMYVLTNQKHN

VEEVs+.structPs.uniq.EG-3.1-noCP
(SEQ ID NO: 17)
TAVCLLANVTFPCSTPPICYDRAPAETLMMLSKNIDNPGYDELLEAVLKCPGRQKRSTEE

LFKEYKLTKPYMAKCIRCAVGSCHSPIAIEAVRSEGHDGYVRLQTSSQYGLDPSGNVKS

RVMRYNMYGKIVEVPLHQVSLHTSRPCQIVDGHGYFLLARCPPGDSITMEFKKGSVTHS

CSVPYEVKFTPVGRELYSHPPEHGTEHPCRVYVHDAQQKDAYVEMHLPGSEVDSSLLS

-continued

```
MSGSAVRVTPPSGQSVLVECNCGSAVSETINTAKSYSQCTKTSQCRAYRLQSDKWVFNS

DKLPKAAGETLKGKLHVPYLLSEAKCTVPLAPEPIVTFGFRFVSLKLHPRNPTYLTTRQL

DGEPNYTHELISEPTIRNFTVTEHGWEYVWGNHPPQRYWAQETAPGDPHGLPHEVIKHY

YHRYPMSTTLGLSICAAVVTTSIAASTWLLCKSRVSCLTPYRLTPNAQLPVCLAFLCCAR

TARAETAWESLDHLWNNNQQMFWTQLLIPLAALIVVTRLLRCVCCVVPFLVLAGAASV

GAYEHATTMPSQVGIPYNTVVNRAGYAPLAISIIPTKIRLIPTLNLEYITCHYKTGLDSPSI

KCCGTQECPKVNRPDEQCKVFAGVYPFMWGGAYCFCDSENTQISRAYVMKSDDCSAD

HALAYKAHTASIQAFLNITVGEQSTTAVVYVNGETPISFNGVKLVAGPLSTAWTPFDRK

VVQYAGEIYNYDFPEYGAGHAGAFGDLQARTITSNDLYANTNLVLQRPKSGTVHVPYT

QAPSGFEQWKKDKPPSLKFTAPFGCEIYVNPVRAENCAVGSIPLSFDIPDALFTRVSDTPT

LSTAECTLNECVYSSDFGGIASVKYSATKAGKCAVHVPSGTATLKESLVEVVEQGSMTL

HFSTASIHPEFRLQICTSFVTCKGDCHPPKDHIVTHPQHHAQTFTAAVSKTAWTWLSSLL

GGSAAIIIGLVLATLVAMYVLTNQKR N

VEEVs + .structPs.uniq.EG-3.2-noCP
                                         (SEQ ID NO: 18)
TTMCLLANVTFPCAQPPICYDRKPAETLAMLSVNVDNPGYDELLEAAVKCPGRKRRSTE

ELFKEYKLTRPYMARCIRCAVGSCHSPIAIEAVKSDGHDGYVRLQTSSQYGLDSSGNLK

GRTMRYDMHGTIEEIPLHQVSVHTSRPCHIIDGHGYFLLARCPAGDSITMEFKKDSVTHS

CSVPYEVKFNPVGRELYTHPPEHGAEQACQVYAHDAQNRGAYVEMHLPGSEVDSSLVS

LSGSSVTVTPPAGTSALVECECGGTKISETINTAKQFSQCTKKEQCRAYRLQNDKWVYN

SDKLPKAAGATLKGKLHVPFLLADGKCTVPLAPEPMITFGFRSVSLKLHPKNPTYLTTR

QLADEPHYTHELISEPAVRNFTVTEKGWEFVWGNHPPKRFWAQETAPGNPHGLPHEVIT

HYYHRYPMSTILGLSICAAIVTTSIAASVWLFCKSRISCLTPYRLTPNARMPLCLAVLCCA

RTARAETTWESLDHLWNHNQQMFWSQLLIPLAALIVATRLLKCVCCVVPFLVVAGAAG

AGAYEHATTMPNQVGIPYNTIVNRAGYAPLPISITPTKIKLIPTVNLEYVTCHYKTGMDSP

AIKCCGSQECTPTYRPDEQCKVFTGVYPFMWGGAYCFCDTENTQVSKAYVMKSDDCL

ADHAEAYKAHTASVQAFLNITVGEHSIVTTVYVNGETPVNFNGVKLTAGPLSTAWTPFD

RKIVQYAGEIYNYDFPEYGAGQPGAFGDIQSRTVSSSDLYANTNLVLQRPKAGAIHVPY

TQAPSGFEQWKKDKAPSLKFTAPFGCEIYTNPIRAENCAVGSIPLAFDIPDALFTRVSETP

TLSAAECTLNECVYSSDFGGIATVKYSASKSGKCAVHVPSGTATLKEAAVELTEQGSATI

HFSTANIHPEFRLQICTSYVTCKGDCHPPRDHIVTHPQYHAQTFTAAVSKTAWTWLTSLL

GGSAVIIIGLVLATIVAMYVLTNQ KHN

VEEVs + .structPs.uniq.EG-3.3-noCP
                                         (SEQ ID NO: 19)
TTLCLLANVTFPCTQPPICYDRKPAETLSMLSHNIDNPGYDELLEAVLKCPGRGKRSTEE

LFKEYKLTRPYMAKCVRCAVGSCHSPIAIEAVRSDGHDGYIRIQTSSQYGLDPSGNLKGR

TMRYDMHGTIKEIPLHQVSLHTSRPCHIVDGHGYFLLARCPEGDSITMEFKKESVTHSCS

VPYEVKFNPAGRELYTHPPEHGAEQPCHVYAHDAQNRGAYVEMHLPGSEVDSTLLSMS

GSSVHVTPPAGQSVQVECECGGTKISETINSAKQYSQCSKTSQCRAYRTQNDKWVYNS

DKLPKASGETLKGKLHVPFVLTEAKCTVPLAPEPIITFGFRSVSLKLHPKNPTFLTTRQLD

GEPAYTHELITHPVVRNFSVTEKGWEFVWGNHPPQRYWSQETAPGNPHGLPHEVIVHY

YHRYPMSTIVGLSICAAIVTVSVAASTWLFCRSRVACLTPYRLTPNARIPFCLAVLCCAR
```

```
TAKAETTWESLDHLWNNNQQMFWIQLLIPLAALIVVTRLLKCMCCVVPFLVVAGAVGA

GAYEHATTMPSQAGISYNTIVNRAGYAPLPISIVPTKVKLIPTVNLEYITCHYKTGMDSPA

IKCCGTQECSPTYRPDEQCKVFSGVYPFMWGGAYCFCDTENTQISKAYVTKSEDCVTD

HAQAYKAHTASIQAFLNITVGGHSTTAVVYVNGETPVNFNGIKLVAGPLSTAWSPFDKK

IVQYAGEVYNYDFPEYGAGHAGAFGDIQARTISSSDVYANTNLVLQRPNTGTIHVPYTQ

APSGYEQWKKDKPPSLKYTAPFGCEIHVNPVRAENCAVGFIPLAFDIPDALFTRVSETPT

LSSAECSLNECTYSTDFGGIATVKYSASKAGKCAVHIPSGTATLKEAAVELAEQGSATIH

FSTASIHPEFKLQICTKVLTCKGDCHPPKDHIVTHPQYHAQSFTAAVSKTAWTWITSLLG

GSAIIIIGLVLATVVAMYVLTNQRHN
```

F. WEEV—Sequences without CP Gene

```
WEEVs + .structPs.uniq.EG-1.1-noCP
                                              (SEQ ID NO: 20)
TALCVLSNVTFPCDKPPVCYSLAPERTLDVLEENVDNPNYDTLLENVLKCPSRRPKRSIT

DDFTLTSPYLGFCPYCRHSTPCFSPIKIENVWDESDDGSIRIQVSAQFGYNQAGTADVTKF

RYMSFDHDHDIKEDSMEKIAISTSGPCRRLGHKGYFLLAQCPPGDSVTVSITSGASENSC

TVEKKIRRKFVGREEYLFPPVHGKLVKCHVYDHLKETSAGYITMHRPGPHAYKSYLEEA

SGEVYIKPPSGKNVTYECKCGDYSTGIVSTRTKMNGCTKAKQCIAYKSDQTKWVFNSP

DLIRHTDHSVQGKLHIPFRLTPTVCPVPLAHTPTVTKWFKGITLHLTATRPTLLTTRKLGL

RADATAEWITGTTSRNFSVGREGLEYVWGNHEPVRVWAQESAPGDPHGWPHEIIIHYY

HRHPVYTVIVLCGVALAILVGTASSAACIAKARRDCLTPYALAPNATVPTALAVLCCIRP

TNAETFGETLNHLWFNNQPFLWAQLCIPLAALVILFRCFSCCMPFLLVAGVCLGKVDAF

EHATTVPNVPGIPYKALVERAGYAPLNLEITVVSSELTPSTNKEYVTCKFHTVIPSPQVKC

CGSLECKASSKADYTCRVFGGVYPFMWGGAQCFCDSENTQLSEAYVEFAPDCTIDHAV

ALKVHTAALKVGLRIVYGNTTAHLDTFVNGVTPGSSRDLKVIAGPISAAFSPFDHKVVIR

KGLVYNYDFPEYGAMKPGAFGDIQASSLDATDIVARTDIRLLKPSVKNIHVPYTQAVSG

YEMWKNNSGRPLQETAPFGCKIEVEPLRASNCAYGHIPISIDIPDAAFVRSSESPTILEVSC

TVADCIYSADFGGSLTLQYKADREGHCPVHSHSTTAVLKEATTHVTAVGSITLHFSTSSP

QANFIVSLCGKKTTCNAECKPPADHIIGEPHKVDQEFQAAVSKTSWNWLLALFGGASSL

IVVGLIVLVCSSMLINTRR

WEEVs + .structPs.uniq.EG-2.1-noCP
                                              (SEQ ID NO: 21)
TAMCVLANVTFPCDKPPVCYSLTPERTLDVLEENVDNPGYDTLLENVLKCPSRRQKRSI

TDDFTLTSPYLGHCPYCLHATPCFSPIKIEKVWDESDDGTIRIQVSAQLGYNQAGTADPT

KFRYMSYEQDHDIKEASMDKIAISTSGPCSRLGHKGYFLLARCPPGDSVTVSITSGTSENS

CTVERKIRRKFVGREEYLLPPVHGKLIKCHVYDHLKETTAGYITMHRPGPHAYATYVEE

SSGEVYIRPPSGKNVTYECKCGDYSTGTVNTRTKMPGCTKKKQCIAYKHDQTKWVFNS

PDLIRHSDHAVQGKLHIPFKLTATACPVPLAHTPTVEKWFKGVTLHLTASHPTLLTTRKL

GPRAEPTSEWIVGTVSRNFSVGREGLEYTWGNHDPVRVWSQESAPGDPHGWPHEIIVH

YYHRHPLYTIAVLCGLVLITVIGIASAAACISKARRDCLTPYALAPNAAVPTLLAVLCCIR

PTHAETLGESLGHLWLNNQPLLWAQLCLPLAALIILFRFFSCCLPFLLVAGVCLGKADAY

EHATTVPNVPGVPYKALVERSGYAPLNLEVTVVSSELIPSTNKEYVTCKFHTIIPSPQVKC

CGSLECQASRKADYTCRVFGGVYPFMWGGAQCSCDSENTQLSEAYVEFAPDCTADHA
```

-continued

```
VALKVHTAALKVGLQIVYGNTSTRLDTFVNGVTPGISGALKVIAGPISAAFTPFDHKVVI

RKGKVYNYDFPEYGAMKPGVFGDIQASSLDSTDIVARTDVRLLKPSVKSIHVPYTQAAS

GYEMWKNNSGRPLQDTAPFGCKIEVDPLRAVDCAYGHIPLSIDIPDAAFVRTSEAPTVLE

MSCTVTACIYSADFGGSLTLQYKADKEGNCPVHSHSSTAVLKEATTHVVHSGSVTLHFS

TSSPQVNFIVSLCGKKTTCDAECKPPSDHIIGEPHKVNQEFQAAVSKTSWNWLFAMLGG

ASSLIVVGLLVLACSSMIINTRR

WEEVs + .structPs.uniq.EG-2.2-noCP
                                                   (SEQ ID NO: 22)
TALCVLSNVTFPCDKPPVCYSLAPERTLDVLEENVDNPNYDTLLENVLKCPSRRPKRSIT

DDFTLTSPYLGFCPYCRHSTPCFSPIKIENVWDESDDGSIRIQVSAQFGYNQAGTADVTKF

RYMSFDHDHDIKEDSMEKIAISTSGPCRRLGHKGYFLLAQCPPGDSVTVSITSGASENSC

TVEKKIRRKFVGREEYLFPPVHGKLVKCHVYDHLKETSAGYITMHRPGPHAYKSYLEEA

SGEVYIKPPSGKNVTYECKCGDYSTGIVSTRTKMNGCTKAKQCIAYKSDQTKWVFNSP

DLIRHTDHSVQGKLHIPFRLTPTVCPVPLAHTPTVTKWFKGITLHLTATRPTLLTTRKLGL

RADATAEWITGTTSRNFSVGREGLEYVWGNHEPVRVWAQESAPGDPHGWPHEIIIHYY

HRHPVYTVIVLCGVALAILVGTASSAACIAKARRDCLTPYALAPNATVPTALAVLCCIRP

TNAETFGETLNHLWFNNQPFLWAQLCIPLAALVILFRCFSCCMPFLLVAGVCLGKVDAF

EHATTVPNVPGIPYKALVERAGYAPLNLEITVVSSELTPSTNKEYVTCKFHTVIPSPQVKC

CGSLECKASSKADYTCRVFGGVYPFMWGGAQCFCDSENTQLSEAYVEFAPDCTIDHAV

ALKVHTAALKVGLRIVYGNTTAHLDTFVNGVTPGSSRDLKVIAGPISAAFSPFDHKVVIR

KGLVYNYDFPEYGAMKPGAFGDIQASSLDATDIVARTDIRLLKPSVKNIHVPYTQAVSG

YEMWKNNSGRPLQETAPFGCKIEVEPLRASNCAYGHIPISIDIPDAAFVRSSESPTILEVSC

TVADCIYSADFGGSLTLQYKADREGHCPVHSHSTTAVLKEATTHVTAVGSITLHFSTSSP

QANFIVSLCGKKSTCNAECKPPADHIIGEPHKVDQEFQAAVSKTSWNWLLALFGGASSLI

VVGLIVLVCSSMLINTRR
```

G. EEEV—Sequences without CP Gene

```
EEEVs + .structPs.uniq.EG-1.1-noCP
                                                   (SEQ ID NO: 23)
TVMCVLANITFPCDQPPCMPCCYEKNPHETLTMLEQNYDSRAYDQLLDAAVKCNARRT

RRDLDTHFTQYKLARPYIADCPNCGHSRCDSPIAIEEVRGDAHAGVIRIQTSAMFGLKTD

GVDLAYMSFMNGKTQKSIKIDNLHVRTSAPCSLVSHHGYYILAQCPPGDTVTVGFHDGP

NRHTCTVAHKVEFRPVGREKYRHPPEHGVELPCNRYTHKRADQGHYVEMHQPGLVAD

HSLLSIHSAKVKITVPSGAQVKYYCKCPDVREGITSSDHTTTCTDVKQCRAYLIDNKKW

VYNSGRLPRGEGDTFKGKLHVPFVPVKAKCIATLAPEPLVEHKHRTLILHLHPDHPTLLT

TRSLGSDANPTRQWIERPTTVNFTVTGEGLEYTWGNHPPKRVWAQESGEGNPHGWPHE

VVVYYYNRYPLTTIIGLCTCVAIIMVSCVTSVWLLCRTRNLCITPYKLAPNAQVPILLALL

CCIKPTRADDTLQVLNYLWNNNQNFFWMQTLIPLAALIVCMRMLRCLFCCGPAFLLVC

GALGAAAYEHTAVMPNKVGIPYKALVERPGYAPVHLQIQLVNTRIIPSTNLEYITCKYKT

KVPSPVVKCCGATQCTSKPHPDYQCQVFTGVYPFMWGGAYCFCDTENTQMSEAYVER

SEECSIDHAKAYKVHTGTVQAMVNITYGSVSWRSADVYVNGETPAKIGDAKLIIGPLSS

AWSPFDNKVVVYGHEVYNYDFPEYGTGKAGSFGDLQSRTSTSNDLYANTNLKLQRPQ
```

-continued

AGIVHTPFTQAPSGFERWKRDKGAPLNDVAPFGCSIALEPLRAENCAVGSIPISIDIPDAA

FTRISETPTVSDLECKITECTYASDFGGIATVAYKSSKAGNCPIHSPSGVAVIKENDVTLA

ESGSFTFHFSTANIHPAFKLQVCTSAVTCKGDCKPPKDHIVDYPAQHTESFTSAISATAW

SWLKVLVGGTSAFIVLGLIATAVVALVLFFHRH

EEEVs + .structPs.uniq.EG-2.1-noCP
(SEQ ID NO: 24)
TVMCVLANITFPCEQPPCMPCCYEKNPHETLSMLEQNYDSQAYDQLLEAAVKCNGRRT

RRDLETHFTQYKLARPYIADCSNCGHGRCDSPIAIEDVRGDAHAGYIRIQTSAMFGLKSD

GVDLAYMSFMNGKTLKAIKIEHLYARTSAPCSLVSYHGYYLLAQCPPGDTVTVGFQDG

ANKHMCTIAHKVEFKPVGREKYRHPPAHGVELPCNKYTHKRADQGYYVEMHQPGVV

ADHSLLSLSSTKVKITVPSGSQVKYYCKCPDVQEGTTSGDHTTTCTDLKQCRAYLIDNK

KWVFNSGKLPRGEGETFKGKLHVPFVPVTSKCTATLAPEPLVEHKHRSLILHLHPEHPTL

LTTRALGNDARPTRQWVDQPTTVNFTVTGEGFEYTWGNHPPKKIWAQESGEGNPHGW

PHEVVIYYYNRYPMTTIVGLCTCAAIIMVSCITSVWLLCRARNLCITPYRLAPNAQVPILL

AVLCCVKPTRADDTLQVLGYLWNHNQNFFWMQTLLPLAALIVCMRMLRCLLCCGPAF

LLVCGAWAAAYEHTAVMSNKVGIPYKALVERPSYAPVHLQIQLVTTKIIPSANLEYITCK

YKTKVLSPVVKCCGATQCTSKQHPDYQCQVFAGVYPFMWGGAYCFCDTENTQMSEA

YIERAEECSVDQAKAYKVHTGTVQAVVNITYGSVTWRSADVYVNGETPAKIGDAKLTI

GPLSSAWTPFDSKVVVYGHEVHNYDFPEYGTGRAGSFGDLQSRTLTSNDLYANTNLKL

QRPQPGVVHTPYTQAPSGFERWKKDRGAPLNDIAPFGCTIALDPLRAENCAVGNIPLSID

IPDAAFTRIAETPTVSDLECKVTECTYASDFGGIATVAYKASKAGNCPIHSPSGIAVIKEN

DVTLADSGSFTFHFSTASIHPAFKMQVCTSVVTCKGDCKPPKDHILDYPAQHTETFTSAV

SATAWSWLKVLVGSTSAFIVLGIIATAVVALVLFTHKH

EEEVs + .structPs.uniq.EG-2.2-noCP
(SEQ ID NO: 25)
TVMCVLANITFPCDQPPCMPCCYEKNPHETLTMLEQNYDSRAYDQLLDAAVKCNARRT

RRDLDTHFTQYKLARPYIADCPNCGHSRCDSPIAIEEVRGDAHAGVIRIQTSAMFGLKTD

GVDLAYMSFMNGKTQKSIKIDNLHVRTSAPCSLVSHHGYYILAQCPPGDTVTVGFHDGP

NRHTCTVAHKVEFRPVGREKYRHPPEHGVELPCNRYTHKRADQGHYVEMHQPGLVAD

HSLLSIHSAKVKITVPSGAQVKYYCKCPDVREGITSSDHTTTCTDVKQCRAYLIDNKKW

VYNSGRLPRGEGDTFKGKLHVPFVPVKAKCIATLAPEPLVEHKHRTLILHLHPDHPTLLT

TRSLGSDANPTRQWIERPTTVNFTVTGEGLEYTWGNHPPKRVWAQESGEGNPHGWPHE

VVVYYYNRYPLTTIIGLCTCVAIIMVSCVTSVWLLCRTRNLCITPYKLAPNAQVPILLALL

CCIKPTRADDTLQVLNYLWNNNQNFFWMQTLIPLAALIVCMRMLRCLFCCGPAFLLVC

GALGAAAYEHTAVMPNKVGIPYKALVERPGYAPVHLQIQLVNTRIIPSTNLEYITCKYKT

KVPSPVVKCCGATQCTSKPHPDYQCQVFTGVYPFMWGGAYCFCDTENTQMSEAYVER

SEECSIDHAKAYKVHTGTVQAMVNITYGSVSWRSADVYVNGETPAKIGDAKLIIGPLSS

AWSPFDNKVVVYGHEVYNYDFPEYGTGKAGSFGDLQSRTSTSNDLYANTNLKLQRPQ

AGIVHTPFTQAPSGFERWKRDKGAPLNDVAPFGCSIALEPLRAENCAVGSIPISIDIPDAA

FTRISETPTVSDLECKITECTYASDFGGIATVAYKSSKAGNCPIHSPSGVAVIKENDVTLA

ESGSFTFHFSTANIHPAFKLQVCTSAVTCKGDCKPPKDHIVDYPAQHTESFTSAISATAW

SWLKVLVGGTSAFIVLGLIATAVVALVLFFHRH

H. CHK—Sequence without CP Gene

CHKs + .structPs.uniq.EG-1.1-noCP
(SEQ ID NO: 26)

```
VMCLLANTTFPCSQPPCTPCCYEKEPEKTLRMLEDNVMRPGYYQLLQASL
TCSPHRQRRSTKDNFNVYKATRPYLAHCPDCGEGHSCHSPVALERIRNEA
TDGTLKIQVSLQIGIKTDDSHDWTKLRYMDNHMPADAERAGLFVRTSAPC
TITGTMGHFILARCPKGETLTVGFTDSRKISHSCTHPFHHDPPVIGREKF
HSRPQHGKELPCSTYVQSTAATTEEIEVHMPPDTPDRTLMSQQSGNVKIT
VNGQTVRYKCNCGGSNEGLTTTDKVINNCKVDQCHAAVTNHKKWQYNSPL
VPRNAELGDRKGKIHIPFPLANVTCRVPKARNPTVTYGKNQVIMLLYPDH
PTLLSYRNMGEEPNYQEEWVTHKKEIRLTVPTEGLEVTWGNNEPYKYWPQ
LSTNGTAHGHPHEIILYYYELYPTMTVVVVSVATFILLSMVGVAVGMCMC
ARRRCITPYELTPGATVPFLLSLICCIRTAKAATYQEAAVYLWNEQQPLF
WLQALIPLAALIVLCNCLRLLPCCCKTLAFLAVMSVGAHTVSAYEHVTVI
PNTVGVPYKTLVNRPGYSPMVLEMELLSVTLEPTLSLDYITCEYKTVIPS
PYVKCCGTAECKDKSLPDYSCKVFTGVYPFMWGGAYCFCDAENTQLSEAH
VEKSESCKTEFASAYRAHTASASAKLRVLYQGNNITVTAYANGDHAVTVK
DAKFIVGPMSSAWTPFDNKIVVYKGDVYNMDYPPFGAGRPGQFGDIQSRT
PESEDVYANTQLVLQRPSAGTVHVPYSQAPSGFKYWLKERGASLQHTAPF
GCQIATNPVRAMNCAVGNMPISIDIPDAAFTRVVDAPSLTDMSCEVPACT
HSSDFGGVAIIKYAASKKGKCAVHSMTNAVTIREAEIEVEGNSQLQISFS
TALASAEFRVQVCSTQVHCAAECHPPKDHIVNYPASHTTLGVQDISATAM
SWVQKITGGVGLVV
```

V. Nucleic Acid Molecules

Nucleic acid molecules encoding the disclosed synthetic immunogenic polypeptides (e.g., SEQ ID NOs: 1-26, or immunogenic portion(s) thereof) are also disclosed herein. Unless otherwise specified, a "nucleic acid molecule encoding a polypeptide" includes all nucleotide sequences that are degenerate versions of each other and encode the same amino acid sequence. For example, a polynucleotide encoding a disclosed immunogenic polypeptide includes a nucleic acid sequence that is degenerate as a result of the genetic code. There are 20 natural amino acids, most of which are specified by more than one codon. Therefore, all degenerate nucleotide sequences are included as long as the amino acid sequence of the polypeptide encoded by the nucleotide sequence is unchanged. In some embodiments, the disclosed polypeptide sequences are back-translated to codon optimized DNA using standard methods.

The nucleic acids encoding a disclosed polypeptide include a recombinant DNA which is incorporated into a vector, such as an autonomously replicating plasmid or virus, or into the genomic DNA of a prokaryote or eukaryote, or which exists as a separate molecule (such as a cDNA) independent of other sequences. Methods for the manipulation and insertion of the nucleic acids of this disclosure into vectors are well known in the art (see for example, Sambrook et al., *Molecular Cloning, a Laboratory Manual*, 2d edition, Cold Spring Harbor Press, Cold Spring Harbor, N.Y., 1989, and Ausubel et al., *Current Protocols in Molecular Biology*, Greene Publishing Associates and John Wiley & Sons, New York, N.Y., 1994). DNA sequences encoding the polypeptide can be expressed in vitro or in vivo by DNA transfer into a suitable host cell. The cell may be prokaryotic or eukaryotic. Methods of stable transfer, meaning that the foreign DNA is continuously maintained in the host, are known in the art.

Polynucleotide sequences encoding the disclosed polypeptides can be operably linked to expression control sequences, such as heterologous expression control sequences (such as a heterologous promoter). An expression control sequence operably linked to a coding sequence is joined such that expression of the coding sequence is achieved under conditions compatible with the expression control sequences. The expression control sequences include, but are not limited to, appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

Hosts can include microbial, yeast, insect and mammalian organisms. Methods of expressing DNA sequences having eukaryotic or viral sequences in prokaryotes are well known in the art. Non-limiting examples of suitable host cells include bacteria, archaea, insect, fungi (for example, yeast), plant, and animal cells (for example, mammalian cells, such as human). Exemplary cells of use include *Escherichia coli, Bacillus subtilis, Saccharomyces cerevisiae, Salmonella typhimurium*, SF9 cells, C129 cells, *Neurospora*, and immortalized mammalian myeloid and lymphoid cell lines. Techniques for the propagation of mammalian cells in culture are well-known (see, Jakoby and Pastan (eds), 1979, Cell Culture, Methods in Enzymology, volume 58, Academic Press, Inc., Harcourt Brace Jovanovich, N.Y.). Examples of commonly used mammalian host cell lines are VERO and HeLa cells, CHO cells, HEK 293 cells, and WI38, BHK, and COS cell lines, although other cell lines may be used, such as cells designed to provide higher expression, desirable glycosylation patterns, or other features.

A number of viral vectors have been constructed, that can be used to express the disclosed polypeptides, including polyoma, i.e., SV40 (Madzak et al., 1992, *J. Gen. Virol.*, 73:1533-1536); adenovirus (Berkner, 1992, *Cur. Top. Microbiol. Immunol.*, 158:39-6; Berliner et al., 1988, *Bio Techniques*, 6:616-629; Gorziglia et al., 1992, *J. Virol.*, 66:4407-4412; Quantin et al., 1992, *Proc. Natl. Acad. Sci. USA*, 89:2581-2584; Rosenfeld et al., 1992, *Cell*, 68:143-155; Wilkinson et al., 1992, *Nucl. Acids Res.*, 20:2233-2239; Stratford-Perricaudet et al., 1990, *Hum. Gene Ther.*, 1:241-256); non-replicating adenoviruses of chimpanzee origin (ChAdv; Tatsis et al., *Gene Ther.* 13:421-429, 2006); vaccinia virus (Mackett et al., 1992, *Biotechnology*, 24:495-499); modified vaccinia Ankara (MVA) virus (Kremer et al., *Methods Mol. Biol.* 890:59-92, 2012); adeno-associated virus (Muzyczka, 1992, *Curr. Top. Microbiol. Immunol.*, 158:91-123; On et al., 1990, *Gene*, 89:279-282); herpes viruses, including HSV and EBV (Margolskee, 1992, *Curr. Top. Microbiol. Immunol.*, 158:67-90; Johnson et al., 1992, *J. Virol.*, 66:2952-2965; Fink et al., 1992, *Hum. Gene Ther.* 3:11-19; Breakfield et al., 1987, *Mol. Neurobiol.*, 1:337-371; Fresse et al., 1990, *Biochem. Pharmacol.*, 40:2189-2199); Sindbis viruses (Herweijer et al., 1995, *Human Gene Therapy* 6:1161-1167; U.S. Pat. Nos. 5,091,309 and 5,2217,879); alphaviruses (Schlesinger, 1993, *Trends Biotechnol.* 11:18-22; Frolov et al., 1996, *Proc. Natl. Acad. Sci. USA*

93:11371-11377); and retroviruses of avian (Brandyopadhyay et al., 1984, *Mol. Cell Biol.*, 4:749-754; Petropoulos et al., 1992, *J. Virol.*, 66:3391-3397), murine (Miller, 1992, *Curr. Top. Microbiol. Immunol.*, 158:1-24; Miller et al., 1985, *Mol. Cell Biol.*, 5:431-437; Sorge et al., 1984, *Mol. Cell Biol.*, 4:1730-1737; Mann et al., 1985, *J. Virol.*, 54:401-407), and human origin (Page et al., 1990, *J. Virol.*, 64:5370-5276; Buchschalcher et al., 1992, *J. Virol.*, 66:2731-2739). Baculovirus (*Autographa californica* multinuclear polyhedrosis virus; AcMNPV) vectors are also known in the art, and may be obtained from commercial sources (such as PharMingen, San Diego, Calif.; Protein Sciences Corp., Meriden, Conn.; Stratagene, La Jolla, Calif.).

In some embodiments, the nucleic acid is mRNA, such as mRNA formulated with a lipid nanoparticle (LNP).

VI. Therapeutic Methods and Pharmaceutical Compositions

The immunogenic polypeptides disclosed herein (such as SEQ ID NOs: 1-26, or polypeptides having at least 95% sequence identity to SEQ ID NOs: 1-26, or immunogenic portions thereof), or nucleic acids encoding the disclosed immunogenic polypeptides, can be administered to a subject to elicit an immune response in the subject, such as an immune response to one or more alphaviruses, such as one or more VEEV, WEEV, EEEV and CHIKV. In some embodiments, one or more of the disclosed polypeptides (or one or more nucleic acids or vectors encoding the disclosed polypeptides) is administered to a subject with an alphavirus infection or at risk of an alphavirus infection. In other embodiments, the one or more immunogenic polypeptides are administered to a subject as part of an immunization regimen. The one or more immunogenic polypeptides are administered in an amount sufficient to elicit an immune response to one or more alphaviruses in the subject. In some examples, administration of the immunogenic peptide inhibits (or in some instances even prevents) infection with one or more alphaviruses and/or reduces the signs and symptoms of alphavirus in an infected subject. In some embodiments, the subject is a mammal. In some examples, the subject is human. In some examples, the subject is an equine species, such as a horse.

In particular embodiments, two or more of the disclosed polypeptides or nucleic acids (or vectors) encoding the polypeptides are administered to the subject. In some examples, the methods include administering to the subject one or more immunogenic polypeptides (or nucleic acids encoding at least two polypeptides), for example, as a polyvalent immunogenic composition. In particular examples, the methods include administering to the subject one or more of the immunogenic polypeptides (for example, 2, 3, 4, 5, 6, 7, or more polypeptides) disclosed herein.

In some examples, the two or more immunogenic polypeptides (such as a set of immunogenic polypeptides) are administered simultaneously (for example, as a mixture), substantially simultaneously (for example, within a few minutes of one another, such as within less than 5 minutes of one another), or sequentially (for example, within 5 minutes, 10 minutes, 15 minutes, 30 minutes, 1 hour, 2 hours, 4 hours, 12 hours, 24 hours, or more of one another).

One or more of the disclosed polypeptides or nucleic acids encoding the polypeptides (including vectors including the nucleic acid) can be administered by any means known to one of skill in the art (see Banga, "Parenteral Controlled Delivery of Therapeutic Peptides and Proteins," in *Therapeutic Peptides and Proteins*, Third Edition, CRC Press, Boca Raton, 2015) either locally or systemically, such as by intramuscular, subcutaneous, or intravenous injection, but even oral, nasal, or anal administration is contemplated. In one embodiment, administration is by subcutaneous or intramuscular injection. To extend the time during which the disclosed polypeptides are available to stimulate a response, the polypeptide or nucleic acid encoding the polypeptide can be provided as an implant, an oily injection, or as a particulate system. The particulate system can be a microparticle, a microcapsule, a microsphere, a nanocapsule, or similar particle. (see, e.g., Banga, supra). A particulate carrier based on a synthetic polymer has been shown to act as an adjuvant to enhance the immune response, in addition to providing a controlled release. Aluminum salts can also be used as adjuvants to produce an immune response.

Optionally, one or more cytokines, such as interleukin (IL)-2, IL-6, IL-12, IL-15, RANTES, granulocyte macrophage colony stimulating factor (GM-CSF), tumor necrosis factor (TNF)-α, interferon (IFN)-α or IFN-γ, one or more growth factors, such as GM-CSF or G-CSF, one or more costimulatory molecules, such as ICAM-1, LFA-3, CD72, B7-1, B7-2, or other B7 related molecules; one or more molecules such as OX-40L or 41 BBL, or combinations of these molecules, can be used as biological adjuvants (see, for example, Salgaller et al., 1998, *J. Surg. Oncol.* 68(2): 122-38; Lotze et al., 2000, *Cancer J Sci. Am.* 6(Suppl 1):S61-6; Cao et al., 1998, *Stem Cells* 16(Suppl 1):251-60; Kuiper et al., 2000, *Adv. Exp. Med. Biol.* 465:381-90) with the disclosed immunogenic polypeptides. These molecules can be administered systemically (or locally) to the host. In several examples, IL-2, RANTES, GM-CSF, TNF-α, IFN-7, G-CSF, LFA-3, CD72, B7-1, B7-2, B7-1 B.7-2, OX-40L, 41 BBL, and/or ICAM-1 are administered.

Pharmaceutical compositions including the disclosed polypeptides, and/or nucleic acids encoding the polypeptides are also disclosed herein. The pharmaceutical compositions can include one or more of pharmaceutically acceptable carriers, adjuvants (such as those described above), a stabilizing detergent (such as polysorbate 80 (TWEEN® 80) (Sorbitan-mono-9-octadecenoate-poly(oxy-1,2-ethanediyl); manufactured by ICI Americas, Wilmington, DE), TWEEN® 40, TWEEN® 20, TWEEN® 60, ZWITTERGENT® 3-12, TEEPOL® HB7, and SPAN® 85 detergents, for example, in an amount of approximately 0.05 to 0.5%, such as at about 0.2%), a micelle-forming agent (such as PLURONIC® L62LF, L101, and L64 block copolymer, polyethylene glycol 1000, and TETRONIC® 1501, 150R1, 701, 901, 1301, and 130R1 block copolymer, for example, between 0.5 and 10%, or in an amount between 1.25 and 5%), and an oil (squalene, squalane, eicosane, tetratetracontane, glycerol, and peanut oil or other vegetable oils, for example, in an amount between 1 and 10%, or between 2.5 and 5%). In one embodiment, the pharmaceutical composition includes a mixture of stabilizing detergents, micelleforming agent, and oil available under the name PROVAX® (IDEC Pharmaceuticals, San Diego, CA).

In some embodiments, a pharmaceutical composition includes one or more nucleic acids, such as DNA, RNA or mRNA, encoding a disclosed polypeptide. A therapeutically effective amount of the nucleic acid(s) can be administered to a subject in order to generate an immune response. In various embodiments, a nucleic acid encoding a biological adjuvant (such as those described above) can be cloned into the same vector as a nucleic acid encoding a disclosed polypeptide, or the nucleic acid can be cloned into one or more separate vectors for co-administration. In addition, nonspecific immunomodulating factors such as Bacillus Calmette-Guerin (BCG) and levamisole can be co-administered.

One approach to administration of nucleic acids is direct immunization with plasmid DNA, such as with a mammalian expression plasmid. As described above, a nucleotide sequence encoding a disclosed polypeptide can be placed under the control of a promoter (such as a heterologous promoter) to increase expression of the molecule. Immunization by nucleic acid constructs is well known in the art and taught, for example, in U.S. Pat. No. 5,643,578 (which describes methods of immunizing vertebrates by introducing DNA encoding a desired antigen to elicit a cell-mediated or a humoral response), and U.S. Pat. Nos. 5,593,972 and 5,817,637 (which describe operably linking a nucleic acid sequence encoding an antigen to regulatory sequences enabling expression). U.S. Pat. No. 5,880,103 describes several methods of delivery of nucleic acids encoding immunogenic peptides or other antigens to an organism. The methods include liposomal delivery of the nucleic acids (or of the synthetic peptides themselves), and immune-stimulating constructs, or ISCOMs, negatively charged cage-like structures of 30-40 nm in size formed spontaneously on mixing cholesterol and Quil A™ (saponin).

In some embodiments, the nucleic acid is mRNA. In some examples, the nucleic acid (such as an mRNA) is formulated with a lipid nanoparticle (LNP). See, e.g., Pardi et al., *Nat. Commun.* 9:3361, 2018; Pardi et al., *Mol. Ther. Nucleic Acids* 15:36-47, 2019; both of which are incorporated herein by reference in their entirety. The mRNA may include one or more modified nucleosides, which in non-limiting examples may be 1-methylpseudouridine, 5-methylcytidine, or both. Such modifications may reduce innate immune responses that can inhibit synthesis of the encoded immunogen. The mRNA is incorporated in a lipid nanoparticle, which may decrease degradation of the mRNA and/or facilitate cellular uptake, for example, compared to naked mRNA. Exemplary lipid nanoparticles that can be used include, but are not limited to, Lipid H (see, e.g., Hassett et al., *Mol. Ther. Nucleic Acids* 15:1-11, 2019), Acuitas ALC-0315 (see, e.g., International Pat. Publ. WO 2017/075531), imidazole cholesterol ester (ICE) based lipids (see e.g., U.S. Pat. Publ. 2020/0155691), cystine cationic lipids (e.g., International Pat. Publ. No. WO 2020/214946), Lipid 2,2 (8,8)4C CH3 (see, e.g., U.S. Pat. No. 9,670,152), Acuitas A9 (see, e.g., U.S. Pat. No. 10,221,127), and Genevant CL1 (see, e.g., International Pat. Publ. WO 2020/219941).

In another approach to using nucleic acids for immunization, a disclosed immunogenic polypeptide can also be expressed by attenuated viral hosts or vectors or bacterial vectors. Recombinant vaccinia virus, adeno-associated virus (AAV), herpes virus, retrovirus, cytomegalovirus or other viral vectors (such as those described above) can be used to express the peptide or protein. For example, vaccinia vectors and methods useful in immunization protocols are described in U.S. Pat. No. 4,722,848. BCG (Bacillus Calmette Guerin) provides another vector for expression of the peptides (see Stover, *Nature* 351:456-460, 1991).

In one embodiment, a nucleic acid encoding a disclosed immunogenic polypeptide is introduced directly into cells. For example, the nucleic acid can be loaded onto gold microspheres by standard methods and introduced into the skin by a device such as Bio-Rad's HELIOS™ Gene Gun. The nucleic acids can be "naked," consisting of plasmids under control of a strong promoter. Typically, the DNA is injected into muscle, although it can also be injected directly into other sites The amount of the disclosed immunogenic polypeptide, or nucleic acid molecule encoding the immunogenic polypeptide can vary depending upon the specific polypeptide(s), the route and protocol of administration, and the target population. In some embodiments, each dose includes about 1 μg to 1 mg of protein, such as from about 1 μg to about 500 μg, for example, from about 1 μg to about 100 μg, or about 1 μg to about 50 μg, such as about 1 μg, about 2 μg, about 5 μg, about 10 μg, about 15 μg, about 20 μg, about 25 μg, about 30 μg, about 40 μg, about 50 μg, about 75 μg, about 100 μg, about 200 μg, about 300 μg, about 400 μg, or about 500 μg. An optimal amount for a particular composition can be ascertained by standard studies involving observation of antibody titers and other responses in subjects (such as CTL or helper T cell responses).

The disclosed immunogenic polypeptides (such as a set of two or more polypeptides) and/or nucleic acids encoding these proteins can be used in a multistep immunization regime. In some examples, the regime includes administering to a subject a therapeutically effective amount of a first immunogenic polypeptide (or mixture or set of immunogenic polypeptides) and boosting the immunogenic response with a second immunogenic polypeptide (or mixture or set of immunogenic polypeptides) after an appropriate period of time. This method of eliciting such an immune reaction is referred to as a "prime-boost" immunization regimen. Different dosages can be used in a series of sequential inoculations. Thus, a practitioner may administer a relatively large dose in a primary inoculation (prime) and then boost with relatively smaller doses. In some examples, the immunogenic polypeptide or mixture thereof administered in both the prime and boost inoculations are the same immunogenic polypeptide or mixture thereof. In other examples, the immunogenic polypeptide or mixture thereof administered in the boost is different from that administered in the prime inoculation.

The prime can be administered as a single dose or multiple doses, for example two doses, three doses, four doses, five doses, six doses, or more can be administered to a subject over days, weeks or months. The boost can be administered as a single dose or multiple doses, for example two to six doses or more can be administered to a subject over a day, a week or months. Multiple boosts can also be given, such one to five, or more. Different dosages can be used in a series of sequential inoculations. For example, a relatively large dose in a primary inoculation and then a boost with relatively smaller doses. In some examples, there are weeks (for example, at least one week, at least 2 weeks, at least 3 weeks, at least 4 weeks, at least 6 weeks, at least 8 weeks, at least 12 weeks, at least 16 weeks, at least 24 weeks, or more) between administration of a prime and a boost or between administration of two boosts in a prime-boost regimen. The immune response against one or more of the synthetic alphavirus polypeptides can be generated by one or more inoculations of a subject with an immunogenic composition disclosed herein.

The following examples are provided to illustrate certain particular features and/or embodiments. These examples should not be construed to limit the disclosure to the particular features or embodiments described.

EXAMPLES

Example 1: Multivalent Alphavirus Vaccines Immunogens

This example describes the design of synthetic immunogenic polypeptides derived from alphavirus polypeptide sequences.

Methods

A graph-theory-based algorithm (Theiler and Korber, *Stat Med* doi:10.1002/sim.7203, 2017) was used to generate sets of high-matching synthetic sequences to cover a curated set of natural alphavirus structural protein sequences. This curated set was generated from an alignment of all VEEV-clade, WEEV-clade, EEEV-clade, and Chikungunya virus (CHKV) sequences available in GenBank (as of Dec. 11, 2018) by removal of highly similar sequences.

In these types of studies (Fischer et al., *Nat Med* 13, 100-106, 2007; Kong et al., *J Virol* 83, 2201-2215, 2009; Barouch et al., *Nat Med* 16, 319-323, 2010; Santra et al., *Nat Med* 16, 324-328, 2010; Yusim et al., *J Gen Virol* 91, 1194-1206, 2010; Fenimore et al., *PLoS One* 7, e44769, 2012; Yusim et al., *Clin Vaccine Immunol* 20, 302-305, 2013; Fischer et al., *J Virol* 86, 13217-13231, 2012; Korber et al., *J Virol* 83, 8300-8314, 2009), potential epitope coverage of a vaccine is generally evaluated in terms of the fraction of short amino acid sub-sequences (k-mers, where 8≤k≤15, k representing the number of amino acids) shared between natural strains and a vaccine candidate. Fragments of 9 amino acids (9-mers) are convenient, since cytotoxic T cell epitopes are typically 9 amino acids long, but optimization of 9-mers inevitably enriches for longer lengths as well (Korber et al., *J Virol* 83, 8300-8314, 2009). Optimization includes generating sequences of full- or near full-length proteins, with extremely rare 9-mers replaced with common ones, and (non-rare) alternative 9-mers distributed among the several different members of each protein cocktail. This enables maximal numbers of common variants to be presented in a single vaccine formulation, and helps ensure that any immune responses induced by the vaccine will correspond to circulating (potentially infective) virus.

Initial analysis showed very little overlap in 9-mers between the several clades of interest (VEEV, EEEV, WEEV, and CHK). Cocktail sets were therefore generated separately for each clade, with 1, 2, or 3 sequences per cocktail, and coverages were computed for various combinations. Sequence subsets were uploaded to the Epigraph tool (online at hiv_lanl_gov/content/sequence/EPIGRAPH/epigraph) with the default parameters excepting trial count and iterative refinement (both set to 10). In addition to the full-length structural polyprotein sequences disclosed herein (referred to as "Sequences (full length)"), sequences truncated at the N-terminal end to remove the capsid (CP) protein are also disclosed (referred to herein as "Sequences (without capsid (CP) gene)").

Results

Figure 1A:
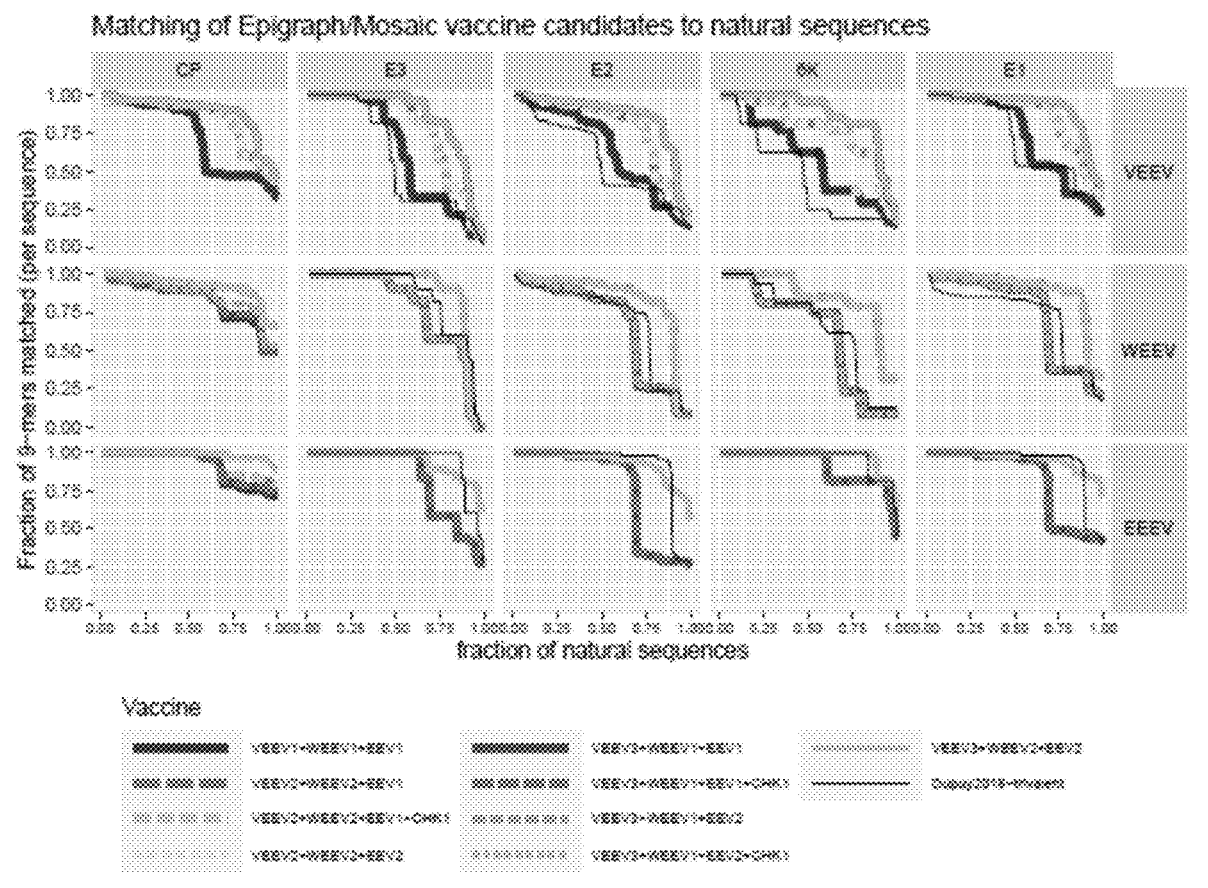
Figure 1B:
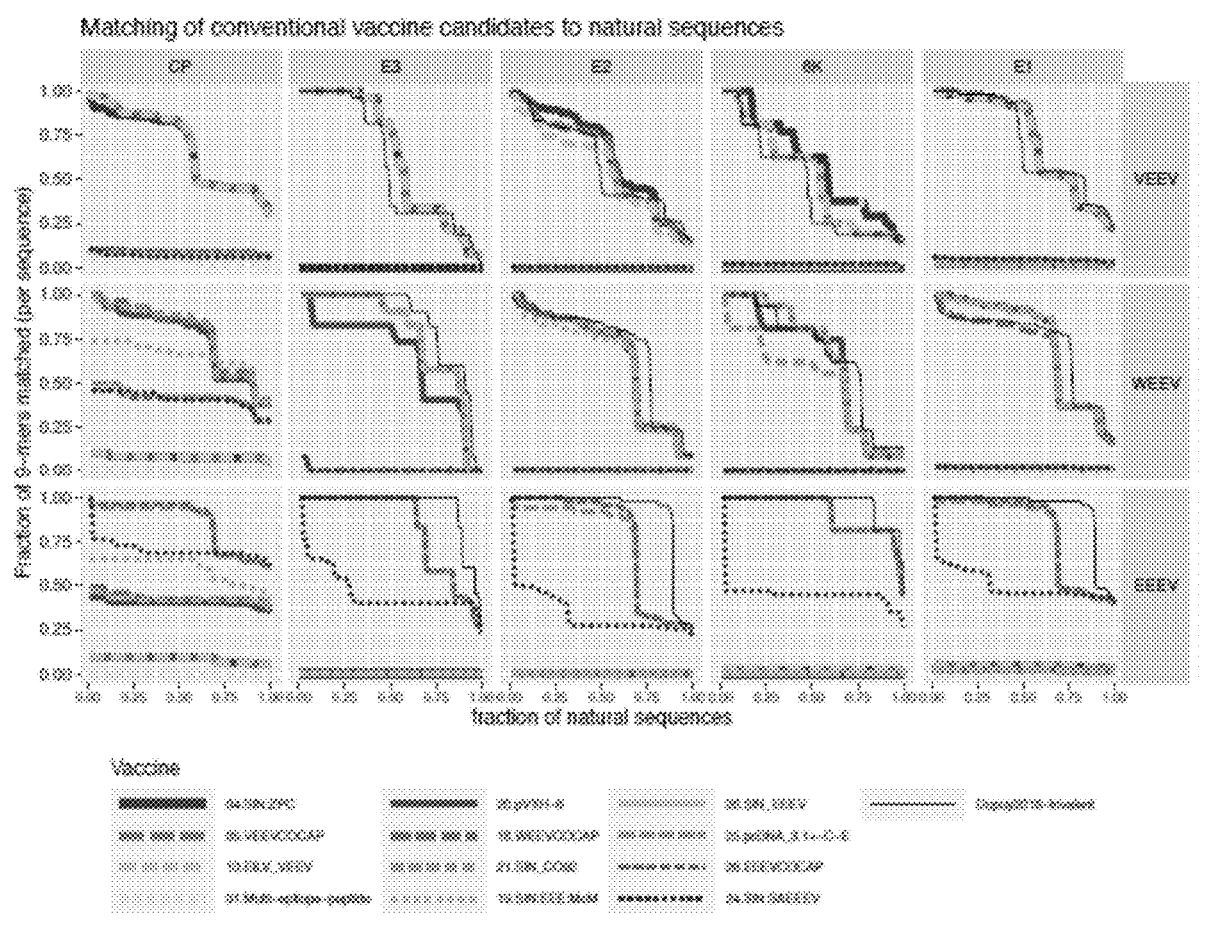

The multi-element compositions or cocktails disclosed herein present a larger fraction of potential epitopes from native virus isolates than conventional vaccine candidates (FIG. 1A), which are based on natural strains (FIG. 1B). These coverage values correspond to different combinations of vaccine immunogens (Table 1). Either the "full length" or "without capsid" sequences can be used in the compositions or cocktails.

TABLE 1

Immunogen content of different cocktails

| Individual immunogen(s) | SEQ ID NO: |
|---|---|
| VEEV1 + WEEV1 + EEV1 | |
| VEEVs + .structPs.uniq.EG-1.1 | 1 |
| WEEVs + .structPs.uniq.EG-1.1 | 7 |
| EEEVs + .structPs.uniq.EG-1.1 | 10 |
| VEEV2 + WEEV2 + EEV1 + CHK1 | |
| VEEVs + .structPs.uniq.EG-2.1 | 2 |
| VEEVs + .structPs.uniq.EG-2.2 | 3 |
| WEEVs + .structPs.uniq.EG-2.1 | 8 |
| WEEVs + .structPs.uniq.EG-2.2 | 9 |
| EEEVs + .structPs.uniq.EG-1.1 | 10 |
| CHKs + .structPs.uniq.EG-1.1 | 13 |
| VEEV2 + WEEV2 + EEV1 | |
| VEEVs + .structPs.uniq.EG-2.1 | 2 |
| VEEVs + .structPs.uniq.EG-2.2 | 3 |
| WEEVs + .structPs.uniq.EG-2.1 | 8 |
| WEEVs + .structPs.uniq.EG-2.2 | 9 |
| EEEVs + .structPs.uniq.EG-1.1 | 10 |
| VEEV2 + WEEV2 + EEV2 | |
| VEEVs + .structPs.uniq.EG-2.1 | 2 |
| VEEVs + .structPs.uniq.EG-2.2 | 3 |
| WEEVs + .structPs.uniq.EG-2.1 | 8 |
| WEEVs + .structPs.uniq.EG-2.2 | 9 |
| EEEVs + .structPs.uniq.EG-2.1 | 11 |
| EEEVs + .structPs.uniq.EG-2.2 | 12 |
| VEEV3 + WEEV1 + EEV1 + CHK1 | |
| VEEVs + .structPs.uniq.EG-3.1 | 4 |
| VEEVs + .structPs.uniq.EG-3.2 | 5 |
| VEEVs + .structPs.uniq.EG-3.3 | 6 |
| WEEVs + .structPs.uniq.EG-1.1 | 7 |
| EEEVs + .structPs.uniq.EG-1.1 | 10 |
| CHKs + .structPs.uniq.EG-1.1 | 13 |
| VEEV3 + WEEV1 + EEV1 | |
| VEEVs + .structPs.uniq.EG-3.1 | 4 |
| VEEVs + .structPs.uniq.EG-3.2 | 5 |
| VEEVs + .structPs.uniq.EG-3.3 | 6 |
| WEEVs + .structPs.uniq.EG-1.1 | 7 |
| EEEVs + .structPs.uniq.EG-1.1 | 10 |
| VEEV3 + WEEV1 + EEV2 + CHK1 | |
| VEEVs + .structPs.uniq.EG-3.1 | 4 |
| VEEVs + .structPs.uniq.EG-3.2 | 5 |
| VEEVs + .structPs.uniq.EG-3.3 | 6 |
| WEEVs + .structPs.uniq.EG-1.1 | 7 |
| EEEVs + .structPs.uniq.EG-2.1 | 11 |
| EEEVs + .structPs.uniq.EG-2.2 | 12 |
| CHKs + .structPs.uniq.EG-1.1 | 13 |
| VEEV3 + WEEV1 + EEV2 | |
| VEEVs + .structPs.uniq.EG-3.1 | 4 |
| VEEVs + .structPs.uniq.EG-3.2 | 5 |
| VEEVs + .structPs.uniq.EG-3.3 | 6 |
| WEEVs + .structPs.uniq.EG-1.1 | 7 |
| EEEVs + .structPs.uniq.EG-2.1 | 11 |
| EEEVs + .structPs.uniq.EG-2.2 | 12 |
| VEEV3 + WEEV2 + EEV2 | |
| VEEVs + .structPs.uniq.EG-3.1 | 4 |
| VEEVs + .structPs.uniq.EG-3.2 | 5 |
| VEEVs + .structPs.uniq.EG-3.3 | 6 |
| WEEVs + .structPs.uniq.EG-2.1 | 8 |
| WEEVs + .structPs.uniq.EG-2.2 | 9 |
| EEEVs + .structPs.uniq.EG-2.1 | 11 |
| EEEVs + .structPs.uniq.EG-2.2 | 12 |

In view of the many possible embodiments to which the principles of the disclosed subject matter may be applied, it should be recognized that the illustrated embodiments are only examples of the disclosure and should not be taken as limiting the scope of the disclosure. Rather, the scope of the disclosure is defined by the following claims. We therefore claim all that comes within the scope and spirit of these claims.

The invention claimed is:

1. A synthetic immunogenic polypeptide comprising:
an amino acid sequence at least 99% identical to any one of SEQ ID NOs: 2, 4-6, 8, 11, 15, 17, 19,21 and 24; or
the amino acid sequence set forth as any one of SEQ ID NOs: 1, 3, 9, 13, 18 and 264-26.

2. The synthetic immunogenic polypeptide of claim 1, wherein the amino acid sequence of the polypeptide comprises or consists of any one of SEQ ID NOs: 1-6, 8, 9, 11, 13, 15, 17-19, 21, 24 and 26.

3. A set of synthetic immunogenic polypeptides comprising two or more polypeptides selected from polypeptides comprising:
an amino acid sequence having at least 99% identity to the amino acid sequence set forth as any one of SEQ ID NOs: 2, 4-6, 8, 11, 15, 17, 19, 21 and 24; or
the amino acid sequence set forth as any one of SEQ ID NOs: 1, 3, 9, 13, 18 and 26.

4. The set of synthetic immunogenic polypeptides of claim 3, further comprising one or more additional polypeptides selected from polypeptides comprising the amino acid sequence set forth as any one of SEQ ID NOs: 7, 10, 12, 14, 16, 20, 22, 23 and 25.

5. The set of synthetic immunogenic polypeptides of claim 3, wherein the two or more polypeptides are selected from polypeptides having an amino acid sequence consisting of the amino acid sequences set forth as any one of SEQ ID NOs: 1-6, 8, 9, 11, 13, 15, 17-19, 21, 24 and 26.

6. A set of synthetic immunogenic polypeptides, comprising:
three synthetic polypeptides having amino acid sequences comprising or consisting of the amino acid sequences of SEQ ID NO: 6, SEQ ID NO: 9 and SEQ ID NO: 12;
three synthetic polypeptides having amino acid sequences comprising or consisting of the amino acid sequences of SEQ ID NO: 1, SEQ ID NO: 7 and SEQ ID NO: 10;
six synthetic polypeptides having amino acid sequences comprising or consisting of the amino acid sequences of SEQ ID NO: 2, SEQ ID NO: 3, SEQ ID NO: 8, SEQ ID NO: 9, SEQ ID NO: 10 and SEQ ID NO: 13;
five synthetic polypeptides having amino acid sequences comprising or consisting of the amino acid sequences of SEQ ID NO: 2, SEQ ID NO: 3, SEQ ID NO: 8, SEQ ID NO: 9 and SEQ ID NO: 10;
six synthetic polypeptides having amino acid sequences comprising or consisting of the amino acid sequences of SEQ ID NO: 2, SEQ ID NO: 3, SEQ ID NO: 8, SEQ ID NO: 9, SEQ ID NO: 11 and SEQ ID NO: 12;
six synthetic polypeptides having amino acid sequences comprising or consisting of the amino acid sequences of SEQ ID NO: 4, SEQ ID NO; 5, SEQ ID NO: 6, SEQ ID NO: 7, SEQ ID NO: 10 and SEQ ID NO: 13;
five synthetic polypeptides having amino acid sequences comprising or consisting of the amino acid sequences of SEQ ID NO: 4, SEQ ID NO; 5, SEQ ID NO: 6, SEQ ID NO: 7 and SEQ ID NO: 10;
seven synthetic polypeptides having amino acid sequences comprising or consisting of the amino acid sequences of SEQ ID NO: 4, SEQ ID NO; 5, SEQ ID NO: 6, SEQ ID NO: 7, SEQ ID NO: 11, SEQ ID NO: 12 and SEQ ID NO: 13;
six synthetic polypeptides having amino acid sequences comprising or consisting of the amino acid sequences of SEQ ID NO: 4, SEQ ID NO; 5, SEQ ID NO: 6, SEQ ID NO: 7, SEQ ID NO: 11 and SEQ ID NO: 12; or
seven synthetic polypeptides having amino acid sequences comprising or consisting of the amino acid sequences of SEQ ID NO: 4, SEQ ID NO; 5, SEQ ID NO: 6, SEQ ID NO: 8, SEQ ID NO: 9, SEQ ID NO: 11 and SEQ ID NO: 12.

7. A nucleic acid molecule or vector encoding the synthetic immunogenic polypeptide of claim 1.

8. A recombinant host cell comprising the nucleic acid molecule or vector of claim 7.

9. A nucleic acid molecule or vector encoding the set of synthetic immunogenic polypeptides of claim 6.

10. A recombinant host cell comprising the nucleic acid molecule or vector of claim 9.

11. A set of isolated nucleic acid molecules comprising two or more nucleic acid molecules, wherein each nucleic acid molecule encodes an immunogenic polypeptide selected from polypeptides comprising:
an amino acid sequence having at least 99% identity to the amino acid sequence set forth as any one of SEQ ID NOs: 2, 4-6, 8, 11, 15, 17, 19, 21 and 24; or
the amino acid sequence set forth as any one of SEQ ID NOs: 1, 3, 9, 13, 18 and 26.

12. The set of isolated nucleic acid molecules of claim 11, further comprising one or more additional nucleic acid molecules, wherein the one or more additional nucleic acid molecules encodes an immunogenic polypeptide selected from polypeptides comprising the amino acid sequence set forth as any one of SEQ ID NOs: 7, 10, 12, 14, 16, 20, 22, 23 and 25.

13. The set of isolated nucleic acid molecules of claim 11, wherein the two or more nucleic acid molecules each encode an immunogenic polypeptide selected from polypeptides having an amino acid sequence consisting of the amino acid sequences set forth as any one of SEQ ID NOs: 1-6, 8, 9, 11, 13, 15, 17-19, 21, 24 and 26.

14. A set of isolated nucleic acid molecules, comprising:
three nucleic acid molecules encoding polypeptides having amino acid sequences comprising or consisting of the amino acid sequences of SEQ ID NO: 6, SEQ ID NO: 9 and SEQ ID NO: 12;
three nucleic acid molecules encoding polypeptides having amino acid sequences comprising or consisting of the amino acid sequences of SEQ ID NO: 1, SEQ ID NO: 7 and SEQ ID NO: 10;
six nucleic acid molecules encoding polypeptides having amino acid sequences comprising or consisting of the amino acid sequences of SEQ ID NO: 2, SEQ ID NO: 3, SEQ ID NO: 8, SEQ ID NO: 9, SEQ ID NO: 10 and SEQ ID NO: 13;
five nucleic acid molecules encoding polypeptides having amino acid sequences comprising or consisting of the amino acid sequences of SEQ ID NO: 2, SEQ ID NO: 3, SEQ ID NO: 8, SEQ ID NO: 9 and SEQ ID NO: 10;
six nucleic acid molecules encoding polypeptides having amino acid sequences comprising or consisting of the amino acid sequences of SEQ ID NO: 2, SEQ ID NO: 3, SEQ ID NO: 8, SEQ ID NO: 9, SEQ ID NO: 11 and SEQ ID NO: 12;
six nucleic acid molecules encoding polypeptides having amino acid sequences comprising or consisting of the amino acid sequences of SEQ ID NO: 4, SEQ ID NO; 5, SEQ ID NO: 6, SEQ ID NO: 7, SEQ ID NO: 10 and SEQ ID NO: 13;
five nucleic acid molecules encoding polypeptides having amino acid sequences comprising or consisting of the amino acid sequences of SEQ ID NO: 4, SEQ ID NO; 5, SEQ ID NO: 6, SEQ ID NO: 7 and SEQ ID NO: 10;
seven nucleic acid molecules encoding polypeptides having amino acid sequences comprising or consisting of the amino acid sequences of SEQ ID NO: 4, SEQ ID NO; 5, SEQ ID NO: 6, SEQ ID NO: 7, SEQ ID NO: 11, SEQ ID NO: 12 and SEQ ID NO: 13;

six nucleic acid molecules encoding polypeptides having amino acid sequences comprising or consisting of the amino acid sequences of SEQ ID NO: 4, SEQ ID NO; 5, SEQ ID NO: 6, SEQ ID NO: 7, SEQ ID NO: 11 and SEQ ID NO: 12; or seven nucleic acid molecules encoding polypeptides having amino acid sequences comprising or consisting of the amino acid sequences of SEQ ID NO: 4, SEQ ID NO; 5, SEQ ID NO: 6, SEQ ID NO: 8, SEQ ID NO: 9, SEQ ID NO: 11 and SEQ ID NO: 12.

15. A vector or a plurality of vectors comprising the set of isolated nucleic acid molecules of claim 14.

16. A recombinant host cell comprising the vector or plurality of vectors of claim 15.

17. A composition comprising the set of synthetic immunogenic polypeptides of claim 6.

18. The composition of claim 17, further comprising a pharmaceutically acceptable carrier and/or an adjuvant.

19. A method of eliciting an immune response against one or more alphaviruses in a subject, comprising administering to the subject an effective amount of the set of synthetic immunogenic polypeptides of claim 6.

20. The method of claim 19, wherein the one or more alphaviruses comprises Venezuelan equine encephalitis virus, Western equine encephalitis virus, Eastern equine encephalitis virus, Chikungunya virus, or any combination thereof.

* * * * *